US008168200B2

(12) United States Patent
Minke et al.

(10) Patent No.: US 8,168,200 B2
(45) Date of Patent: May 1, 2012

(54) VACCINE AGAINST AFRICAN HORSE SICKNESS VIRUS

(75) Inventors: Jules Maarten Minke, Corbas (FR); Jean-Christophe Audonnet, Lyon (FR); Alan John Guthrie, Gauteng (ZA); Nigel James MacLachlan, Davis, CA (US); Jiansheng Yao, Ontario (CA)

(73) Assignees: Merial Limited, Duluth, GA (US); The Regents of the University of California, Oakland, CA (US); University of Pretoria, Pretoria (ZA)

( * ) Notice: Subject to any disclaimer, the term of this patent is extended or adjusted under 35 U.S.C. 154(b) by 61 days.

(21) Appl. No.: 12/604,048

(22) Filed: Oct. 22, 2009

(65) Prior Publication Data

US 2010/0119546 A1 May 13, 2010

Related U.S. Application Data

(60) Provisional application No. 61/108,075, filed on Oct. 24, 2008, provisional application No. 61/163,517, filed on Mar. 26, 2009.

(51) Int. Cl.
*A61K 39/15* (2006.01)
*A61K 39/295* (2006.01)
*C12N 15/85* (2006.01)
*C12N 15/863* (2006.01)
*C12N 5/10* (2006.01)
*C12N 7/01* (2006.01)

(52) U.S. Cl. ............... 424/199.1; 424/215.1; 424/232.1; 435/235.1; 435/320.1; 435/325; 536/23.72

(58) Field of Classification Search ........................ None
See application file for complete search history.

(56) References Cited

U.S. PATENT DOCUMENTS

| | | | | |
|---|---|---|---|---|
| 5,494,807 A | 2/1996 | Paoletti | 435/69.3 |
| 5,505,941 A | 4/1996 | Paoletti | 424/93.2 |
| 5,756,103 A | 5/1998 | Paoletti | 424/199.1 |
| 5,766,599 A | 6/1998 | Paoletti | 424/199.1 |
| 7,163,926 B1 | 1/2007 | Audonnet | 514/44 A |
| 7,862,821 B2 * | 1/2011 | Audonnet et al. | 424/185.1 |
| 2005/0255127 A1 * | 11/2005 | Loosmore et al. | 424/199.1 |

FOREIGN PATENT DOCUMENTS

| | | |
|---|---|---|
| WO | WO96/40241 | 12/1996 |
| ZA | 9 706 424 A | 1/1999 |

OTHER PUBLICATIONS

MacLachlan et al (Vaccine 25:5577-5582, 2007).*
Boone et al (Vaccine 25:672-678, 2007).*
Cook et al (Veterinary Microbiology 108:23-37, 2005).*
Database EMBL: Oct. 15, 1992, Iwata H, et al.: "African Horse Sickness Virus 4, capsid protein VP2"—XP002574276 Database accession No. M94680 abstract.
Antoine G., Virology, 1998, 244, 365-396 Complete Genomic Sequence of the Modified Vaccinia Ankara Strain.
Boone JD, et al. 25 (2007) 672-678 Recombinant canarypox virus vaccine co-expressing genes encoding the VP2 and VP5 . . . .
Bremer, CW, et al. (1990); Journal of General Virology (1990), 71, 793-799.
Grubman, M. J. & Lewis, S. A. (1992); Virology 186, 444-451 (1992).
Guo P. et al. J. Virol., 1989, 63, 4189-4198.
Huismans, H. & Els, H. J. Virology 92, 397-406 (1979); Characterization of the Tubules Associated with the Replication of Three . . . .
Huismans, H Virology 92 (1979) 385-396.
Lewis SA and Grubman MJ, (1991); Journal of Virology, Dec. 1991, p. 6572-6580.
Martinez-Torrecuadrada JL et al. (1999); Virology 257, 449-459 (1999).
Minke JM, et al., 2004 a Vet. Res. 35 (2004) 425-443.
Minke JM, et al. 2004b *Arch Virol Suppl* 2004;(18):221-30, (Abstract only).
Minke JM, et al. (2007); J.Comp. Path.2007,vol. 137, S76-S80.
Mizukoshi, N. et al. (1992) Journal of General Virology (1992), 73, 2425-2428.
Pearson LD, Roy P, (1993) *Immunology and Cell Biology* (1993) 71, 381-389.
Perkus M. et al., J. Virol., 1989, 63, 3829-3836—Cloning and Expression of Foreign Genes in Vaccinia Virus, Using a Host Range Selection System.
Poulet H, et al. (2003)—The Veterinary Record, Aug. 2, 2003—Efficacy of a canarypox virus—vectored vaccine against feline leukaemia.
Roy P., et al. (1995) Orbivirus Structure and Assembly. Virology 216, 1-11 (1996).
Scanlen M, et al. (2002) The protective efficacy of a recombinant VP2-based African horsesickness subunit vaccine candidate is determined by adjuvant. Vaccine 20 (2002) 1079-1088.
Taylor J. et al., Vaccine, 1988, 6, 504-508;—Fowlpox virus as a vector in non-avian species.
Taylor J. et al. Recombinant fowlpox virus inducing protective immunity in non-avian species, Vaccine, 1988, 6, 497-503.
van Staden, V. & Huismans, H. (1991); Journal of General Virology (1991), 72, 1073-1079.
Wilson and Mecham. Molecular evolution of orbiviruses. Proc. U.S. Animal Health Assoc. 104:169-180. 2000.

* cited by examiner

*Primary Examiner* — Mary E Mosher
(74) *Attorney, Agent, or Firm* — Judy Jarecki-Black; Chad Kitchen; Merial Limited

(57) ABSTRACT

The present invention provides vectors that contain and express in vivo the genes encoding VP2 and VP5 of African Horse Sickness Virus or an epitope thereof that elicits an immune response in a horse against African horse sickness virus, compositions comprising said vectors, methods of vaccination against African horse sickness virus, and kits for use with such methods and compositions.

15 Claims, 56 Drawing Sheets

FIGURE 1 (1/2)
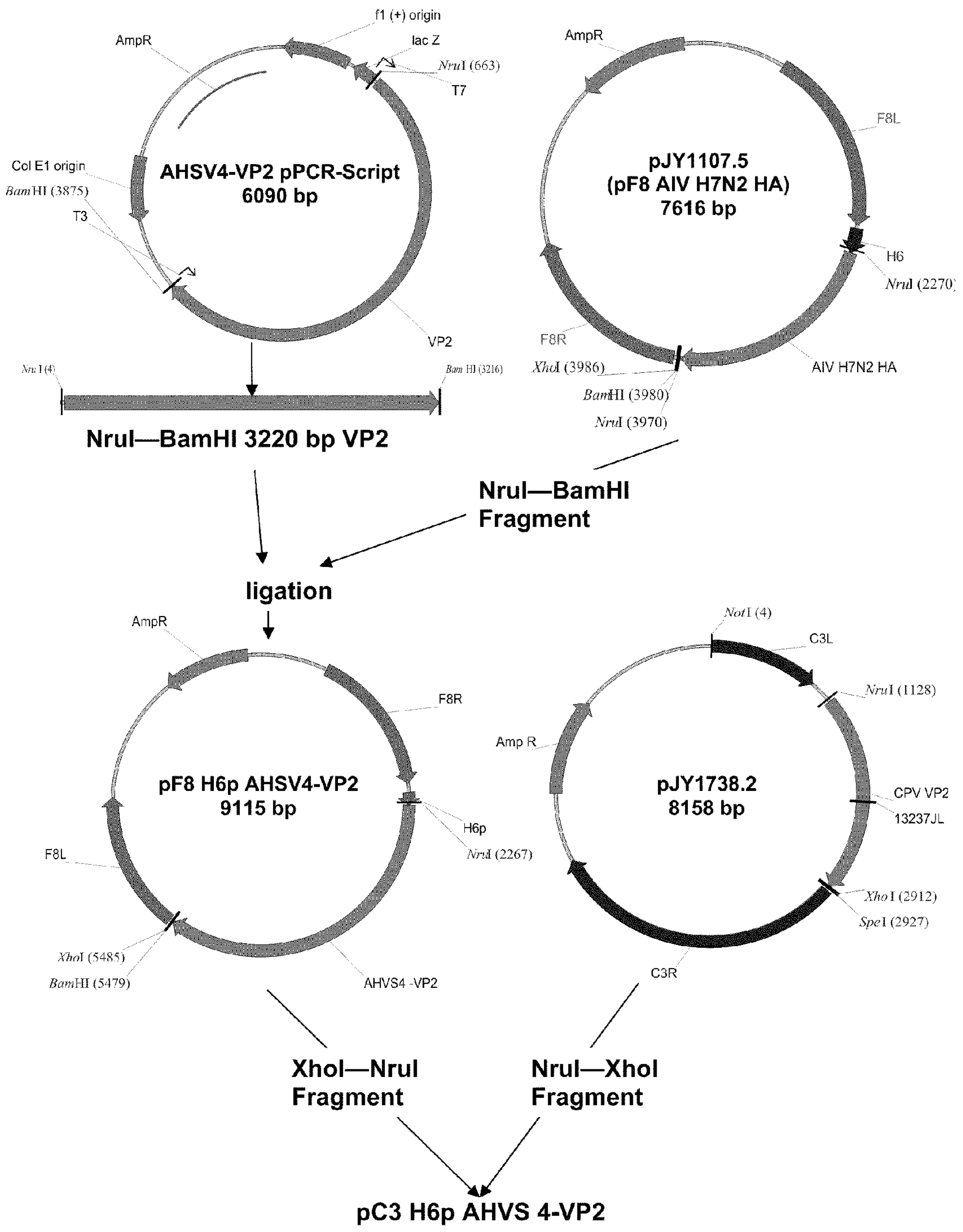

FIGURE 1 (2/2)
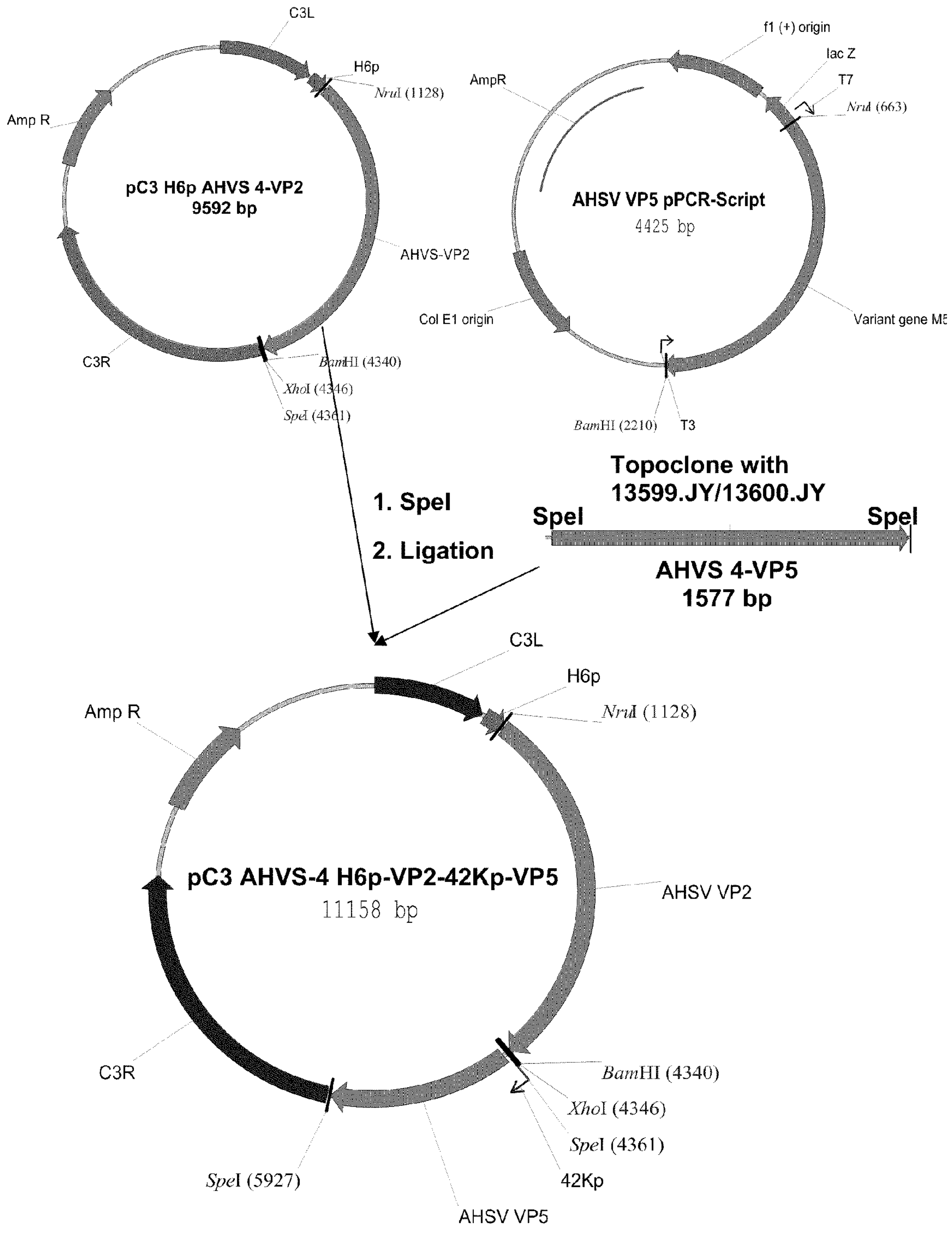

| | |
|---|---|
| C3 left arm: | 3-942 |
| H6 promoter: | 966-1152 |
| AHSV 4-VP2: | 1153-4338 |
| 42K promoter: | 4365-4397 |
| AHSV 4-VP5: | 4398-5912 |
| C3 right arm: | 5947-8509 |

pLHD3460.4-SEQ ID NO:6
AHSV-4 VP2 DNA (pLHD3460.4)-SEQ ID NO:4
AHSV-4 VP5 DNA (pLHD3460.4)-SEQ ID NO:5
Predicted AA Seq. for AHSV-4 VP2 PRT (pLHD3460.4)-SEQ ID NO:1
Predicted AA Seq. for AHSV-4 VP5 PRT (pLHD3460.4)-SEQ ID NO:2 vCP2377 Restriction digestion

Lane 1: (KB markers) 40.0, 20.0, 15.0, 10.0, 8.0, 7.0, 6.0, 5.0, 4.0, 3.0, 2.0, 1.65, 1.0
Lane 2: ALVAC-1 digested with BamHI
Lane 3: vCP2377 digested with BamHI
Lane 4: ALVAC-1 digested with HindIII
Lane 5: vCP2377 digested with HindIII
Lane 6: ALVAC-1 digested with PstI
Lane 7: vCP2377 digested with PstI Unique restriction fragments which hybridize with AHSV4-VP2 specific probe ( ■ ■ ■ ):

vCP2377
BamH I: 16047, 6971 bp
HindIII: 20660 bp
PstI: 13658, 4061 bp vCP2377 RE gel

Lane 1: ALVAC-1 digested with BamHI

Lane 2: vCP2377.6.1.1 digested with BamHI

Lane 3: ALVAC-1 digested with HindIII

Lane 4: vCP2377.6.1.1 digested with HindIII

Lane 5: ALVAC-1 digested with PstI

Lane 6: vCP2377.6.1.1 digested with PstI vCP2377 Southern blot

Lane 1: ALVAC-1 digested with BamHI

Lane 2: vCP2377.6.1.1 digested with BamHI

Lane 3: ALVAC-1 digested with HindIII

Lane 4: vCP2377.6.1.1 digested with HindIII

Lane 5: ALVAC-1 digested with PstI

Lane 6: vCP2377.6.1.1 digested with PstI

Unique restriction fragments which hybridize with AHSV4-VP2 specific probe (refer to FIGURE 4):

vCP2377
BamHI: 16047, 6971 bp
HindIII: 20660 bp
PstI: 13658, 4061 bp vCP2377 Western blot

Lane 1: ALVAC cell pellet

Lane 2: vCP2377.6.1.1 cell pellet

Lane 3: ALVAC culture media

Lane 4: vCP2377.6.1.1 culture medium

Primary antibody: mouse anti-VP5
AHSV 10AE12 antibody (1:100)

vCP2377 IP using anti-VP5 AHSV
10AE12 Passage 9 antibody (1:100)

AHSV-4 VP2/5 in C3 Locus (vCP2377.6.1.1)
9020 bp

FIGURE 10 (1/2)
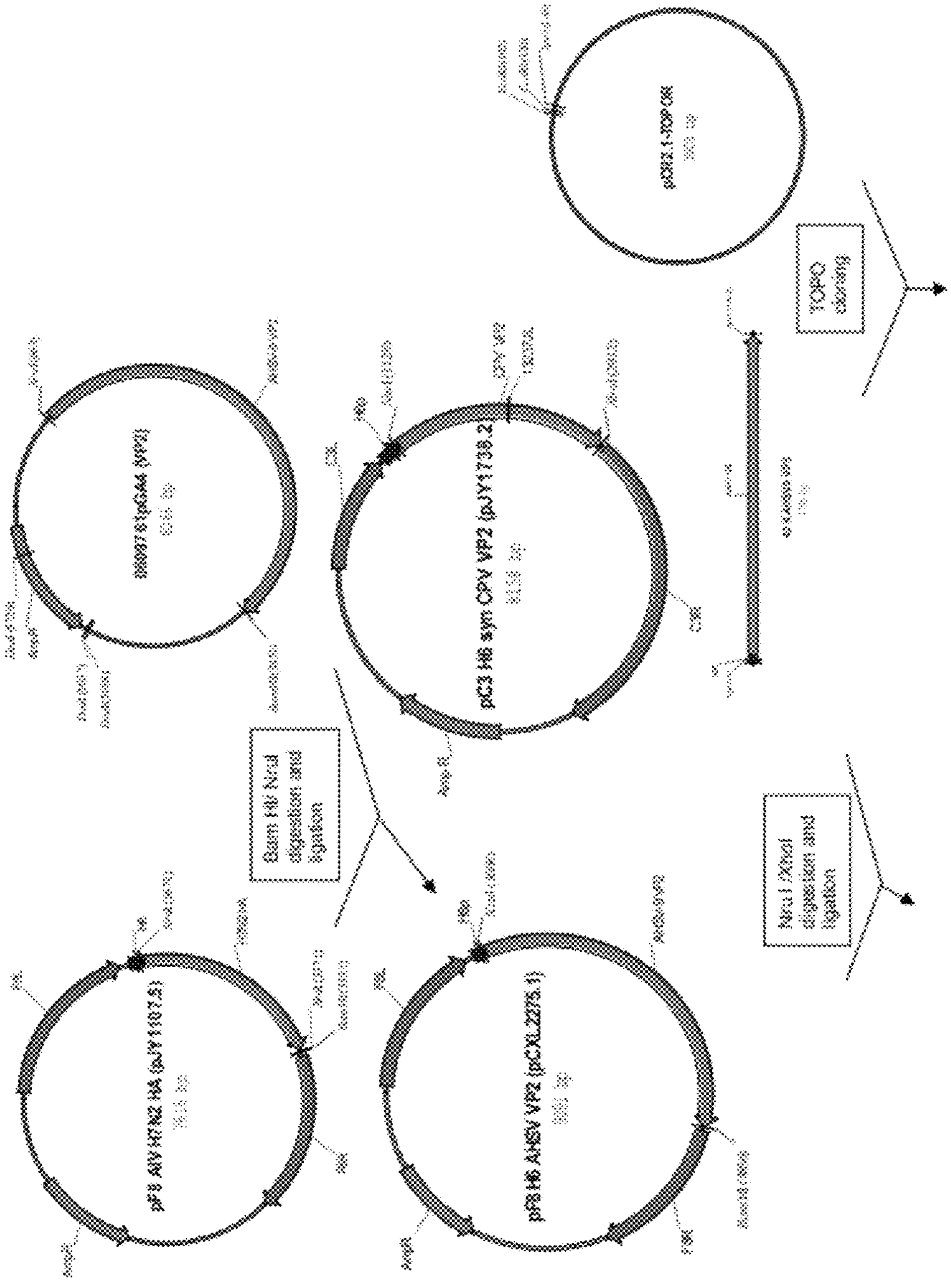

FIGURE 10 (2/2)
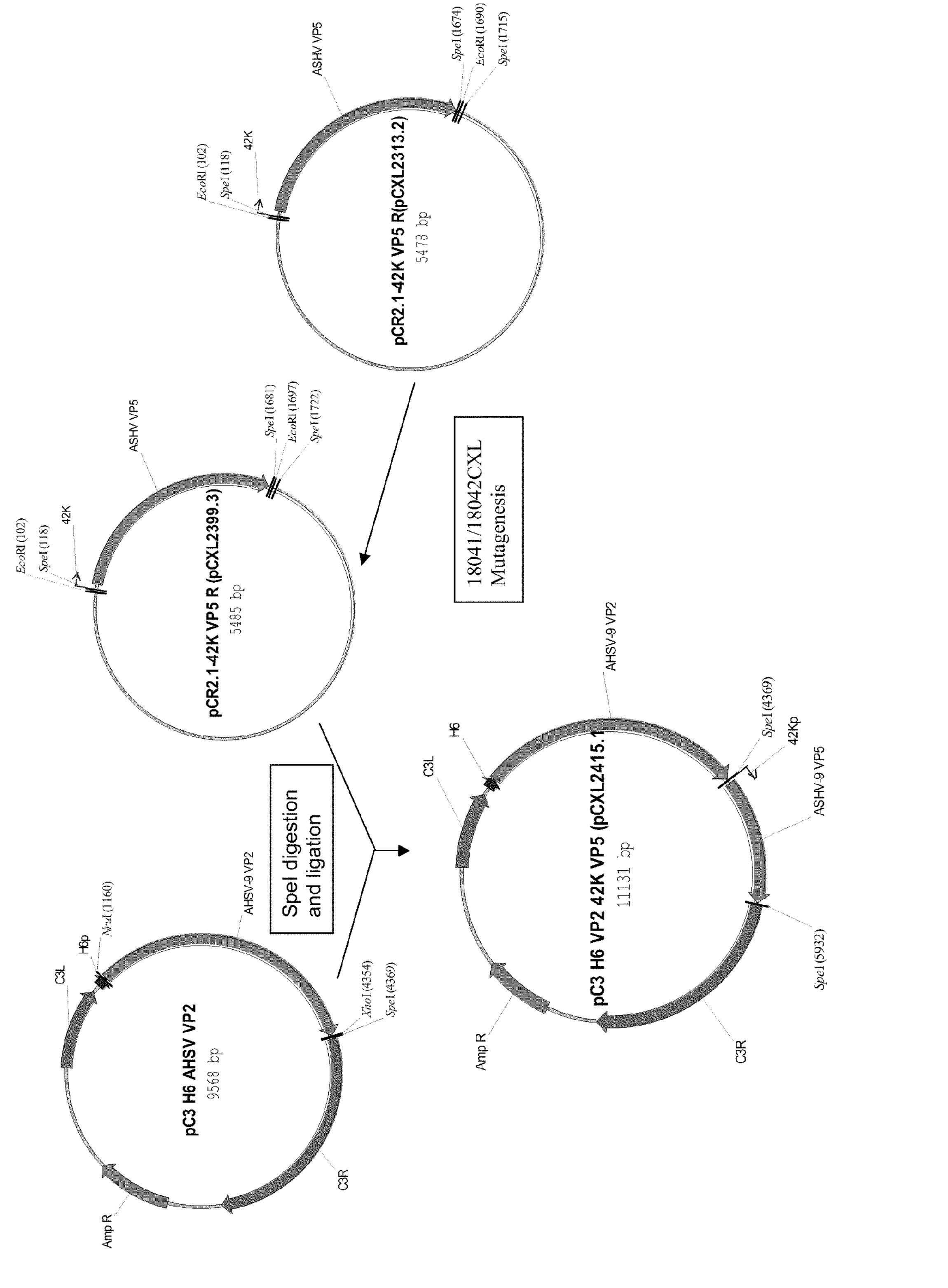

| | |
|---|---|
| C3L: | 58-972 |
| H6 promoter: | 1061-1184 |
| AHSV-9 VP2: | 1185-4340 |
| 42K promoter: | 4374-4405 |
| AHSV-9 VP5: | 4406-5917 |
| C3R: | 5943-8514 |

| |
|---|
| AHSV-9 VP2 DNA in pCXL2415.1-SEQ ID NO:18 |
| AHSV-9 VP5 DNA in pCXL2415.1-SEQ ID NO:19 |
| Predicted AA Sequence for AHSV-9 VP2 PRT in pCXL2415.1-SEQ ID NO:20 |
| Predicted AA Sequence for AHSV-9 VP5 PRT in pCXL2415.1-SEQ ID NO:21 |

FIGURE 12 (1/2)
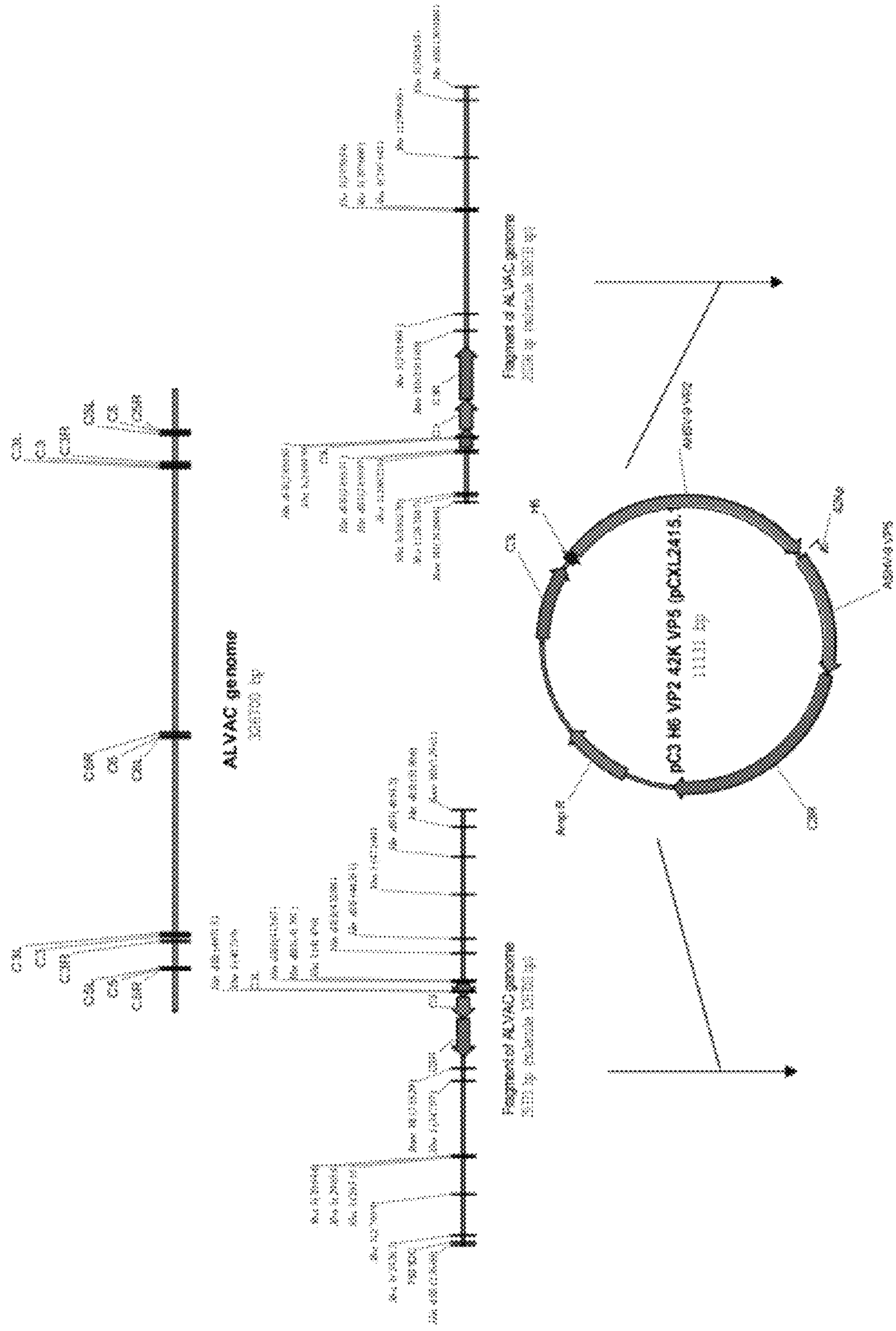

FIGURE 12 (2/2)
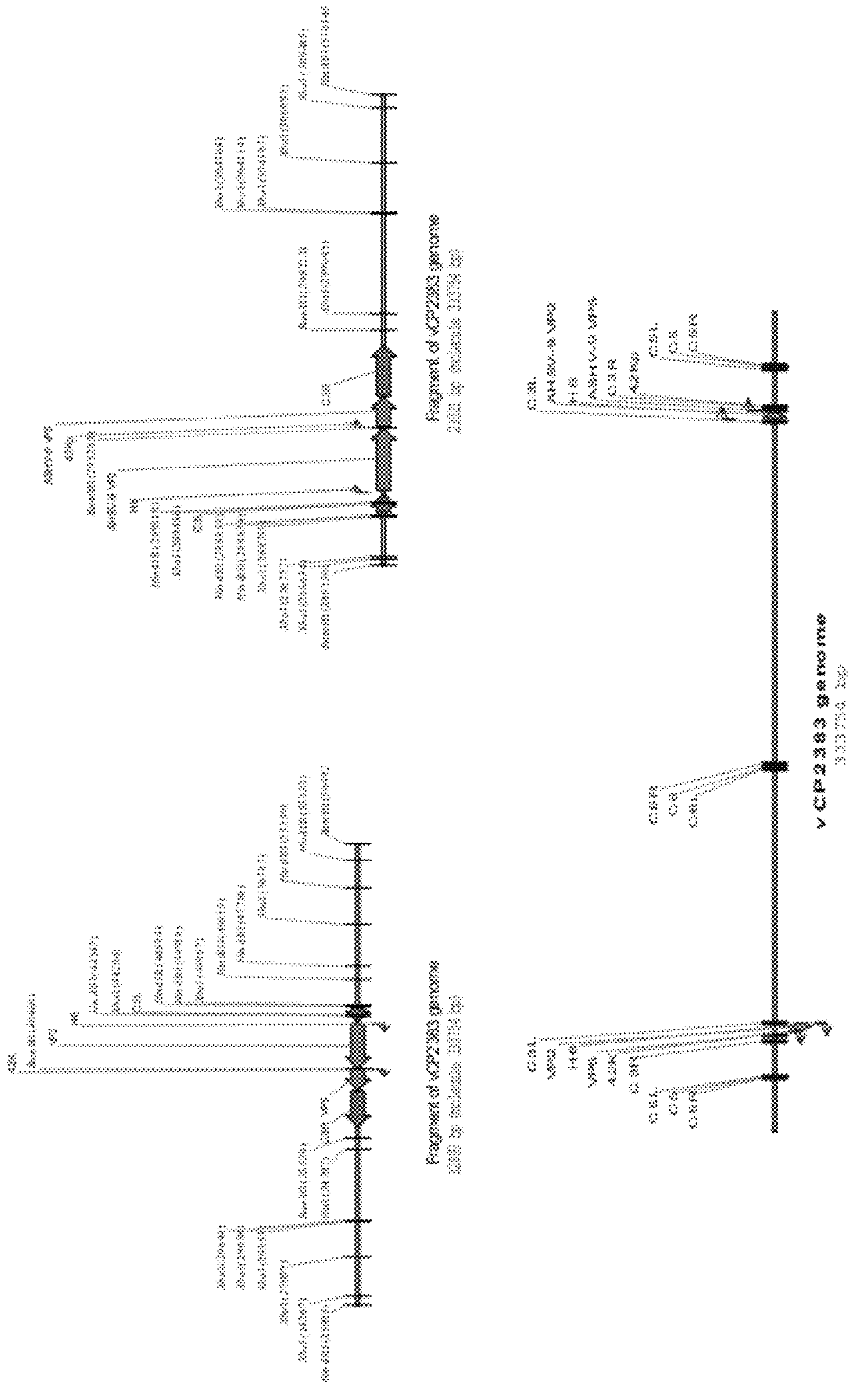

Appendix II: vCP2383 restriction analysis 1. 1Kb+ DNA ladder
2. ALVAC-Bam HI
3. vCP2383.3111-Bam HI
4. vCP2383.9111-Bam HI
5. ALVAC-Hind III
6. vCP2383.3111-Hind III
7. vCP2383.9111-Hind III
8. ALVAC-Xba I
9. vCP2383.3111-Xba I
10. vCP2383.9111-Xba I
11. 1Kb DNA extension ladder Difference between ALVAC and vCP2383
(***** band hybridized with AHSV-VP5 probe, see FIGURE 13)

BamHI ALVAC: 8360 bp
BamHI vCP2383: 6947, 4940 bp

HindIII ALVAC: 17106 bp
HindIII vCP2383: 20633 bp

XbaI ALVAC: 6032 bp
XbaI vCP2383: 9559 bp vCP2383 Left Arm to Right Arm - SEQ ID:27
AHSV-9 VP2 DNA - SEQ ID:28
AHSV-9 VP2 PRT - SEQ ID:30
AHSV-9 VP5 DNA - SEQ ID:29
AHSV-9 VP2 PRT - SEQ ID:31

C3 left arm: 73-997
H6 promoter: 1086-1209
AHSV-9 VP2: 1210-4365
42 K promoter: 4398-4430
AHSV-9-VP5: 4431-5942
C3 right arm: 5968-8539

FIGURE 19
| CEP | vCP EIV (vCP1533 + vCP2242 ) | vCP2377 9A011 | vCP2377 9A021 | vCP2377 9A031 | vCP2377 Before formulation |
|---|---|---|---|---|---|
| Anti VP5 | Negative 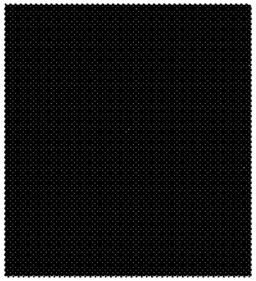 | Positive 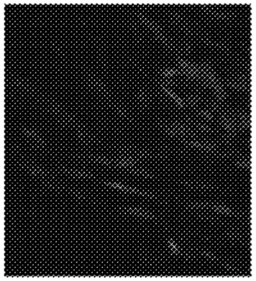 | Positive 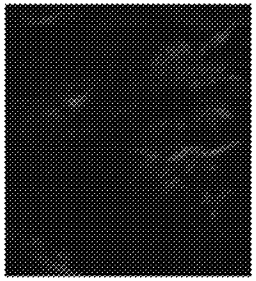 | Positive 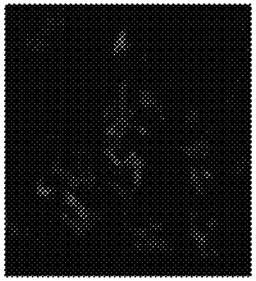 | Positive 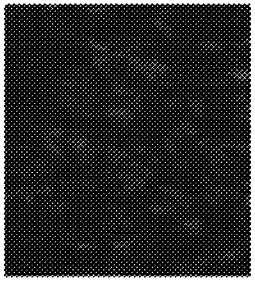 |
| 3 sera anti VP2 St 4 | Negative 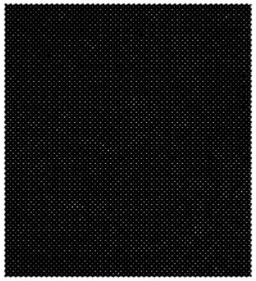 | Positive 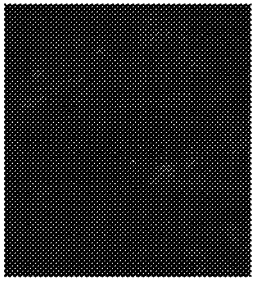 | Positive 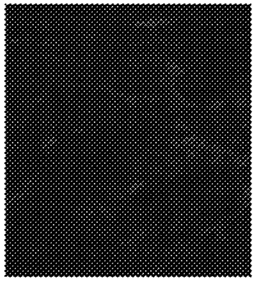 | Positive 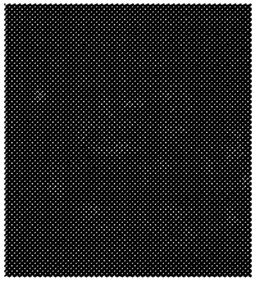 | Positive 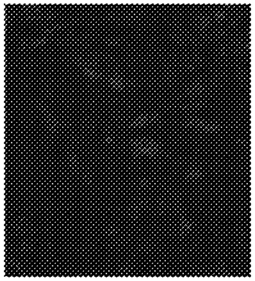 |

FIGURE 21 cpAHSV4 (vCP2377) Neutralizing Antibody Titres against AHSV4

| Horse | Day 0 | Day 28 | Day 42 | Vaccine | |
|---|---|---|---|---|---|
| | | | | Batch | Titration ($Log_{10}CCID_{50}$/ml) |
| **54365** | Neg | 1:28 | 1:224 | 87859A011 | 7.3 |
| **24903** | Neg | 1:56 | 1:224 | | |
| **73420** | Neg | 1:56 | 1:224 | 87859A021 | 6.96 |
| **45671** | Neg | Neg | 1:160 | | |
| **54017** | Neg | Neg | 1:40 | 87859A031 | 6.28 |
| **53761** | Neg | Neg | Neg | | |

Day 0: 3 doses of vaccine. Two doses administered IM on one site of the neck and one dose on the other site.

Day 28: 1 dose of vaccine administered IM in the neck

Blood samples on D0, D28 and D42 pC3 H6p-AHSV 5-VP2/42Kp-VP5 (pJSY2247.2) – SEQ ID NO: 32

CDS (3 total)

VP2 - Start: 1153 End: 4329 – SEQ ID NO: 33
Predicted Amino Acid Sequence for AHSV-5 VP2 – SEQ ID NO: 35
VP5 - Start: 4383 End: 5903 – SEQ ID NO: 34
Predicted Amino Acid Sequence for AHSV-5 VP5 – SEQ ID NO: 36

Amp R - Start: 9105 End: 9961

Misc. Feature (2 total)

C3L - Start: 3 End: 942; C3R - Start: 5932 End: 8494

Promoter Eukaryotic (2 total)

H6p - Start: 967 End: 1152; 42Kp - Start: 4351 End: 4382 vCP2398 Restriction digestion

Lane 1: markers : 40.0, 20.0, 15.0, 10.0, 8.0, 7.0, 6.0, 5.0, 4.0, 3.0, 2.0, 1.65, 1.0, Kb
Lane 2: ALVAC-1 digested with *BamH I*
Lane 3: vCP2398 digested with *BamH I*
*Lane 4:* ALVAC-1 digested with *Hind III*
Lane 5: vCP2398 digested with *Hind III*
*Lane 6*: ALVAC-1 digested with *Pst I*
Lane 7: vCP2398 digested with *Pst I*

Unique restriction fragments which hybridize with AHSV5-VP2 specific probe (■■■■■):

vCP2398 BamHI: 20975 11899 bp
vCP2398 HindIII: 4980 bp
vCP2398 PstI: 1818 bp vCP2398 RE gel Lane 1: ALVAC-1 digested with BamHI Lane 2: vCP2398.2.1.1 digested with BamHI Lane 3: vCP2398.3.1.1 digested with BamHI Lane 4: ALVAC-1 digested with HindIII Lane 5: vCP2398.2.1.1 digested with HindIII Lane 6: vCP2398.3.1.1 digested with HindIII Lane 7: ALVAC-1 digested with PstI Lane 8: vCP2398.2.1.1 digested with PstI Lane 9: vCP2398.3.1.1 digested with PstI

FIGURE 27 vCP2398 Southern blot

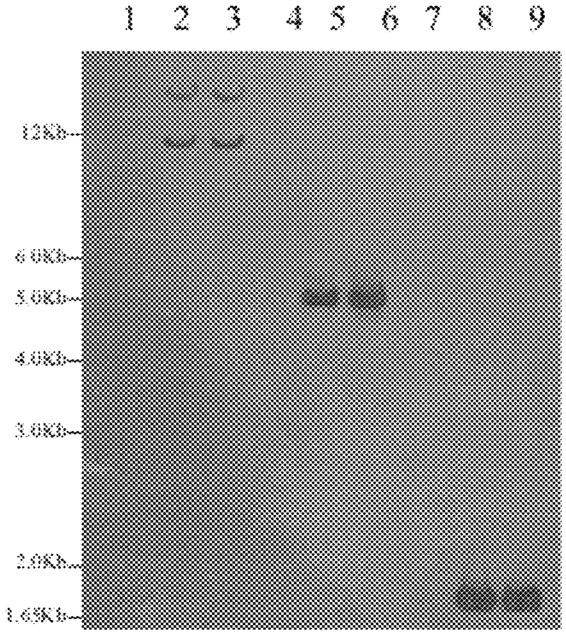

Lane 1: ALVAC-1 digested with BamHI

Lane 2: vCP2398.2.1.1 digested with BamHI

Lane 3: vCP2398.3.1.1 digested with BamHI

Lane 4: ALVAC-1 digested with HindIII

Lane 5: vCP2398.2.1.1 digested with HindIII

Lane 6: vCP2398.3.1.1 digested with HindIII

Lane 7: ALVAC-1 digested with PstI

Lane 8: vCP2398.2.1.1 digested with PstI

Lane 9: vCP2398.3.1.1 digested with PstI

Unique restriction fragments which hybridize with AHSV5-VP2 specific probe ( ):

vCP2398 BamHI: 20975,11899 bp
vCP2398 HindIII: 4980 bp
vCP2398 PstI: 1818 bp vCP2398 Western blot Lane 1: ALVAC culture media
Lane 2: vCP2398.2.1.1 culture media Lane 3: ALVAC cell lysate
Lane 4: vCP2398.2.1.1 cell lysate Primary antibody: mouse anti-VP5
AHSV 10AE12 antibody (1:100)

vCP2398 IP using anti-VP5 AHSV
10AE12 Passage 9 antibody (1:100)

```
C3 left arm:      211-1137
H6 promoter:     1162-1347
AHSV5-VP2(SEQ ID NO:42): 1348-4524
42K promoter:    4542-4573
AHSV5-VP5(SEQ ID NO:43): 4574-6094
C3 right arm:    6123-8685
```

C3 AHSV-5 H6p-VP2 / 42Kp-VP5

Panel A

Panel B

Panel C

FIGURE 32 (1/2)

| SEQ ID NO. | TYPE | Description |
|---|---|---|
| 1 | PRT | AHSV-4 VP2 from pLHD3460.4 |
| 2 | PRT | AHSV-4 VP5 from pLHD3460.4 |
| 3 | DNA | Left Arm to Right Arm Nucleotide Sequence for pLHD3460.4 |
| 4 | DNA | AHSV-4 – VP2 gene in pLHD3460.4 |
| 5 | DNA | AHSV-4 – VP5 gene in pLHD3460.4 |
| 6 | DNA | pLHD3460.4 (pC3 H6p synthetic AHSV4 VP2/42Kp synthetic AHSV4 VP5) entire plasmid |
| 7 | DNA | 13599.JY Primer for amplification of 42Kp-AHSV4 VP5 expressing cassette |
| 8 | DNA | 13600.JY Primer for amplification of 42Kp-AHSV4 VP5 expressing cassette |
| 9 | DNA | 13625.LH Primer for amplifying the AHSV-4 VP2 probe |
| 10 | DNA | 13632.LH Primer for amplifying the AHSV-4 VP2 probe |
| 11 | DNA | 13615.LH Primer for amplifying the AHSV-4 VP5 probe |
| 12 | DNA | 13620.LH Primer for amplifying the AHSV-4 VP5 probe |
| 13 | DNA | 8103.JY Primer for PCR amplification of the vCP2377/vCP2383/vCP2398 C3 arms + insert |
| 14 | DNA | 8104.JY Primer for PCR amplification of the vCP2377/vCP2383/vCP2398 C3 arms + insert |
| 15 | DNA | 13616.LH Primer for PCR amplification of the vCP2377 C3 arms plus insert |
| 16 | DNA | 13637.LH Primer for PCR amplification of the vCP2377 C3 arms plus insert |
| 17 | DNA | vCP2377.6.1.1 viral vector (H6p, synthetic AHSV-4 VP2, 42Kp, synthetic AHSV-4 VP5) |
| 18 | DNA | AHSV-9 VP2 in pCXL2415.1 |
| 19 | DNA | AHSV-9 VP5 in pCXL2415.1 |
| 20 | PRT | Predicted AHSV-9 amino acid seq VP2 in pCXL2415.1 |
| 21 | PRT | Predicted AHSV-9 amino acid seq VP5 in pCXL2415.1 |
| 22 | DNA | Entire plasmid pCXL2415.1 |
| 23 | DNA | 18020CXL Primer for amplifying the AHSV-9 VP5 probe for the vCP2383.3.1.1.1 vector |
| 24 | DNA | 18021CXL Primer for amplifying the AHSV-9 VP5 probe for the vCP2383.3.1.1.1 vector |
| 25 | DNA | 13660CXL Primer for amplifying the AHSV-9 VP2 probe for the vCP2383.3.1.1.1 vector |
| 26 | DNA | 13665CXL Primer for amplifying the AHSV-9 VP2 probe for the vCP2383.3.1.1.1 vector |
| 27 | DNA | vCP2383 viral vector sequence from left arm to right arm |
| 28 | DNA | AHSV-9 VP2 of vCP2383 |
| 29 | DNA | AHSV-9 VP5 of vCP2383 |
| 30 | PRT | Predicted AA sequence for AHSV-9 VP2 of vCP2383 |
| 31 | PRT | Predicted AA sequence for AHSV-9 VP5 of vCP2383 |
| 32 | DNA | pJSY2247.2 plasmid |
| 33 | DNA | AHSV-5 VP2 in pC3 H6p-AHSV 5-VP2/42Kp-VP5 (pJSY2247.2) |
| 34 | DNA | AHSV-5 VP5 in pC3 H6p-AHSV 5-VP2/42Kp-VP5 (pJSY2247.2) |
| 35 | PRT | Predicted AA Seq for AHSV-5 VP2 in pC3 H6p-AHSV 5-VP2/42Kp-VP5 (pJSY2247.2) |
| 36 | PRT | Predicted AA Seq for AHSV-5 VP5 in pC3 H6p-AHSV 5-VP2/42Kp-VP5 (pJSY2247.2) |
| 37 | DNA | 18098.JY Primer for amplifying the AHSV-5 VP2 probe for the vCP2398.2.1.1 viral vector |
| 38 | DNA | 18103.JY Primer for amplifying the AHSV-5 VP2 probe for the vCP2398.2.1.1 viral vector |
| 39 | DNA | 18115.JY Primer for amplifying the AHSV-5 VP5 probe for the vCP2398.2.1.1 viral vector |
| 40 | DNA | 18120.JY Primer for amplifying the AHSV-5 VP5 probe for the vCP2398.2.1.1 viral vector |
| 41 | DNA | vCP2398 viral vector sequence from left arm to right arm |
| 42 | DNA | AHSV-5 VP2 of vCP2398 |
| 43 | DNA | AHSV-5 VP5 of vCP2398 |
| 44 | PRT | Predicted Amino Acid Sequence for AHSV-5 VP2 of vCP2398 |
| 45 | PRT | Predicted Amino Acid Sequence for AHSV-5 VP5 of vCP2398 |

FIGURE 32 (2/2)

| SEQ ID NO. | TYPE | Description |
|---|---|---|
| 46 | DNA | 18041 CXL primer |
| 47 | DNA | 18042 CXL primer |
| 48 | DNA | AHSV4-Jane Strain-L2/VP2 gene |
| 49 | PRT | AHSV4-Jane Strain-VP2 predicted AA sequence |
| 50 | DNA | AHSV4-Jane Strain-L2/VP5 gene |
| 51 | PRT | AHSV4-Jane Strain-VP5 predicted AA sequence |
| 52 | PRT | *AHSV4-VP5 - B4UUP0 |
| 53 | PRT | *AHSV4-VP5 - B4UUP1 |
| 54 | PRT | *AHSV4-VP5 - B4UUP2 |
| 55 | PRT | *AHSV4-VP5 - B4UUP3 |
| 56 | PRT | *AHSV4-VP5 - B4XIE4 |
| 57 | PRT | *AHSV4-VP5 - B4XIE5 |
| 58 | PRT | *AHSV4-VP5 - B4XIE7 |
| 59 | PRT | *AHSV4-VP2 - B4UUN4_9REOV |
| 60 | PRT | *AHSV4-VP2 - B4UUN5_9REOV |
| 61 | PRT | *AHSV4-VP2 - B4UUN6_9REOV |
| 62 | PRT | *AHSV4-VP2 - B4UUN7_9REOV |
| 63 | PRT | *AHSV4-VP2 - B4UUN8_9REOV |
| * = Sequences are described in "Variation within the VP2, VP5 and NS3 proteins of five recent African horse sickness virus field isolates." - Rutkowska D.A. et al. Submitted (JUL-2006) to the EMBL/GenBank/DDBJ databases. | | |

FIGURE 33 (1/2)

```
                      1                                                50
SEQ ID NO:01    (1)   MASEFGILMTNEKFDPSLEKTICDVIVTKKGRVKHKEVDGVCGYEWDETN
SEQ ID NO:44    (1)   MASEFGVLLTDKVEGDALEKTNCEVILTRSGRVRRREVDGVKGYEWEFTD
SEQ ID NO:30    (1)   MAFEFGILQTDKIRENTLEKTNCDVILTRENRVRAREVDGVKGYYWEDTD
                      51                                              100
SEQ ID NO:01   (51)   HRFGLCEVEHDMSISEFMYNEIRCEGAYPIFPRYIIDTLKYEKFIDRNDH
SEQ ID NO:44   (51)   HRLGLCEIEHTMSMADFFYNQIKCEGAYPIFPHYITDVLKYGKMVDRNDH
SEQ ID NO:30   (51)   HRLGLCEVEHTVSVRDFMYKQTKCEGSYPVVPLYMIDAIKYGRMIDRNDH
                      101                                             150
SEQ ID NO:01  (101)   QIRVDRDDNEMRKILIQPYAGEMYFSPECYPSVFLRREARSQKLDRIRNY
SEQ ID NO:44  (101)   QIRVDRDVKELSKILIQPYFGEAYFSPEFYTSTFSKRQAIQMNVEMLRAF
SEQ ID NO:30  (101)   QIRVDKDDKTLFKIQVQPYLGDAYFSPEHYTATFFKREPLPIHVDTIRDY
                      151                                             200
SEQ ID NO:01  (151)   IGKRVEFYEEESKRKAILDQNKMSKVEQWRDAVNERIVSIEPKRGECYDH
SEQ ID NO:44  (151)   VPKRVAFYEDDMRRGGTIDGNWIGALQAWKKKADLQMSREGNSQTNCVDH
SEQ ID NO:30  (151)   IGKRINYFERELG-SGVRDANLETIVGKWKDNTYKRIE--GEKTTMCVRH
                      201                                             250
SEQ ID NO:01  (201)   GTDIIYQFIKKLRFGMMYPHYYVLHSDYCIVPNKGGTSIGSWHIRKRTEG
SEQ ID NO:44  (201)   NADVIYQHMKKLRFGLLYPHYYMLNSEYTVEEKSKGGLIANWLVKEKAAG
SEQ ID NO:30  (198)   EPDSVLQILKKMRFGMLYPNYYMLNTGYIVTESSKGAPLNRWLVKERTVG
                      251                                             300
SEQ ID NO:01  (251)   DAKASAMYSGKGPLNDLRVKIERDDLSRETIIQIIEYGKKFNSSAGDKQG
SEQ ID NO:44  (251)   RAENSPMYSGVGPLNTLRERIERDELDEKVIQEIIAYGSKFSTYAGTRTG
SEQ ID NO:30  (248)   KVKAAEAFAGNSLLKNLASRMEDEELSREIIVAVINYGSKFGTRSGKKKD
                      301                                             350
SEQ ID NO:01  (301)   NISIEKLVEYCDFLTTFVHAKKKEEGEDDTARQEIRKAWVKGMPYMDFSK
SEQ ID NO:44  (301)   DLTLNELVKYCESLTTFVHKKKKE-GEDETAREFFKSKWIQGMPKMNFEN
SEQ ID NO:30  (298)   LMTIDKLEKYCESLTTFVHRKKRDEGDDETARAIIRNQWIKGMPSMNLKK
                      351                                             400
SEQ ID NO:01  (351)   PMKITRGFNRNMLFFAALDSFRKRNGVDVDPNKGKWKEHIKEVTEKLKKA
SEQ ID NO:44  (350)   EMIMSRKSWANTKFFWSIDMFKRNNGVDIDPNGKNWKDYKKKIQEQLDEA
SEQ ID NO:30  (348)   EMKVSRGPIQNWSFFMSLEVFKRNNKVDIDPNHDTWKNHVKEIRERMQKE
                      401                                             450
SEQ ID NO:01  (401)   QTENGGQPCQVSIDGVNVLTNVDYGTVNHWIDWVTDIIMVVQTKRLVKEY
SEQ ID NO:44  (400)   QKKNNNEPYKVMVDGVNIMTNKKYGSVENWVDWVVNYIMLSHVKRLVKDY
SEQ ID NO:30  (398)   QSANSNSPLKIQVDGVSLSTSEFYGTVEHWIDWVVDLIMLAQVKRLIKEY
                      451                                             500
SEQ ID NO:01  (451)   AFKKLKSENLLAGMNSLVGVLRCYMYCLALAIYDFYEGTIDGFKKGSNAS
SEQ ID NO:44  (450)   KFKRLKPDNLMSGMNKLVGALRCYAYCLILALYDHFGEDIEGFKKGTNAA
SEQ ID NO:30  (448)   KFIRLETTNLMAGMNKLVGALRCYAYCLILALYDFYGADIEGFEKGSNSS
                      501                                             550
SEQ ID NO:01  (501)   AIIETVAQMFPDFRRELVEKFGIDLRMKEITRELFVGKSMTSKFMEEGEY
SEQ ID NO:44  (500)   SIVETVSQMFPQFRKEVSETFGITLNTKDVKYELFIARDMSAKEAQSGEV
SEQ ID NO:30  (498)   AIVETVVQMFPNFKQEIQANFGINLNIKDKKQVLFVRMDMDSEFSEDEQK

                      551                                             600
SEQ ID NO:01  (551)   GYKFAYGWRRDGFAVMEDYGEILTEKVEDLYKGVLLGRKWEDEVDDPESY
SEQ ID NO:44  (550)   GYKFQYGWRKTDQKVMSDYADILSEKVEALYQALLSGRKWSDIADDTEEY
SEQ ID NO:30  (548)   GYMFEYGWAKREERIWTNYGDILTDLVEQLYKSILDHEEWEKIVDDPERY
                      601                                             650
SEQ ID NO:01  (601)   FYDDLYTNEPHRVFLSAGKDVDNNITLRSISQAETTYLSKRFVSYWYRIS
SEQ ID NO:44  (600)   FIDDLYVNKPDRVFERAGLDPERHIKVKGVMNELTTYFSKRFVSYWYKIT
SEQ ID NO:30  (598)   FYDELFNASPETVFISKGYDLDNNIVIEGKVGQDVTYFSKRFVSYWYRVR
```

FIGURE 33 (2/2)

```
                         651                                              700
SEQ ID NO:01    (651)    QVEVTKARNEVLDMNEKQKPYFEFEYDDFKPCSIGELGIHASTYIYQNLL
SEQ ID NO:44    (650)    KVEARNLLTLTDIGG-DAKKYTQFDPDDFKPMAVAELGAHASTYVYQNLI
SEQ ID NO:30    (648)    QVQTSKGIERRSIED---VKYREFDIESFKPYAIGEIGIHASTYKYQDLL
                         701                                              750
SEQ ID NO:01    (701)    VGRNRGEEILDSKELVWMDMSLLNFGAVRSHDRCWISSSVAIEVNLRHAL
SEQ ID NO:44    (699)    LGRNRGEKIDDAKEIVWYDLSLTNFGCSRSLDSCWVGSVARSELNLRFHL
SEQ ID NO:30    (695)    AGRNRGEKVKDSQALVWYDLALTNYTLVRPQDRCWIMSCTDSEYTLRFAM
                         751                                              800
SEQ ID NO:01    (751)    IVRIFSHFDMMSERETFSTILEKVMEDVKELRFFPTYRHYYLETLQRVFN
SEQ ID NO:44    (749)    ISAIFERYQHDARRSSFYEIIFDLPS--KKEKIFPSYKHYYVALLQNIFN
SEQ ID NO:30    (745)    ITMIFERLSEETDLSYHDILLRVREYP---IQSFASYKHFYVRVLQHVFR
                         801                                              850
SEQ ID NO:01    (801)    DERRLEVDDFYMRLYDVQTREQALNTFTDFHRCVESELLLPTLKLNFLLW
SEQ ID NO:44    (797)    DTQRLEVMDYCERLMNPETRMSALLSLQGFKNCVESEFVAPTLKMNALLW
SEQ ID NO:30    (792)    DYQEIDVLEFCTRMLDPRTRESGLNKFSRFKQWRESEFLIDALKMNFLLW
                         851                                              900
SEQ ID NO:01    (851)    IVFEMENVEVNAAYKRHPLLISTAKGLRVIGVDIFNSQLSISMSGWIPYV
SEQ ID NO:44    (847)    VLADMENIDINYSNKRMPLLLSTEKGLRVISIDMFNGMLGVSYSGWIPYL
SEQ ID NO:30    (842)    VVFELENIDVDYSKKRHPLLISTDKGLRVVPVDLFNSMLSVSSSGWIPYV
                         901                                              950
SEQ ID NO:01    (901)    ERMCAESKVQTKLTADELKLKRWFISYYTTLKLDRRAEPRMSFKFEGLST
SEQ ID NO:44    (897)    ERICSEVNLQRRLRADELKLKKWFISYYATYEVERRAEPRMSFKMEGIST
SEQ ID NO:30    (892)    ERVCERSEIKRRLNADELKLKNWFIAYYITLPLLRRAEPRMSFKYEGITT
                         951                                             1000
SEQ ID NO:01    (951)    WIGSNCGGVRDYVIQMLPTRKPKPGALMVVYARDSRIEWIEAELSQWLQM
SEQ ID NO:44    (947)    WIGSNCGGVQDYVLHLIPSRRPKPGLLFLIYADDGDVDWVANMLSDVIGS
SEQ ID NO:30    (942)    WIGSNCGGVRDYLIQMLPARKPKPGVLILAYGAETNVAWLNHALRDILSL
                         1001                                            1050
SEQ ID NO:01   (1001)    EGSLGLILVHDSGIINKSVLRARTLKIYNRGSMDTLILISSGVYTFGNKF
SEQ ID NO:44    (997)    EGSLGFIFINDRTFVNKSQLKVRTLKIYNRGMLDRLILISGGNYTFGNKF
SEQ ID NO:30    (992)    EGSLGMIIISDGSVVNKSKLRVRDMKIYNRGEVDRLILISSGDYTFGNKY
                         1051    1061
SEQ ID NO:01   (1051)    LLSKLLAKTE-
SEQ ID NO:44   (1047)    LLSKLLAKTEK
SEQ ID NO:30   (1042)    LLSKLMAKIE-
```

Percent Identity for Above Sequence Alignment:

| | SEQ ID NO:1 | SEQ ID NO:44 | SEQ ID NO:30 |
|---|---|---|---|
| AHSV4 VP2 - SEQ ID NO:1 | | 53 | 52 |
| AHSV5 VP2 - SEQ ID NO:44 | | | 53 |
| AHSV9 VP2 - SEQ ID NO:30 | | | |

FIGURE 34

```
                        1                                                50
SEQ ID NO:02     (1)    MGKFTSFLKRAGNATKRALTSDSAKKMYKLAGKTLQRVVESEVGSAAIDG
SEQ ID NO:45     (1)    MGKFTSFLKRAGSATKKALTSDTAKRMYKMAGKTLQKVVENEVGSAAIDG
SEQ ID NO:31     (1)    MGKFTSFLKRAGSATKKALTSDAAKRMYKMAGKTLQKVVESEVGSAAIDG
                        51                                              100
SEQ ID NO:02    (51)    VMQGAIQSIIQGENLGDSIKQAVILNVAGTLESAPDPLSPGEQLLYNKVS
SEQ ID NO:45    (51)    VMQGTIQSIIQGENLGDSIRQAVILNVAGTLESAPDPLSPGEQLLYNKVS
SEQ ID NO:31    (51)    VMQGTIQSIIQGENLGDSIKQAVILNVAGTLESAPDPLSPGEQLLYNKVS
                        101                                             150
SEQ ID NO:02   (101)    EIEKMEKEDRVIETHNAKIEEKFGKDLLAIRKIVKGEVDAEKLEGNEIKY
SEQ ID NO:45   (101)    ELERAEKEDRVIETHNEKIIEKYGEDLLKIRKIMKGEAKAEQLEGKEIEY
SEQ ID NO:31   (101)    EIERAEKEDRVIETHNKKIIEKYGEDLLKIRKIMKGEAEAEQLEGKEMEY
                        151                                             200
SEQ ID NO:02   (151)    VEKALSGLLEIGKDQSERITKLYRALQTEEDLRTRDETRMINEYREKFDA
SEQ ID NO:45   (151)    VEMALKGMLKIGKDQSERITQLYRALQTEEDLRTSDETRMINEYREKFDA
SEQ ID NO:31   (151)    VEKALKGMLRIGKDQSERITRLYRALQTEEDLRTSDETRMISEYREKFEA
                        201                                             250
SEQ ID NO:02   (201)    LKEAIEIEQQATHDEAIQEMLDLSAEVIETASEEVPIFGAGAANVIATTR
SEQ ID NO:45   (201)    LKQAIELEQQATHEEAVQEMLDLSAEVIETAAEEVPIFGAGAANVVATTR
SEQ ID NO:31   (201)    LKQAIELEQQATHEEAVQEMLDLSAEVIETAAEEVPVFGAGAANVVATTR
                        251                                             300
SEQ ID NO:02   (251)    AIQGGLKLKEIVDKLTGIDLSHLKVADIHPHIIEKAMLRDTVTDKDLAMA
SEQ ID NO:45   (251)    AVQGGLKLKEIIDKLTGIDLSHLKVADIHPHIIEKAMLKDKIPDNELAMA
SEQ ID NO:31   (251)    AIQGGLKLKEIIDKLTGIDLSHLKVADIHPHIIEKAMLKNKIPDNELAMA
                        301                                             350
SEQ ID NO:02   (301)    IKSKVDVIDEMNVETQHVIDAVLPIVKQEYERHDNKYHVRIPGALKIHSE
SEQ ID NO:45   (301)    IKSKVEVIDEMNTETEHVIESIMPLVKKEYEKHDNKYHVNIPSVLKIHSE
SEQ ID NO:31   (301)    IKSKVEVIDEMNTETEHVIESIMPLVKKEYEKHDNKYHVNIPSALKIHSE
                        351                                             400
SEQ ID NO:02   (351)    HTPKIHIYTTPWDSDSVPMCRAIAPHHQQRSFFIGFDLEIEYVHFEDTSV
SEQ ID NO:45   (351)    HTPKVHIYTTPWDSDKVFICRCIAPHHQQKSFMIGFDLEIEFVFYEDTSV
SEQ ID NO:31   (351)    HTPKVHIYTTPWDSDKVFICRCIAPHHQQRSFMIGFDLEIEFVFYEDTSV
                        401                                             450
SEQ ID NO:02   (401)    EGHILHGGAITVEGRGFRQAYTEFMNAAWGMPTTPELHKRKLQRSMGTHP
SEQ ID NO:45   (401)    EGHIMHGGAVLIEGRGFRQAYSEFMNAAWSMPSTPELHKRRLQRSLGSHP
SEQ ID NO:31   (401)    EGHIMHGGAVSIEGRGFRQAYSEFMNAAWSMPSTPELHKRRLQRSLGSHP
                        451                                             500
SEQ ID NO:02   (451)    IYMGSMDYAISYEQLVSNAMRLVYDSELQMHCLRGPLKFQRRTLMNALLY
SEQ ID NO:45   (451)    IYMGSMDYTVSYDQLVSNAMKLVYDTELQMHCLRGPLKFQRRTLMNALLF
SEQ ID NO:31   (451)    IYMGSMDYTVSYEQLVSNAMKLVYDTDLQMHCLRGPLKFQRRTLMNALLF
                        501
SEQ ID NO:02   (501)    GVKIA
SEQ ID NO:45   (501)    GVKIA
SEQ ID NO:31   (501)    GVK--
```

Percent Identity for Above Sequence Alignment:

| | SEQ ID NO:2 | SEQ ID NO:45 | SEQ ID NO:31 |
|---|---|---|---|
| AHSV4 VP5 - SEQ ID NO:2 | | 84 | 84 |
| AHSV5 VP5 - SEQ ID NO:45 | | | 96 |
| AHSV9 VP5 - SEQ ID NO:31 | | | |

FIGURE 35 (1/2)

Synthetic AHSV4-VP2 versus field isolate (Jane Strain) AHSV4-VP2

```
                    1                                       40
 SEQ ID NO:1     (1) MASEFGILMTNEKFDPSLEKTICDVIVTKKGRVKHKEVDG
SEQ ID NO:49     (1) MASEFGILMTNEKFDPSLEKTICDVIVTKKGRVKHKEVDG
                    41                                      80
 SEQ ID NO:1    (41) VCGYEWDETNHRFGLCEVEHDMSISEFMYNEIRCEGAYPI
SEQ ID NO:49    (41) VCGYEWDETNHRFGLCKVEHDMSISEFMYNEIRCEGAYPI
                    81                                     120
 SEQ ID NO:1    (81) FPRYIIDTLKYEKFIDRNDHQIRVDRDDNEMRKILIQPYA
SEQ ID NO:49    (81) FPRYIIDTLKYEKFIDRNDHQIRVDRDDNEMRKILIQPYA
                    121                                    160
 SEQ ID NO:1   (121) GEMYFSPECYPSVFLRREARSQKLDRIRNYIGKRVEFYEE
SEQ ID NO:49   (121) GEMYFSPECYPSVFLRREARSQKLDRIRNYIGKRVEFYEE
                    161                                    200
 SEQ ID NO:1   (161) ESKRKAILDQNKMSKVEQWRDAVNERIVSIEPKRGECYDH
SEQ ID NO:49   (161) ESKRKAILDQNKMSKVEQWRDAVNERIVSIEPKRGECYDH
                    201                                    240
 SEQ ID NO:1   (201) GTDIIYQFIKKLRFGMMYPHYYVLHSDYCIVPNKGGTSIG
SEQ ID NO:49   (201) GTDIIYQFIKKLRFGMMYPHYYVLHSDYCIVPNKGGTSIG
                    241                                    280
 SEQ ID NO:1   (241) SWHIRKRTEGDAKASAMYSGKGPLNDLRVKIERDDLSRET
SEQ ID NO:49   (241) SWHIRKRTEGDAKASAMYSGKGPLNDLRVKIERDDLSRET
                    281                                    320
 SEQ ID NO:1   (281) IIQIIEYGKKFNSSAGDKQGNISIEKLVEYCDFLTTFVHA
SEQ ID NO:49   (281) IIQIIEYGKKFNSSAGDKQGNISIEKLVEYCDFLTTFVHA
                    321                                    360
 SEQ ID NO:1   (321) KKKEEGEDDTARQEIRKAWVKGMPYMDFSKPMKITRGFNR
SEQ ID NO:49   (321) KKKEEGEDDTARQEIRKAWVKGMPYMDFSKPMKITRGFNR
                    361                                    400
 SEQ ID NO:1   (361) NMLFFAALDSFRKRNGVDVDPNKGKWKEHIKEVTEKLKKA
SEQ ID NO:49   (361) NMLFLAALDSFRKRNGVDVDPNKGKWKEHIKEVTEKLKKA
                    401                                    440
 SEQ ID NO:1   (401) QTENGGQPCQVSIDGVNVLTNVDYGTVNHWIDWVTDIIMV
SEQ ID NO:49   (401) QTENGGQPCQVSIDGVNVLTNVDYGTVNHWIDWVTDIIMV
                    441                                    480
 SEQ ID NO:1   (441) VQTKRLVKEYAFKKLKSENLLAGMNSLVGVLRCYMYCLAL
SEQ ID NO:49   (441) VQTKRLVKEYAFKKLKSENLLAGMNSLVGVLRCYMYCLAL
                    481                                    520
 SEQ ID NO:1   (481) AIYDFYEGTIDGFKKGSNASAIIETVAQMFPDFRRELVEK
SEQ ID NO:49   (481) AIYDFYEGTIDGFKKGSNASAIIETVAQMFPDFRRELVEK
                    521                                    560
 SEQ ID NO:1   (521) FGIDLRMKEITRELFVGKSMTSKFMEEGEYGYKFAYGWRR
SEQ ID NO:49   (521) FGIDLRMKEITRELFVGKSMTSKFMEEGEYGYKFAYGWRR
                    561                                    600
 SEQ ID NO:1   (561) DGFAVMEDYGEILTEKVEDLYKGVLLGRKWEDEVDDPESY
SEQ ID NO:49   (561) DGFAVMEDYGEILTEKVEDLYKGVLLGRKWEDEVDDPESY
                    601                                    640
 SEQ ID NO:1   (601) FYDDLYTNEPHRVFLSAGKDVDNNITLRSISQAETTYLSK
SEQ ID NO:49   (601) FYDDLYTNEPHRVFLSAGKDVDNNITLRSISQAETTYLSK
                    641                                    680
 SEQ ID NO:1   (641) RFVSYWYRISQVEVTKARNEVLDMNEKQKPYFEFEYDDFK
SEQ ID NO:49   (641) RFVSYWYRISQVEVTKARNEVLDMNEKQKPYFEFEYDDFK
```

FIGURE 35 (2/2)

```
                          681                                     720
  SEQ ID NO:1    (681)    PCSIGELGIHASTYIYQNLLVGRNRGEEILDSKELVWMDM
  SEQ ID NO:49   (681)    PCSIGELGIHASTYIYQNLLVGRNRGEEILDSKELVWMDM
                          721                                     760
  SEQ ID NO:1    (721)    SLLNFGAVRSHDRCWISSSVAIEVNLRHALIVRIFSRFDM
  SEQ ID NO:49   (721)    SLLNFGAVRSHDRCWISSSVAIEVNLRHALIVRIFSRFDM
                          761                                     800
  SEQ ID NO:1    (761)    MSERETFSTILEKVMEDVKELRFFPTYRHYYLETLQRVFN
  SEQ ID NO:49   (761)    MSERETFSTILEKVMEDVKELRFFPTYRHYYLETLQRVFN
                          801                                     840
  SEQ ID NO:1    (801)    DERRLEVDDFYMRLYDVQTREQALNTFTDFHRCVESELLL
  SEQ ID NO:49   (801)    DERRLEVDDFYMRLYDVQTREQALNTFTDFHRCVESELLL
                          841                                     880
  SEQ ID NO:1    (841)    PTLKLNFLLWIVFEMENVEVNAAYKRHPLLISTAKGLRVI
  SEQ ID NO:49   (841)    PTLKLNFLLWIVFEMENVEVNAAYKRHPLLISTAKGLRVI
                          881                                     920
  SEQ ID NO:1    (881)    GVDIFNSQLSISMSGWIPYVERMCAESKVQTKLTADELKL
  SEQ ID NO:49   (881)    GVDIFNSQLSISMSGWIPYVERMCAESKVQTKLTADELKL
                          921                                     960
  SEQ ID NO:1    (921)    KRWFISYYTTLKLDRRAEPRMSFKFEGLSTWIGSNCGGVR
  SEQ ID NO:49   (921)    KRWFISYYTTLKLDRRAEPRMSFKFEGLSTWIGSNCGGVR
                          961                                    1000
  SEQ ID NO:1    (961)    DYVIQMLPTRKPKPGALMVVYARDSRIEWIEAELSQWLQM
  SEQ ID NO:49   (961)    DYVIQMLPTRKPKPGALMVVYARDSRIEWIEAELSQWLQM
                          1001                                   1040
  SEQ ID NO:1   (1001)    EGSLGLILVHDSGIINKSVLRARTLKIYNRGSMDTLILIS
  SEQ ID NO:49  (1001)    EGSLGLILVHDSGIINKSVLRARTLKIYNRGSMDTLILIS
                          1041             1060
  SEQ ID NO:1   (1041)    SGVYTFGNKFLLSKLLAKTE
  SEQ ID NO:49  (1041)    SGVYTFGNKFLLSKLLAKTE
```

Percent Identity = 99.8%

FIGURE 36

Synthetic AHSV4-VP5 versus field isolate AHSV4-VP5

```
SEQ ID NO:02   (1)    MGKFTSFLKRAGNATKRALTSDSAKKMYKLAGKTLQRVVESEVGSAAIDG
SEQ ID NO:51   (1)    MGKFTSFLKRAGNATKRALTSDSAKKMYKLAGKTLQRVVESEVGSAAIDG
                      51                                                100
SEQ ID NO:02   (51)   VMQGAIQSIIQGENLGDSIKQAVILNVAGTLESAPDPLSPGEQLLYNKVS
SEQ ID NO:51   (51)   VMQGAIQSIIQGENLGDSIKQAVILNVAGTLESAPDPLSPGEQLLYNKVS
                      101                                               150
SEQ ID NO:02   (101)  EIEKMEKEDRVIETHNAKIEEKFGKDLLAIRKIVKGEVDAEKLEGNEIKY
SEQ ID NO:51   (101)  EIEKMEKEDRVIETHNAKIEEKFGKDLLAIRKIVKGEVDAEKLEGNEIKY
                      151                                               200
SEQ ID NO:02   (151)  VEKALSGLLEIGKDQSERITKLYRALQTEEDLRTRDETRMINEYREKFDA
SEQ ID NO:51   (151)  VEKALSGLLEIGKDQSERITKLYRALQTEEDLRTRDETRMINEYREKFDA
                      201                                               250
SEQ ID NO:02   (201)  LKEAIEIEQQATHDEAIQEMLDLSAEVIETASEEVPIFGAGAANVIATTR
SEQ ID NO:51   (201)  LKEAIEIEQQATHDEAIQEMLDLSAEVIETASEEVPIFGAGAANVIATTR
                      251                                               300
SEQ ID NO:02   (251)  AIQGGLKLKEIVDKLTGIDLSHLKVADIHPHIIEKAMLRDTVTDKDLAMA
SEQ ID NO:51   (251)  AIQGGLKLKEIVDKLTGIDLSHLKVADIHPHIIEKAMLRDTVTDKDLAMA
                      301                                               350
SEQ ID NO:02   (301)  IKSKVDVIDEMNVETQHVIDAVLPIVKQEYERHDNKYHVRIPGALKIHSE
SEQ ID NO:51   (301)  IKSKVDVIDEMNVETQHVIDAVLPIVKQEYERHDNKYHVRIPGALKIHSE
                      351                                               400
SEQ ID NO:02   (351)  HTPKIHIYTTPWDSDSVFMCRAIAPHHQQRSFFIGFDLEIEYVHFEDTSV
SEQ ID NO:51   (351)  HTPKIHIYTTPWDSDSVFMCRAIAPHHQQRSFFIGFDLEIEYVHFEDTSV
                      401                                               450
SEQ ID NO:02   (401)  EGHILHGGAITVEGRGFRQAYTEFMNAAWGMPTTPELHKRKLQRSMGTHP
SEQ ID NO:51   (401)  EGHILHGGAITVEGRGFRQAYTEFMNAAWGMPTTPELHKRKLQRSMGTHP
                      451                                               500
SEQ ID NO:02   (451)  IYMGSMDYAISYEQLVSNAMRLVYDSELQMHCLRGPLKFQRRTLMNALLY
SEQ ID NO:51   (451)  IYMGSMDYAISYEQLVSNAMRLVYDSELQMHCLRGPLKFQRRTLMNALLY
                      501
SEQ ID NO:02   (501)  GVKIA
SEQ ID NO:51   (501)  GVKIA

Percent Identity = 100%
```

FIGURE 37 (1/4)

Synthetic AHSV4-VP2 versus other deposited AHSV4-VP2 proteins

```
                         1                                                  50
SEQ ID NO:01      (1)    MASEFGILMTNEKFDPSLEKTICDVIVTKKGRVKHKEVDGVCGYEWDETN
SEQ ID NO:61      (1)    MASEFGILMTNEKFDPSLEKTICDVIVTKKGRVKHKEVDGVCGYEWDETN
SEQ ID NO:59      (1)    MASEFGILLTIQIYDQTYEKEKCDVIITAENAVRRVEVAGVYGYEWGATN
SEQ ID NO:60      (1)    MASEFGILICDKLKENTLEKTNCDVIITGVGKVSVREEDGILGYEWEETN
SEQ ID NO:63      (1)    MAFEFGILQTDKIRENTLEKTNCDVILTKENRVRMKEVEGVKGYYWEDTD
SEQ ID NO:62      (1)    MAFEFGILLTEKVEGDALEKTNCEVIITKNGRVKHKEVDGVKGYEWEFTD
                         51                                                100
SEQ ID NO:01     (51)    HRFGLCEVEHDMSISEFMYNEIRCEGAYPIFPRYIIDTLKYEKFIDRNDH
SEQ ID NO:61     (51)    HRFGLCEVEHDMSISEFMYNEIRCEGAYPIFPRYIIDTLKYEKFIDRNDH
SEQ ID NO:59     (51)    HRLGLCEIENTKSIGRMIYEQIRCEGAYPIFPHYITDTLKYGKSIDRNDN
SEQ ID NO:60     (51)    HRLGLCEIENTVSISDFVYKQIRCEGAYPILPHYVTDVIKYGMVIDRNDH
SEQ ID NO:63     (51)    HRLGLCEVEHTVSVRDFVYKQTKCEGSYPVVPLYMIDAIKYGRMIDRNDH
SEQ ID NO:62     (51)    HRLGLCEESYLMKMAEYVYTQTKCEGAYPVFPHYITDVLKYGVMVDRNDH
                         101                                               150
SEQ ID NO:01    (101)    QIRVDRDDNEMRKILIQPYAGEMYFSPECYPSVFLRREARSQKLDRIRNY
SEQ ID NO:61    (101)    QIRVDRDDNEMRKILIQPYAGEMYFSPECYPSVFLRREARSQKLDRIRNY
SEQ ID NO:59    (101)    QIRVDRDDERLRKIKIQPYFGEMYFSPENYITVFCKRQAISGQIEVSRSI
SEQ ID NO:60    (101)    QIRVDRDEKSIGKIQIQPYFGDMYFSPEYYPATFVKREPLPISVDMIRDY
SEQ ID NO:63    (101)    QIRVDKDDKILSKIQVQPYLGDAYFSPEYYTATFFKREPLPIHVDMIRDY
SEQ ID NO:62    (101)    QIRVDRDVKELGKILIQPYFGEVFFSPEFYTSTFLKRQAINSDVEMLRRS
                         151                                               200
SEQ ID NO:01    (151)    IGKRVEFYEEESKRKAILDQNKMSKVEQWRDAVNERIVSIEPKRGECYDH
SEQ ID NO:61    (151)    IGKRVEFYEEESKRKAILDQNKMSKVEQWRDAVNERIVSIEPKRGECYDH
SEQ ID NO:59    (151)    IGRRMKYEESAEQTKGTINANKYRLLEKWRDLAYEQIEMEG-SSERCLTH
SEQ ID NO:60    (151)    IGARMRKIEARAGRIKEGGGNLLECARRWEKAAYERIENE--RALRCVVH
SEQ ID NO:63    (151)    IGKRINYFERELSGG-VRDANLEMIVEKWKDNTYKRIEGE--KTTMCVRH
SEQ ID NO:62    (151)    IPKRIKYFEDQMELRKSVNGNWIGTLHKWKESVDARMLEEGVGKKVCVSH
                         201                                               250
SEQ ID NO:01    (201)    GTDIIYQFIKKLRFGMMYPHYYVLHSDYCIVPNKGGTSIGSWHIRKRTEG
SEQ ID NO:61    (201)    GTDIIYQFIKKLRFGMMYPHYYVLPSDYCIVPNKGGTSIGSWHIRKRTEG
SEQ ID NO:59    (200)    NTDPIYQLIKKMRFGMMYPVHYILNDKYKVVQERADMGIEKWLLQKIGRG
SEQ ID NO:60    (199)    ETDPTYQILKKLRFGFIYPHYYVLNTDYNPTTVTRTSRINDWLLKEKTQG
SEQ ID NO:63    (198)    EPDSVLQMLKKMRFGMLYPNYYMLNTDYIVTESSKEAPLNRWLVKEKTVG
SEQ ID NO:62    (201)    ETDVVYQLMKKMRFGLLYPHYYMLNNEYVVKKENVDALIGSWLIKERSSG
                         251                                               300
SEQ ID NO:01    (251)    DAKASAMYSGKGPLNDLRVKIERDDLSRETIIQIIEYGKKFNSSAGDKQG
SEQ ID NO:61    (251)    DAKVSAMYSGKGPLNDLRVKIERDDLSRETIIQIIEYGKKFNSSAGDKQG
SEQ ID NO:59    (250)    TQRRKADDGDNDTLLQLERMMSSEELERPVIESVIRFGSLYNAHAGKKTG
SEQ ID NO:60    (249)    VVKAAEAYSDNAELKTLAERMEEEELTVDIIRAVIRYGAKYATRSGMRED
SEQ ID NO:63    (248)    KVKAAEAFAGNSLLKSLASRMEDEELSREIIIAVINYGSKFGTRSGKKKD
SEQ ID NO:62    (251)    KAEYSQMYSGVGPLSGLRERIEKDELDEKVIQEIIAYGSKFSTYTGAKHG
                         301                                               350
SEQ ID NO:01    (301)    NISIEKLVEYCDFLTTFVHAKKKEEGEDDTARQEIRKAWVKGMPYMDFSK
SEQ ID NO:61    (301)    NISIEKLVEYFDFLTTFVHAKKKEEGEDDTARQEIRKAWVKGMPYMDFSK
SEQ ID NO:59    (300)    DIPLEVLIKYCDSLTTFVHKKNREGGDNQTARDEIRRAMVKNIPSMKQEN
SEQ ID NO:60    (299)    TLSLQELDRYCDSLTTFVHKKKKDEGDDETARTIIRNQWIKGMPRMDFKK
SEQ ID NO:63    (298)    LMTIDKLEKYCDSLTTFVHKKKRDEGDDETARAIIRNQWIKGMPSMNLKK
SEQ ID NO:62    (301)    DISLKDLVEYCESLTTFVHKKK-KDGEEETARQFFKNKWIQGMPKMNFES
```

Figure 37:
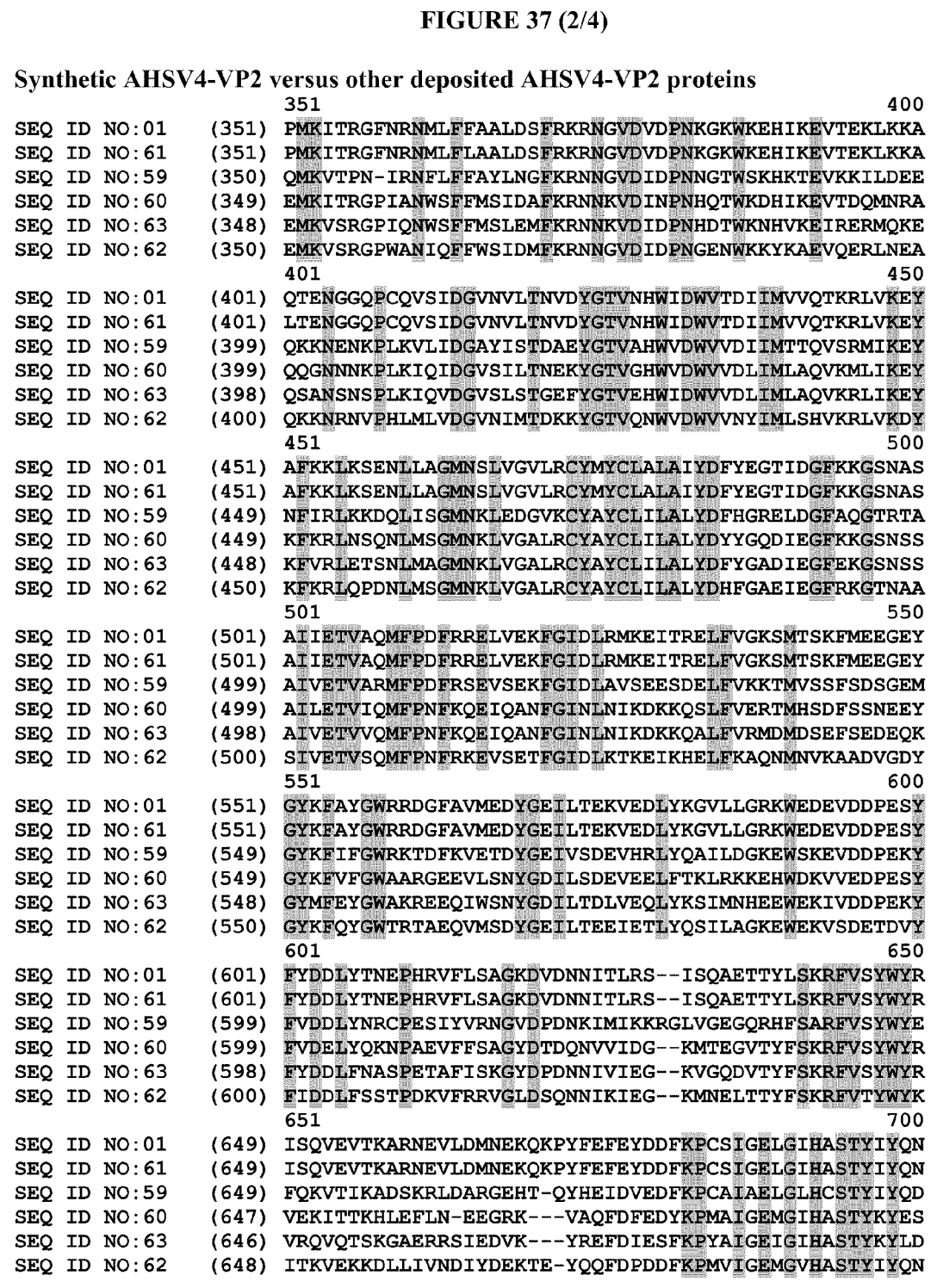

FIGURE 37 (2/4)

Synthetic AHSV4-VP2 versus other deposited AHSV4-VP2 proteins

```
                          351                                              400
SEQ ID NO:01    (351)  PMKITRGFNRNMLFFAALDSFRKRNGVDVDPNKGKWKEHIKEVTEKLKKA
SEQ ID NO:61    (351)  PMKITRGFNRNMLFLAALDSFRKRNGVDVDPNKGKWKEHIKEVTEKLKKA
SEQ ID NO:59    (350)  QMKVTPN-IRNFLFFAYLNGFKRNNGVDIDPNNGTWSKHKTEVKKILDEE
SEQ ID NO:60    (349)  EMKITRGPIANWSFFMSIDAFKRNNKVDINPNHQTWKDHIKEVTDQMNRA
SEQ ID NO:63    (348)  EMKVSRGPIQNWSFFMSLEMFKRNNKVDIDPNHDTWKNHVKEIRERMQKE
SEQ ID NO:62    (350)  EMKVSRGPWANIQFFWSIDMFKRNNGVDIDPNGENWKKYKAEVQERLNEA
                          401                                              450
SEQ ID NO:01    (401)  QTENGGQPCQVSIDGVNVLTNVDYGTVNHWIDWVTDIIMVVQTKRLVKEY
SEQ ID NO:61    (401)  LTENGGQPCQVSIDGVNVLTNVDYGTVNHWIDWVTDIIMVVQTKRLVKEY
SEQ ID NO:59    (399)  QKKNENKPLKVLIDGAYISTDAEYGTVAHWVDWVVDIIMTTQVSRMIKEY
SEQ ID NO:60    (399)  QQGNNNKPLKIQIDGVSILTNEKYGTVGHWVDWVVDLIMLAQVKMLIKEY
SEQ ID NO:63    (398)  QSANSNSPLKIQVDGVSLSTGEFYGTVEHWIDWVVDLIMLAQVKRLIKEY
SEQ ID NO:62    (400)  QKKNRNVPHLMLVDGVNIMTDKKYGTVQNWVDWVVNYIMLSHVKRLVKDY
                          451                                              500
SEQ ID NO:01    (451)  AFKKLKSENLLAGMNSLVGVLRCYMYCLALAIYDFYEGTIDGFKKGSNAS
SEQ ID NO:61    (451)  AFKKLKSENLLAGMNSLVGVLRCYMYCLALAIYDFYEGTIDGFKKGSNAS
SEQ ID NO:59    (449)  NFIRLKKDQLISGMNKLEDGVKCYAYCLILALYDFHGRELDGFAQGTRTA
SEQ ID NO:60    (449)  KFKRLNSQNLMSGMNKLVGALRCYAYCLILALYDYYGQDIEGFKKGSNSS
SEQ ID NO:63    (448)  KFVRLETSNLMAGMNKLVGALRCYAYCLILALYDFYGADIEGFEKGSNSS
SEQ ID NO:62    (450)  KFKRLQPDNLMSGMNKLVGALRCYAYCLILALYDHFGAEIEGFRKGTNAA
                          501                                              550
SEQ ID NO:01    (501)  AIIETVAQMFPDFRRELVEKFGIDLRMKEITRELFVGKSMTSKFMEEGEY
SEQ ID NO:61    (501)  AIIETVAQMFPDFRRELVEKFGIDLRMKEITRELFVGKSMTSKFMEEGEY
SEQ ID NO:59    (499)  AIVETVARMFPDFRSEVSEKFGIDLAVSEESDELFVKKTMVSSFSDSGEM
SEQ ID NO:60    (499)  AILETVIQMFPNFKQEIQANFGINLNIKDKKQSLFVERTMHSDFSSNEEY
SEQ ID NO:63    (498)  AIVETVVQMFPNFKQEIQANFGINLNIKDKKQALFVRMDMDSEFSEDEQK
SEQ ID NO:62    (500)  SIVETVSQMFPNFRKEVSETFGIDLKTKEIKHELFKAQNMNVKAADVGDY
                          551                                              600
SEQ ID NO:01    (551)  GYKFAYGWRRDGFAVMEDYGEILTEKVEDLYKGVLLGRKWEDEVDDPESY
SEQ ID NO:61    (551)  GYKFAYGWRRDGFAVMEDYGEILTEKVEDLYKGVLLGRKWEDEVDDPESY
SEQ ID NO:59    (549)  GYKFIFGWRKTDFKVETDYGEIVSDEVHRLYQAILDGKEWSKEVDDPEKY
SEQ ID NO:60    (549)  GYKFVFGWAARGEEVLSNYGDILSDEVEELFTKLRKKEHWDKVVEDPESY
SEQ ID NO:63    (548)  GYMFEYGWAKREEQIWSNYGDILTDLVEQLYKSIMNHEEWEKIVDDPEKY
SEQ ID NO:62    (550)  GYKFQYGWTRTAEQVMSDYGEILTEEIETLYQSILAGKEWEKVSDETDVY
                          601                                              650
SEQ ID NO:01    (601)  FYDDLYTNEPHRVFLSAGKDVDNNITLRS--ISQAETTYLSKRFVSYWYR
SEQ ID NO:61    (601)  FYDDLYTNEPHRVFLSAGKDVDNNITLRS--ISQAETTYLSKRFVSYWYR
SEQ ID NO:59    (599)  FVDDLYNRCPESIYVRNGVDPDNKIMIKKRGLVGEGQRHFSARFVSYWYE
SEQ ID NO:60    (599)  FVDELYQKNPAEVFFSAGYDTDQNVVIDG--KMTEGVTYFSKRFVSYWYR
SEQ ID NO:63    (598)  FYDDLFNASPETAFISKGYDPDNNIVIEG--KVGQDVTYFSKRFVSYWYR
SEQ ID NO:62    (600)  FIDDLFSSTPDKVFRRVGLDSQNNIKIEG--KMNELTTYFSKRFVTYWYK
                          651                                              700
SEQ ID NO:01    (649)  ISQVEVTKARNEVLDMNEKQKPYFEFEYDDFKPCSIGELGIHASTYIYQN
SEQ ID NO:61    (649)  ISQVEVTKARNEVLDMNEKQKPYFEFEYDDFKPCSIGELGIHASTYIYQN
SEQ ID NO:59    (649)  FQKVTIKADSKRLDARGEHT-QYHEIDVEDFKPCAIAELGLHCSTYIYQD
SEQ ID NO:60    (647)  VEKITTKHLEFLN-EEGRK---VAQFDFEDYKPMAIGEMGIHASTYKYES
SEQ ID NO:63    (646)  VRQVQTSKGAERRSIEDVK---YREFDIESFKPYAIGEIGIHASTYKYLD
SEQ ID NO:62    (648)  ITKVEKKDLLIVNDIYDEKTE-YQQFDPDDFKPMVIGEMGVHASTYIYQN
```

FIGURE 37 (3/4)

Synthetic AHSV4-VP2 versus other deposited AHSV4-VP2 proteins

```
                          701                                              750
SEQ ID NO:01      (699)   LLVGRNRGEEILDSKELVWMDMSLLNFGAVRSHDRCWISSSVAIEVNLRH
SEQ ID NO:61      (699)   LLVGRNRGEEILDSKELVWMDMSLLNFGAVRSHDRCWISSSVAIEVNLRH
SEQ ID NO:59      (698)   LLVGANRGEYVKDAKELVWFDIANTNYNITRPFDRCWPSSCAEAELSLRF
SEQ ID NO:60      (693)   LLLGKNRGQKVKDSIALCNYDLALTNFEVSRRQDCCWISSCSAIELSMRA
SEQ ID NO:63      (693)   LLAGRNRGEKVKDSQALVWYDFALTNYTLVRPQDRCWIMSCTDCEYTLRF
SEQ ID NO:62      (697)   LILGRNRGERIVDSKEIVWYDLSLTNFGLVRSQNQCWIGSISNFELSMRY
                          751                                              800
SEQ ID NO:01      (749)   ALIVRIFSRFDMMSERETFSTILEKVMEDVKELRFFPTYRHYYLETLQRV
SEQ ID NO:61      (749)   ALIVRIFSRFDMMSERETFSTILEKVMEDVKELRFFPTYRHYYLETLQRV
SEQ ID NO:59      (748)   HLITKIFTRYRGER--TSFVDIINELSERGYVKHNFPSYKHYYLSVIQTV
SEQ ID NO:60      (743)   NITIAIFRR-IEDRRYESFAKILSGLSQ--QQDLYFPTYKHYYLFVLQKV
SEQ ID NO:63      (743)   ATITMIFER-LSEEADLSYHDILLKVRE--YPIQSFASYKHFYVRVLQHV
SEQ ID NO:62      (747)   HIITEIFQRYRVDSAHKSYHEIISGLTK--KDVILFPSYKHYYVRVIQDV
                          801                                              850
SEQ ID NO:01      (799)   FNDERRLEVDDFYMRLYDVQTREQALNTFTDFHRCVESELLLPTLKLNFL
SEQ ID NO:61      (799)   FNDERRLEVDDFYMRLYDVQTREQALNTFTDFHRCVESELLLPTLKLNFL
SEQ ID NO:59      (796)   FEDQRAIDPLDFCAMISRNETRESTLKGFSMFAAIVKSERLIDTLFLNFL
SEQ ID NO:60      (790)   LRDERRIDQNRMCTELFDIQRRRGILLSFTTLRFWNDSEFLGDTLMMNFL
SEQ ID NO:63      (790)   FRDNQEIDVLEFCTRMLDPRTREAGLNKFSRFRQWRESEFLIDALKMNFL
SEQ ID NO:62      (795)   FQDSQKVDVLDFCLRIANPETRLSTLLKIQGFRACVESEFLLPTLHLNFL
                          851                                              900
SEQ ID NO:01      (849)   LWIVFEMENVEVNAAYKRHPLLISTAKGLRVIGVDIFNSQLSISMSGWIP
SEQ ID NO:61      (849)   LWIVFEMENVEVNAAYKRHPLLISTAKGLRVIGVDIFNSQLSISMSGWIP
SEQ ID NO:59      (846)   LWIVFEMENVDVSAANKRHPLLISHEKGLRLIGVDLFNGALSISTGGWIP
SEQ ID NO:60      (840)   LWVVFEMENIDVDYGKKWHPLLVSSEKGLRVIAVDVFNSMMGVSTSGWLP
SEQ ID NO:63      (840)   LWVVFELENIDVDYSKKRHPLLISTDKGLRVVSVDLFNSMLSVSLSGWIP
SEQ ID NO:62      (845)   IWLLIDMENGDINYSKKRLPLLISTTNGLRVMAVDAFNNMIAMSYSGWLP
                          901                                              950
SEQ ID NO:01      (899)   YVERMCAESKVQTKLTADELKLKRWFISYYTTLKLDRRAEPRMSFKFEGL
SEQ ID NO:61      (899)   YVERMCAESKVQTKLTADELKLKRWFISYYTTLKLDRRAEPRMSFKFEGL
SEQ ID NO:59      (896)   YLERICSEEKAQRRLNADELKIKSWFLTYYMNLSLERRAEPRMSFKFEGL
SEQ ID NO:60      (890)   YVERICSESDMRRRLNADELELKRWFFDYYATLLLERRGEPRLSFKYEGL
SEQ ID NO:63      (890)   YVERVCERSEAKRRLNADELKLKNWFIAYYVTLPLLRRAEPRMSFKYEGI
SEQ ID NO:62      (895)   YLERICHETKQRTRLNADELKLKKWFLNYVTKYEVERRAEPRMSFKMEGI
                          951                                             1000
SEQ ID NO:01      (949)   STWIGSNCGGVRDYVIQMLPTRKPKPGALMVVYARDSRIEWIEAELSQWL
SEQ ID NO:61      (949)   STWIGSNCGGVRDYVIQMLPTRKPKPGALMVVYARDSRIEWIEAELSQWL
SEQ ID NO:59      (946)   TTWIGSNCGGVRDYVVQALPMRKPKPGLLMVIYGDDGDARWVEWAMKNFT
SEQ ID NO:60      (940)   TTWIGSNCGGVRDYVVQLLPMRKPKPGLLCIAYGDDVNVQWVEHELRDFL
SEQ ID NO:63      (940)   TTWIGSNCGGVRDYLIQMLPARKPKPGVLILAHGAEINVAWLNHALRDIL
SEQ ID NO:62      (945)   TTWIGSNCGGVQDYILHLIPSRKPKPGLLFLIYTDAGDVDWVTRMLYDVC
                          1001                                            1050
SEQ ID NO:01      (999)   QMEGSLGLILVHDSGIINKSVLRARTLKIYNRGSMDTLILISSGVYTFGN
SEQ ID NO:61      (999)   QMEGSLGLILVHDSGIINKSVLRARTLKIYNRGSMDTLILISSGVYTFGN
SEQ ID NO:59      (996)   AVDGSLGFIYIDRHKLVNKSDFRVREMKIYNRGRLDRLILISSGHYTFGN
SEQ ID NO:60      (990)   THEGSLGLVVISGKMLVNKSKLRVRNLKIYNRGTLDSLFLISGGSYTFGN
SEQ ID NO:63      (990)   SLEGSLGIIIVSDGSVVNKSKLRVRDMKIYNRWEVDRLILISSGDYTFGN
SEQ ID NO:62      (995)   RLEGSLGFILIDDRVMVNKSQLRARILKIYNRGKLDKLILISGGNYTFGN
```

FIGURE 37 (4/4)

Synthetic AHSV4-VP2 versus other deposited AHSV4-VP2 proteins

```
                            1051       1063
SEQ ID NO:01   (1049)  KFLLSKLLAKTE~
SEQ ID NO:61   (1049)  KFLLSKLLAKTE~
SEQ ID NO:59   (1046)  KFLMSKLLAKTE~
SEQ ID NO:60   (1040)  KFLLSKLMAKAE~
SEQ ID NO:63   (1040)  KYLLSKLMAKIEQ
SEQ ID NO:62   (1045)  KFLLSKLLAKTEK
```

Percent Identity for the above aligned sequences:

| | SEQ ID NO:01 | SEQ ID NO:61 | SEQ ID NO:59 | SEQ ID NO:60 | SEQ ID NO:63 | SEQ ID NO:62 |
|---|---|---|---|---|---|---|
| SEQ ID NO:01 | 100 | 100 | 52 | 51 | 52 | 52 |
| SEQ ID NO:61 | | 100 | 51 | 51 | 52 | 51 |
| SEQ ID NO:59 | | | 100 | 51 | 51 | 51 |
| SEQ ID NO:60 | | | | 100 | 62 | 52 |
| SEQ ID NO:63 | | | | | 100 | 53 |
| SEQ ID NO:62 | | | | | | 100 |

FIGURE 38 (1/3)

Synthetic AHSV4-VP5 versus other deposited AHSV4-VP5 proteins 50

```
SEQ ID NO:02     (1) MGKFTSFLKRAGNATKRALTSDSAKKMYKLAGKTLQRVVESEVGSAAIDG
SEQ ID NO:52     (1) MGKFTSFLKRAGNATKRALTSDSAKKMYKLAGKTLQRVVESEVGSAAIDG
SEQ ID NO:58     (1) MGKFTSFLKRAGNATKRALTSDSAKKMYKLAGKTLQRVVESEVGSAAIDG
SEQ ID NO:54     (1) MGKFTSFLKRAGSATKKALTSDTAKRMYKMAGKTLQKVVESEVGSAAIDG
SEQ ID NO:56     (1) MGKFTSFLKRAGSATKKALTSDAAKRMYKMAGKTLQKVVDSEVGSAAIDG
SEQ ID NO:53     (1) MGKFTSFLKRTGSATKKALTSDAAKRMYKMAGKTLQKVVESEVGSAAIDG
SEQ ID NO:55     (1) MGKFTSFLKRAGSATKKALTSDAAKRMYKMAGKALQKVVESEVGSAAIDG
SEQ ID NO:57     (1) MGKFTSFLKRAGSATKKALTSDAAKRMYKMAGKTLQKVVESEVGSAAIDG
                     51                                             100
SEQ ID NO:02    (51) VMQGAIQSIIQGENLGDSIKQAVILNVAGTLESAPDPLSPGEQLLYNKVS
SEQ ID NO:52    (51) VMQGAIQSIIQGENLGDSIKQAVILNVAGTLESAPDPLSPGEQLLYNKVS
SEQ ID NO:58    (51) VMQGAIQSIIQGENLGDSIKQAVILNVAGTLESAPDPLSPGERLLYNKVS
SEQ ID NO:54    (51) VMQGTIQSIIQGENLGDSIRQAVILNVAGTLESAPDPLSPGEQLLYNKVA
SEQ ID NO:56    (51) VMQGTIQSIIQGENLGDSIKQAVILNVAGTLESPPDPLSPGEQLLYNKVS
SEQ ID NO:53    (51) VMQGTIQSIIQGENLGDSIKQAVILNVAGTLESAPDPLSPGEQLLYNKVS
SEQ ID NO:55    (51) VMQGTFQSIIQGENLGDSIKQAVILNVAGTLESAPDPLSPGEQLLYNKVS
SEQ ID NO:57    (51) VMQGTIQSIIQGENLGDSIKQAVILNVAGTLESAPDPLSPGEQLLYNKVS
                     101                                            150
SEQ ID NO:02   (101) EIEKMEKEDRVIETHNAKIEEKFGKDLLAIRKIVKGEVDAEKLEGNEIKY
SEQ ID NO:52   (101) EIEKMEKEDRVIETHNAKIEEKFGKDLLAIRKIVKGEVDAEKLEGNEIKY
SEQ ID NO:58   (101) EIEKMEKEDRVIETHNAKIEEKFGKDLLAIRKIVKGEVDAEKLEGNEIKY
SEQ ID NO:54   (101) ELERAEKEDRVIETHNEKIIQEYGKDLLKIRKIMKGEAKAEQLEGKEIEY
SEQ ID NO:56   (101) KIERAEKEDRVIETHNEKIIEKYGEDLLKIRKIMKGEAEAEQLEGKEMEY
SEQ ID NO:53   (101) EIERAEKEDRVIEIHNKKIVEKYGEDLLKIRKIMKGEAEAEQLEGKEMEY
SEQ ID NO:55   (101) EIERAEKEDRVIETHNKKIVEKYGEDLLKIRKIMKGEAEAEQLEGKEMEY
SEQ ID NO:57   (101) EIERAEKEDRVIETHNKKIVEKYGEDLLKIRKIMKGEAEAEQLEGKEMEY
                     151                                            200
SEQ ID NO:02   (151) VEKALSGLLEIGKDQSERITKLYRALQTEEDLRTRDETRMINEYREKFDA
SEQ ID NO:52   (151) VEKALSGLLEIGKDQSERITKLYRALQTEEDLRTRDETRMINEYREKFDA
SEQ ID NO:58   (151) VEKALSGLLEIGKDQSERITKLYRALQTEEDLRTRDETRMINEYREKFDA
SEQ ID NO:54   (151) VEMALKGMLKIGKDQSERITQLYRALQTEEDLRTSDETRMINEYREKFDA
SEQ ID NO:56   (151) VEKALKGMLKIGKDQSERITRLYRALQTEEDLRTSDETRMISEYREKFDA
SEQ ID NO:53   (151) VEKALRGMLKIGKDQSERITRLYRALQTEEDLRTSDETRIISEYREKFDA
SEQ ID NO:55   (151) VEKALRGMLKIGKDQSERITRLYRALQTEEDLRTSDETRIISEYREKFDA
SEQ ID NO:57   (151) VEKALRGMLKIGKDQSERITRLYRALQTEEDLRTSDETRIISEYREKFDA
                     201                                            250
SEQ ID NO:02   (201) LKEAIEIEQQATHDEAIQEMLDLSAEVIETASEEVPIFGAGAANVIATTR
SEQ ID NO:52   (201) LKEAIEIEQQATHDEAIQEMLDLSAEVIETASEEVPIFGAGAANVIATTR
SEQ ID NO:58   (201) LKEAIEIEQQATHDEAIQEMLDLSAEVIETASEEVPIFGAGAANVIATTR
SEQ ID NO:54   (201) LKQAIELEQQATHEEAVQEMLDLSAEVIETAAEEVPIFGAGAANVVATTR
SEQ ID NO:56   (201) LKQAIELEQQATHEEAVQEMLDLSAEVIETAAEDLPIFGAGAANVVATTR
SEQ ID NO:53   (201) LKQAIELEQQATHEEAVQEMLDLSAEVIETAAEEVPVFGAGAANVVATTR
SEQ ID NO:55   (201) LKQAIELEQQATHEEAVQEMLDLSAEVIETAAEEVPVFGAGAANVVATTR
SEQ ID NO:57   (201) LKQAIELEQQATHEEAVQEMLDLSAEVIETAAEEVPVFGAGAANVVATTR
                     251                                            300
SEQ ID NO:02   (251) AIQGGLKLKEIVDKLTGIDLSHLKVADIHPHIIEKAMLRDTVTDKDLAMA
SEQ ID NO:52   (251) AIQGGLKLKEIVDKLTGIDLSHLKVADIHPHIIEKAMLRDTVTDKDLAMA
SEQ ID NO:58   (251) AIQGGLKLKEIVDKLTGIDLSHLKVADIHPHIIEKAMLRDTVTDKDLAMA
SEQ ID NO:54   (251) AVQGGLKLKEIIDKLTGIDLSHLKVADIHPHIIEKAILKDKIPDSELAMA
SEQ ID NO:56   (251) AIQGGLKLKEIIDKLTGIDLSHLKVADIHPHIIEKAMLKDKIPDNELAMA
SEQ ID NO:53   (251) AIQGGLKLKEIIDKLTGIDLSHLKVADIHPHIIEKAMLKVKIPDNELAMA
SEQ ID NO:55   (251) AIQGGLKLKEIIDKLTGIDLSHLKVADIHPHIIEKAMLKDKIPDNELAMA
SEQ ID NO:57   (251) AIQGGLKLKEIIDKLTGIDLSHLKVADIHPHIIEKAMLKDKIPDNELAMA
```

FIGURE 38 (2/3)

```
                          301                                              350
SEQ ID NO:02    (301)  IKSKVDVIDEMNVETQHVIDAVLPIVKQEYERHDNKYHVRIPGALKIHSE
SEQ ID NO:52    (301)  IKSKVDVIDEMNVETQHVIDAVLPIVKQEYEKHDNKYHVRIPGALKIHSE
SEQ ID NO:58    (301)  IKSKVDVIDEMNVETQHVIDAVLPIVKQEYEKHDNKYHVRIPGALKIHSE
SEQ ID NO:54    (301)  IKSKVEVIDEMNTETEHVIKSIMPLVKKEYEKHDNKYHVNIPSVLKIHSE
SEQ ID NO:56    (301)  IKSKVEVIDEMNTETEHVIESIMPLVKKEYEKHDNKYHVNIPSALKIHSE
SEQ ID NO:53    (301)  IKSKVEVVDEMNTETEHVIESIMPLVKKEYEKHDNKYHVNIPSALKIHSE
SEQ ID NO:55    (301)  IKSKVEVVDEMNTEMEHVIESIMPLVKKEYEKHDNKYHVNIPSALKIHSE
SEQ ID NO:57    (301)  IKSKVEVVDEMNTETEHVIESIMPLVKKEYEKHDNKYHVNIPSALKIHSE
                          351                                              400
SEQ ID NO:02    (351)  HTPKIHIYTTPWDSDSVFMCRAIAPHHQQRSFFIGFDLEIEYVHFEDTSV
SEQ ID NO:52    (351)  HTPKIHIYTTPWDSDSVFMCRAIAPHHQQRSFFIGFDLEIEYVHFEDTSV
SEQ ID NO:58    (351)  HTPKIHIYTTPWDSDSVFMCRAIAPHHQQRSFFIGFDLEIEYVHFEDTSV
SEQ ID NO:54    (351)  HTPKVHIYTTPWDSDKVFICRCIAPHHQQKSFMIGFDLEIEFVFYEDTSV
SEQ ID NO:56    (351)  HTPKVHIYTTPWDSDKVFICRCIAPHHQQRSFMIGFDLEIEFVFYEDTSV
SEQ ID NO:53    (351)  QTPKVHIYTTPWDSDKVFICRCIAPHHQQKSFMIGFDLEIEFVFYEDTSV
SEQ ID NO:55    (351)  HTPKVHIYTTPWDSDKVFICRCIAPHHQQRSFMIGFDLGIEFVFYEDTSV
SEQ ID NO:57    (351)  HTPKVHIYTTPWDSDKVFICRCIAPHHQQRSFMIGFDLEIEFVFYEDTSV
                          401                                              450
SEQ ID NO:02    (401)  EGHILHGGAITVEGRGFRQAYTEFMNAAWGMPTTPELHKRKLQRSMGTHP
SEQ ID NO:52    (401)  EGHILHGGAITVEGRGFRQAYTEFMNAAWGMPTTPELHKRKLQRSMGTHP
SEQ ID NO:58    (401)  EGHILHGGAITVEGRGFRQAYTEFMNAAWGMPTTPELHKRKLQRSMGTHP
SEQ ID NO:54    (401)  EGHIMHGGAVSIEGRGFRQAYSEFMNAAWSMPSTPELHKRRLQRSLGSHP
SEQ ID NO:56    (401)  EGHIMHGGAVSIEGRGFRQAYSEFMNAAWSMPSTPELHKRRLQRSLGSHP
SEQ ID NO:53    (401)  EGHIMHGGAVSIEGRGFRQAYSEFMNAAWSMPLTPELHKRRLQRSLGSHP
SEQ ID NO:55    (401)  EGHIMHGGAVSIEGRGFRQAYSEFMNAAWSMPSTPELHKRRLQRSLGSHP
SEQ ID NO:57    (401)  EGHIMHGGAVSIEGRGFRQAYSEFMNAAWSMPSTPELHKRRLQRSLGSHP
                          451                                              500
SEQ ID NO:02    (451)  IYMGSMDYAISYEQLVSNAMRLVYDSELQMHCLRGPLKFQRRTLMNALLY
SEQ ID NO:52    (451)  IYMGSMDYAISYEQLVSNAMRLVYDSELQMHCLRGPLKFQRRTLMNALLY
SEQ ID NO:58    (451)  IYMGSMDYAISYEQLVSNAMRLVYDSELQMHCLRGPLKFQRRTLMNALLY
SEQ ID NO:54    (451)  IYMGSMDYTVSYDQLVSNAMKLVYDTELQMHCLRGPLKFQRRTLMNALLF
SEQ ID NO:56    (451)  IYMGSMDYTVSYEQLVSNAMKLVYDTDLQMHCLRGPLKFQRRTLMNALLF
SEQ ID NO:53    (451)  IYMGSMDYTISYEQLVSNAMKLVYDTDLQMHCLRGPLKFQRRTLMNALLF
SEQ ID NO:55    (451)  IYMGSMDYTISYEQLVSNAMKLVYDTDLQMHCLRGPLKLQRRTLMNALLF
SEQ ID NO:57    (451)  IYMGSMDYTISYEQLVSNAMKLVYDTDLQMHCLRGPLKFQRRTLMNALLF
                          501
SEQ ID NO:02    (501)  GVKIA
SEQ ID NO:52    (501)  GVKIA
SEQ ID NO:58    (501)  GVKIA
SEQ ID NO:54    (501)  GVKIA
SEQ ID NO:56    (501)  GVKVA
SEQ ID NO:53    (501)  GVKVA
SEQ ID NO:55    (501)  GVKVA
SEQ ID NO:57    (501)  GVKVA
```

FIGURE 38 (3/3)

Percent Identity for the above aligned sequences:

| | SEQ ID NO:02 | SEQ ID NO:52 | SEQ ID NO:58 | SEQ ID NO:54 | SEQ ID NO:56 | SEQ ID NO:53 | SEQ ID NO:55 | SEQ ID NO:57 |
|---|---|---|---|---|---|---|---|---|
| SEQ ID NO:02 | 100 | 100 | 100 | 84 | 84 | 83 | 83 | 84 |
| SEQ ID NO:52 | | 100 | 100 | 84 | 84 | 84 | 84 | 84 |
| SEQ ID NO:58 | | | 100 | 84 | 84 | 83 | 83 | 84 |
| SEQ ID NO:54 | | | | 100 | 95 | 94 | 93 | 94 |
| SEQ ID NO:56 | | | | | 100 | 96 | 97 | 98 |
| SEQ ID NO:53 | | | | | | 100 | 98 | 99 |
| SEQ ID NO:55 | | | | | | | 100 | 99 |
| SEQ ID NO:57 | | | | | | | | 100 |

FIGURE 39 (1/4)

Codon-optimized AHSV4-VP2 (SEQ ID NO:04) vs. field isolate AHSV4-VP2 (SEQ ID NO:48)

```
                         1                                                50
SEQ ID NO:04       (1)  ATGGCCAGCGAGTTCGGCATCCTGATGACCAACGAGAAGTTCGACCCCAG
SEQ ID NO:48       (1)  ATGGCGTCCGAGTTTGGAATATTGATGACAAATGAAAAATTTGACCCAAG
                         51                                              100
SEQ ID NO:04      (51)  CCTGGAAAAGACCATCTGCGACGTGATCGTGACCAAGAAGGGCCGGGTCA
SEQ ID NO:48      (51)  CTTAGAGAAAACCATTTGCGATGTTATAGTTACGAAGAAGGGAAGAGTGA
                         101                                             150
SEQ ID NO:04     (101)  AGCACAAGGAAGTGGACGGCGTGTGCGGCTACGAGTGGGACGAGACCAAC
SEQ ID NO:48     (101)  AGCATAAAGAGGTGGATGGCGTATGTGGATACGAGTGGGATGAAACGAAT
                         151                                             200
SEQ ID NO:04     (151)  CACCGGTTCGGCCTGTGCGAGGTGGAGCACGACATGAGCATCAGCGAGTT
SEQ ID NO:48     (151)  CACCGATTCGGATTGTGTAAGGTGGAACACGACATGTCTATATCGGAATT
                         201                                             250
SEQ ID NO:04     (201)  CATGTACAACGAGATCAGATGCGAGGGCGCCTACCCCATCTTCCCCCGGT
SEQ ID NO:48     (201)  TATGTACAATGAGATCAGATGTGAGGGGGCATATCCAATTTTTCCGCGTT
                         251                                             300
SEQ ID NO:04     (251)  ACATCATCGACACCCTGAAGTATGAGAAGTTCATCGACCGGAACGACCAC
SEQ ID NO:48     (251)  ATATAATTGATACGTTAAAATACGAGAAATTTATTGATAGGAATGACCAT
                         301                                             350
SEQ ID NO:04     (301)  CAGATCCGGGTGGACCGGGACGACAACGAGATGCGGAAGATCCTGATCCA
SEQ ID NO:48     (301)  CAAATTAGAGTGGATAGAGATGATAACGAAATGAGGAAAATATTGATACA
                         351                                             400
SEQ ID NO:04     (351)  GCCCTACGCCGGCGAGATGTACTTCAGCCCCGAGTGCTACCCCAGCGTGT
SEQ ID NO:48     (351)  GCCGTATGCAGGTGAGATGTACTTTTCGCCGGAATGTTATCCGAGCGTTT
                         401                                             450
SEQ ID NO:04     (401)  TCCTGCGGCGGGAGGCCAGAAGCCAGAAGCTGGACCGGATCAGGAACTAC
SEQ ID NO:48     (401)  TTCTTCGGAGGGAAGCGCGAAGTCAAAAGCTTGATCGGATTCGGAATTAT
                         451                                             500
SEQ ID NO:04     (451)  ATCGGCAAGCGGGTGGAGTTCTACGAGGAAGAGAGCAAGCGGAAGGCCAT
SEQ ID NO:48     (451)  ATTGGAAAGAGAGTCGAATTTTATGAAGAGGAGAGTAAGAGAAAAGCAAT
                         501                                             550
SEQ ID NO:04     (501)  CCTGGACCAGAACAAGATGAGCAAGGTGGAACAGTGGCGGGACGCCGTGA
SEQ ID NO:48     (501)  CCTTGATCAGAATAAGATGTCTAAGGTTGAACAATGGAGAGATGCGGTTA
                         551                                             600
SEQ ID NO:04     (551)  ACGAGCGGATCGTGAGCATCGAGCCCAAGCGGGGCGAGTGCTACGACCAC
SEQ ID NO:48     (551)  ATGAAAGGATTGTGAGTATCGAACCAAAGCGAGGTGAGTGCTATGATCAC
                         601                                             650
SEQ ID NO:04     (601)  GGCACCGACATCATCTACCAGTTCATCAAGAAGCTGCGGTTCGGCATGAT
SEQ ID NO:48     (601)  GGAACCGACATTATCTACCAATTCATAAAAAAGCTGAGATTTGGAATGAT
                         651                                             700
SEQ ID NO:04     (651)  GTACCCCCACTACTACGTGCTGCACAGCGACTACTGCATCGTGCCCAACA
SEQ ID NO:48     (651)  GTACCCACACTATTATGTTTTGCATAGTGATTACTGTATTGTACCAAATA
                         701                                             750
SEQ ID NO:04     (701)  AGGGCGGCACCAGCATCGGCAGCTGGCACATCCGGAAGCGGACCGAGGGC
SEQ ID NO:48     (701)  AGGGGGGAACTAGTATTGGATCATGGCATATAAGAAAACGTACTGAGGGT
                         751                                             800
SEQ ID NO:04     (751)  GACGCCAAGGCCAGCGCCATGTACAGCGGCAAGGGCCCCCTGAACGACCT
SEQ ID NO:48     (751)  GATGCGAAAGCTTCTGCTATGTATTCTGGAAAAGGTCCACTGAATGACTT
                         801                                             850
SEQ ID NO:04     (801)  GCGGGTGAAGATCGAGCGGGACGACCTGAGCCGGGAGACCATCATCCAGA
SEQ ID NO:48     (801)  ACGAGTTAAAATTGAGCGGGATGATTTATCTCGAGAGACAATTATTCAGA
```

FIGURE 39 (2/4)

```
                             851                                              900
SEQ ID NO:04      (851)  TCATCGAGTACGGCAAGAAGTTCAACAGCTCTGCCGGCGACAAGCAGGGC
SEQ ID NO:48      (851)  TCATTGAGTACGGTAAGAAATTTAATTCATCAGCAGGTGATAAGCAGGGG
                             901                                              950
SEQ ID NO:04      (901)  AACATCAGCATCGAGAAGCTGGTCGAGTACTGCGACTTCCTGACCACCTT
SEQ ID NO:48      (901)  AACATTTCAATTGAAAAATTGGTAGAGTATTGTGATTTTTTGACAACATT
                             951                                             1000
SEQ ID NO:04      (951)  CGTGCACGCCAAGAAGAAGGAAGAGGGCGAGGACGACACCGCCAGGCAGG
SEQ ID NO:48      (951)  CGTTCATGCGAAGAAGAAAGAAGAGGGTGAGGATGATACTGCTCGACAGG
                             1001                                            1050
SEQ ID NO:04     (1001)  AAATCCGGAAGGCCTGGGTGAAGGGAATGCCCTACATGGACTTCAGCAAG
SEQ ID NO:48     (1001)  AGATAAGAAAAGCATGGGTTAAGGGGATGCCTTATATGGATTTCTCAAAA
                             1051                                            1100
SEQ ID NO:04     (1051)  CCCATGAAGATCACCCGGGGCTTCAACCGGAATATGCTGTTCTTCGCCGC
SEQ ID NO:48     (1051)  CCGATGAAAATCACGCGTGGATTCAACAGAAATATGCTTTTCCTTGCGGC
                             1101                                            1150
SEQ ID NO:04     (1101)  CCTGGACAGCTTCCGGAAGAGGAACGGCGTGGACGTGGACCCCAATAAGG
SEQ ID NO:48     (1101)  GCTCGATTCATTCAGAAAGAGGAACGGTGTAGATGTTGATCCGAATAAGG
                             1151                                            1200
SEQ ID NO:04     (1151)  GCAAGTGGAAAGAGCACATCAAAGAGGTCACCGAGAAGCTGAAGAAGGCC
SEQ ID NO:48     (1151)  GTAAGTGGAAAGAACATATAAAGGAGGTAACCGAAAAATTGAAGAAAGCG
                             1201                                            1250
SEQ ID NO:04     (1201)  CAGACCGAGAACGGCGGCCAGCCCTGCCAGGTGTCCATCGACGGCGTGAA
SEQ ID NO:48     (1201)  CAAACCGAAAATGGAGGACAACCATGCCAAGTGTCGATCGATGGAGTAAA
                             1251                                            1300
SEQ ID NO:04     (1251)  CGTGCTGACCAACGTGGACTACGGCACCGTGAACCACTGGATCGACTGGG
SEQ ID NO:48     (1251)  CGTCTTGACTAACGTAGATTACGGTACGGTTAATCATTGGATAGATTGGG
                             1301                                            1350
SEQ ID NO:04     (1301)  TGACAGACATCATCATGGTGGTGCAGACCAAGCGGCTGGTGAAAGAGTAC
SEQ ID NO:48     (1301)  TAACAGATATAATTATGGTTGTACAAACTAAACGTTTGGTGAAAGAGTAT
                             1351                                            1400
SEQ ID NO:04     (1351)  GCCTTTAAGAAGCTGAAAAGCGAGAACCTGCTGGCCGGCATGAACAGCCT
SEQ ID NO:48     (1351)  GCATTTAAAAAACTAAAGAGCGAAAACTTACTTGCTGGAATGAATAGTTT
                             1401                                            1450
SEQ ID NO:04     (1401)  GGTCGGCGTGCTGCGGTGCTACATGTACTGCCTGGCCCTGGCCATCTACG
SEQ ID NO:48     (1401)  AGTTGGGGTATTAAGATGTTATATGTATTGCTTAGCTTTAGCGATCTATG
                             1451                                            1500
SEQ ID NO:04     (1451)  ACTTCTACGAGGGCACCATCGATGGCTTCAAGAAGGGCAGCAACGCCTCC
SEQ ID NO:48     (1451)  ATTTTTATGAAGGGACTATTGATGGTTTTAAGAAAGGCTCGAATGCTTCC
                             1501                                            1550
SEQ ID NO:04     (1501)  GCCATCATCGAGACCGTGGCCCAGATGTTCCCCGACTTCCGGCGGGAACT
SEQ ID NO:48     (1501)  GCTATCATTGAAACTGTCGCGCAGATGTTTCCGGACTTTCGCAGAGAGCT
                             1551                                            1600
SEQ ID NO:04     (1551)  GGTGGAGAAGTTTGGCATCGACCTGCGCATGAAAGAGATCACCCGCGAGC
SEQ ID NO:48     (1551)  TGTCGAAAAATTCGGTATAGATTTAAGGATGAAGGAAATCACGCGTGAGT
                             1601                                            1650
SEQ ID NO:04     (1601)  TGTTCGTGGGCAAGAGCATGACCAGCAAGTTCATGGAAGAGGGGGAGTAC
SEQ ID NO:48     (1601)  TGTTTGTTGGTAAGAGCATGACGTCAAAATTTATGGAGGAAGGTGAATAT
                             1651                                            1700
SEQ ID NO:04     (1651)  GGCTACAAGTTCGCCTACGGCTGGCGGAGGGACGGCTTCGCCGTGATGGA
SEQ ID NO:48     (1651)  GGATATAAGTTCGCCTATGGATGGCGTAGGGATGGCTTCGCGGTGATGGA
                             1701                                            1750
SEQ ID NO:04     (1701)  AGATTACGGCGAGATCCTGACAGAGAAGGTGGAGGACCTGTACAAGGGGG
SEQ ID NO:48     (1701)  AGATTACGGAGAAATTTTGACAGAAAAAGTGGAGGACCTATATAAGGGTG
```

FIGURE 39 (3/4)

```
                  1751                                               1800
SEQ ID NO:04 (1751) TGCTGCTGGGCCGGAAGTGGGAGGACGAGGTGGACGACCCCGAGAGCTAC
SEQ ID NO:48 (1751) TACTTTTAGGACGAAAGTGGGAGGATGAGGTTGATGATCCAGAGAGTTAT
                  1801                                               1850
SEQ ID NO:04 (1801) TTCTACGACGACCTGTACACCAACGAGCCCCACCGGGTGTTCCTGAGCGC
SEQ ID NO:48 (1801) TTTTATGATGATCTTTATACTAATGAGCCCCACAGAGTGTTTCTAAGCGC
                  1851                                               1900
SEQ ID NO:04 (1851) CGGCAAGGACGTGGACAACAACATCACCCTGCGGAGCATCAGCCAGGCCG
SEQ ID NO:48 (1851) AGGAAAGGATGTGGATAATAATATCACGCTTCGATCGATTTCGCAGGCGG
                  1901                                               1950
SEQ ID NO:04 (1901) AGACCACCTACCTGAGCAAGCGGTTCGTGAGCTACTGGTACAGGATCAGC
SEQ ID NO:48 (1901) AAACCACGTATCTATCGAAACGTTTCGTATCATATTGGTATAGAATATCA
                  1951                                               2000
SEQ ID NO:04 (1951) CAGGTGGAGGTGACCAAGGCCCGGAACGAGGTGCTGGACATGAACGAGAA
SEQ ID NO:48 (1951) CAAGTTGAAGTAACGAAGGCGCGTAATGAAGTTCTGGACATGAATGAGAA
                  2001                                               2050
SEQ ID NO:04 (2001) GCAGAAGCCCTACTTCGAGTTCGAGTACGACGACTTCAAGCCCTGCTCCA
SEQ ID NO:48 (2001) ACAGAAGCCGTATTTTGAATTTGAATATGATGATTTCAAACCCTGTTCAA
                  2051                                               2100
SEQ ID NO:04 (2051) TCGGCGAGCTGGGCATCCACGCCAGCACCTACATCTACCAGAATCTGCTG
SEQ ID NO:48 (2051) TTGGAGAGTTGGGGATCCATGCATCCACATATATATATCAGAACCTACTG
                  2101                                               2150
SEQ ID NO:04 (2101) GTCGGCAGGAACCGGGGCGAGGAAATCCTGGACAGCAAAGAACTGGTCTG
SEQ ID NO:48 (2101) GTCGGACGTAATAGAGGTGAGGAAATACTTGATTCGAAAGAGCTCGTCTG
                  2151                                               2200
SEQ ID NO:04 (2151) GATGGACATGAGCCTGCTGAACTTCGGCGCCGTGCGGAGCCACGACCGGT
SEQ ID NO:48 (2151) GATGGATATGTCACTTTTAAATTTTGGAGCGGTCAGATCTCACGATAGGT
                  2201                                               2250
SEQ ID NO:04 (2201) GCTGGATCTCTAGCAGCGTGGCCATCGAGGTGAACCTGCGGCACGCCCTG
SEQ ID NO:48 (2201) GCTGGATCTCCTCAAGCGTCGCGATTGAGGTGAATTTACGTCATGCACTA
                  2251                                               2300
SEQ ID NO:04 (2251) ATCGTGCGGATCTTCAGCAGATTCGACATGATGAGCGAGAGAGAGACCTT
SEQ ID NO:48 (2251) ATAGTTAGGATTTTTTCACGCTTTGACATGATGTCGGAAAGAGAAACGTT
                  2301                                               2350
SEQ ID NO:04 (2301) CAGCACCATCCTGGAAAAGGTCATGGAAGATGTGAAAGAGCTGCGGTTCT
SEQ ID NO:48 (2301) TTCAACCATTTTAGAAAAAGTCATGGAGGATGTGAAAGAGTTGAGATTTT
                  2351                                               2400
SEQ ID NO:04 (2351) TCCCCACCTACCGGCACTACTACCTGGAAACCCTGCAGCGGGTGTTCAAC
SEQ ID NO:48 (2351) TCCCGACATATCGTCATTATTATTTGGAAACTCTCCAACGTGTCTTTAAC
                  2401                                               2450
SEQ ID NO:04 (2401) GACGAGCGGCGGCTGGAAGTGGATGACTTCTACATGCGGCTGTACGACGT
SEQ ID NO:48 (2401) GATGAGAGACGCTTAGAAGTTGATGACTTTTATATGAGGTTATATGATGT
                  2451                                               2500
SEQ ID NO:04 (2451) GCAGACCCGGGAGCAGGCCCTGAACACCTTCACCGACTTCCACAGATGCG
SEQ ID NO:48 (2451) GCAGACAAGGGAGCAGGCACTAAATACTTTCACGGATTTTCACAGGTGTG
                  2501                                               2550
SEQ ID NO:04 (2501) TGGAGAGCGAGCTGCTGCTGCCCACCCTGAAGCTGAACTTCCTGCTGTGG
SEQ ID NO:48 (2501) TTGAGTCGGAACTGCTCTTACCGACACTTAAACTTAACTTTCTGCTGTGG
                  2551                                               2600
SEQ ID NO:04 (2551) ATCGTGTTCGAGATGGAAAACGTGGAGGTGAACGCCGCCTACAAGCGGCA
SEQ ID NO:48 (2551) ATTGTTTTTGAAATGGAAAATGTTGAAGTGAACGCGGCGTACAAGCGTCA
                  2601                                               2650
SEQ ID NO:04 (2601) CCCCCTGCTGATCTCTACCGCCAAGGGCCTGAGGGTGATCGGCGTGGACA
SEQ ID NO:48 (2601) TCCGCTTTTAATCTCAACTGCCAAAGGGTTAAGGGTTATCGGCGTTGATA
```

FIGURE 39 (4/4)

```
                       2651                                              2700
SEQ ID NO:04   (2651)  TCTTCAACAGCCAGCTGTCCATCAGCATGAGCGGCTGGATTCCCTACGTG
SEQ ID NO:48   (2651)  TTTTCAACTCACAGCTTTCGATATCAATGAGCGGATGGATTCCGTATGTC
                       2701                                              2750
SEQ ID NO:04   (2701)  GAGCGGATGTGCGCCGAGAGCAAAGTGCAGACCAAACTGACCGCCGACGA
SEQ ID NO:48   (2701)  GAACGGATGTGCGCGGAGAGTAAAGTTCAAACAAAATTGACGGCTGATGA
                       2751                                              2800
SEQ ID NO:04   (2751)  GCTGAAACTGAAGCGGTGGTTCATCAGCTACTACACCACACTGAAGCTGG
SEQ ID NO:48   (2751)  GCTGAAATTGAAGAGGTGGTTCATCTCATATTATACGACGTTGAAATTGG
                       2801                                              2850
SEQ ID NO:04   (2801)  ACAGAAGAGCCGAGCCCCGGATGAGCTTCAAGTTCGAGGGCCTGAGCACC
SEQ ID NO:48   (2801)  ACCGCAGAGCGGAGCCACGTATGAGTTTCAAATTTGAGGGGTTGAGTACA
                       2851                                              2900
SEQ ID NO:04   (2851)  TGGATCGGCAGCAACTGTGGCGGCGTGCGGGACTACGTGATCCAGATGCT
SEQ ID NO:48   (2851)  TGGATCGGTTCGAACTGCGGAGGTGTTAGGGATTACGTAATACAGATGCT
                       2901                                              2950
SEQ ID NO:04   (2901)  GCCTACCCGGAAGCCCAAGCCTGGCGCCCTGATGGTGGTGTACGCCCGGG
SEQ ID NO:48   (2901)  TCCTACCAGAAAACCTAAACCGGGAGCTTTGATGGTGGTATACGCGCGGG
                       2951                                              3000
SEQ ID NO:04   (2951)  ACAGCCGGATCGAGTGGATCGAGGCCGAGCTGTCCCAGTGGCTGCAGATG
SEQ ID NO:48   (2951)  ATTCGAGAATCGAGTGGATCGAAGCAGAGCTATCACAGTGGCTGCAAATG
                       3001                                              3050
SEQ ID NO:04   (3001)  GAAGGCAGCCTGGGCCTGATCCTGGTGCACGACAGCGGCATCATCAACAA
SEQ ID NO:48   (3001)  GAAGGTTCGCTTGGTTTGATCCTCGTTCATGATTCAGGTATAATAAATAA
                       3051                                              3100
SEQ ID NO:04   (3051)  GAGCGTGCTGAGGGCCCGGACCCTGAAAATCTACAACCGGGGCAGCATGG
SEQ ID NO:48   (3051)  GAGCGTATTGAGAGCGAGAACTCTGAAAATTTACAATAGGGGTTCGATGG
                       3101                                              3150
SEQ ID NO:04   (3101)  ACACCCTGATCCTGATCAGCTCCGGCGTGTACACCTTCGGCAACAAGTTC
SEQ ID NO:48   (3101)  ATACTTTAATTCTAATTTCGAGTGGAGTTTACACTTTCGGAAATAAATTC
                       3151                          3180
SEQ ID NO:04   (3151)  CTGCTGTCCAAGCTGCTGGCCAAGACCGAG
SEQ ID NO:48   (3151)  TTGTTGTCGAAGTTACTCGCAAAAACAGAA
```

Percent Identity for above-aligned sequences = 73%

FIGURE 40 (1/2)

Codon-optimized AHSV4-VP5 (SEQ ID NO:05) vs. field isolate AHSV4-VP5 (SEQ ID NO:50)

```
                          1                                                  50
SEQ ID NO:05      (1)    ATGGGCAAGTTTACCAGCTTCCTGAAGAGGGCCGGCAACGCCACCAAGCG
SEQ ID NO:50      (1)    ATGGGAAAGTTCACATCTTTTTTGAAGCGCGCGGGCAATGCGACCAAGAG
                          51                                                 100
SEQ ID NO:05     (51)    GGCCCTGACCAGCGACAGCGCCAAGAAGATGTACAAGCTGGCCGGCAAGA
SEQ ID NO:50     (51)    GGCGCTGACGTCGGATTCAGCAAAGAAGATGTATAAGTTGGCGGGGAAAA
                          101                                                150
SEQ ID NO:05    (101)    CCCTGCAGCGGGTGGTGGAGAGCGAAGTGGGCAGCGCCGCCATCGACGGC
SEQ ID NO:50    (101)    CGTTACAGAGAGTGGTAGAAAGTGAAGTTGGAAGTGCAGCGATCGATGGC
                          151                                                200
SEQ ID NO:05    (151)    GTGATGCAGGGCGCCATCCAGAGCATCATCCAGGGCGAGAACCTGGGCGA
SEQ ID NO:50    (151)    GTGATGCAGGGGCGATACAAAGCATAATACAAGGCGAAAACCTTGGTGA
                          201                                                250
SEQ ID NO:05    (201)    CAGCATCAAGCAGGCCGTGATCCTGAACGTGGCCGGCACCCTGGAAAGCG
SEQ ID NO:50    (201)    TTCAATTAAGCAGGCGGTTATTTTAAATGTTGCGGGGACATTGGAATCGG
                          251                                                300
SEQ ID NO:05    (251)    CCCCTGACCCCCTGAGCCCTGGCGAGCAGCTGCTGTACAACAAGGTGTCC
SEQ ID NO:50    (251)    CGCCAGACCCGTTGAGCCCAGGGGAGCAGCTCCTTTACAATAAGGTTTCT
                          301                                                350
SEQ ID NO:05    (301)    GAGATCGAGAAGATGGAAAAGGAAGATCGGGTGATCGAGACCCACAACGC
SEQ ID NO:50    (301)    GAAATCGAGAAAATGGAAAAAGAGGATCGAGTGATTGAAACACACAATGC
                          351                                                400
SEQ ID NO:05    (351)    CAAGATCGAGGAAAAGTTCGGCAAGGACCTGCTGGCCATCCGGAAGATCG
SEQ ID NO:50    (351)    GAAAATAGAAGAAAAATTTGGTAAAGATTTATTAGCGATTCGAAAGATTG
                          401                                                450
SEQ ID NO:05    (401)    TGAAGGGCGAGGTGGACGCCGAGAAGCTGGAAGGCAACGAGATCAAGTAC
SEQ ID NO:50    (401)    TGAAAGGCGAGGTTGATGCAGAAAAGCTGGAAGGTAACGAAATTAAGTAC
                          451                                                500
SEQ ID NO:05    (451)    GTGGAGAAGGCCCTGAGCGGCCTGCTGGAAATCGGCAAGGATCAGAGCGA
SEQ ID NO:50    (451)    GTAGAAAAGCGCTTAGCGGTTTGCTGGAGATAGGGAAAGATCAGTCAGA
                          501                                                550
SEQ ID NO:05    (501)    GCGGATCACCAAGCTGTACCGGGCCCTGCAGACCGAAGAGGACCTGCGGA
SEQ ID NO:50    (501)    ACGCATTACAAAGCTATATCGCGCGTTACAAACAGAGGAAGATTTGCGGA
                          551                                                600
SEQ ID NO:05    (551)    CCCGGGACGAGACCCGGATGATCAACGAGTACCGGGAGAAGTTCGACGCC
SEQ ID NO:50    (551)    CACGAGATGAGACTAGAATGATAAACGAATATAGAGAAAAATTTGACGCG
                          601                                                650
SEQ ID NO:05    (601)    CTGAAAGAGGCCATCGAGATCGAGCAGCAGGCCACCCACGACGAGGCCAT
SEQ ID NO:50    (601)    TTGAAAGAAGCGATTGAAATCGAGCAGCAAGCGACACATGATGAGGCGAT
                          651                                                700
SEQ ID NO:05    (651)    CCAGGAAATGCTGGACCTGAGCGCCGAGGTGATCGAAACCGCCAGCGAGG
SEQ ID NO:50    (651)    TCAAGAGATGCTCGACTTAAGCGCGGAAGTAATTGAGACTGCGTCGGAGG
                          701                                                750
SEQ ID NO:05    (701)    AAGTGCCCATCTTTGGCGCCGGAGCCGCCAACGTGATCGCCACCACCCGG
SEQ ID NO:50    (701)    AGGTACCAATCTTCGGCGCTGGGGCGGCGAACGTTATCGCCACAACCCGC
                          751                                                800
SEQ ID NO:05    (751)    GCCATTCAGGGCGGCCTGAAGCTGAAGGAAATCGTGGACAAGCTGACAGG
SEQ ID NO:50    (751)    GCAATACAGGGGGGGTTAAAACTAAAGGAAATTGTTGATAAGCTTACGGG
```

FIGURE 40 (2/2)

```
                 801                                                850
SEQ ID NO:05  (801) CATCGACCTGAGCCACCTGAAGGTGGCCGACATCCACCCCCACATCATCG
SEQ ID NO:50  (801) CATAGATTTGAGCCATTTGAAGGTGGCCGACATTCATCCACACATCATTG
                 851                                                900
SEQ ID NO:05  (851) AGAAGGCCATGCTGCGGGACACCGTGACCGACAAGGACCTGGCTATGGCC
SEQ ID NO:50  (851) AAAAGGCAATGCTACGTGATACTGTAACGGACAAAGATTTGGCGATGGCA
                 901                                                950
SEQ ID NO:05  (901) ATCAAGAGCAAGGTGGACGTGATCGACGAGATGAACGTGGAGACCCAGCA
SEQ ID NO:50  (901) ATTAAGTCAAAAGTGGATGTAATTGACGAGATGAACGTAGAAACGCAGCA
                 951                                               1000
SEQ ID NO:05  (951) CGTGATCGATGCCGTGCTGCCCATCGTGAAGCAGGAATACGAGCGGCACG
SEQ ID NO:50  (951) CGTAATCGATGCCGTTCTACCGATAGTTAAACAAGAATATGAGAGACATG
                1001                                               1050
SEQ ID NO:05 (1001) ACAACAAGTACCACGTGAGAATCCCTGGCGCCCTGAAGATCCACAGCGAG
SEQ ID NO:50 (1001) ATAACAAATATCATGTTAGGATCCCAGGTGCATTGAAGATACATTCAGAG
                1051                                               1100
SEQ ID NO:05 (1051) CACACCCCCAAGATCCACATCTACACCACCCCCTGGGACAGCGACTCCGT
SEQ ID NO:50 (1051) CACACGCCTAAGATACATATATATACGACCCCATGGGATTCGGATAGCGT
                1101                                               1150
SEQ ID NO:05 (1101) GTTCATGTGCCGGGCCATCGCCCCCCACCATCAGCAGCGGAGCTTCTTCA
SEQ ID NO:50 (1101) CTTCATGTGTAGAGCCATTGCACCGCATCATCAACAACGAAGCTTTTTCA
                1151                                               1200
SEQ ID NO:05 (1151) TCGGCTTCGACCTGGAAATCGAGTACGTGCACTTCGAGGACACCAGCGTG
SEQ ID NO:50 (1151) TTGGATTTGATCTAGAAATTGAATATGTCCATTTTGAAGATACTTCAGTT
                1201                                               1250
SEQ ID NO:05 (1201) GAGGGCCACATCCTGCACGGCGGAGCCATCACCGTGGAGGGCAGGGGCTT
SEQ ID NO:50 (1201) GAGGGACATATATTACATGGAGGGGCAATAACCGTTGAGGGTAGAGGATT
                1251                                               1300
SEQ ID NO:05 (1251) CCGGCAGGCCTACACCGAGTTCATGAACGCCGCCTGGGGCATGCCTACCA
SEQ ID NO:50 (1251) TCGACAGGCGTATACTGAGTTCATGAATGCAGCGTGGGGGATGCCAACAA
                1301                                               1350
SEQ ID NO:05 (1301) CCCCCGAGCTGCACAAGCGGAAGCTGCAGCGGAGCATGGGCACCCACCCC
SEQ ID NO:50 (1301) CCCCAGAGCTCCATAAACGTAAGCTACAAAGGAGTATGGGAACTCATCCG
                1351                                               1400
SEQ ID NO:05 (1351) ATCTACATGGGCAGCATGGACTACGCCATCAGCTACGAGCAGCTGGTGTC
SEQ ID NO:50 (1351) ATCTATATGGGATCGATGGATTACGCTATAAGCTACGAACAGCTGGTTTC
                1401                                               1450
SEQ ID NO:05 (1401) CAATGCCATGCGGCTGGTGTACGACAGCGAGCTGCAGATGCACTGCCTGA
SEQ ID NO:50 (1401) TAACGCGATGAGATTAGTTTATGATTCCGAGTTACAAATGCATTGTCTCC
                1451                                               1500
SEQ ID NO:05 (1451) GAGGCCCCCTGAAGTTCCAGCGGCGGACCCTGATGAACGCCCTGCTGTAC
SEQ ID NO:50 (1451) GTGGGCCTCTAAAATTTCAACGCCGCACGCTAATGAACGCGCTTCTATAT
                1501     1515
SEQ ID NO:05 (1501) GGCGTGAAGATCGCC
SEQ ID NO:50 (1501) GGTGTGAAAATAGCT
```

Percent Identity for above-aligned sequences = 73%

VACCINE AGAINST AFRICAN HORSE SICKNESS VIRUS

INCORPORATION BY REFERENCE

This application claims benefit of the U.S. provisional application Ser. No. 61/108,075 filed on Oct. 24, 2008, and of U.S. provisional application Ser. No. 61/163,517 filed on Mar. 26, 2009.

The foregoing applications, and all documents cited therein or during their prosecution ("appln cited documents") and all documents cited or references in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to vaccination of a subject against African Horse Sickness Virus (AHSV). In particular, the invention pertains to the construction and use of recombinant vectors containing and expressing, in a host, one or more immunogenic proteins of African Horse Sickness Virus. The invention further relates to immunological compositions or vaccines which induce an immune response directed to African Horse Sickness Virus. The invention further relates to such compositions or vaccines which confer protective immunity against infection by African Horse Sickness Virus.

Several publications are referenced in this application. Full citation to these documents is found at the end of the specification preceding the claims, and/or where the document is cited. These documents pertain to the field of this invention; and, each of the documents cited or referenced in this application ("herein cited documents"), and each document cited or referenced in herein cited documents, are hereby incorporated herein by reference.

BACKGROUND OF THE INVENTION

African Horse Sickness (AHS) is a serious, often fatal, arthropod-borne viral disease of horses and mules (African Horse Sickness, The Merck Veterinary Manual). The mortality rate can be as high as 95% in some forms of this disease. Asymptomatic or mild infections can occur in horses, as well as zebras and donkeys, especially horses that were previously infected with a different serotype of the virus. Infected animals or vectors may carry the virus into AHS-free regions. Some authors speculate that climate change could increase the risk for spread of arthropod-borne diseases such as African Horse Sickness, as recently has occurred with related bluetongue virus (Wilson A et al., Parasitol. Res. 2008; 103: 69-77). *Culicoides imicola*, the principal vector for this disease, has made incursions into North Africa and southern Europe. Potential arthropod vectors also exist throughout virtually all regions of the world, including much of the United States and the rest of the Americas.

African Horse Sickness results from infection with the African Horse Sickness Virus, a member of the genus Orbivirus in the family Reoviridae. To date, 9 serotypes of African Horse Sickness Virus are known. African Horse Sickness Virus serotype 9 is widespread in endemic regions, while serotypes 1 to 8 are found primarily in limited geographic areas. Serotype 9 has been responsible for the majority of African Horse Sickness outbreaks outside Africa. Serotype 4 caused one outbreak in Spain and Portugal between 1987 and 1990 (Lubroth J., Equine Pract. 1988; 10:26-33).

Initial research on African Horse Sickness Virus resulted in the development of mouse-brain attenuated modified live virus vaccine to African Horse Sickness Virus in the 1930's. These vaccines were refined and resulted in the development of a tissue culture attenuated modified live virus (MLV) vaccine in the 1960's.

Despite the efficacy of this vaccine, it has some inherent limitations including vaccine reactions (including death) in individual animals, varied immune response in individual animals, difficulty in immunizing young animals with passive maternal immunity, possibility of reversion to virulence of vaccine virus, and recombination of vaccine strains following vaccination with possible reversion to virulence (du Plessis M. et al. 1998, Onderstepoort Journal of Veterinary Research 65: 321-329). There are also socio-economic implications with using the MLV vaccine. South Africa has a protocol that allows it to export horses to the European Union and a number of other countries. This protocol also makes it possible for horses from other countries to enter South Africa to compete in various events or stand at stud for a temporary period. The protocol is based on ensuring that horses are adequately vaccinated against African Horse Sickness Virus. Veterinary Authorities are aware of the possible dangers of using the MLV vaccine. Most of these problems would be greatly reduced by the development of alternate African Horse Sickness Virus vaccines.

The African Horse Sickness Virus genome is composed of ten double-stranded RNA segments (Oellermann, R. A. et al., 1970; Bremer, C. W. et al., 1976), which encode at least ten viral proteins. The genome segments are numbered 1-10 in order of their migration in PAGE. Seven of the viral proteins are structural and form the double-shelled virus particle. The outer capsid is composed of two major viral proteins, VP2 and VP5, which determine the antigenic variability of the African Horse Sickness Viruses, while the inner capsid is comprised of two major (VP3 and VP7) and three minor (VP1, VP4 and VP6) viral proteins (Lewis S A and Grubman M J, 1991); Martinez-Torrecuadrada J L et al., 1994); Bremer, C W, et al. 1990; Grubman, M. J. & Lewis, S. A., 1992). VP3 and VP7 are highly conserved among the nine serotypes (Oellermann et al., 1970; Bremer et al., 1990). At least three non-structural proteins, NS1, NS2 and NS3, have been identified (Huismans, H. & Els, H. J., 1979); van Staden, V. & Huismans, H., 1991); Mizukoshi, N. et al., 1992).

Recombinant canarypox viruses derived from attenuated viruses have been developed as vectors for the expression of heterologous viral genes. A number of these canarypox constructs have since been licensed as vaccines in many countries, including South Africa, the European Union and the United States of America for use in horses (Minke J M, et al., 2004a and b; Minke J M, et al., 2007; Siger L, et al. 2006) and other species (Poulet H, et al., 2003).

The fact that these vaccines only contain genes of the organism of interest makes them inherently safe (Minke J M, et al., 2004b). Furthermore, the onset of detectable neutralizing antibody is rapid even after a single dose of vaccine (Minke J M et al., 2004b). The inherent safety of such vaccines and the nature of the development of neutralizing antibody make such vaccines particularly attractive for use in epizootics (Minke J M et al., 2004a).

Previous studies have shown that horses develop neutralizing antibodies to AHS when they are inoculated with exogenously expressed VP2 and an appropriate adjuvant (Scanlen M, et al., 2002). Studies in sheep have shown that the neutralizing antibody response to Bluetongue Virus is enhanced by inoculation of sheep with virus-like particles in which VP2 and VP5 are co-expressed (Pearson L D, Roy P, 1993). A recombinant canarypox virus vaccine co-expressing the genes encoding for VP2 and VP5 outer capsid proteins of Bluetongue Virus has recently been shown to induce high levels of protection in sheep (Boone J D, et al., 2007).

It has not been shown that horses develop neutralizing antibodies to African Horse Sickness Virus when inoculated with a vector containing and co-expressing AHSV VP2 and VP5. It can thus be appreciated that the present invention fulfills a need in the art by providing a recombinant poxvirus including compositions and products therefrom, particularly ALVAC-based recombinants and compositions and products therefrom, especially such recombinants expressing AHSV VPs 2 and 5 or any combination thereof and compositions and products therefrom.

Citation or identification of any document in this application does not constitute an admission that such document is available as prior art to the present invention.

SUMMARY OF THE INVENTION

An object of this invention can be any one or all of providing recombinant vectors or viruses as well as methods for making such recombinant vectors or viruses, and providing compositions and/or vaccines as well as methods for treatment and prophylaxis of infection by African Horse Sickness Virus.

The invention provides a recombinant vector, such as a recombinant virus, e.g., a recombinant poxvirus, that comprises and expresses at least one exogenous nucleic acid molecule, wherein the at least one exogenous nucleic acid molecule may comprise a nucleic acid molecule encoding an immunogen or epitope of interest from an African Horse Sickness Virus especially a viral protein or portion thereof of an African Horse Sickness Virus.

The present invention further provides recombinant vectors wherein the African Horse Sickness Virus strain is 1, 2, 4, or 9.

The invention further provides immunological (or immunogenic), or vaccine compositions comprising such a virus or the expression product(s) of such a virus.

The invention further provides methods for inducing an immunological (or immunogenic) or protective response against African Horse Sickness Virus, as well as methods for preventing or treating African Horse Sickness Virus or disease state(s) caused by African Horse Sickness Virus, comprising administering the virus or an expression product of the virus, or a composition comprising the virus, or a composition comprising an expression product of the virus.

The invention also comprehends expression products from the virus as well as antibodies generated from the expression products or the expression thereof in vivo and uses for such products and antibodies, e.g., in diagnostic applications.

The invention further provides AHSV VP2 and VP5 polypeptides and polynucleotides encoding AHSV VP2 and VP5 polypeptides. The invention also provides a new AHS strain AHSV4-Jane.

These and other embodiments are described in, or are obvious from and encompassed by, the following Detailed Description.

BRIEF DESCRIPTION OF THE DRAWINGS

The following detailed description, given by way of example but not intended to limit the invention solely to the specific embodiments described, may best be understood in conjunction with the accompanying drawings, in which:

FIG. 1 provides the construction scheme for pLHD3460.4, the C3 donor plasmid for generation of an ALVAC recombinant expressing synthetic AHSV-4-VP2 (SEQ ID NO:1) and synthetic AHSV-4-VP5 (SEQ ID NO:2) proteins.

FIG. 10 shows the construction scheme for pCXL2415.1 (SEQ ID NO:22), the C3 donor plasmid for generation of an ALVAC recombinant expressing AHSV9-VP2 (SEQ ID NO:20) and AHSV9-VP5 (SEQ ID NO:21) proteins.

FIG. 12 provides the in vitro recombination scheme for vCP2383 (ALVAC C3 H6-synthetic AHSV9 VP2/42K-synthetic AHSV9 VP5).

FIG. 19 provides the immunofluorescence results of anti-VP2 and anti-VP5 IFI from infected CEF cells.

FIG. 21 gives the results of the serum-virus neutralization test against AHSV-4 for 6 horses that were vaccinated using cpAHSV-4 (vCP2377). Results are shown for days 0, 28, and 42.

FIG. 27 provides the Southern blot analysis of vCP2398 using an AHSV5 VP2 specific probe.

Figure 2:
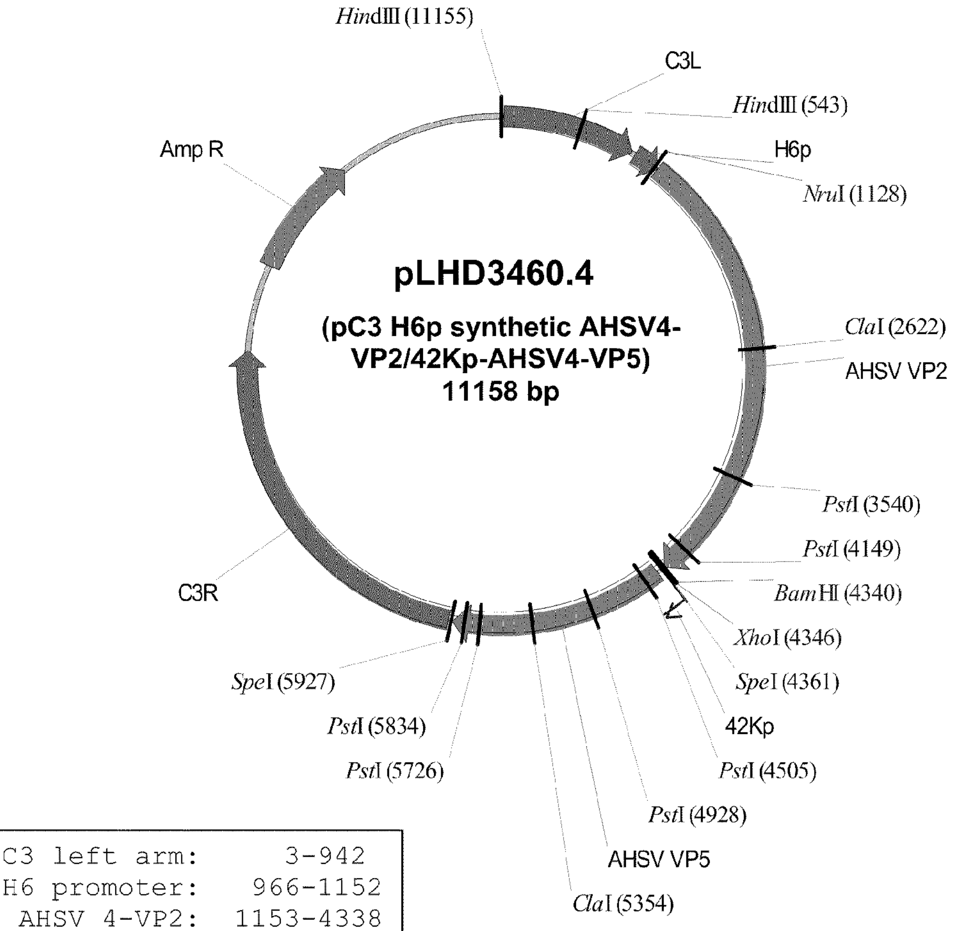
FIG. 2 provides the map and relevant SEQ ID NOs for pLHD3460.4 (pC3 H6p synthetic AHSV-4-VP2/42Kp synthetic AHSV-4-VP5). pLHD3460.4=SEQ ID NO:6; AHSV-4 VP2 DNA (pLHD3460.4)—SEQ ID NO:4; AHSV-4 VP5 DNA (pLHD3460.4)—SEQ ID NO:5; predicted AA Seq. for AHSV-4 VP2 PRT (pLHD3460.4)—SEQ ID NO:1; predicted AA Seq. for AHSV-4 VP5 PRT (pLHD3460.4)=SEQ ID NO:2.

Panel A: Cycle threshold of qRT-PCR's for genes that encode AHSV NS2 and VP7 proteins (average of NS2 and VP7 profile shown). The presence of AHSV in the blood of the horse was determined by qRT-PCR assays that detect the individual genes encoding the VP7 and NS2 proteins of AHSV with samples being classified as positive if the fluorescence exceeded the threshold of 0.1 within a maximum of 40 cycles.

Panel B: Body temperature, IDEM

Panel C: Platelet count of 8 vaccinated with vCP2377 and an unvaccinated control horse after challenge with a virulent field strain of AHSV serotype 4.IDEM FIG. 32 provides a chart that summarizes the SEQ ID NOs present in the sequence listing.

FIG. 33 provides a ClustalW alignment of AHSV-4/5/9 VP2 proteins (SEQ ID NOs:1, 44, 30).

FIG. 34 provides a ClustalW alignment of AHSV-4/5/9 VP5 proteins (SEQ ID NOs:2, 45, 31).

FIG. 35 provides a ClustalW alignment of synthetic AHSV-4-VP2 protein (SEQ ID NO:1) vs. the field isolate AHSV4 Jane Strain (SEQ ID NO:49). Percent identity is also indicated.

FIG. 36 provides a ClustalW alignment of synthetic AHSV-4-VP5 protein (SEQ ID NO:2) vs. the field isolate AHSV4 Jane Strain (SEQ ID NO:51). Percent identity is also indicated.

FIG. 37 provides a ClustalW alignment of synthetic AHSV-4-VP2 protein (SEQ ID NO:1) vs. multiple deposited AHSV-4-VP2 proteins (SEQ ID NOs:59-63). Percent identity table is provided.

FIG. 38 provides a ClustalW alignment of synthetic AHSV-4-VP5 protein (SEQ ID NO:2) vs. multiple deposited AHSV-4-VP5 proteins (SEQ ID NOs:52-58). Percent identity table is provided.

FIG. 39 provides a ClustalW alignment of codon-optimized AHSV4-VP2 (SEQ ID NO:04) vs. field isolate AHSV4-VP2 (SEQ ID NO:48). Percent identity is provided.

FIG. 40 provides a ClustalW alignment of codon-optimized AHSV4-VP5 (SEQ ID NO:05) vs. field isolate AHSV4-VP5 (SEQ ID NO:50). Percent identity is provided.

DETAILED DESCRIPTION

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The target species or subject (host) includes animal and human. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

The terms "polypeptide" and "protein" are used interchangeably herein to refer to a polymer of consecutive amino acid residues.

The term "nucleic acid", "nucleotide", and "polynucleotide" refers to RNA or DNA and derivatives thereof, such as those containing modified backbones. It should be appreciated that the invention provides polynucleotides comprising sequences complementary to those described herein. Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term “immunogenic polypeptide” or “immunogenic fragment” as used herein refers to a polypeptide or a fragment of a polypeptide which comprises an allele-specific motif, an epitope or other sequence such that the polypeptide or the fragment will bind an MHC molecule and induce a cytotoxic T lymphocyte (“CTL”) response, and/or a B cell response (for example, antibody production), and/or T-helper lymphocyte response, and/or a delayed type hypersensitivity (DTH) response against the antigen from which the immunogenic polypeptide or the immunogenic fragment is derived. A DTH response is an immune reaction in which T cell-dependent macrophage activation and inflammation cause tissue injury. A DTH reaction to the subcutaneous injection of antigen is often used as an assay for cell-mediated immunity.

By definition, an epitope is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. Specific, non-limiting examples of an epitope include a tetra- to penta-peptide sequence in a polypeptide, a tri- to penta-glycoside sequence in a polysaccharide. In the animal most antigens will present several or even many antigenic determinants simultaneously. Such a polypeptide may also be qualified as an immunogenic polypeptide and the epitope may be identified as described further.

The term “purified” as used herein does not require absolute purity; rather, it is intended as a relative term. Thus, for example, a purified polypeptide preparation is one in which the polypeptide is more enriched than the polypeptide is in its natural environment. A polypeptide preparation is substantially purified such that the polypeptide represents several embodiments at least 60%, at least 70%, at least 80%, at least 90%, at least 95%, or at least 98%, of the total polypeptide content of the preparation. The same applies to polynucleotides. The polypeptides disclosed herein can be purified by any of the means known in the art.

A recombinant polynucleotide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In one embodiment, a recombinant polynucleotide encodes a fusion protein.

In one aspect, the present invention provides polypeptides from the African Horse Sickness Virus. In another aspect, the present invention provides a polypeptide having a sequence as set forth in SEQ ID NO: 1, 2, 20, 21, 30, 31, 35, 36, 44, 45, 49, 51, 52, 53, 54, 55, 56, 57, 58, 59, 60, 61, 62, or 63, and variant or fragment thereof.

As used herein, the term “African Horse Sickness Virus protein or African Horse Sickness Virus polypeptide (AHSV VP)” may include AHSV VP1, VP2, VP3, VP4, NS1, VP5, VP6, VP7, NS2, NS3, and their homologs, fragments and variants.

Homologs of viral proteins from African Horse Sickness virus are intended to be within the scope of the present invention. As used herein, the term “homologs” includes orthologs, analogs and paralogs. The term “analogs” refers to two polynucleotides or polypeptides that have the same or similar function, but that have evolved separately in unrelated organisms. The term “orthologs” refers to two polynucleotides or polypeptides from different species, but that have evolved from a common ancestral gene by speciation. Normally, orthologs encode polypeptides having the same or similar functions. The term “paralogs” refers to two polynucleotides or polypeptides that are related by duplication within a genome. Paralogs usually have different functions, but these functions may be related. Analogs, orthologs, and paralogs of a wild-type African Horse Sickness virus polypeptide can differ from the wild-type African Horse Sickness virus polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type African Horse Sickness virus polypeptide or polynucleotide sequences, and will exhibit a similar function.

In another aspect, the present invention provides an AHSV VP having at least 70%, at least 75%, at least 80%, at least 85%, at least 90%, at least 95%, 96%, 97%, 98% or 99% sequence identity to a polypeptide having a sequence as set forth in SEQ ID NO: 1, 2, 20, 21, 30, 31, 35, 36, 44, 45, 49, 51, 52, 53, 54, 55, 56, 57, 58, 59, 60, 61, 62, or 63.

In yet another aspect, the present invention provides fragments and variants of the AHSV VPs identified above (SEQ ID NO: 1, 2, 20, 21, 30, 31, 35, 36, 44, 45, 49, 51, 52, 53, 54, 55, 56, 57, 58, 59, 60, 61, 62, or 63) which may readily be prepared by one of skill in the art using well-known molecular biology techniques.

Variants are homologous AHSV VPs having an amino acid sequence at least 75%, 80%, 85%, 90%, 95%, 96%, 97%, 98%, or 99% identity to the amino acid sequence as set forth in SEQ ID NO: 1, 2, 20, 21, 30, 31, 35, 36, 44, 45, 49, 50, 51, 52, 53, 54, 55, 56, 57, 58, 59, 60, 61, 62, or 63.

Variants include allelic variants. The term “allelic variant” refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene if interest, are intended to be within the scope of the invention.

A variant is any polypeptide from African Horse Sickness virus, capable of inducing in animals, such as equines, vaccinated with this polypeptide a specific cell-based immune response characterized by secretion of interferon gamma (IFN-gamma) upon stimulation by African Horse Sickness virus. Such IFN-gamma secretion may be demonstrated using in vitro methodology (i.e. QUANTIKINE® immunoassay from R&D Systems Inc. (catalog number# CAIF00); Djoba Siawaya J F et al.).

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the African Horse Sickness virus polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

An immunogenic fragment of an African Horse Sickness virus polypeptide includes at least 8, 10, 15, or 20 consecutive amino acids, at least 21 amino acids, at least 23 amino acids, at least 25 amino acids, or at least 30 amino acids of an African Horse Sickness virus polypeptide having a sequence as set forth in SEQ ID NO: 1, 2, 20, 21, 30, 31, 35, 36, 44, 45, 49, 51, 52, 53, 54, 55, 56, 57, 58, 59, 60, 61, 62, 63, or variants thereof. In another embodiment, a fragment of an African Horse Sickness virus includes a specific antigenic epitope found on a full-length African Horse Sickness virus polypeptide.

Procedures to determine fragments of polypeptide and epitope such as, generating overlapping peptide libraries (Hemmer B. et al.), Pepscan (Geysen H. M. et al., 1984; Geysen H. M. et al., 1985; Van der Zee R. et al.; Geysen H. M.) and algorithms (De Groot A. et al.; Hoop T. et al.; Parker K. et al.), can be used in the practice of the invention, without undue experimentation. Generally, antibodies specifically bind a particular antigenic epitope. Specific, non-limiting examples of epitopes include a tetra- to penta-peptide sequence in a polypeptide, a tri- to penta-glycoside sequence in a polysaccharide. In animals most antigens will present several or even many antigenic determinants simultaneously. Preferably wherein the epitope is a protein fragment of a larger molecule it will have substantially the same immunological activity as the total protein.

In another aspect, the present invention provides a polynucleotide encoding an AHSV VP, such as a polynucleotide encoding an AHSV VP having a sequence as set forth in SEQ ID NO: 1, 2, 20, 21, 30, 31, 35, 36, 44, 45, 49, 51, 52, 53, 54, 55, 56, 57, 58, 59, 60, 61, 62, 63. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 2, 20, 21, 30, 31, 35, 36, 44, 45, 49, 51, 52, 53, 54, 55, 56, 57, 58, 59, 60, 61, 62, 63, or a conservative variant, an allelic variant, a homolog or an immunogenic fragment comprising at least eight or at east ten consecutive amino acids of one of these polypeptides, or a combination of these polypeptides.

In another aspect, the present invention provides a polynucleotide having a nucleotide sequence as set forth in SEQ ID NO: 3, 4, 5, 6, 17, 18, 19, 22, 27, 28, 29, 32, 33, 34, 41, 42, 43, 48, 50, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 3, 4, 5, 6, 17, 18, 19, 22, 27, 28, 29, 32, 33, 34, 41, 42, 43, 48, 50, or a variant thereof.

These polynucleotides may include DNA, cDNA, and RNA sequences that encode an AHSV VP. It is understood that all polynucleotides encoding an African Horse Sickness virus polypeptide are also included herein, as long as they encode a polypeptide with the recognized activity, such as the binding to an antibody that recognizes the polypeptide, the induction of an immune response to the polypeptide, or an effect on survival of African Horse Sickness when administered to a subject exposed to African Horse Sickness virus or who undergoes a decrease in a sign or a symptom of African Horse Sickness.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for African Horse Sickness polypeptides, the DNA sequence of the African Horse Sickness virus protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of African Horse Sickness protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the African Horse Sickness virus polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

Sequence identity between two nucleotide sequences also may be determined using the "Align" program of Myers and Miller, ("Optimal Alignments in Linear Space", CABIOS 4, 11-17, 1988) and available at NCBI, as well as the same or other programs available via the Internet at sites thereon such as the NCBI site.

Alternatively or additionally, the term "identity", for instance, with respect to a nucleotide or amino acid sequence, may indicate a quantitative measure of homology between two sequences. The percent sequence homology may be calculated as: $(N_{ref}-N_{dif})*100/N_{ref}$ wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences, can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

The African Horse Sickness virus polynucleotides may include a recombinant DNA which is incorporated into a vector, into an autonomously replicating plasmid or virus, or into the genomic DNA of a prokaryote or eukaryote, or which exists as a separate molecule (for example, a cDNA) independent of other sequences.

Recombinant vectors disclosed herein may include a polynucleotide encoding a polypeptide, a variant thereof or a fragment thereof. Recombinant vectors may include plasmids and viral vectors and may be used for in vitro or in vivo expression. Recombinant vectors may include further a signal peptide. Signal peptides are short peptide chain (3-60 amino acids long) that direct the post-translational transport of a protein (which are synthesized in the cytosol) to certain organelles such as the nucleus, mitochondrial matrix, endoplasmic reticulum, chloroplast, apoplast and peroxisome. The signal sequence may be the natural sequence from the African Horse Sickness virus protein or a peptide signal from a secreted protein e.g. the signal peptide from the tissue plasminogen activator protein (tPA), in particular the human tPA (S. Friezner Degen et al.; R. Rickles et al.; D. Berg. et al.), or the signal peptide from the Insulin-like growth factor 1 (IGF1), in particular the equine IGF1 (K. Otte et al.), the canine IGF1 (P. Delafontaine et al.), the feline IGF1 (WO03/022886), the bovine IGF1 (S. Lien et al.), the porcine IGF1 (M. Muller et al.), the chicken IGF1 (Y. Kajimoto et al.), the turkey IGF1 (GenBank accession number AF074980). The signal peptide from IGF1 may be natural or optimized which may be achieved by removing cryptic splice sites and/or by adapting the codon usage. Upon translation, the unprocessed polypeptide may be cleaved at a cleavage site to lead to the mature polypeptide. The cleavage site may be predicted using the method of Von Heijne (1986).

A plasmid may include a DNA transcription unit, for instance a nucleic acid sequence that permits it to replicate in a host cell, such as an origin of replication (prokaryotic or eukaryotic). A plasmid may also include one or more selectable marker genes and other genetic elements known in the art. Circular and linear forms of plasmids are encompassed in the present disclosure.

In a further aspect, the present invention relates to a vaccine composition or a pharmaceutical composition for inducing an immunological or protective response in a host animal inoculated with the composition. The composition includes a carrier or diluent or excipient and/or adjuvant, and a recombinant vector, such as a recombinant virus. The recombinant virus can be a modified recombinant virus; for instance, a recombinant of a virus that has inactivated therein (e.g., disrupted or deleted) virus-encoded genetic functions. A modified recombinant virus can have inactivated therein virus-encoded non-essential genetic functions; for instance, so that the recombinant virus has attenuated virulence and enhanced safety. The virus used in the composition according to the present invention is advantageously a poxvirus, such as a vaccinia virus or raccoonpox virus or preferably an avipox virus, e.g., a fowlpox virus or more preferably a canarypox virus; and more advantageously, an ALVAC virus. It is advantageous that the recombinant vector or recombinant virus have expression without replication in mammalian species. In another aspect, the present invention relates to recombinant vectors comprising at least one nucleic acid molecule encoding one or more African Horse Sickness Virus (AHSV) antigen(s). It further relates to vaccines or immunogenic compositions comprising an effective amount to elicit a protective immune response in a subject of a recombinant avipox vector comprising at least one nucleic acid molecule encoding one or more African Horse Sickness Virus (AHSV) antigen(s). It further relates to corresponding methods of vaccinating a subject against African Horse Sickness Virus.

The pharmaceutically acceptable vehicles or excipients of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides, plasmids, viral vectors herein disclosed. In general, the nature of the vehicle or excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, freeze-dried pastille, powder, pill, tablet, or capsule forms), conventional non-toxic solid vehicles or excipients can include, for example, pharmaceutical grades of mannitol, lactose, starch, or magnesium stearate. In addition to biologically neutral vehicles or excipients, immunogenic compositions to be administered can contain minor amounts of non-toxic auxiliary substances, such as wetting or emulsifying agents, preservatives, and pH buffering agents and the like, for example sodium acetate or sorbitan monolaurate.

The compositions or vaccines according to the instant invention may include vectors comprising one or more polynucleotide(s) encoding one or more AHSV VP(s) according to the present invention as described above.

Multiple insertions may be done in the same vector using different insertion sites or using the same insertion site. When the same insertion site is used, each polynucleotide insert, which may be any polynucleotide of the present invention aforementioned, may be inserted under the control of the same and/or different promoters. The insertion can be done tail-to-tail, head-to-head, tail-to-head, or head-to-tail. IRES elements (Internal Ribosome Entry Site, see EP 0803573) can also be used to separate and to express multiple inserts operably linked to the same and/or different promoters.

In one embodiment, the present invention relates to an expression vector comprising one or more polynucleotide(s) aforementioned. The expression vector may be an in vivo expression vector, or an in vitro expression vector.

In one embodiment, the recombinant vector or virus may include one or more heterologous nucleic acid molecule(s) that encodes one or more African Horse Sickness Virus (AHSV) antigen(s), immunogens, including epitopes or fragments thereof. The recombinant vector or modified recombinant virus may include, e.g., within the virus genome, such as within a non-essential region of the virus genome, a heterologous DNA sequence that encodes an immunogenic protein, e.g., derived from African Horse Sickness Virus viral protein(s), e.g., AHSV VP1, VP2, VP3, VP4, NS1, VP5, VP6, VP7, NS2, NS3 or any combination thereof, preferably AHSV VPs 2 and 5, (wherein the immunogenic protein can be an epitope of interest, e.g., an epitope of interest from a protein expressed by any one or more of AHSV VP1, VP2, VP3, VP4, NS1, VP5, VP6, VP7, NS2, NS3, e.g., an epitope of interest from AHSV VPs 2 and/or 5). The vector or virus is advantageously a poxvirus, such as a vaccinia virus or preferably an avipox virus, e.g., a fowlpox virus or more preferably a canarypox virus; and more advantageously, an ALVAC virus.

In another embodiment, the heterologous nucleic acid molecule that encodes one or more African Horse Sickness Virus (AHSV) antigen(s), immunogens, including epitopes or fragments thereof, e.g., derived from African Horse Sickness Virus viral protein(s), e.g., AHSV VP1, VP2, VP3, VP4, NS1, VP5, VP6, VP7, NS2, NS3 or any combination thereof, preferably AHSV VPs 2 and 5, (wherein the immunogenic protein can be an epitope of interest, e.g., an epitope of interest from a protein expressed by any one or more of AHSV VP1, VP2, VP3, VP4, NS1, VP5, VP6, VP7, NS2, or NS3, e.g., an epitope of interest from AHSV VPs 2 and/or 5) is operably linked to a promoter sequence and optionally to an enhancer. In an advantageous embodiment, the promoter sequence is selected from the group consisting of H6 vaccinia promoter, I3L vaccinia promoter, 42K poxyiral promoter, 7.5K vaccinia promoter, and Pi vaccinia promoter. More advantageously, the promoter sequence is the H6 vaccinia promoter or the 42K poxyiral promoter. More preferably, VP2 is operably linked to the H6 vaccinia promoter and VP5 is operably linked to the 42K poxyiral promoter.

In another embodiment, the heterologous nucleic acid molecule that encodes one or more African Horse Sickness Virus (AHSV) antigen(s), immunogens, including epitopes or fragments thereof, e.g., derived from African Horse Sickness Virus viral protein(s), e.g., AHSV VP1, VP2, VP3, VP4, NS1, VP5, VP6, VP7, NS2, NS3, or any combination thereof, preferably AHSV VPs 2 and 5, (wherein the immunogenic protein can be an epitope of interest, e.g., an epitope of interest from a protein expressed by any one or more of AHSV VP1, VP2, VP3, VP4, NS1, VP5, VP6, VP7, NS2, or NS3, e.g., an epitope of interest from AHSV VPs 2 and/or 5) is inserted into a vector comprising an insertion loci where in said loci comprise C5 and/or C6 and/or C3, and wherein the flanking sequences of the C6, C5 and/or C3 insertion loci promote homologous recombination of the African Horse Sickness Virus antigens with the cognate insertion locus.

In another embodiment, the heterologous nucleic acid molecule that encodes one or more African Horse Sickness Virus (AHSV) antigen(s), immunogens, including epitopes or fragments thereof, e.g., derived from African Horse Sickness Virus viral protein(s), e.g., AHSV VP1, VP2, VP3, VP4, NS1, VP5, VP6, VP7, NS2, NS3, or any combination thereof, preferably AHSV VPs 2 and 5, (wherein the immunogenic protein can be an epitope of interest, e.g., an epitope of interest from a protein expressed by any one or more of AHSV VP1, VP2, VP3, VP4, NS1, VP5, VP6, VP7, NS2, or NS3, e.g., an epitope of interest from AHSV VPs 2 and/or 5) is inserted into a vector comprising an insertion loci where in said loci comprise C5 and/or C6 and/or C3, and wherein the flanking sequences of the C6, C5 and/or C3 insertion loci promote homologous recombination of the African Horse Sickness Virus antigens with the cognate insertion locus further wherein the flanking sequences comprise C3L and C3R open reading frames of avipox.

In another embodiment, the avipox vector is vCP2377 or vCP2383 or vCP2398.

The practice of the present invention will employ, unless otherwise indicated, conventional techniques of molecular biology, microbiology, bacteriology, recombinant DNA technology, and immunology, which are within the skill of the art. Such techniques are explained fully in the literature. See, e.g., Sambrook, et al. (1989); 1985); (M. J. Gait ed. 1984); (B. D. Hames & S. J. Higgins eds. 1984); (R. K. Freshney ed. 1986); (IRL press, 1986); Perbal, B., (1984); t (D. M. Weir and C. C. Blackwell eds., 1986.

In one aspect, the present invention provides a recombinant vector, e.g., virus such as a recombinant poxvirus containing therein a DNA sequence from African Horse Sickness Virus, e.g., in the virus (such as poxvirus) genome, advantageously a non-essential region of the virus, e.g., poxvirus genome. The poxvirus can be a vaccinia virus such as a NYVAC or NYVAC-based virus; and, the poxvirus is advantageously an avipox virus, such as fowlpox virus, especially an attenuated fowlpox virus, e.g., TROVAC, or a canarypox virus, preferably an attenuated canarypox virus, such as ALVAC. However, the vector in the invention may be any suitable recombinant virus or viral vector, such as a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, etc. (as in documents incorporated herein by reference); or the vector may be a plasmid.

The recombinant virus can be a modified recombinant virus; for instance, a recombinant of a virus that has inactivated therein (e.g., disrupted or deleted) virus-encoded genetic functions. A modified recombinant virus can have inactivated therein virus-encoded nonessential genetic functions; for instance, so that the recombinant virus has attenuated virulence and enhanced safety. The virus used in the composition according to the present invention is advantageously a poxvirus, such as a vaccinia virus or preferably an avipox virus, e.g., a fowlpox virus or more preferably a canarypox virus; and more advantageously, an ALVAC virus. It is advantageous that the recombinant vector or recombinant virus have expression without replication in mammalian species.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

Recombinant poxviruses can be constructed in two steps known in the art and analogous to the methods for creating synthetic recombinants of poxviruses such as the vaccinia virus and avipox virus described in U.S. Pat. Nos. 4,769,330; 4,722,848; 4,603,112; 5,110,587; 5,174,993; 5,494,807; 5,942,235, and 5,505,941, the disclosures of which are incorporated herein by reference. Alternatively, methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 6,130,066, 5,494,807, 5,514,375, 5,744,140, 5,744,141, 5,756,103, 5,762,938, 5,766,599, 5,990,091, 6,004,777, 6,130,066, 6,497,883, 6,464,984, 6,451,770, 6,391,314, 6,387,376, 6,376,473, 6,368,603, 6,348,196, 6,306,400, 6,228,846, 6,221,362, 6,217,883, 6,207,166, 6,207,165, 6,159,477, 6,153,199, 6,090,393, 6,074,649, 6,045,803, 6,033,670, 6,485,729, 6,103,526, 6,224,882, 6,312,682, 6,312,683, 6,348,450, 4,603,112; 4,769,330; 5,174,993; 5,505,941; 5,338,683; 5,494,807; 4,394,448; 4,722,848; 4,745,051; 4,769,331; 5,591,639; 5,589,466; 4,945,050; 5,677,178; 5,591,439; 5,552,143; 5,580,859; WO 94/16716; WO 96/39491; WO91/11525; WO 98/33510; WO 90/01543; EP 0 370 573; EP 265785; (Paoletti 1996); (Moss 1996); Richardson (Ed) (1995); (Smith, Summers et al. 1983); (Pennock, Shoemaker et al. 1984); (Roizman 1996); (Andreansky, He et al. 1996); (Robertson, Ooka et al. 1996); (Frolov, Hoffman et al. 1996); (Kitson, Burke et al. 1991); (Ballay, Levrero et al. 1985); (Graham 1990); (Prevec, Schneider et al. 1989); (Feigner, Kumar et al. 1994); (Ulmer, Donnelly et al. 1993); (McClements, Armstrong et al. 1996); (Ju, Edelstein et al. 1998); and (Robinson and Tones 1997).

Elements for the expression of the polynucleotide or polynucleotides are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a protein fragment, e.g., advantageously, in the vector, an ATG is placed at 5' of the reading frame and a stop codon is placed at 3'. Other elements for controlling expression may be present, such as enhancer sequences, stabilizing sequences and signal sequences permitting the secretion of the protein.

Patent applications WO 90/11092, WO 93/19183, WO 94/21797 and WO 95/20660 have made use of the recently developed technique of polynucleotide vaccines. It is known that these vaccines use a plasmid capable of expressing, in the host cells, the antigen inserted into the plasmid. All routes of administration have been proposed (intraperitoneal, intravenous, intramuscular, transcutaneous, intradermal, mucosal and the like). Various means of vaccination can also be used, such as DNA deposited at the surface of gold particles and projected so as to penetrate into the animal's skin (Tang et al., 1992) and liquid jet injectors which make it possible to transfect the skin, muscle, fatty tissues as well as the mammary tissues (Furth et al., 1992). (See also U.S. Pat. Nos. 5,846,946, 5,620,896, 5,643,578, 5,580,589, 5,589,466, 5,693,622, and 5,703,055; Ulmer, J. B., et al., 1993; Robinson et al., 1997; Luke et al. 1997; Norman et al. 1997; Bourne et al., 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.)

According to another embodiment of the invention, the poxvirus vector is a canarypox virus or a fowlpox virus vector, advantageously an attenuated canarypox virus or fowlpox virus. In this regard, reference is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the attenuated fowlpox strain TROVAC.

When the expression vector is a vaccinia virus, insertion site or sites for the polynucleotide or polynucleotides to be expressed can be at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, the insertion site or sites can be ORF(s) C3, C5 and/or C6; see also documents cited herein, especially those pertaining to canarypox virus. In the case of fowlpox, the insertion site or sites can be ORFs F7 and/or F8; see also documents cited herein, especially those pertaining to fowlpox virus. The insertion site or sites for MVA virus area can be as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

In another embodiment of the present invention the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

In another embodiment the viral vector is an adenovirus, such as a human adenovirus (HAV) or a canine adenovirus (CAV).

The recombinant viral vector-based vaccine may be combined with fMLP (N-formyl-methionyl-leucyl-phenylalanine; U.S. Pat. No. 6,017,537) and/or CARBOMER adjuvant (Pharmeuropa Vol.)

In another embodiment the viral vector may be, but is not limited to, an adenovirus of humans, porcines, opines, bovines, or avians. For the human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in GenBank under the accession number M73260 and in the referenced publication J. Chroboczek et al Virol. 1992, 186, 280-285. The deleted adenovirus is propagated in E1-expressing 293 (F. Graham et al J. Gen. Virol. 1977, 36, 59-72) or PER cells, in particular PER.C6 (F. Falloux et al Human Gene Therapy 1998, 9, 1909-1917). The human adenovirus can be deleted in the E3 region, in particular from about nucleotide 28592 to about nucleotide 30470. The deletion in the E1 region can be done in combination with a deletion in the E3 region (see, e.g. J. Shriver et al. Nature, 2002, 415, 331-335, F. Graham et al Methods in Molecular Biology Vol 0.7: Gene Transfer and Expression Protocols Edited by E. Murray, The Human Press Inc, 1991, p 109-128; Y. Ilan et al Proc. Natl. Acad. Sci. 1997, 94, 2587-2592; U.S. Pat. No. 6,133,028; U.S. Pat. No. 6,692, 956; S. Tripathy et al Proc. Natl. Acad. Sci. 1994, 91, 11557-11561; B. Tapnell Adv. Drug Deliv. Rev. 1993, 12, 185-199; X. Danthinne et al Gene Therapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci (region) eventually after a partial or complete deletion of the E1 and/or E3 regions. When the expression vector is an adenovirus, the polynucleotide to be expressed may be inserted under the control of a promoter functional in eukaryotic cells, such as a strong promoter, such as a cytomegalovirus immediate-early gene promoter (CMV-IE promoter), in particular the enhancer/promoter region from about nucleotide −734 to about nucleotide +7 in M. Boshart et al Cell 1985, 41, 521-530 or the enhancer/promoter region from the pCI vector from Promega Corp. The CMV-IE promoter is advantageously of murine or human origin. The promoter of the elongation factor 1α can also be used. A muscle specific promoter can also be used (X. Li et al Nat. Biotechnol. 1999, 17, 241-245). Strong promoters are also discussed herein in relation to plasmid vectors. In one embodiment, a splicing sequence can be located downstream of the enhancer/promoter region. For example, the intron 1 isolated from the CMV-IE gene (R. Stenberg et al J. Virol. 1984, 49, 190), the intron isolated from the rabbit or human β-globin gene, in particular the intron 2 from the β-globin gene, the intron isolated from the immunoglobulin gene, a splicing sequence from the SV40 early gene or the chimeric intron sequence isolated from the pCI vector from Promega Corp. comprising the human β-globin gene donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone releasing hormone gene, in particular from about nucleotide 2339 to about nucleotide 2550 in Genbank under the accession number BOVGHRH (AF242855), a rabbit β-globin gene or a SV40 late gene polyadenylation signal.

In another embodiment the viral vector is a canine adenovirus, in particular a CAV-2 (see, e.g. L. Fischer et al. Vaccine, 2002, 20, 3485-3497; U.S. Pat. No. 5,529,780; U.S. Pat. No. 5,688,920; PCT Application No. WO95/14102). For CAV, the insertion sites can be in the E3 region and/or in the region located between the E4 region and the right ITR region (see U.S. Pat. No. 6,090,393; U.S. Pat. No. 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as an equine herpesvirus (EHV1-5), a porcine herpesvirus (PRV), a canine herpesvirus (CHV) or a feline herpesvirus (FHV). The insertion sites may be in the thymidine kinase gene, in the ORF3, or in the UL43 ORF (for CHV see U.S. Pat. No. 6,159,477). In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

More generally, the present invention encompasses in vivo expression vectors including any plasmid (EP-A2-1001025; Chaudhuri P.) containing and expressing in vivo in a host the polynucleotide or gene of African Horse Sickness virus polypeptide, variant thereof or fragment thereof and elements necessary for its in vivo expression.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

As used herein, the term "plasmid" may include any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention. The plasmids may also comprise other transcription-regulating elements such as, for example, stabilizing sequences of the intron type. In several embodiments, the plasmids may include the first intron of CMV-IE (WO 89/01036), the intron II of the rabbit beta-globin gene (van Ooyen et al.), the signal sequence of the protein encoded by the tissue plasminogen activator (tPA; Montgomery et al.), and/or a polyadenylation signal (polyA), in particular the polyA of the bovine growth hormone (bGH) gene (U.S. Pat. No. 5,122,458) or the polyA of the rabbit beta-globin gene or of SV40 virus.

Each plasmid comprises or contains or consists essentially of, in addition to the polynucleotide encoding an AHSV antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell., 1985, 41, 521-530) or murine CMV-IE. A strong cellular promoter that may be usefully employed in the practice of the invention is the promoter of a gene of the cytoskeleton, such as the desmin promoter (Kwissa M. et al.), or the actin promoter (Miyazaki J. et al.). Functional sub fragments of these promoters, i.e., portions of these promoters that maintain adequate promoter activity, are included within the present invention, e.g. truncated CMV-IE promoters according to WO 98/00166 or U.S. Pat. No. 6,156,567 and may be used in the practice of the invention. A promoter useful in the practice of the invention consequently may include derivatives and/or sub fragments of a full-length promoter that maintain adequate promoter activity and hence function as a promoter, and which may advantageously have promoter activity that is substantially similar to that of the actual or full-length promoter from which the derivative or sub fragment is derived, e.g., akin to the activity of the truncated CMV-IE promoters of U.S. Pat. No. 6,156,567 in comparison to the activity of full-length CMV-IE promoters. Thus, a CMV-IE promoter in the practice of the invention may comprise or consist essentially of or consist of the promoter portion of the full-length promoter and/or the enhancer portion of the full-length promoter, as well as derivatives and/or sub fragments thereof.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

Isolation and purification of recombinantly expressed polypeptide may be carried out by conventional means including preparative chromatography (for example, size exclusion, ion exchange, affinity), selective precipitation and ultra-filtration. Examples of state of the art techniques that can be used, but not limited to, may be found in "Protein Purification Applications", Second Edition, edited by Simon Roe and available at Oxford University Press. Such a recombinantly expressed polypeptide is part of the present disclosure. The methods for production of any polypeptide according to the present invention as described above are also encompassed, in particular the use of a recombinant expression vector comprising a polynucleotide according to the disclosure and of a host cell.

The vaccines containing recombinant viral vectors according to the invention may be freeze-dried, advantageously with a stabilizer. Freeze-drying can be done according to well-known standard freeze-drying procedures. The pharmaceutically or veterinary acceptable stabilizers may be carbohydrates (e.g. sorbitol, mannitol, lactose, sucrose, glucose, dextran, trehalose), sodium glutamate (Tsvetkov T et al.; Israeli E et al.), proteins such as peptone, albumin, lactalbumin or casein, protein containing agents such as skimmed milk (Mills C K et al.; Wolff E et al.), and buffers (e.g. phosphate buffer, alkaline metal phosphate buffer). An adjuvant may be used to make soluble the freeze-dried preparations.

Any composition or vaccine according to the invention can also advantageously contain one or more adjuvant.

The plasmid-based vaccines may be formulated with cationic lipids, advantageously with DMRIE (N-(2-hydroxyéthyl)-N,N-diméthyl-2,3-bis(tetradecyloxy)-1-propanammonium; WO96/34109), or in association with a neutral lipid, for example DOPE (dioleoyl-phosphatidyl-ethanolamine; Behr J. P.) to form DMRIE-DOPE. In one embodiment, the mixture is made extemporaneously, and before its administration it is advantageous to wait about 10 min to about 60 min, for example, about 30 min, for the appropriate complexation of the mixture. When DOPE is used, the molar ratio of DMRIE/DOPE can be from 95/5 to 5/95 and is advantageously 1/1. The weight ratio plasmid/DMRIE or DMRIE-DOPE adjuvant is, for example, from 50/1 to 1/10, from 10/1 to 1/5 or from 1/1 to 1/2.

Optionally a cytokine may be added to the composition, especially GM-CSF or cytokines inducing Th1 (e.g. IL12). These cytokines can be added to the composition as a plasmid encoding the cytokine protein. In one embodiment, the cytokines are from canine origin, e.g. canine GM-CSF which gene sequence has been deposited at the GenBank database (accession number S49738). This sequence can be used to create said plasmid in a manner similar to what was made in WO 00/77210.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Advantageous host cells include, but are not limited to, baby hamster kidney (BHK) cells, colon carcinoma (Caco-2) cells, COST cells, MCF-7 cells, MCF-10A cells, Madin-Darby canine kidney (MDCK) lines, mink lung (Mv1Lu) cells, MRC-5 cells, U937 cells and VERO cells. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

The polynucleotide vaccines may use both naked DNAs and DNAs formulated, for example, inside liposomes or cationic lipids or with CpG's.

Nucleic acids which differ from native African Horse Sickness Virus nucleic acids due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. DNA sequence variations that lead to changes in the amino acid sequences of the subject African Horse Sickness Virus proteins encoded by the recombinant vectors of the present invention are also encompassed by the present invention. Any and all such nucleotide variations and resulting amino acid variations are within the scope of this invention.

It is also possible to modify the structure of the subject African Horse Sickness Virus polypeptides encoded by the recombinant vectors of the present invention for such purposes as enhancing therapeutic or prophylactic efficacy (e.g., increasing immunogenicity of the polypeptide). Such modified polypeptides, when designed to retain at least one activity of the naturally-occurring form of the protein, are considered functional equivalents of the African Horse Sickness Virus polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W.H. Freeman and Co., 1981). Whether a change in the amino acid sequence of a polypeptide results in a functional homolog can be readily determined by assessing the ability of the variant polypeptide to produce a response in cells in a fashion similar to the wild-type protein.

As to epitopes of interest, reference is made to Kendrew, THE ENCYCLOPEDIA OF MOLECULAR BIOLOGY (Blackwell Science Ltd., 1995) and Sambrook, et al. 1982. An epitope of interest is an immunologically relevant region of an immunogen or immunologically active fragment thereof, e.g., from a pathogen or toxin of veterinary or human interest, e.g., African Horse Sickness Virus. One skilled in the art can determine an epitope or immunodominant region of a peptide or polypeptide and ergo the coding DNA therefore from the knowledge of the amino acid and corresponding DNA sequences of the peptide or polypeptide, as well as from the nature of particular amino acids (e.g., size, charge, etc.) and the codon dictionary, without undue experimentation.

The DNA sequence preferably encodes at least regions of the peptide that generate an antibody response or a T cell response. One method to determine T and B cell epitopes involves epitope mapping. The protein of interest is synthesized in short overlapping peptides (PEPSCAN). The individual peptides are then tested for their ability to bind to an antibody elicited by the native protein or to induce T cell or B cell activation. Janis Kuby, (1992).

Another method for determining an epitope of interest is to choose the regions of the protein that are hydrophilic. Hydrophilic residues are often on the surface of the protein and are therefore often the regions of the protein which are accessible to the antibody. Janis Kuby, (1992). Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response.

Some guidelines in determining whether a protein is an epitope of interest which will stimulate a T cell response, include: Peptide length—the peptide should be at least 8 or 9 amino acids long to fit into the MHC class I complex and at least 13-25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al; Englehard, V H, (1994)). This can be done, without undue experimentation, by comparing the sequence of the protein of interest with published structures of peptides associated with the MHC molecules.

Further, the skilled artisan can ascertain an epitope of interest by comparing the protein sequence with sequences listed in the protein data base.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro.

In further embodiments, the invention provides a recombinant vector comprising one or more nucleic acid(s) encoding one or more African Horse Sickness Virus protein, e.g., VP2 and or VP5, which has been modified from its native form to overcome an immunodominant non-neutralizing epitope. Immunodominant non-neutralizing epitopes act as decoys against neutralizing epitopes, for example, by directing an immune response away from a neutralizing epitope. Immunodominant non-neutralizing epitopes may be found in immunogenic proteins of pathogens, such as African Horse Sickness Virus.

The present invention encompasses recombinant vectors and modified recombinant viruses comprising nucleic acids encoding one or more African Horse Sickness Virus proteins that have been modified from their native form, e.g., by deletion(s) and/or insertion(s) and/or substitution of amino acid residue(s) in the native sequence.

As to “immunogenic composition”, “immunological composition” and “vaccine”, an immunological composition containing the vector (or an expression product thereof) elicits an immunological response—local or systemic. The response can, but need not be protective. An immunogenic composition containing the inventive recombinant or vector (or an expression product thereof) likewise elicits a local or systemic immunological response which can, but need not be, protective. A vaccine composition elicits a local or systemic protective response. Accordingly, the terms “immunological composition” and “immunogenic composition” include a “vaccine composition” (as the two former terms can be protective compositions). The invention comprehends immunological, immunogenic or vaccine compositions.

According to the present invention, the recombinant vector, e.g., virus such as poxvirus, expresses gene products of the foreign African Horse Sickness Virus gene(s) or nucleic acid molecule(s). Specific viral proteins of African Horse Sickness Virus or specific nucleic acid molecules encoding epitope(s) from specific African Horse Sickness Virus viral proteins is/are inserted into the recombinant vector e.g., virus such as poxvirus vector, and the resulting vector, e.g., recombinant virus such as poxvirus, is used to infect an animal or express the product(s) in vitro for administration to the animal. Expression in the animal of African Horse Sickness Virus gene products results in an immune response in the animal to African Horse Sickness Virus. Thus, the recombinant vector, e.g., virus such as recombinant poxvirus of the present invention may be used in an immunological composition or vaccine to provide a means to induce an immune response.

The administration procedure for a recombinant vector, e.g., recombinant virus such as recombinant poxvirus-AHSV or expression product thereof, as well as for compositions of the invention such as immunological or vaccine compositions or therapeutic compositions (e.g., compositions containing the recombinant vector or recombinant virus such as poxvirus or the expression product therefrom), can be via a parenteral route (intradermal, intramuscular or subcutaneous). Such an administration enables a systemic immune response, or humoral or cell-mediated responses.

The vector or recombinant virus-AHSV, e.g., poxvirus-AHSV, or expression product thereof, or composition containing such an expression product and/or vector or virus, can be administered to horses of any age or sex; for instance, to elicit an immunological response against African Horse Sickness Virus, e.g., to thereby prevent African Horse Sickness Virus and/or other pathologic sequelae associated with African Horse Sickness Virus. Advantageously, the vector or recombinant virus-AHSV, e.g., poxvirus-AHSV, or expression product thereof, or composition containing such an expression product and/or vector or virus, is administered to horses, including a newborn and/or to a pregnant mare to confer active immunity during gestation and/or passive immunity to the newborn through maternal antibodies. In a preferred embodiment, the invention provides for inoculation of a female horse (e.g., mare) with a composition comprising an immunogen from African Horse Sickness Virus or an epitope of interest from such an immunogen, e.g., an immunogen from AHSV VP2 and/or VP5 and/or an epitope of interest expressed by any one or more of these VPs or combinations of VPs, and/or with a vector expressing such an immunogen or epitope of interest. The inoculation can be prior to breeding; and/or prior to serving; and/or during gestation (or pregnancy), and/or prior to the perinatal period; and/or repeatedly over a lifetime. Advantageously, at least one inoculation is done before serving. It is also advantageously followed by an inoculation to be performed during gestation, e.g., at about mid-gestation (at about 5-6 months of gestation) and/or at the end of gestation (or at about 10-11 months of gestation). Thus, an advantageous regimen is an inoculation before serving and a booster inoculation during gestation. Thereafter, there can be reinoculation before each serving and/or during gestation at about mid-gestation (at about 5-6 months of gestation) and/or at the end of gestation (or at about 10-11 months of gestation). Preferably, reinoculation can be during gestation only. In another preferred embodiment, foals, such as foals from vaccinated females (e.g., inoculated as herein discussed), are inoculated within the first months of life, e.g., inoculation at three and/or four, and/or four and/or five, and five and/or six and six months of life. Even more advantageous, such foals are then boosted two (2) to eight (8) weeks later (after being first inoculated). Thus, both offspring, as well as the female horse (e.g., mare) can be administered compositions of the invention and/or can be the subject of performance of methods of the invention. Inoculations can be in the doses as herein described. With respect to the administration of poxvirus or virus compositions and maternal immunity, reference is made to U.S. Pat. No. 5,338,683.

With respect to dosages, routes of administration, formulations, adjuvants, and uses for recombinant viruses and expression products there of, compositions of the invention may be used for parenteral or mucosal administration, preferably by intradermal, subcutaneous or intramuscular routes.

When mucosal administration is used, it is possible to use oral, ocular or nasal routes. The invention in yet a further aspect relates to the product of expression of the inventive recombinant or vector, e.g., virus, for instance, recombinant poxvirus, and uses therefore, such as to form an immunological or vaccine compositions for treatment, prevention, diagnosis or testing; and, to DNA from the recombinant or inventive virus, e.g., poxvirus, which is useful in constructing DNA probes and PCR primers.

The inventive recombinant vector or virus-AHSV (e.g., poxvirus-AHSV recombinants) immunological or vaccine compositions or therapeutic compositions, can be prepared in accordance with standard techniques well known to those skilled in the pharmaceutical or veterinary art. Such compositions can be administered in dosages and by techniques well known to those skilled in the veterinary arts taking into consideration such factors as the age, sex, weight, and the route of administration. The compositions can be administered alone, or can be co-administered or sequentially administered with compositions, e.g., with "other" immunological composition, or attenuated, inactivated, recombinant vaccine or therapeutic compositions thereby providing multivalent or "cocktail" or combination compositions of the invention and methods employing them. The composition may contain combinations of the African Horse Sickness Virus component (e.g., recombinant vector such as a plasmid or virus or poxvirus expressing an African Horse Sickness Virus immunogen or epitope of interest and/or African Horse Sickness Virus immunogen or epitope of interest) and one or more unrelated equine pathogen vaccines (e.g., epitope(s) of interest, immunogen(s) and/or recombinant vector or virus such as a recombinant virus, e.g., recombinant poxvirus expressing such epitope(s) or immunogen(s)) such as one or more immunogen or epitope of interest from one or more equine bacterial and/or viral pathogen(s), e.g., an epitope of interest or immunogen from one or more of: equine herpes virus (EHV), equine influenza virus (EIV), West Nile Virus (WNV) in horses, Eastern Equine Encephalomyelitis (EEE), Western Equine Encephalomyelitis (WEE), and Venezuelan Equine Encephalomyelitis (VEE), tetanus, rabies, and Potomac horse fever+EPM. Again, the ingredients and manner (sequential or co-administration) of administration, as well as dosages can be determined taking into consideration such factors as the age, sex, weight, and, the route of administration. In this regard, reference is made to U.S. Pat. No. 5,843,456, incorporated herein by reference, and directed to rabies compositions and combination compositions and uses thereof.

Examples of compositions of the invention include liquid preparations for mucosal administration, e.g., oral, nasal, ocular, etc., administration such as suspensions and, preparations for parenteral, subcutaneous, intradermal, intramuscular (e.g., injectable administration) such as sterile suspensions or emulsions. In such compositions the recombinant poxvirus or immunogens may be in admixture with a suitable carrier, diluent, or excipient such as sterile water, physiological saline, or the like. The compositions can also be lyophilized or frozen. The compositions can contain auxiliary substances such as wetting or emulsifying agents, pH buffering agents, adjuvants, preservatives, and the like, depending upon the route of administration and the preparation desired.

The compositions can contain at least one adjuvant compound chosen from aluminum hydroxide, a metabolizable oil, comprising terpene hydrocarbons and a polyoxyethylene-polyoxypropylene block copolymer, the polymers of acrylic or methacrylic acid, the copolymers of maleic anhydride and alkenyl derivative and Immune-stimulating Complex Matrix (ISCOM) comprising glycosides of QUIL A, cholesterol, antigen, and/or phospholipids.

The preferred adjuvant compounds are the polymers of acrylic or methacrylic acid which are cross-linked, especially with polyalkenyl ethers of sugars or polyalcohols. These compounds are known by the term CARBOMER (Pharmeuropa Vol. 8, No. 2, June 1996). Persons skilled in the art can also refer to U.S. Pat. No. 2,909,462 (incorporated herein by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL® (BF Goodrich, Ohio, USA) are particularly appropriate. They are cross-linked with allyl sucrose or with allyl pentaerythritol. Among them, there may be mentioned CARBOPOL® 974P, 934P and 971P.

Among the copolymers of maleic anhydride and alkenyl derivative, the copolymers EMA® (Monsanto) which are copolymers of maleic anhydride and ethylene, linear or cross-linked, for example cross-linked with divinyl ether, are preferred. Reference may be made to J. Fields et al., 1960, incorporated herein by reference.

From the point of view of their structure, the polymers of acrylic or methacrylic acid and the copolymers EMA® are preferably formed of basic units of the following formula:

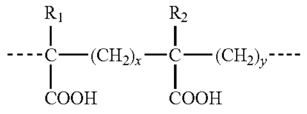

in which:

$R_1$ and $R_2$, which are identical or different, represent H or $CH_3$ x=0 or 1, preferably x=1 y=1 or 2, with x+y=2

For the copolymers EMA®, x=0 and y=2. For the carbomers, x=y=1.

The dissolution of these polymers in water leads to an acid solution which will be neutralized, preferably to physiological pH, in order to give the adjuvant solution into which the vaccine itself will be incorporated. The carboxyl groups of the polymer are then partly in $COO^-$ form.

Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCl 9 g/l) all at once in several portions with concomitant or subsequent neutralization (pH 7.3 to 7.4), preferably with NaOH. This solution at physiological pH will be used as it is for mixing with the vaccine, which may be especially stored in freeze-dried, liquid or frozen form.

The polymer concentration in the final vaccine composition will be 0.01% to 2% w/v, more particularly 0.06 to 1% w/v, preferably 0.1 to 0.6% w/v.

The compositions of the invention can also be formulated as oil in water or as water in oil in water emulsions, e.g. as in V. Ganne et al. (1994).

Standard texts, such as "REMINGTON'S PHARMACEUTICAL SCIENCE", 17th edition, 1985, incorporated herein by reference, may be consulted to prepare suitable preparations, without undue experimentation.

Compositions in forms for various administration routes are envisioned by the invention. And again, the effective dosage and route of administration are determined by known factors, such as age, sex, weight, and other screening procedures which are known and do not require undue experimentation. Dosages of each active agent can be as in herein cited documents (or documents referenced or cited in herein cited documents).

Recombinant vectors can be administered in a suitable amount to obtain in vivo expression corresponding to the dosages described herein and/or in herein cited documents. For instance, suitable ranges for viral suspensions can be determined empirically. The viral vector or recombinant in the invention can be administered to a horse or infected or transfected into cells in an amount of about at least $10^3$ pfu; more preferably about $10^4$ pfu to about $10^{10}$ pfu, e.g., about $10^5$ pfu to about $10^9$ pfu, for instance about $10^6$ pfu to about $10^8$ pfu, per dose, for example, per 2 mL dose. And, if more than one gene product is expressed by more than one recombinant, each recombinant can be administered in these amounts; or, each recombinant can be administered such that there is, in combination, a sum of recombinants comprising these amounts. In recombinant vector compositions employed in the invention, dosages can be as described in documents cited herein or as described herein or as in documents referenced or cited in herein cited documents. For instance, suitable quantities of each DNA in recombinant vector compositions can be 1 μg to 2 mg, preferably 50 μg to 1 mg. Documents cited herein (or documents cited or referenced in herein cited documents) regarding DNA vectors may be consulted by the skilled artisan to ascertain other suitable dosages for recombinant DNA vector compositions of the invention, without undue experimentation.

However, the dosage of the composition(s), concentration of components therein and timing of administering the composition(s), which elicit a suitable immunological response, can be determined by methods such as by antibody titrations of sera, e.g., by ELISA and/or seroneutralization assay analysis and/or by vaccination challenge evaluation in horse. Such determinations do not require undue experimentation from the knowledge of the skilled artisan, this disclosure and the documents cited herein. And, the time for sequential administrations can be likewise ascertained with methods ascertainable from this disclosure, and the knowledge in the art, without undue experimentation.

The African Horse Sickness Virus immunogen or epitope of interest can be obtained from any of the nine serotypes of African Horse Sickness Virus or can be obtained from in vitro recombinant expression of African Horse Sickness Virus gene(s) or portions thereof. Methods for making and/or using vectors (or recombinants) for expression and uses of expression products and products therefrom (such as antibodies) can be by or analogous to the methods disclosed in herein cited documents and documents referenced or cited in herein cited documents.

Suitable dosages can also be based upon the examples below.

The invention in a particular aspect is directed to recombinant poxviruses containing therein a DNA sequence from African Horse Sickness Virus, advantageously in a nonessential region of the poxvirus genome. The recombinant poxviruses express gene products of the foreign African Horse Sickness Virus gene. In particular, VP2 and VP5 genes encoding African Horse Sickness Virus viral proteins were isolated, characterized and inserted into ALVAC (canarypox vector) recombinants.

One embodiment of the invention relates to a new AHSV strain, namely AHSV4-Jane Strain.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989). All the restriction fragments used for the present invention were isolated using the "Geneclean" kit (BIO 101 Inc., La Jolla, Calif.).

Example 1

Construction of the Canarypox Recombinant Viral Vectors

Synthetic genes encoding the VP2 and VP5 proteins of African Horse Sickness Virus were used in the construction of a recombinant canarypox virus vector. Briefly, the L2 and M5 gene segments that respectively encode VP2 and VP5 of African Horse Sickness Virus serotypes 4, 5 and 9 were amplified by reverse-transcriptase polymerase chain reaction (RT-PCR) and sequenced using a protocol previously described by Bonneau K R, Mullens B A, (2001) Bonneau K R, et al. (1999).

The sequences of the L2/VP2 (SEQ ID NO:48) and M5/VP5 (SEQ ID NO:50) genes of a virulent field isolate of AHSV-4 (hereinafter referred to as "the AHSV4 Jane Strain") were compared to the published sequences of the same genes of other strains of AHS serotype 4 available at GenBank, and optimized synthetic sequences were then derived using GeneOptimizer® software (Geneart GmbH) for chemical synthesis of an array of oligonucleotides that encompass each individual gene. The oligonucleotides were assembled using a PCR-based strategy to generate the complete, full length synthetic VP2 and VP5 coding sequences. The synthetic genes encoding VP2 and VP5 were then subcloned into the canarypox virus vector to produce the AHSV-canarypox virus recombinant (AHSV-CP), essentially as previously described for the recombinant canarypox virus vectored West Nile virus (WNV-CP) vaccine (Minke J M, et al. 2004a).

Briefly, the synthetic gene encoding VP2 of AHSV-4 (SEQ ID NO:4) was subcloned into a canarypox C3 insertion vector (plasmid containing a vaccinia virus H6 promoter and the flanking arms of the canarypox C3 locus) to generate an expression cassette containing the VP2 (SEQ ID NO:4) gene under the control of the H6 promoter. Subsequently, an expression cassette containing the synthetic VP5 gene (SEQ ID NO:5) under the control of entomopoxvirus *Amsacta moorei* 42K promoter was constructed and cloned into H6-VP2 donor plasmid. The resultant insertion plasmid contained two expression cassettes, the VP2 gene (SEQ ID NO:4) under the control of the H6 promoter and the VP5 gene (SEQ ID NO:5) under the control of the 42K promoter, in a head-to-tail orientation.

To generate the AHSV-CP virus recombinant, the insertion plasmid was transfected into primary chicken embryo fibroblast (CEF) cells that were subsequently infected with canarypox virus. After 24 hours, the transfected-infected cells were harvested, sonicated and used for recombinant virus screening (Piccini A, et al. (1987)). The recombinant plaques were screened by in situ plaque lift hybridization method (Sambrook et al., 1982) using an AHSV-specific probe. After 4 sequential rounds of plaque purification, the recombinant confirmed by hybridization to be 100% positive for the African Horse Sickness Virus insert was amplified and used to prepare vaccine stocks that were stored at −80° C.

Example 2

Construction of the pLHD3460.4 Donor Plasmid Expressing the H6 Promoter-Driven Synthetic AHSV-4-VP2 and the 42K Promoter-Driven Synthetic AHSV-4-VP5

FIG. 1 shows the construction scheme for pLHD3460.4 (SEQ ID NO:6), the C3 donor plasmid for generation of the ALVAC recombinant expressing AHSV-4-VP2 and AHSV-4-VP5 viral proteins. The genes encoding AHSV-4-VP2 (SEQ ID NO:4) and AHSV-4-VP5 (SEQ ID NO:5) are synthetic with codon optimization for expression in mammalian cells. The synthetic AHSV-4-VP2 (SEQ ID NO:4) gene was placed under the control of vaccinia pC3H6p promoter and the synthetic AHSV-4-VP5 (SEQ ID NO:5) gene was placed under the control of vaccinia 42K promoter. The plasmid contains also a gene conferring ampicillin resistance.

The plasmid containing synthetic AHSV-4-VP2 gene was digested with BamHI and NruI. The resulting 3.2 Kb AHSV-4-VP2 insert was isolated and cloned into the BamHI/NruI sites of a shuttle vector prepared from pJY1107.5 (pF8 AIV H7N2 HA) to create pLHD3410.9 (pF8H6p AHSV-4-VP2), which contains the NruI site of H6 promoter and the full length AHSV-4-VP2 followed by the XhoI site.

pLHD3410.9 was digested again with NruI and XhoI, and a 3.2 Kb DNA fragment comprising 3' NruI of the H6 promoter and the full-length AHSV-4-VP2 gene was isolated and cloned into the NruI/XhoI sites of an ALVAC C3 donor plasmid prepared from pJY1738.2 (pC3H6p CPV-VP2) to create pLHD3426.1, an ALVAC C3 donor plasmid containing the H6p-AHSV-4-VP2 expression cassette.

An expression cassette 42Kp-AHSV-4-VP5 flanked by the SpeI site was PCR amplified using the plasmid containing AHSV-4-VP5 as the template and a pair of primers 13599.JY (SEQ ID NO:7) and 13600.JY (SEQ ID NO:8). Primer 13599.JY (SEQ ID NO:7) comprises the SpeI site and the sequence of 42K promoter followed by the 5' sequence of VP5. Primer 13600.JY (SEQ ID NO:8) consists of the 3' sequence of VP5 followed by T5NT and SpeI site. The amplified expression cassette was then cloned into pCR2.1, a TOPO vector, to create pCR2.1 42Kp AHSV-4-VP5, which was confirmed to contain the correct sequence.

Plasmid pCR2.1 AHSV-4-VP5 was digested with SpeI, and the 42Kp-VP5 expressing cassette was then isolated and cloned into the SpeI site of plasmid pLHD3426.1 to create an ALVAC C3 donor plasmid containing the double expression cassettes H6p-AHSV-4-VP2/42Kp-VP5 (pLHD3460.4), which was sequenced and confirmed to contain the correct sequences at set forth by SEQ ID NO:6.

The primers for amplification of 42Kp-AHSV-4-VP5 expressing cassette were as follows:

```
13599.JY
                                                                   (SEQ ID NO: 7)
5' TGACTAGTTCAAAATTGAAAATATATAATTACAATATAAAATGGGCAAGTTTACCAGCTTCCTGAAG
 SpeI              42 Kp

13600.JY
                                                                   (SEQ ID NO: 8)
5' TTAACTAGTAGAAAAATCATCAGGCGATCTTCACGCCGTACAG
      SpeI    T5NT
```

The predicted molecular weights were 124.3 kDa for AHSV-4-VP2 (SEQ ID NO:1), and 57 KDa for AHSV-4-VP5 (SEQ ID NO:2). The isoelectric points were 6.75 for AHSV-4-VP2 and 5.8 for AHSV-4-VP5. Both viral proteins were expressed primarily in the cytoplasm.

Example 3

Construction of Recombinant Viral Vector vCP2377 (ALVAC C3 H6p-Synthetic AHSV-4-VP2/42Kp-Synthetic AHSV-4-VP5)

Figure 3:
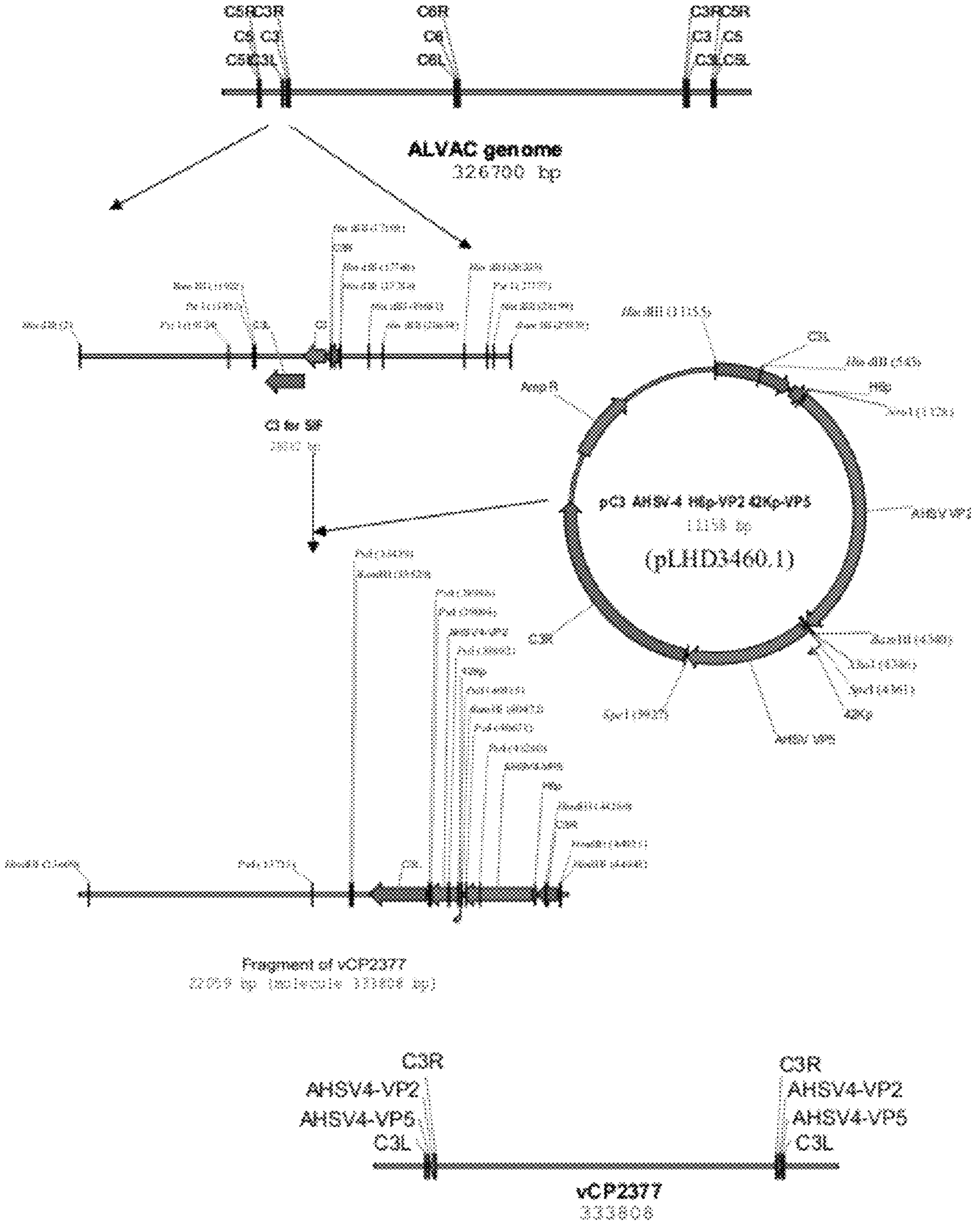
FIG. 3 provides the in vitro recombination scheme for vCP2377 (ALVAC C3 H6p-synthetic AHSV-4-VP2/42Kp-synthetic AHSV-4-VP5).

To produce the vCP2377 recombinant viral vector, the donor plasmid, pLHD3460.4 (SEQ ID NO:6), and the parental virus, ALVAC ($4.4\times10^{10}$ pfu/mL), were recombined in vitro using primary chicken embryo fibroblast (primary CEF, or CEF) cells. FIG. 3 outlines this procedure. Plaque hybridization by AHSV-4-VP5 specific probe was used to confirm recombinant viral vector.

The in vitro recombination (IVR) was performed by transfection of primary CEF cells with NotI-linearized donor plasmid pLHD3460.4 (15 μg) using Fugene reagent (Roche, Palo Alto, Calif. 94304-1353). The transfected cells were subsequently infected with ALVAC ($4.4\times10^{10}$ pfu/mL) as the rescue virus at a multiplicity of infection (MOI) of 10. After 24 hours, the transfected-infected cells were harvested, sonicated and used for recombinant virus screening.

The recombinant plaques were screened based on the plaque lift hybridization method (Sambrook et al., 1982) using an AHSV-4-VP5 specific probe which was labeled with horseradish peroxidase according to the manufacturer's protocol (Amersham, Alpharetta, Ga. 30058, Cat #RPN3001). After 3 sequential rounds of plaque purification, the recombinant designated as vCP2377.6.1.1 (partial sequence given by SEQ ID NO:17) was generated and confirmed by hybridization as 100% positive for the AHSV insert and 100% negative for the empty C3 site.

Figure 7:
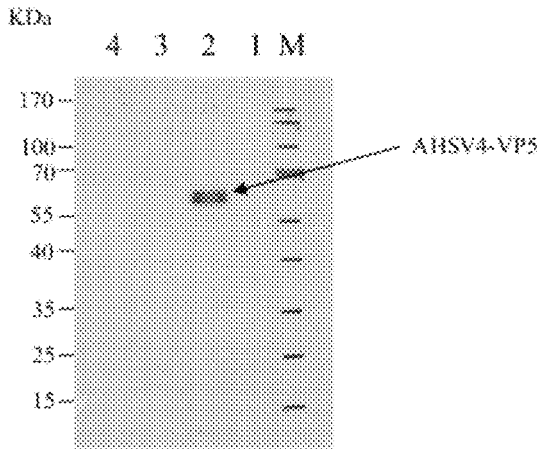
FIG. 7 provides Western blot results of the analysis of recombinant vCP2377 indicating the expression of the AHSV-4-VP5 protein.
Figure 8:
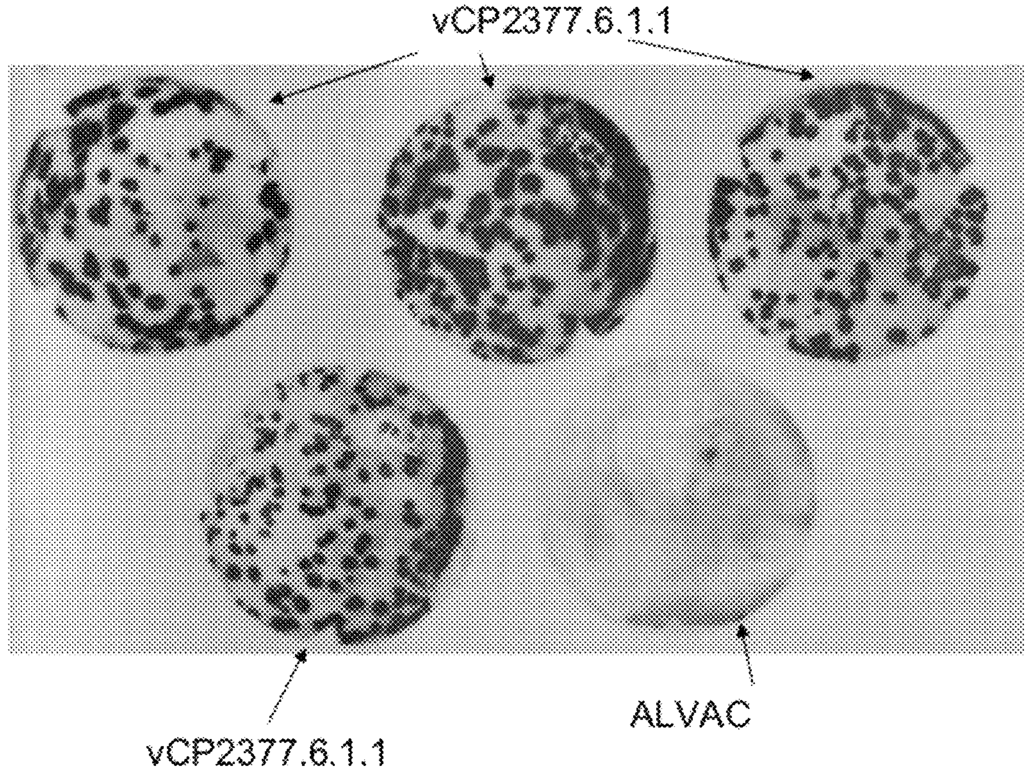
FIG. 8 provides the immunoplaque results indicating 100% homogeneity of the vCP2377.6.1.1 population using mouse anti-AHSV VP5 mAb 10AE12 Passage 9 at a dilution of 1:100.

Single plaques were selected from the final round of plaque purification, and expanded to obtain P1 (T-25 flask), P2 (T-75 flask) and P3 (roller bottle) stocks to amplify vCP2377.6.1.1. The recombinant was re-confirmed at the P2 level by hybridization and found to be 100% positive for the insert and 100% negative for the empty C3 loci. The infected cell culture fluid from the roller bottles was harvested and concentrated to produce the virus stock (3.2 mL of vCP2377.6.1.1 at $1.2\times10^{10}$ pfu/mL). Mouse anti-BTV4-VP2 mAb and mouse anti-VP5 AHSV mAb 10AE12 Passage 9 (Martinez-Torrecuadrada, J et al., Virology 257, 449-459, 1999) were used for Western blot and Immunoplaque (FIG. 7 and FIG. 8, respectively).

The cells used for in vitro recombination were primary chicken embryo fibroblast (primary CEF) cells grown in 10% Fetal bovine serum (FBS) (JRH bioscience, Lenexa, Kans. 66215: γ-irradiated cat #12107, Lot#1L0232), Dulbecco's modified Eagle's medium (DMEM) (Invitrogen/BRL/Gibco, Carlsbad, Calif., 92008-7321, cat #11960) supplemented with 4 mM Glutamine (Invitrogen/BRL/Gibco, Carlsbad, Calif., 92008-7321, cat #25030-081) and 1 mM Sodium Pyruvate (Invitrogen/BRL/Gibco cat #11360-070) in the presence of 1× antibiotics/antimycotics (P/S/A/A, Invitrogen/BRL/Gibco cat #15240-062). Fugene (Roche, Lot #181444). The final virus concentrates was re-suspended in 1 mM Tris, pH9.0.

Example 4

Analysis of Recombinant Viral Vector vCP2377 (ALVAC C3 H6p-Synthetic AHSV-4-VP2/42Kp-Synthetic AHSV-4-VP5)

Figure 4:
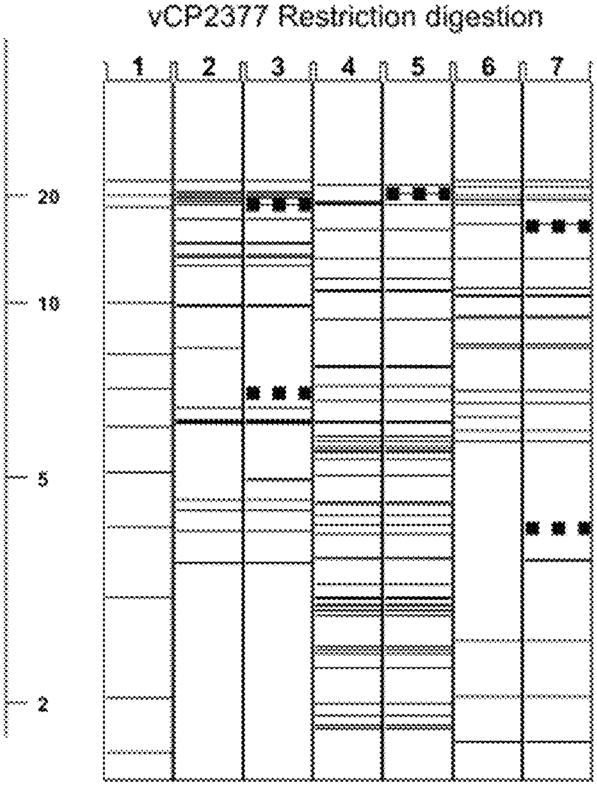
FIG. 4 provides a theoretical restriction enzyme gel for the genomic DNA created in Vector NTI.
Figure 5:
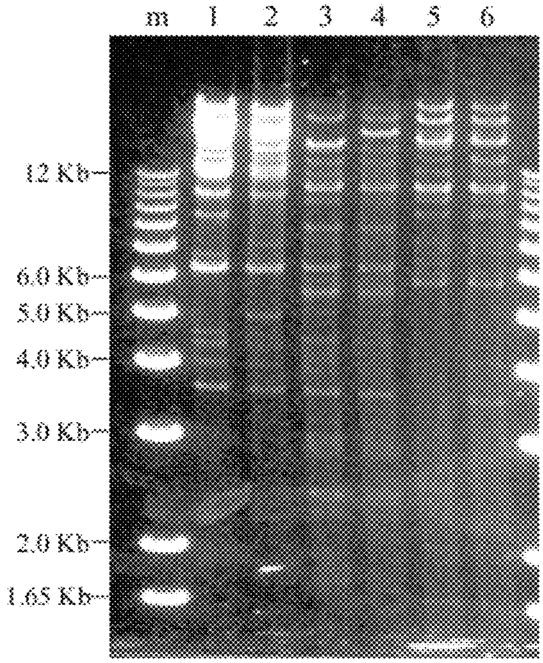
FIG. 5 provides the 0.8% agarose gel electrophoresis results of genomic DNA extraction of the P3 stock from vCP2377.6.1.1, followed by digestion with BamHI, HindIII or PstI.

The P3 stock was re-confirmed by hybridization, as 100% positive for the AHSV-4-VP2 and AHSV-4-VP5 inserts, and 100% negative for the empty C3 loci. A theoretical restriction map of the genomic DNA (FIG. 4) was created in Vector NTI (Invitrogen, Carlsbad, Calif.). To perform the real-life experiment, genomic DNA was extracted from vCP2377.6.1.1 virus concentrates and digested with BamHI, HindIII or PstI, and separated by 0.8% agarose gel electrophoresis (FIG. 5). The results revealed the correct insertion of the foreign gene sequence.

Figure 6:
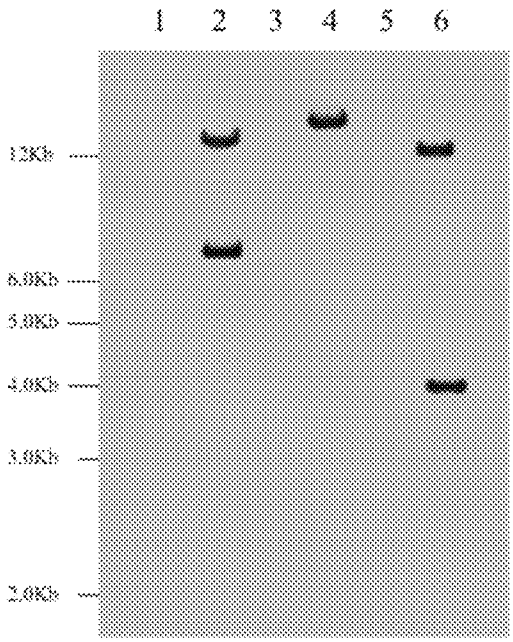
FIG. 6 provides the Southern Blot analysis of vCP2377.6.1.1 using an AHSV-4-VP2 probe.

Southern blot: The genomic DNA digested with BamHI, HindIII, or PstI was transferred to nylon membrane and Southern blot analysis was performed by probing with the AHSV-4-VP2 probe. Bands of expected sizes were observed, namely 16047 bp, 6971 bp BamHI, 20660 bp HindIII and 13658 bp, 4061 bp PstI. The results indicated the correct insertion of AHSV-4-VP2 and AHSV-4-VP5 into the C3 loci. (FIG. 6).

Expression analysis: Primary CEF cells were infected with the P3 stock of vCP2377.6.1.1 at a MOI of 10 and incubated at 37° C. for 24 hrs. The cells and culture supernatant were then harvested. Sample proteins were separated on a 10% SDS-PAGE gel, transferred to IMMOBILON nylon membrane, and probed separately with the mouse anti-VP5 of AHSV (African horse sickness virus) 10AE12 Passage 9 antibody (Martinez-Torrecuadrada, J et al., 1999) at a dilution of 1:100. Peroxidase conjugated goat anti-mouse antiserum was used as a secondary antibody and the bands were visualized using Amersham detection regents. With the use of the mouse anti-AHSV VP5 mAb, the protein bands between 55 to 70 kDa were detected in the cell pellets of vCP2377.6.1.1, indicating the expression of the AHSV-4-VP5 protein. (FIG. 7). AHSV-4-VP5 protein expression was not detected in the culture medium. The expression of AHSV-4-VP2 expression was not detected by the mouse anti-BTV4-VP2 mAb (Merial proprietary material).

Immunoplaque: The homogeneity of the vCP2377.6.1.1 population was 100% as evidenced by an immunoplaque assay, using mouse anti-AHSV VP5 mAb 10AE12 Passage 9 (Martinez-Torrecuadrada, J et al., 1999) at a dilution of 1:100 (FIG. 8). Anti-AHSV VP2 antibody was not available.

Figure 9:
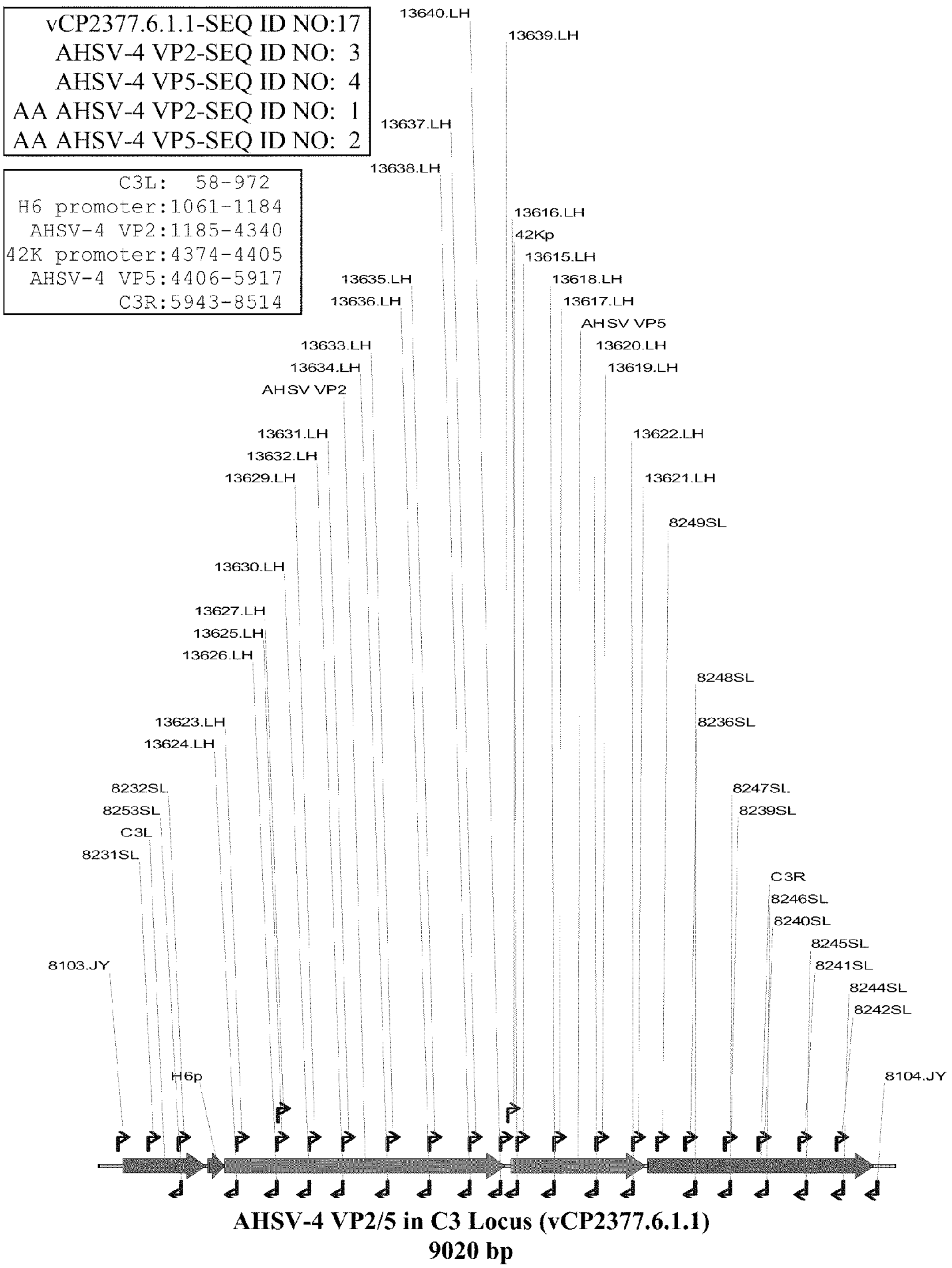
FIG. 9 provides a map of the primers used to amplify the C3R-AHSV insert-C3L fragment and the SEQ ID references for the recombinant vCP2377.6.1.1 sequences (SEQ ID NOs: 17-21).

Sequence analysis: A more detailed analysis of the P3 stock genomic DNA was performed by using PCR amplification and sequence analysis of the flanking arms of the C3 locus and the AHSV-4-VP2 and AHSV-4-VP5 inserts. Primers 8103.JY (SEQ ID NO:13)/13616.LH (SEQ ID NO:15) and 13637.LH (SEQ ID NO:16)/8104.JY (SEQ ID NO:14) were used to amplify the entire C3R-AHSV-4-VP2/VP5-inserts-C3L fragment (FIG. 9). The resulting sequence, namely SEQ ID NO:17, indicated that the sequences of the AHSV-4-VP2 and AHSV-4-VP5 inserts and the C3 left and right arms around the AHSV inserts in vCP2377.6.1.1 were correct.

```
Primers for amplifying the AHSV-4-VP2 probe
13625.LH
                                        (SEQ ID NO: 9)
5' TACGACCACGGCACCGACATCATCT 3'

13632.LH
                                        (SEQ ID NO: 10)
5' TTTTCAGCTTCTTAAAGGCGTACTC 3'

Primers for amplifying the AHSV-4-VP5 probe
13615.LH
                                        (SEQ ID NO: 11)
5'AAGAAGATGTACAAGCTGGCCGGCA 3'

13620.LH
                                        (SEQ ID NO: 12)
5' GCCGCTCGTATTCCTGCTTCACGAT 3'

Primers for PCR amplification of the vCP2377 C3
arms plus insert
8103.JY
                                        (SEQ ID NO: 13)
5' GAGGCATCCAACATATAAAGAAGACTAAAG 3'

8104.JY
                                        (SEQ ID NO: 14)
5' TAGTTAAATACTCATAACTCATATCTG 3'

13616.LH
                                        (SEQ ID NO: 15)
5' TGCCGGCCAGCTTGTACATCTTCTT 3'

13637.LH
                                        (SEQ ID NO: 16)
5' CACCACACTGAAGCTGGACAGAAGA 3'
```

Example 5

Construction of pCXL2415.1 Donor Plasmid Expressing the H6 Promoter-Driven Synthetic AHSV-9-VP2 and the 42K Promoter-Driven Synthetic AHSV-9-VP5

The overall construction scheme for pCXL2415.1 (SEQ ID NO:22) is depicted in FIG. 10. The plasmid containing synthetic AHSV-9-VP2 (SEQ ID NO:28) was digested with NruI/BamHI, and the 3188 bp fragment was isolated and cloned into NruI/BamHI-linearized pJY1107.5 (pF8H6p-AIV H7N2 HA). The resulting plasmid, pCXL2275.1 (pF8H6p-AHSV-9-VP2), contains the NruI site of H6 promoter and the full length AHSV-9-VP2 followed by the XhoI site. After sequence confirmation, pCXL2275.1 was digested with NruI/XhoI, and the 3194 bp AHSV-9-VP2 fragment was isolated and cloned into NruI/XhoI-digested pJY1738.2 (the C3 ALVAC donor plasmid). The resulting plasmid, pCXL2328.4 (pC3 H6p-AHSV-9-VP2), contains the expression cassette H6p-AHSV-9-VP2.

To produce a 42Kp-AHSV-9-VP5 expression cassette, DNA encoding the AHSV-9 synthetic VP5 gene was PCR-amplified using 18020CXL (SEQ ID NO: 23) and 18021CXL (SEQ ID NO: 24) primers. The PCR product was subsequently cloned using TOPO pCR2.1 vector to create plasmid pCXL2313.2 (pCR2.1 42Kp-VP5). However, pCXL2313.2 was found to contain no TN5T sequence at the end of the VP5 gene due the design of primer 18020CXL. Therefore, a new set of primers, 18041CXL (SEQ ID NO:46) and 18042CXL (SEQ ID NO:47), was synthesized and used to introduce the T5NT sequence at the end of the VP5 gene in plasmid pCXL2313.2. The site-directed mutagenesis was carried out using Stratagene's QuickChange kit, and the resulting plasmid, pCXL2399.3, was sequenced and confirmed to contain the correct 42Kp-AHSV-9-VP5 expression cassette flanked by SpeI sites.

Figure 11:
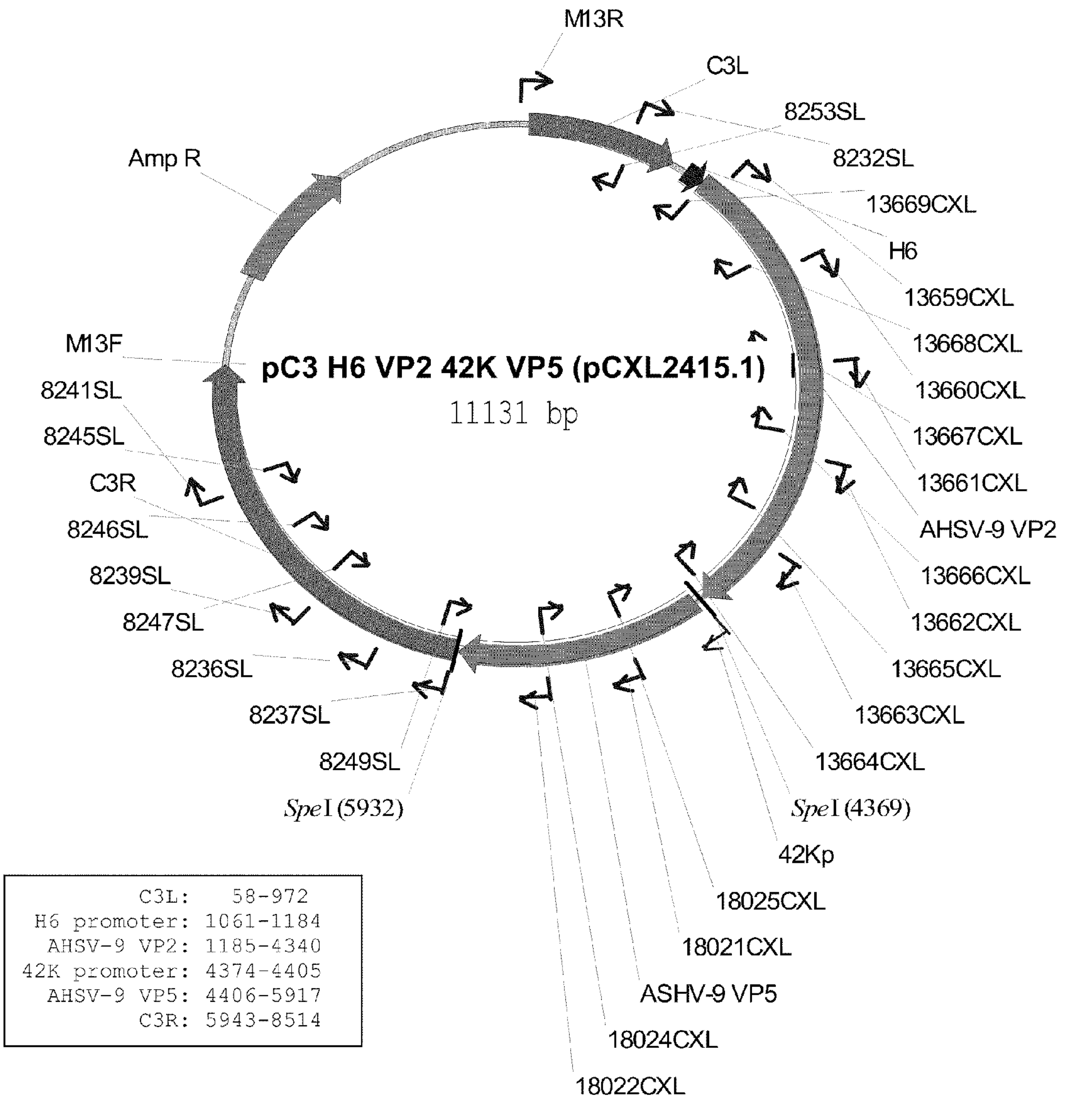
FIG. 11 provides the map and relevant SEQ ID NOs (18-21) for pCXL2415.1 (pALVAC C3 AHSV-9H6 VP2 42K VP5).

Plasmid pCXL2399.3 was subsequently digested with SpeI, and the 1556 bp fragment containing the 42Kp-AHSV-9-VP5 expression cassette was isolated and cloned into the SpeI site of plasmid pCXL2328.4 to create pCXL2415.1 (SEQ ID NO:22), which is an ALVAC C3 donor containing the double expression cassettes H6p-AHSV-9-VP2/42Kp-AHSV-9-VP5 in a head to tail orientation (FIG. 11). The predicted molecular weights for AHSV-9-VP2 and AHSV-9-VP5 are 123.5 kDa and 56.8 kDa, respectively. The isoelectric points for VP2 and VP5 are 8.14 and 5.96, respectively, and the proteins expressed largely in the cytoplasm.

Example 6

Construction of Recombinant Viral Vector vCP2383 (ALVAC C3 H6p-Synthetic AHSV-9-VP2/42Kp-Synthetic AHSV-9-VP5)

The vCP2383 recombinant viral vector was produced according to the in vitro recombination (IVR) scheme depicted in FIG. 12. The IVR was performed by transfecting primary chicken embryonic fibroblast (CEF) cells with 13.2 μg SapI-linearized donor plasmid pCXL2415.1 using FuGENE® HD transfection reagent (Roche, Cat #04709705001). The transfected CEF cells were subsequently infected with ALVAC ($4.4\times10^{10}$ pfu/mL) as the rescue virus at a multiplicity of infection (MOI) of 10. After 24 hours, the transfected-infected cells were harvested, sonicated and used for recombinant virus screening.

The recombinant plaques were screened based on the plaque lift hybridization method (Sambrook et al., 1982) using AHSV-9-VP5 specific probe which was labeled with horseradish peroxidase according to the manufacturer's protocol (Amersham Cat# RPN3001). After 4 sequential rounds of plaque purification, the recombinant designated as vCP2383.3.1.1.1 and vCP2383.9.1.1.1 were generated and confirmed by hybridization as 100% positive for the AHSV insert and 100% negative for C3 loci. Single plaques were selected from the final round of plaque purification, and expanded to obtain P1 (T-25 flask), P2 (T-75 flask) and P3 (6× roller bottle) stocks to amplify vCP2383.3.1.1.1. The infected cell culture fluid from the roller bottles was harvested and concentrated to produce the virus stock (4.5 mL of vCP2383.3.1.1.1 at $2.2\times10^{10}$ pfu/mL).

Example 7

Analysis of Recombinant Viral Vector vCP2383 (ALVAC C3 H6p-Synthetic AHSV-9-VP2/42Kp-Synthetic AHSV-9-VP5)

The P3 stock was re-confirmed by hybridization, as 100% positive for the AHSV-9-VP2 and AHSV-9-VP5 inserts, and 100% negative for the C3 loci.

Figure 13:
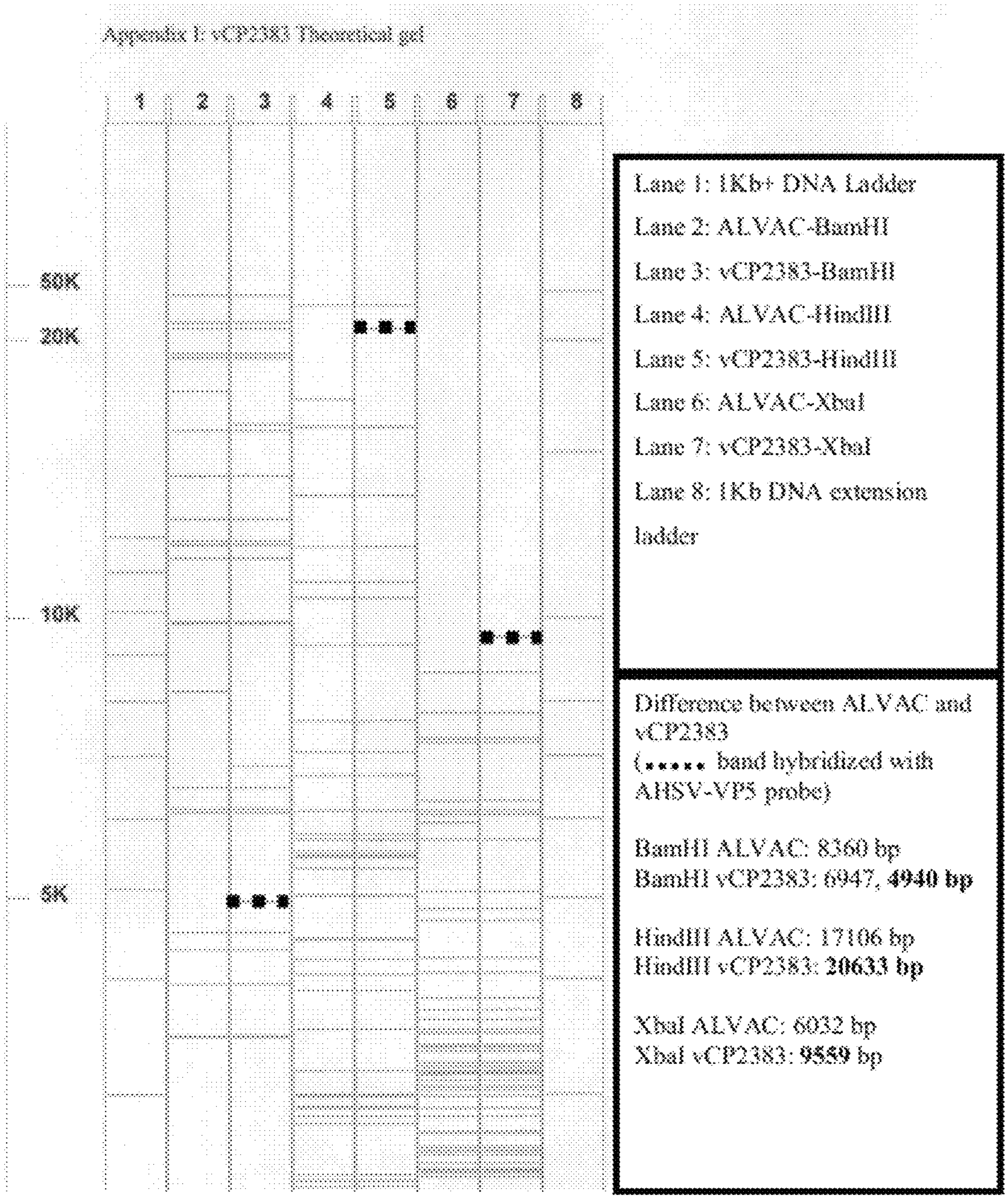
FIG. 13 provides a theoretical restriction enzyme gel for the genomic DNA was created in Vector NTI.
Figure 14:
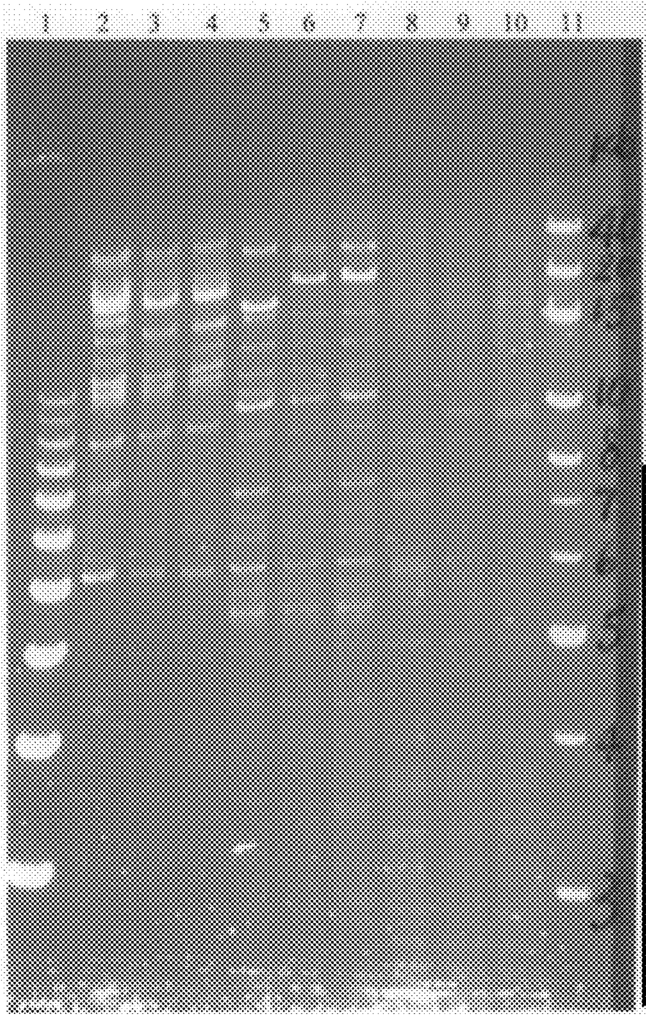
FIG. 14 provides the 0.8% agarose gel electrophoresis results of genomic DNA extraction from vCP2383.3.1.1.1 and vCP2383.9.1.1.1, digested with BamHI, HindIII or XbaI.

Genomic analysis: A theoretical vCP2383 genomic DNA restriction enzyme gel was produced using Vector NTI (FIG. 13). To perform the real-life experiment, genomic DNA was extracted from vCP2383.3.1.1.1 and vCP2383.9.1.1.1, digested with BamHI, HindIII or XbaI, and separated by 0.8% agarose gel electrophoresis. The results revealed the correct insertion of the foreign gene sequence. (FIG. 14).

Figure 15:
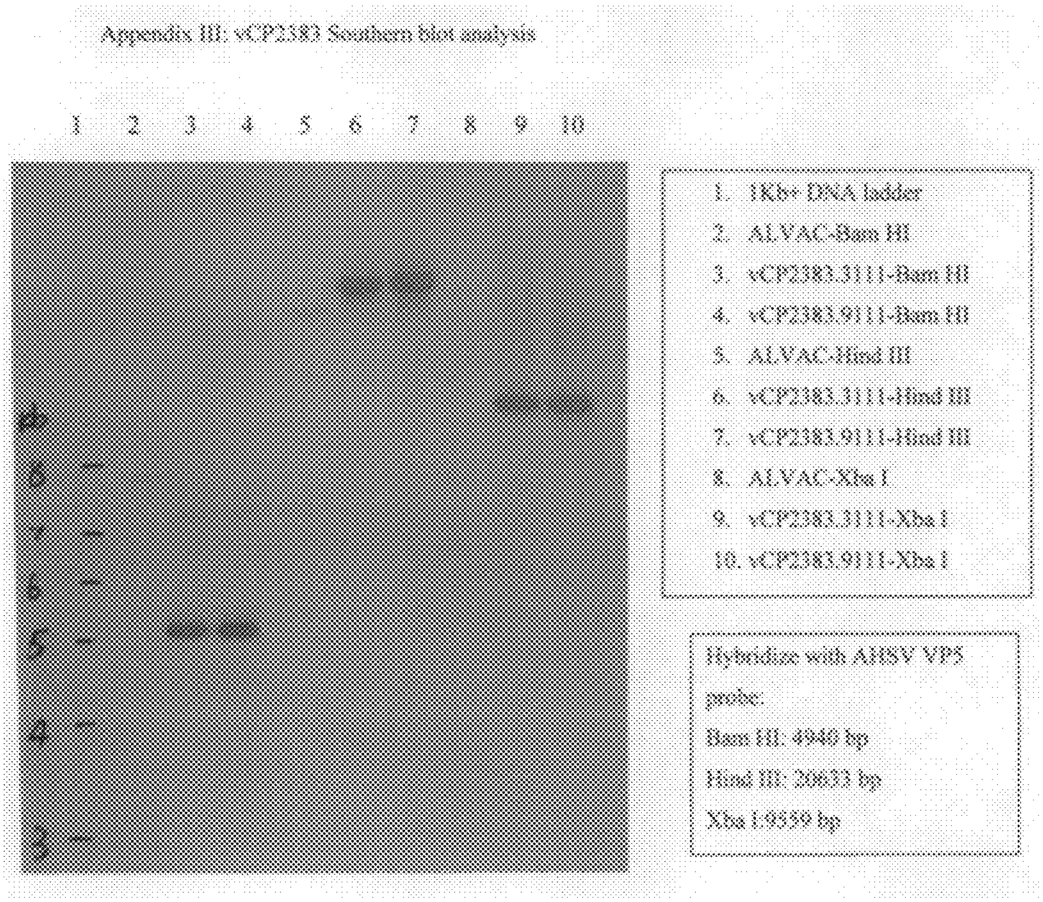
FIG. 15 provides the Southern blot analysis of vCP2383 using an AHSV-4-VP5 probe.

Southern blot: The genomic DNA digested with BamHI, HindIII, or XbaI was transferred to a nylon membrane and Southern blot analysis was performed by probing with the AHSV-9-VP5 probe. Bands of the expected sizes were observed, namely 4940 bp BamHI, 20633 bp HindIII and 9559 bp XbaI. The results indicated the correct insertion of AHSV-9-VP2 and AHSV-9-VP5 into the C3 loci (FIG. 15).

Figure 16:
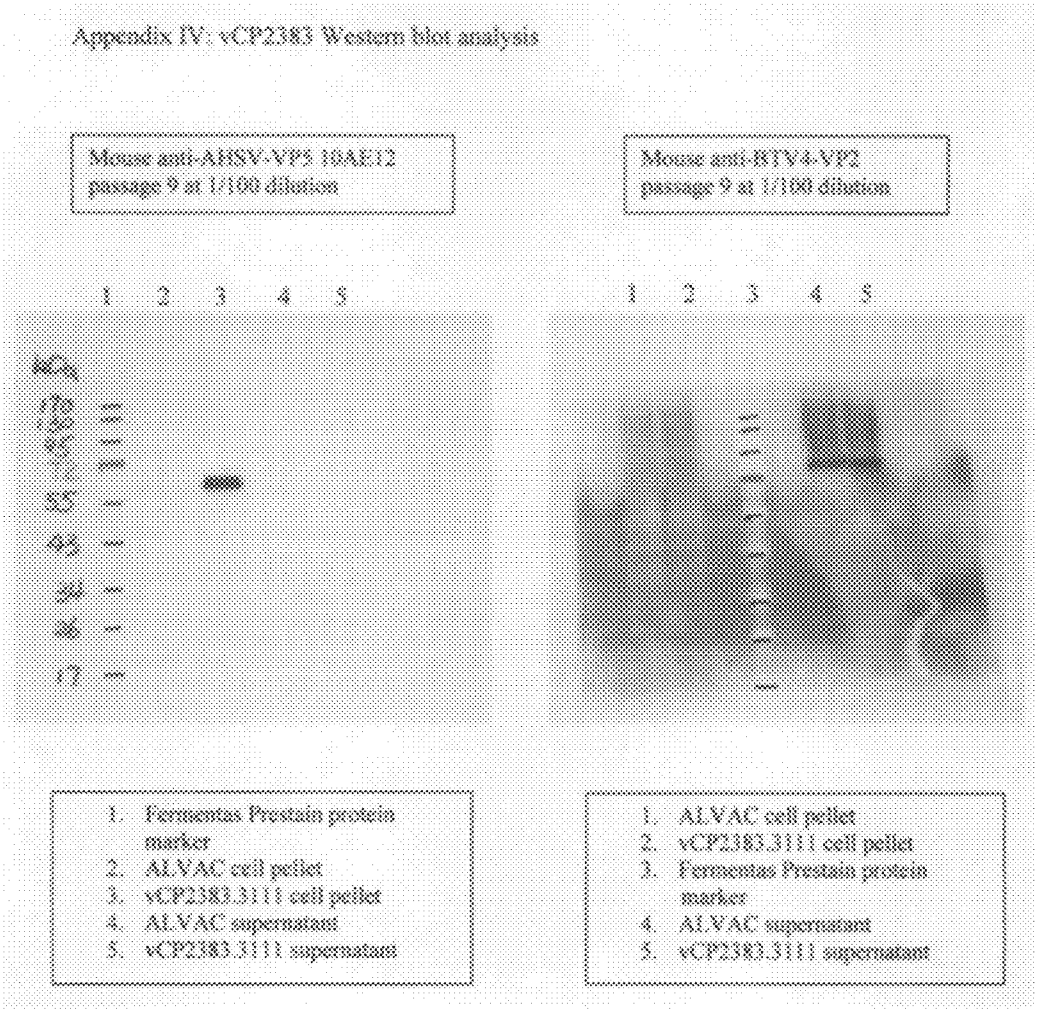
FIG. 16 provides Western blot results of the analysis of recombinant vCP2383 indicating the expression of the AHSV9 VP5 protein.

Expression analysis: Primary CEF cells were infected with the P3 stock of vCP2383.3.1.1.1 at a MOI of 10 and incubated at 37° C. for 26 hrs. The cells and culture supernatant were harvested and sample proteins were separated on a 10% SDS-PAGE gel, transferred to IMMOBILON nylon membrane, and probed separately with the mouse anti-VP5 of AHSV (African horse sickness virus) 10AE12 Passage 9 antibody (Martinez-Torrecuadrada, J et al., 1999) at a dilution of 1:100. Peroxidase conjugated goat anti-mouse antiserum was used as a secondary antibody and the bands were visualized using Amersham detection regents. With the mouse anti-AHSV VP5 mAb, the protein bands between 55 to 72 kDa were detected in the cell pellets of vCP2383.3.1.1.1, indicating the expression of the AHSV-9-VP5 protein (FIG. 16). AHSV9-VP5 protein expression was not detected in the culture medium. The expression of AHSV9-VP2 was not detected by the mouse anti-BTV4-VP2 mAb (Merial proprietary material).

Figure 17:
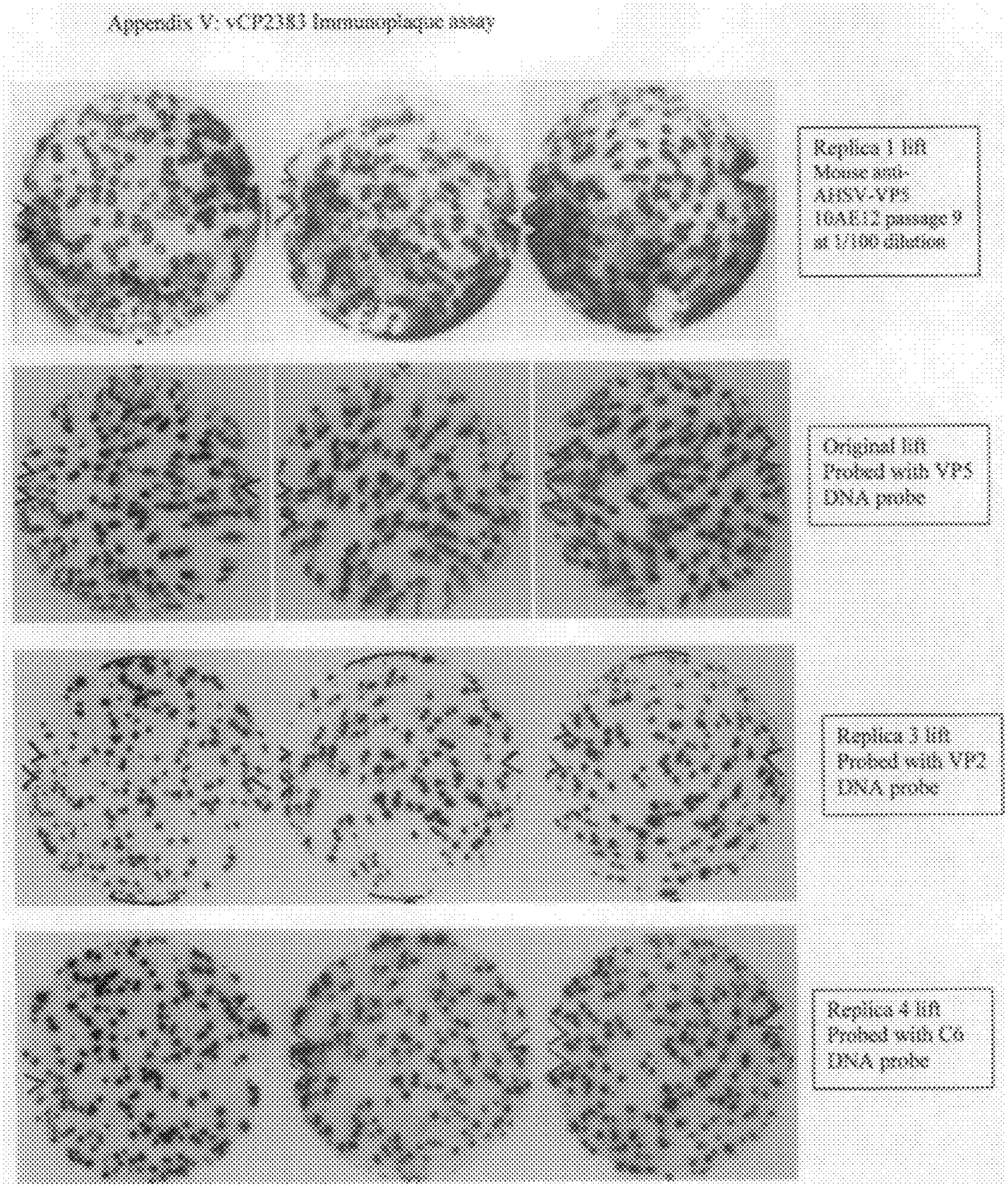
FIG. 17 provides the immunoplaque results indicating 100% homogeneity of the vCP2383.3.1.1.1 population using mouse anti-AHSV VP5 mAb 10AE12 Passage 9 at a dilution of 1:100.

Immunoplaque: The homogeneity of the vCP2383.3.1.1.1 population was 100% as evidenced by an immunoplaque assay, using mouse anti-AHSV VP5 mAb 10AE12 Passage 9 (Martinez-Torrecuadrada, J et al., 1999) at a dilution of 1:100 (FIG. 17).

Figure 18:
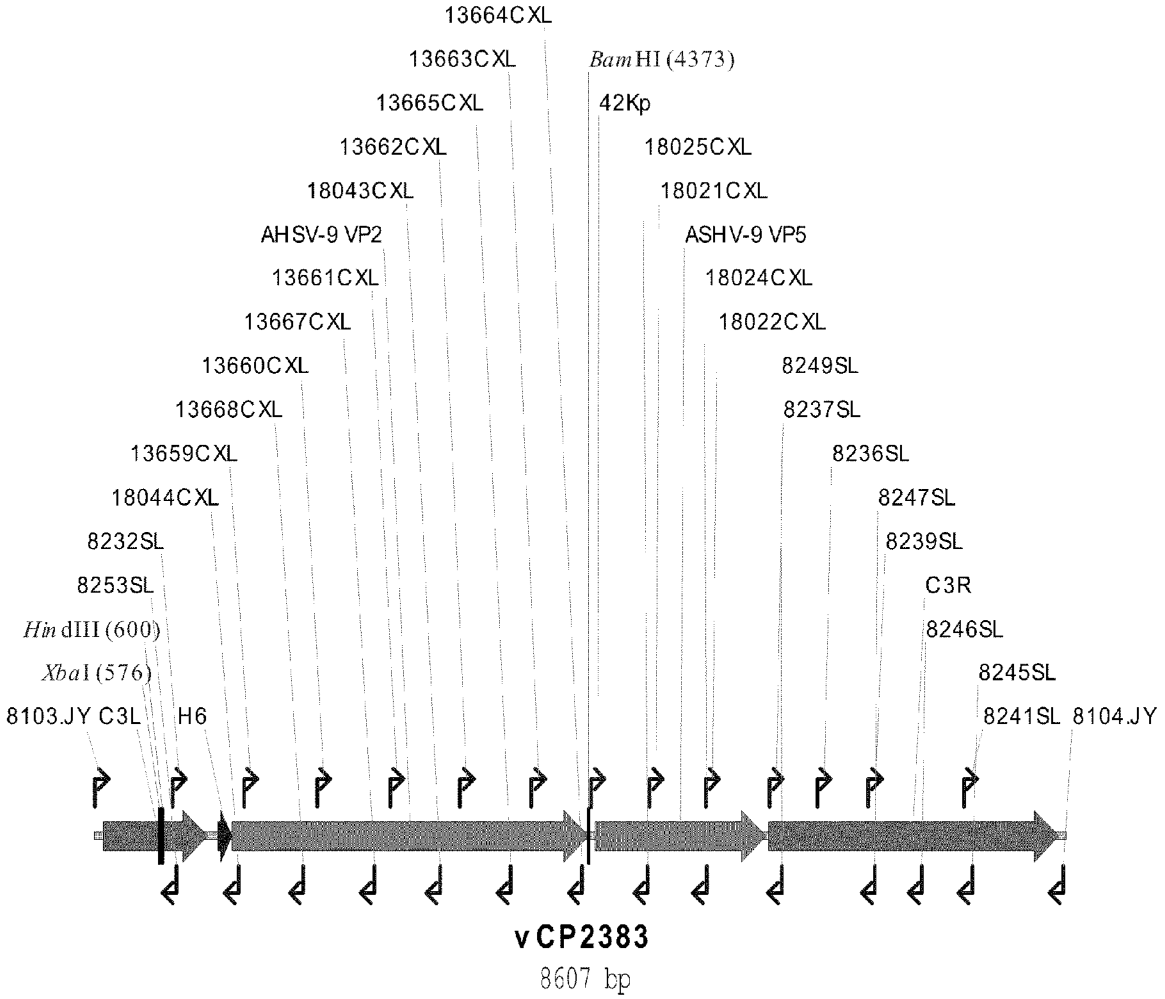
FIG. 18 provides a map of the primers used to amplify the entire C3L-H6 AHSV9 VP2-42K AHSV9 VP5-C3R fragment and the relevant SEQ ID NOs (27-31) for the recombinant vCP2383 sequences.

Sequence analysis: A more detailed analysis of the P3 stock genomic DNA was performed by PCR amplification and sequence analysis of the flanking arms of the C3 locus and the AHSV-9-VP2 (SEQ ID NO:28) and AHSV-9-VP5 (SEQ ID NO:29) inserts. Primers 8103.JY (SEQ ID NO:13) and 8104.JY (SEQ ID NO:14) (FIG. 18) were used to amplify the entire C3L-H6-AHSV-9-VP2-42K-AHSV-9-VP5-C3R fragment. The resulting sequence, namely SEQ ID NO:27, indicated that the sequences of the AHSV-9-VP2 (SEQ ID NO:28) and AHSV-9-VP5 (SEQ ID NO:29) inserts and the C3 left and right arms around the AHSV inserts in vCP2383.3.1.1.1 were correct.

```
Primers for amplifying the AHSV-9-VP5 probe
18020CXL (SEQ ID NO: 23) 5':
CTAGACTAGTTTACTATCATTTCACGCCGAACAGCA
```

-continued

```
18021CXL (SEQ ID NO: 24) 5':
GCAAGGACCAGAGCGAGCGGATCA

Primers for amplifying the AHSV-9-VP2 probe
13660CXL (SEQ ID NO: 25) 5':
AGGCCTTCGCCGGCAACAGCCTGCT

13665CXL (SEQ ID NO: 26) 5':
AGGGCATCGATCAGGAACTCGCTCT

Primers for PCR amplification of the vCP2383 C3
arms plus insert
8103.JY (SEQ ID NO: 13) 5':
GAGGCATCCAACATATAAAGAAGACTAAAG 3'

8104.JY (SEQ ID NO: 14) 5':
TAGTTAAATACTCATAACTCATATCTG 3'
```

Example 8

Construction of pJSY2247.2 (SEQ ID NO:32) Donor Plasmid Expressing the H6 Promoter-Driven Synthetic AHSV-5-VP2 and the 42K Promoter-Driven Synthetic AHSV-5-VP5

Figure 22:
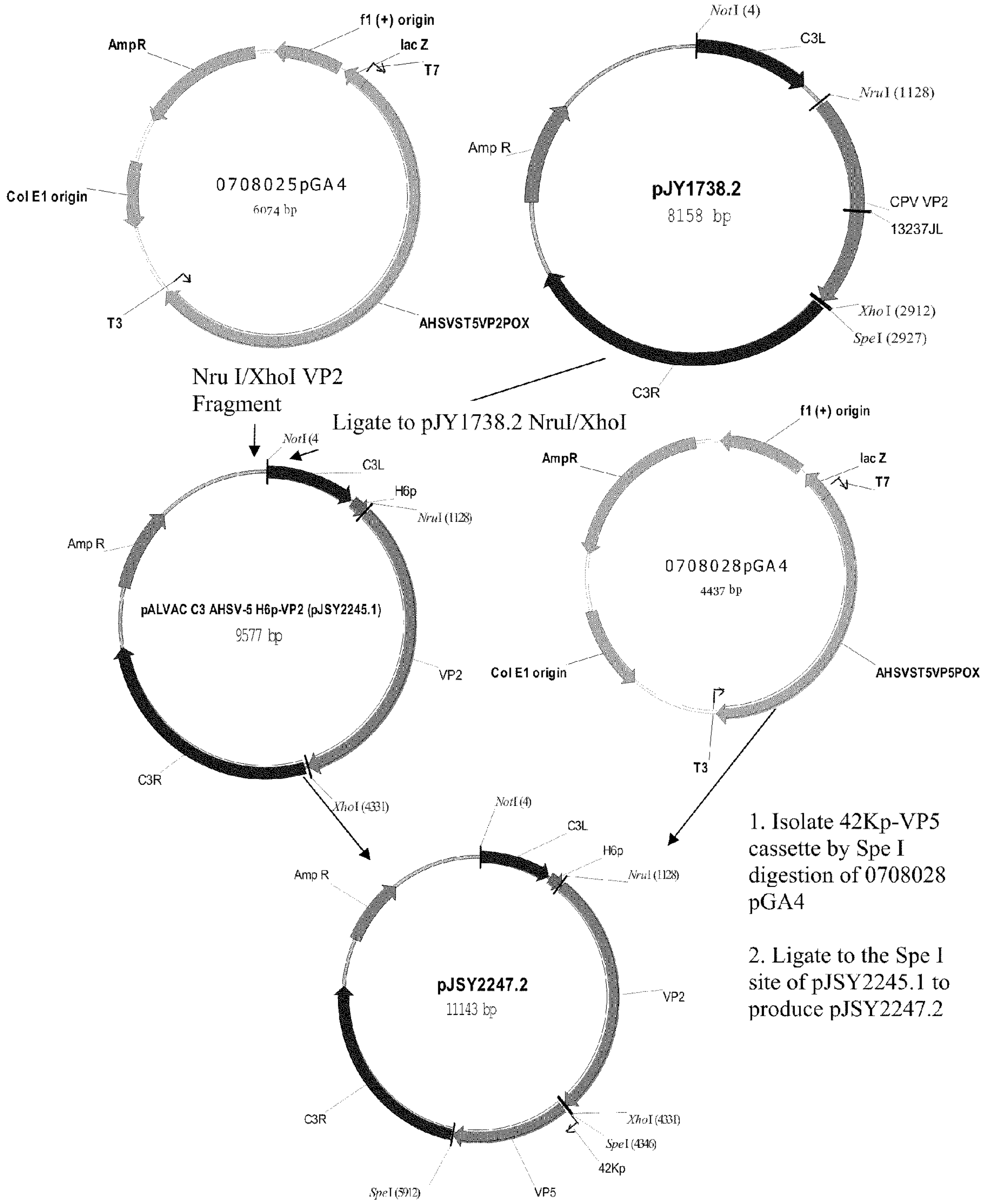
FIG. 22 shows the construction scheme for pJSY2247.2, the C3 donor plasmid for generation of an ALVAC recombinant expressing AHSV5-VP2 and VP5 proteins.

The overall construction scheme for pJSY2247.2 (SEQ ID NO:32) is depicted in FIG. 22. The plasmid containing synthetic AHSV-5-VP2 (SEQ ID NO:33) gene was digested with XhoI and NruI. The resulting AHSV-5-VP2 (SEQ ID NO:33) insert was isolated and cloned into the NruI/XhoI sites of an ALVAC C3 donor plasmid prepared from pJY1738.2 (pC3 H6p CPV-VP2) to create pJSY2245.1, an ALVAC C3 donor plasmid containing the H6p-AHSV-5-VP2 expression cassette.

Figure 23:
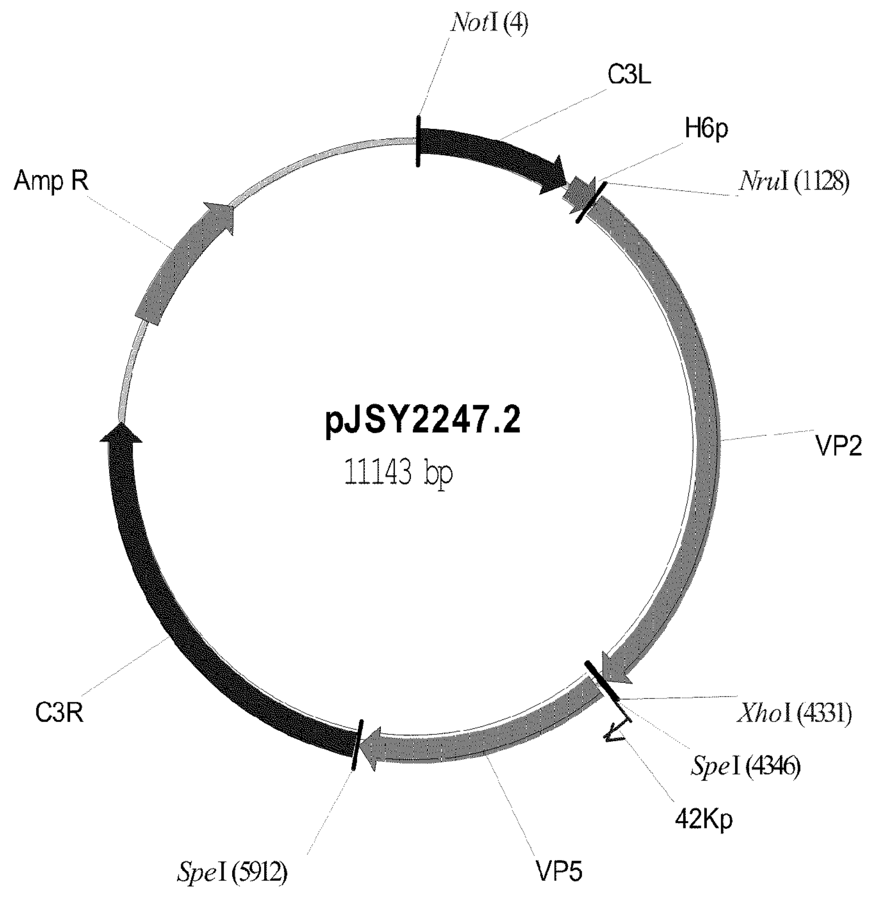
FIG. 23 provides the map and relevant SEQ ID NOs for pJSY2247.2 (pALVAC C3 AHSV5H6 VP2 42K VP5) sequences.

An expression cassette 42Kp-AHSV-5-VP5 flanked by the SpeI site was isolated from the plasmid containing synthetic AHSV-5-VP5 (SEQ ID NO:34) by SpeI digestion, and was then cloned into the SpeI site of plasmid pJSY2245.1 to create an ALVAC C3 donor plasmid containing the double expression cassettes pJSY2247.2 (SEQ ID NO:32; H6p-AHSV-5-VP2/42Kp-VP5), which was sequenced and confirmed to contain the correct sequences. A diagram of the plasmid pJSY2247.2 and corresponding SEQ ID NOs are indicated in FIG. 23. The Molecular Weights for synthetic AHSV-5-VP2 (SEQ ID NO:35) and synthetic AHSV-5-VP5 (SEQ ID NO:36) were about 122.9 kDa and about 57.1 KDa, respectively. The isoelectric points for synthetic AHSV-5-VP2 (SEQ ID NO:35) and synthetic AHSV-5-VP5 (SEQ ID NO:36) were about 8.4 and 5.77, respectively. Both viral proteins were found primarily in the cytoplasm.

Example 9

Construction of Recombinant Viral Vector vCP2398 (SEQ ID NO:41) (H6-Synthetic AHSV-5-VP2-42K-Synthetic AHSV-5-VP5)

Figure 24:
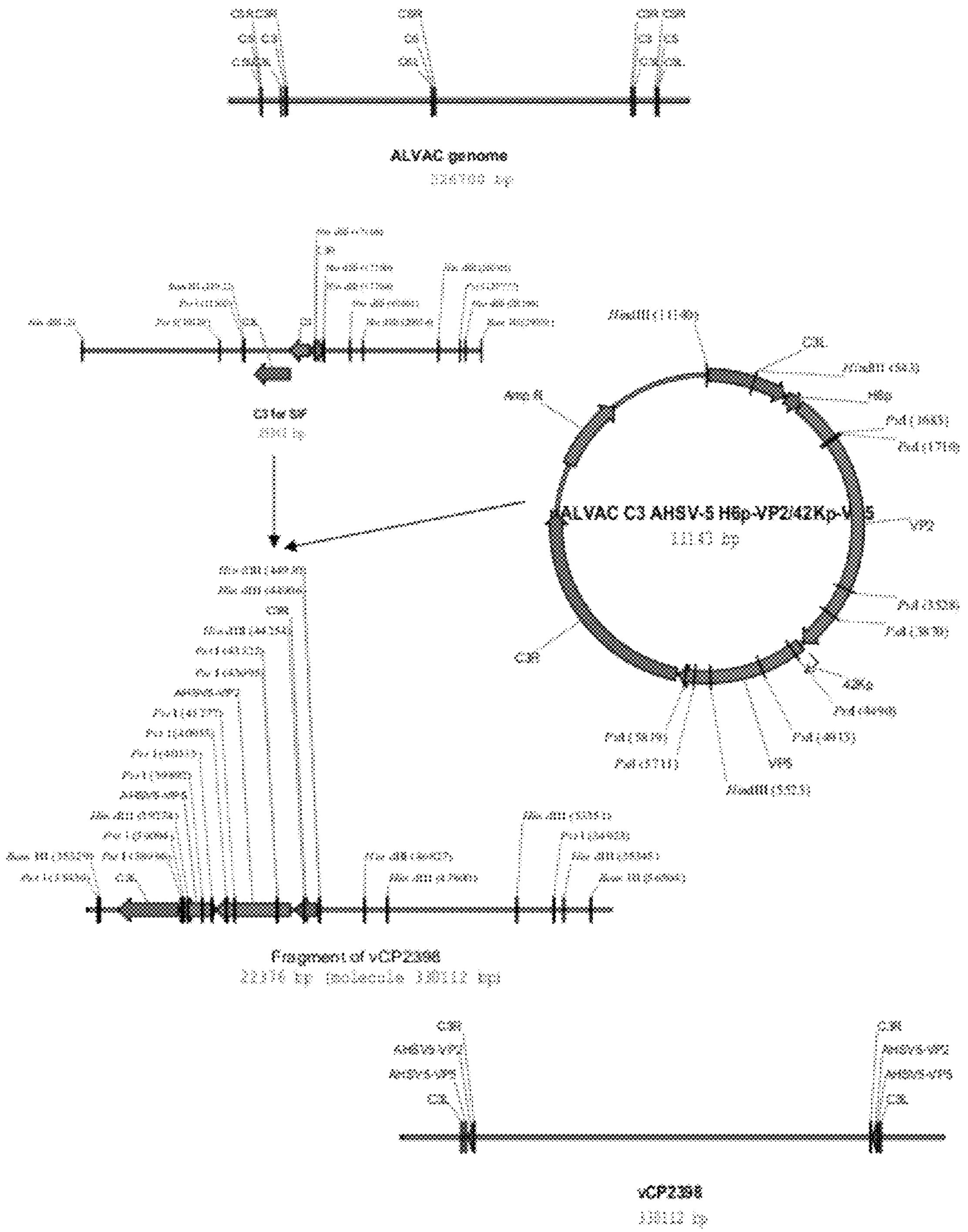
FIG. 24 provides the in vitro recombination scheme for vCP2398 (ALVAC C3 H6-synthetic AHSV5 VP2/42K-synthetic AHSV5 VP5).

The vCP2398 (SEQ ID NO:41) recombinant viral vector was produced according to the in vitro recombination (IVR) scheme depicted in FIG. 24. The IVR was performed by transfecting primary CEF cells with 15 μg NotI-linearized pJSY2247.2 (SEQ ID NO:32) donor plasmid using FuGENE reagent (Roche, Cat #04709705001). The transfected cells were subsequently infected with ALVAC (1) ($2\times10^{10}$ pfu/mL HM1355) as the rescue virus at a MOI of 10. After 24 hours, the transfected-infected cells were harvested, sonicated and used for recombinant virus screening.

The recombinant plaques were screened based on the plaque lift hybridization method (Sambrook et al., 1982) using AHSV-5-VP2 specific probe which was labeled with horseradish peroxidase according to the manufacturer's protocol (Amersham Cat# RPN3001). After 3 sequential rounds of plaque purification, the recombinant designated as vCP2398.2.1.1 was generated and confirmed by hybridization as 100% positive for the AHSV insert and 100% negative for the empty C3 site Single plaques were selected from the final round of plaque purification, and expanded to obtain P1 (T-25 flask), P2 (T-75 flask) and P3 (roller bottle) stocks to amplify vCP2398.2.1.1. The recombinant was re-confirmed at the P2 level by hybridization and found to be 100% positive for the insert and 100% negative for the empty C3 site. The infected cell culture fluid from the roller bottles was harvested and concentrated to produce the virus stock (2.6 mL of vCP2398.2.1.1 at $3.3\times10^{10}$ pfu/mL).

Example 10

Analysis of Recombinant Viral Vector vCP2398 (SEQ ID NO:41) (H6-Synthetic AHSV-5-VP2-42K-Synthetic AHSV-5-VP5)

The P3 stock was re-confirmed by hybridization, as 100% positive for the AHSV-5-VP2 and AHSV-5-VP5 inserts, and 100% negative for the empty C3 site.

Figure 25:
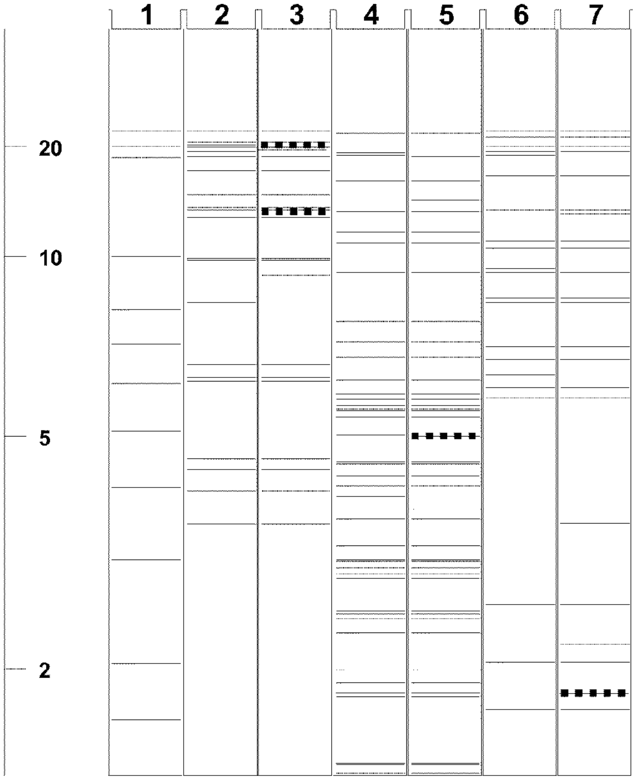
FIG. 25 provides a theoretical restriction enzyme gel for the genomic vCP2398 DNA that was created in Vector NTI.
Figure 26:
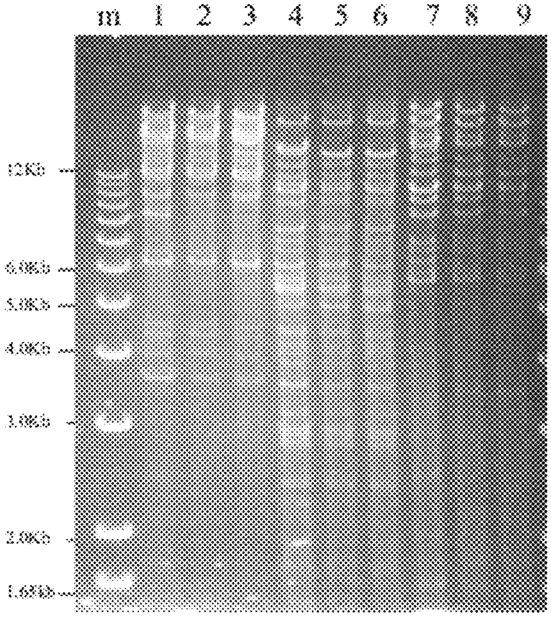
FIG. 26 provides an 0.8% agarose gel electrophoresis result of genomic DNA extraction from vCP2398.2.1.1 and 3.1.1, digested with BamHI, HindIII or PstI.

Genomic analysis: A theoretical restriction enzyme gel for the genomic DNA was created in Vector NTI and is shown in FIG. 25. The genomic DNA was extracted from vCP2398.2.1.1, digested with BamHI, HindIII or PstI, and separated by 0.8% agarose gel electrophoresis. The results revealed the correct insertion of the foreign gene sequence. (FIG. 26).

Southern blot: The genomic DNA digested with BamHI, HindIII, or PstI was transferred to the nylon membrane and Southern blot analysis was performed by probing with the AHSV-5-VP2 probe. Specific 20975 bp and 11899 bp BamHI, 4980 bp HindIII and 1818 bp PstI bands were observed at the expected sizes. The results indicated the correct insertion of AHSV-5-VP2 and AHSV-5-VP5 into the C3 locus (FIG. 27).

Figure 28:
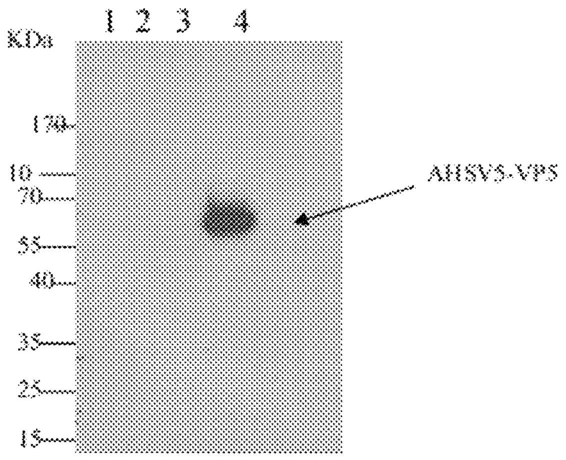
FIG. 28 provides Western blot results of the analysis of recombinant vCP2398 indicating the expression of the AHSV5 VP5 protein.

Expression analysis: Primary CEF cells were infected with the P3 stock of vCP2398.2.1.1 at a MOI of 10 and incubated at 37° C. for 24 hrs. The cells and culture supernatant were then harvested. Sample proteins were separated on a 10% SDS-PAGE gel, transferred to Immobilon nylon membrane, and probed separately with the mouse anti-VP5 of AHSV (African horse sickness virus) 10AE12 Passage 9 antibody (Martinez-Torrecuadrada, J et al., 1999) at a dilution of 1:100. Peroxidase conjugated goat anti-mouse antiserum was used as a secondary antibody and the bands were visualized using Amersham detection regents. With the use of the mouse anti-AHSV VP5 mAb, protein bands between 55 to 72 kDa were detected in the cell pellets of vCP2398.2.1.1, indicating the expression of the AHSV-5-VP5 protein (FIG. 28). AHSV-5-VP5 protein expression was not detected in the culture medium.

Figure 29:
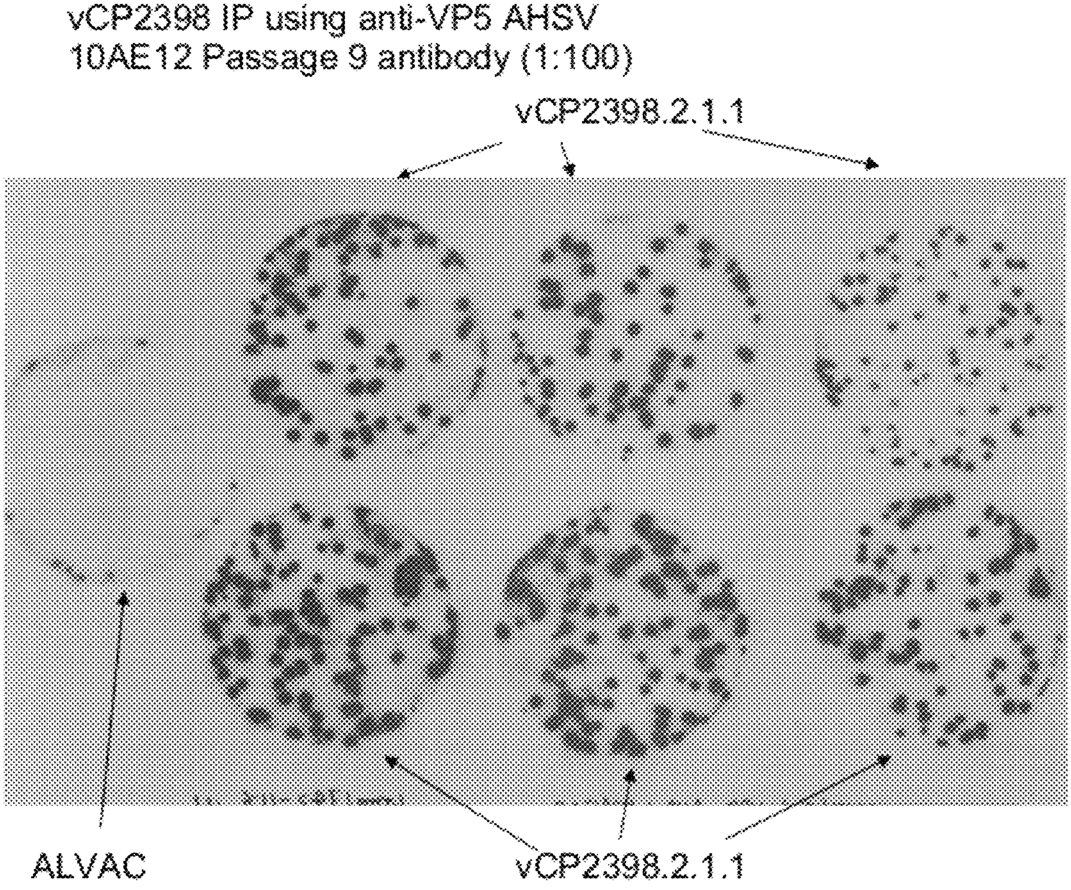
FIG. 29 provides the immunoplaque results indicating 100% homogeneity of the vCP2383.2.1.1 population using mouse anti-AHSV VP5 mAb 10AE12 Passage at a dilution of 1:100.

Immunoplaque: The homogeneity of the vCP2398.2.1.1 population was 100% as evidenced by an immunoplaque assay, using mouse anti-AHSV VP5 mAb 10AE12 Passage 9 (Martinez-Torrecuadrada, J et al., 1999) at a dilution of 1:100 (FIG. 29).

Figure 30:
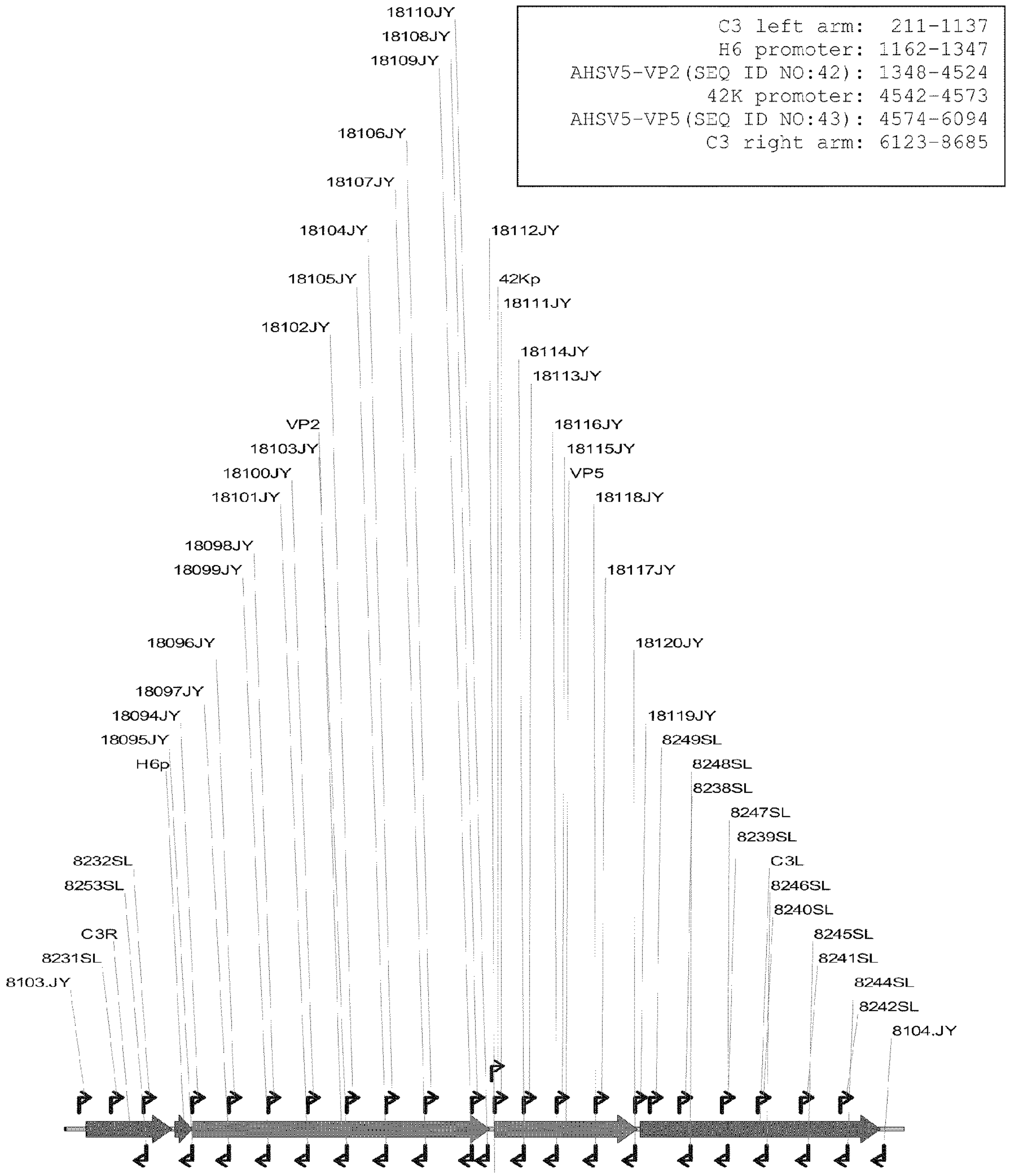
FIG. 30 provides a map of the primers used to amplify the entire C3L-H6 AHSV5 VP2-42K AHSV5 VP5-C3R fragment for the recombinant vCP2398.

Sequence analysis: A more detailed analysis of the P3 stock genomic DNA was performed by PCR amplification and sequence analysis of the flanking arms of the C3 locus and the AHSV-5-VP2 and AHSV-5-VP5 inserts. Primers 8103.JY/8104.JY were used to amplify the entire C3R-AHSV-5-VP2/VP5 inserts-C3L fragment. A primer map is shown in FIG. 30. The resulting sequence, namely SEQ ID NO:41, indicated that the sequences of the AHSV-5-VP2 and AHSV-5-VP5 inserts and the C3 left and right arms around the AHSV inserts in vCP2398.2.1.1 were correct.

```
Primers for amplifying the AHSV-5-VP2 probe:
18098.JY
                                         (SEQ ID NO: 37)
5'GGATCGAGCGGGACGAGCTGGACG 3'

18103.JY
                                         (SEQ ID NO: 38)
5'GCCAGCCGTACTGGAACTTGTAGC 3'

Primers for amplifying the AHSV-5-VP5 probe:
18115.JY
                                         (SEQ ID NO: 39)
5' TGCTGGACCTGAGCGCCGAGGTGA 3'

18120.JY
                                         (SEQ ID NO: 40)
5' TCAGGCGATCTTCACGCCGAACAG 3'

Primers for PCR amplification of the vCP2398 C3
arms plus insert:
8103.JY
                                         (SEQ ID NO: 13)
5' GAGGCATCCAACATATAAAGAAGACTAAAG 3'

8104.JY
                                         (SEQ ID NO: 14)
5' TAGTTAAATACTCATAACTCATATCTG 3'
```

Example 11

Production of Experimental Vaccines

Three different vaccines were produced using an active ingredient produced at the 5th passage after the master seed virus stock (MSV+5) after a culture of 4 days of the vCP2377 (produced according to EXAMPLE 6) on confluent monolayers of chicken embryo fibroblast (CEF) and treatment of the harvest. The MSV+5 passage is representative (from the genomic/genetic structure stability perspective) of the commercial vaccine product, and is typically used for producing commercial batches. The three vaccines (produced in GMP conditions) used CARBOMER as adjuvant (4 mg/mL) and are differentiated by their concentration of antigen. The specific CARBOMER used was CARBOMER®/CARBOPOL® 974P (Pharmaceutical grade, produced by Goodrich Chemicals Europe NV, Belgium). The concentration used was 4 mg/mL with 1 dose=1 mL. CARBOMER® 974P is used interchangeably with CARBOPOL® 974P throughout this application.

The infective titer of the active ingredient vCP2377 used in formulation of the vaccines was 8.89 Log 10 CCID50/mL. The vaccine formulations also contained the following ingredients: an adjuvant made up of a 1.5% solution of carbomer in water for injection containing 0.1% NaCl; a diluent that was physiologically buffered at pH 7.1; and a 0.1N NaOH solution for pH regulation.

The active ingredient stored at −70° C. was thawed in a water bath (37° C.) no more than 72 hours before use. Immediately after thawing, they were stored at +5° C. In a sterile vessel with stirring system, 80% of the buffered physiological saline pH 7.1 for the formulation was introduced at room temperature. Under stirring was added the active ingredient. After homogenization, the 1.5% solution of CARBOMER® 974P was added slowly with pH regulation (pH 7.1) using NaOH 1N. During formulation, the pH value preferably remained between 6.5 and 7.3 and a final concentration of CARBOMER of 4 mg/mL. When all the CARBOMER® 974P was added, the remaining quantity of buffered physiological saline pH 7.1 was added under stirring to complete the final volume.

If necessary, the pH can be adjusted to 7.1±0.2 by addition of sodium hydroxide (1N) or hydrochloric acid (1N). The bulk was homogenized by stiffing at a temperature not lower than +2° C. for at least 2 hours. The bulk obtained was stored at +5° C. (±3° C.) until filling. The composition of the vaccines is summarized in TABLE 1.

TABLE 1

| Code | Name | Batch | Volume (mL) |
|---|---|---|---|
| | Vaccine batch 87859A010 Target Formulation: 7.5 $Log_{10}$ $CCID_{50}$/mL | | |
| | vCP2377 | 8C23775E05 | 40.7 |
| | CARBOMER ® 974P (1.5% solution) | 8CB011311H50 | 266.7 |
| 1045001007 | Buffered physiological saline pH 7.1 | 285142 | 668.6 |
| 1045000842 | NaOH 1N | 283938 | 47.9 |
| | Vaccine batch 87859A020 Target Formulation: 7.2 $Log_{10}$ $CCID_{50}$/mL | | |
| | vCP2377 | 8C23775E05 | 20.4 |
| | CARBOMER ® 974P (1.5% solution) | 8CB011311H50 | 266.7 |
| 1045001007 | Buffered physiological saline pH 7.1 | 285142 | 689.2 |
| 1045000842 | NaOH 1N | 283938 | 47.7 |
| | Vaccine batch 87859A030 Target Formulation: 6.8 $Log_{10}$ $CCID_{50}$/mL | | |
| | vCP2377 | 8C23775E05 | 8.1 |
| | CARBOMER ® 974P (1.5% solution) | 8CB011311H50 | 266.7 |
| 1045001007 | Buffered physiological saline pH 7.1 | 285142 | 701.3 |
| 1045000842 | NaOH 1N | 283938 | 47.9 |

Example 12

Verification of the Identity of 3 Vaccine Batches Containing vCP2377 Recombinant Viral Vector Expressing Synthetic AHSV-4-VP2 and Synthetic AHSV-4-VP5 Capsid Proteins The 3 vaccines containing vCP2377 adjuvanted with ®974P were described according to the following: batch 87859A011, target titer 7.5 log 10 DICC50/mL, batch 87859A021, target titer 7.2 log 10 DICC50/mL, and batch 87859A031, target titer 6.8 log 10 DICC50/mL. The vCP2377 before formulation was vCP2377-1-CEPI 7007/17/07/07 and the titer was 8.3 log 10 DICC50/mL A vaccine comprising two "non relevant" recombinant canarypox (EIV) adjuvanted with CARBOPOL® 974P was used as negative control (batch—76435V191, titer 7.34 log 10 DICC50/mL).

Methods: The expression of viral proteins AHSV-4-VP2 and AHSV-4-VP5 was verified by indirect immunofluorescence and Western blot and was used to confirm the identity of the vaccines. The reagents included the following: anti-AHSV VP5 10AE12 (INGENASA, 28037 Madrid), pig polyclonal serums anti-VP2 serotype 4 AHSV (GENOVAC), anti-cMyc clone 4A6 (mouse monoclonal IgG1, Upstate, cat #05-724), anti-mouse IRDye800, anti-guinea pig IRDye800, anti-mouse Cy3, and anti-guinea pig Cy3. The plasmids encoding the synthetic AHSV-4-VP2 (SEQ ID NO:1) and AHSV-4-VP5 (SEQ ID NO:2) proteins were used as positive controls: pVR1012 (control plasmid without insert); pCG050 (synthetic AHSV-4-VP2 (SEQ ID NO:4) inserted in pVR1012); pCG042 (synthetic AHSV-4-VP5 (SEQ ID NO:5) inserted in pVR1012); and pCG049 (synthetic AHSV-4-VP2 (SEQ ID NO:4)+cMyc-tag inserted in pVR1012).

For the indirect immunofluorescence, recombinant viral vector infected/plasmid transfected chicken embryonic fibroblast (CEF) cells were plated into 96 well-plates (25000 cells/well). The cells were fixed about 24 h after transfection, which equates to about 72 h after infection. The cells were then labeled using anti-VP2 and anti-VP5 primary antibodies, followed by Cy3-linked secondary antibodies. Labeled cells were observed using fluorescent microscopy.

For the Western blot, recombinant viral vector infected/plasmid transfected CEF cells were plated into 6 cm dishes (1.10e6 cells/dish). The cells were harvested about 24 h after transfection which equates to about 72 h after infection. After penetration, the harvested samples were put on acrylamide Tris-Glycine 4-20% gel. After migration, the gels were transferred onto nitrocellulose membrane, probed with anti-VP2, anti-VP5, and anti-cMyc primary antibodies, and thereafter probed with IRDye800-linked secondary antibodies. The reading was performed using an Odyssey-LiCor scanner.

Results: According to the immunofluorescence results, illustrated in FIG. 19, the VP5 protein expressed in CEF-infected cells by the 3 batches of vCP2377 adjuvanted with CARBOPOL, and with the vCP2377 before formulation (with vCP EIV as negative controls). The VP2 protein was correctly detected with a pool of 3 guinea pig serums in the vCP2377 before formulation and after formulation in the 3 batches of vCP. Nevertheless, the fluorescence was lesser with the pool of polyclonal antibodies as compared to the monoclonal anti-VP5 antibodies, and a small noise was shown on the vCP EIV negative controls.

Further, the reagents were validated using CEF transfected by plasmids encoding the individual proteins, including the control plasmid without insert (pVR1012), the synthetic AHSV-4-VP2 (SEQ ID NO:4) in pVR1012 (pCG050), the synthetic AHSV-4-VP5 (SEQ ID NO:5) in pVR1012 (pCG042), and the synthetic AHSV-4-VP2+his-tag in pVR1012 (pCG049). The VP5 protein was only shown in CEF transfected by the pCG042 plasmid. The VP2 protein was correctly detected in the CEF transfected by pCG050 and pCG049 plasmids. These results validated the technique and the reagents.

Figure 20A:
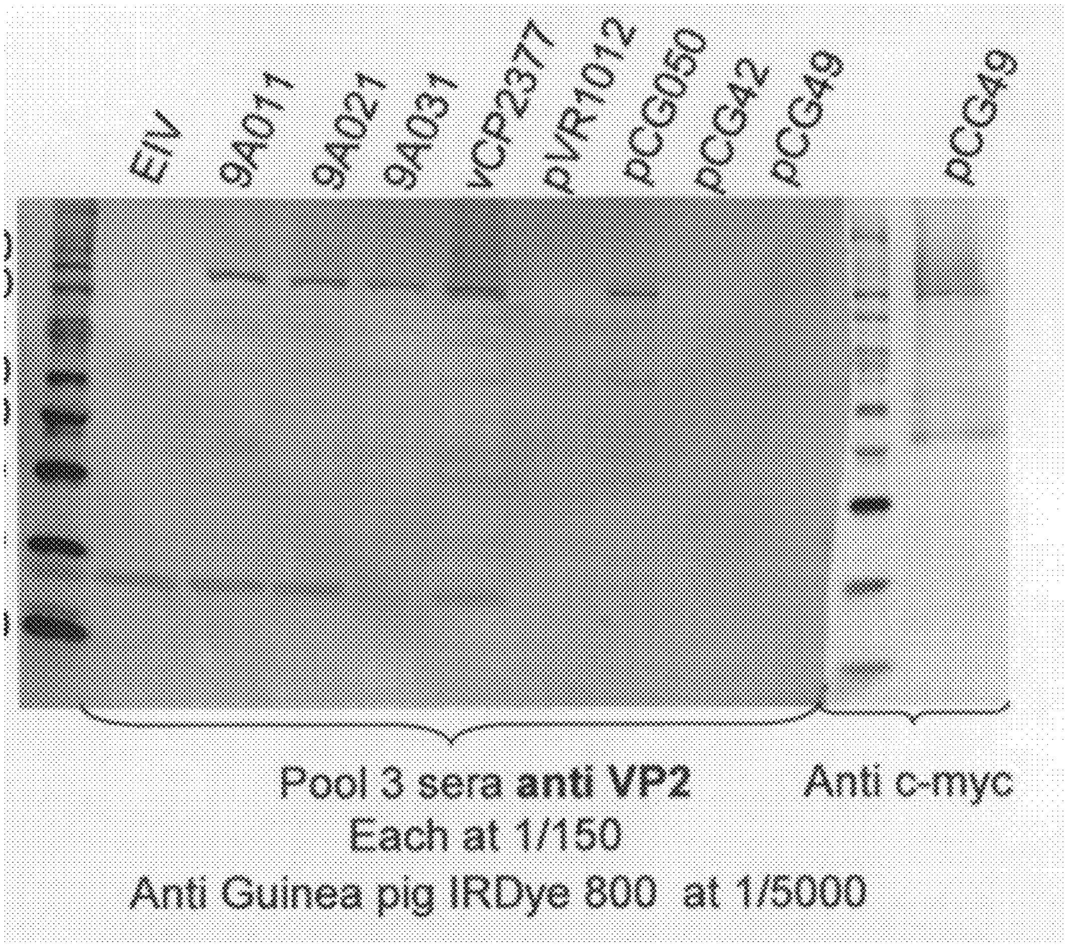
FIG. 20 A&B shows the results of western blot with infected and transfected CEF using anti-VP2 (A) and anti-VP5 (B).

FIG. 20A shows the western blot performed on lysates from infected and transfected CEF, and indicates the expression of the VP2 serotype 4 AHSV protein. The VP2 protein was detected in each of the 3 batches of vCP2377 adjuvanted with CARBOPOL (identified as 9A011, 9A021 and 9A031), and in the vCP2377 before formulation. The CEF transfected by the plasmids pCG050 (VP2 in pVR1012) and pCG049 (VP2+c-myc in pVR1012) were used as positive controls, also expressed VP2. The processing with the anti-c-myc of the CEF transfected by pCG049 plasmid was used as transfection positive control.

As predicted, no signal was detected for CEF infected by vCP EIV, or for CEF transfected by pVR1012 and pCG042. Furthermore the anti-VP2 polyclonal antibodies were specific to the VP2 serotype 4 AHSV protein.

Figure 20B:
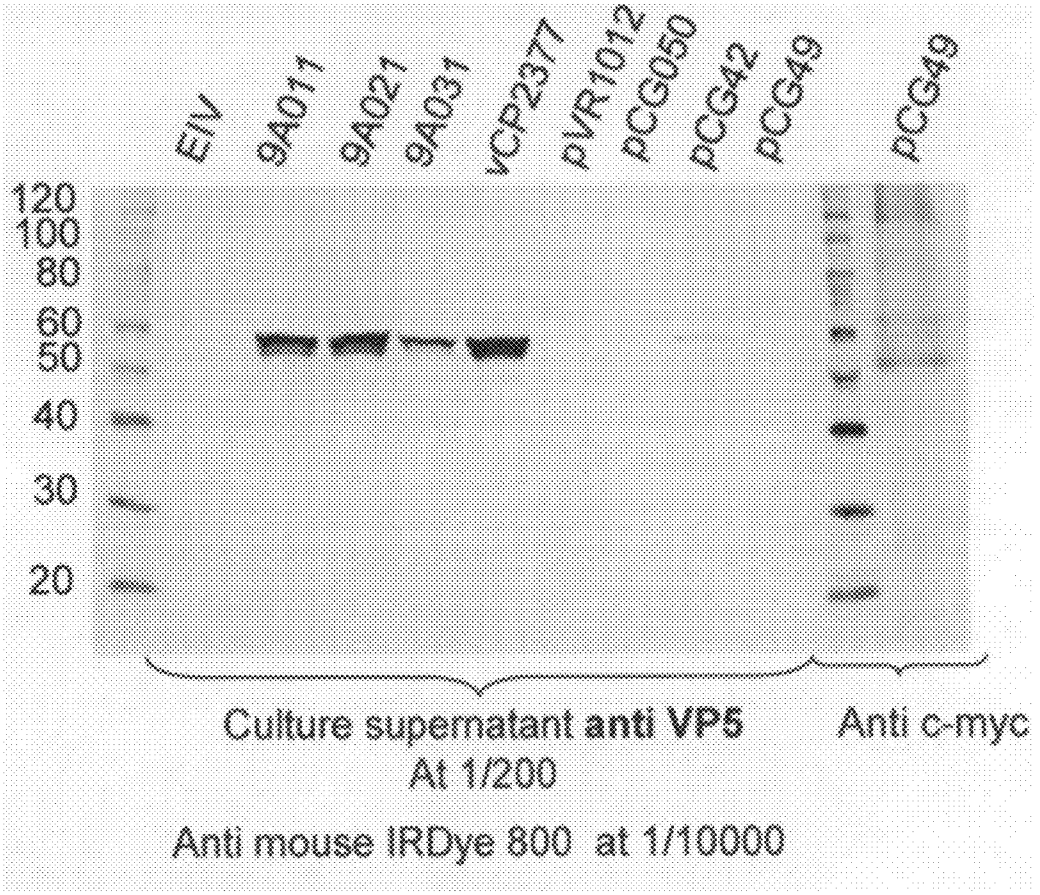

The FIG. 20B shows the western blot performed on lysates of infected and transfected CEF, and indicates the expression of the VP5 serotype 4 AHSV protein.

FIG. 20A shows the results of anti-VP5 western blot on infected and transfected CEF. The VP5 protein was detected in each of the 3 batches of vCP2377 adjuvanted with CARBOPOL® 974P and in the vCP2377 before formulation. The CEF transfected by the plasmids pCG042 (VP5 in pVR1012) also expressed VP5 protein.

As predicted, no signal was detected for CEF infected by vCP EIV, nor for CEF transfected by pVR1012, pCG050 and pCG049, showing that the anti-VP5 antibody is clearly specific to VP5 AHSV protein, as described in literature (Martinez-Torrecuadrada et al.; Virology, 257, 449-459; 1999).

IV. CONCLUSION

All the results given by indirect immunofluorescent and by western blot show that the three vCP2377 vaccines adjuvanted with CARBOPOL® 974P express VP2 and VP5 proteins of serotype 4 AHSV.

Example 13

Vaccine Dose Response in Horses

A. Experimental Animals

A total of 6 previously unvaccinated horses were used for immunogenicity studies. The animals were fed and managed according to standard procedures.

B. Immunogenicity in Unvaccinated Animals

In order to evaluate the immune response of horses to the candidate vaccine 6 previously unvaccinated foals were randomly paired in to 3 groups. Each group of 2 horses was vaccinated on Day 0 with 3 doses from one of three different batch preparations (Batches: 87859A011, 87859A021, and 87859A031) of the candidate vaccine (AHSV-CP). The different batches varied with respect to their target titers as shown in FIG. 21, namely 7.3, 6.96, and 6.28 $Log_{10}$ $CCID_{50}$/mL. In each group, two of the doses were administered Intramuscularly (IM) on one side of the neck, and one dose was administered IM on the other side of the neck. On Day 28 horses were immunized IM in the neck with one dose of the same batch of vaccine administered at Day 0. Prior to receiving the primary dose of vaccine, blood samples were collected (Day 0) by jugular venepuncture into 2×7 mL tubes SST VACUTAINER tubes. In addition, blood samples were collected from all horses by jugular venepuncture into 2×7 ml SST VACUTAINER tubes on Day 28 and Day 42.

C. Analysis

Serum samples collected prior to the first vaccination, during the first vaccination period, at the time of the second vaccination and during the second vaccination period were subject to a group specific Elisa test for antibodies to African Horse Sickness Virus (Hamblin C, et al. (1990) Epidemiology and Infection 104: 303-312) and an AHS serotype 4 specific serum-virus neutralization test (Howell P G, (1962).

The results are shown in FIG. 21. At Day 0, all horses were negative with no detectable serum antibody titers against AHSV-4. On Day 28, four weeks after primary immunization, all of the horses that were immunized with vaccine from the batch with the highest titer ($Log_{10}$ $CCID_{50}$/mL 7.3) developed neutralizing titers. On Day 28, 1 of 2 horses that were immunized with vaccine from the batch with the intermediate titer ($Log_{10}$ $CCID_{50}$/mL 6.96) developed neutralizing titers. Finally, on Day 28, none of the horses that were immunized with vaccine from the batch with the lowest titer ($Log_{10}$ $CCID_{50}$/mL 6.28) developed neutralizing titers. On Day 42, two weeks after administration of the booster dose, 5 of 6 horses had good antibody titers (FIG. 21). One horse (#53761) that was immunized with vaccine from the lowest titer batch (87859A031) was negative for antibodies to African Horse Sickness Virus.

Example 14

Vaccination of Horses with Recombinant Canarypox Viruses

Nine yearling Boerperd horses (5 males, 4 females) were procured from the Northern Cape Province, South Africa, a region free from reported AHS for at least the preceding 12 months. The horses were confirmed to be free of AHSV-specific antibodies by indirect enzyme linked immunosorbent assay (ELISA) that detects antibodies to the VP7 core protein that is common to viruses of the AHSV serogroup (Maree, S. and Paweska, J T., 2005). The horses were housed in vector-protected, isolation facilities throughout these studies. Two groups of four horses each (2 males and 2 females) were inoculated intramuscularly with $10^{7.1}$ or $10^{6.4}$ TCID50/dose, respectively, of AHSV-CP in approximately 1 mL of diluent containing a CARBOPOL adjuvant. For ethical reasons, a single control horse was used to confirm the virulence of the challenge inoculum because this virus strain has previously been shown to cause severe or lethal disease in inoculated horses (Nurton, J. P., et al, 2001). The control horse was vaccinated with recombinant canarypox virus expressing the hemagglutinin protein of equine influenza virus (EI-CP; PROTEQFLU® equine influenza virus vaccine, Merial) that was administered according to the manufacturer's instructions. All horses were revaccinated 28 days later with the respective vaccine construct. The animals were co-housed regardless of vaccine type. All laboratory testing was done independent of knowledge of vaccination status.

A. Methods

AHSV Infection of Horses and Sample Collection

All 9 horses were challenged by intravenous inoculation of $10^{5.5}$$TCID_{50}$ of AHSV-4 at 28 days after the second vaccination. The horses were evaluated daily for manifestations of African horse sickness for 23 days after inoculation. Blood was collected in EDTA VACUTAINER™ tubes (Becton Dickinson) prior to challenge infection and at 2, 5, 7, 9, 12, 14, 16, 19, 21 and 23 days post-infection (DPI) for complete blood counts (CBC). Blood samples were also collected daily in EDTA VACUTAINER™ tubes (Becton Dickinson) on days 0 through 23 DPI for quantitative reverse transcriptase polymerase chain reaction (qRT-PCR) and virus isolation in BHK-21 cells. Serum was collected in SST serum separator tubes (Becton Dickinson) from all horses immediately prior to vaccination and at two weekly intervals thereafter.

Clinical Laboratory Assays

Haematological analysis was done using an electronic cell counter (Coulter Electronics Inc.).

Virus Detection

The presence of AHSV in the blood of the horses was determined using qRT-PCR assays that detect the individual genes encoding the VP7 and NS2 proteins of AHSV (Quan, M. and A J Guthrie, 2009) with samples being classified as positive if the fluorescence exceeded the threshold of 0.1 within a maximum of 40 cycles. Virus isolation from blood was done in BHK-21 cells, as described by Quan, M. et al, 2008.

Serological Assays

Serotype-specific neutralizing antibodies to AHSV were detected by microneutralization assay using AHSV-4 as the challenge virus as described by Howell, P G et al, 2002. Antibody titers were recorded as the reciprocal of the highest final dilution of serum that provided at least 50% protection of the BHK-21 cell monolayer. A titer of >10 was considered significant.

Statistical Analysis

AHSV-4 neutralizing antibody titres at 8 weeks after primary vaccination and 6 weeks after AHSV infection were compared between the vaccine groups by Mann-Whitney U test with a P<0.05 being considered significant.

B. Analysis

Immunogenicity of AHSV-CP

All horses were seronegative by both ELISA and AHSV-4 microneutralization assays prior to vaccination, and all but two horses in TABLE 2 developed neutralizing antibodies to AHSV-4 after immunization with the AHSV-CP recombinant vector whereas the horse immunized with EIV-CP did not develop neutralizing antibodies to AHSV-4 (Table 2). At 8 weeks post-vaccination, AHSV-4 titres were significantly higher (P=0.021) in horses given the high vaccine dose than those in the low dose group, but this difference was less evident (P=0.057) at 6 weeks post infection. All horses remained healthy and showed no adverse effects after vaccination.

TABLE 2

Titers of African horse sickness serotype 4 neutralizing antibodies

| Treatment/ | Post-vaccination titers[a] (weeks after primary vaccination) | | | Post-infection titers[a] (weeks after AHSV infection) | | |
|---|---|---|---|---|---|---|
| Horse ID | 0 | 4 | 8 | 2 | 4 | 6 |
| Vaccinated (AHSV-CP - $10^{7.1}$) | | | | | | |
| 1 | ≦10 | ≦10 | 28 | 20 | 40 | 20 |
| 2 | ≦10 | ≦10 | 40 | 40 | 10 | 14 |
| 3 | ≦10 | ≦10 | 20 | 40 | 28 | 40 |
| 4 | ≦10 | ≦10 | 40 | 80 | 56 | 80 |
| Vaccinated (AHSV-CP - $10^{6.4}$) | | | | | | |
| 5 | ≦10 | ≦10 | ≦10 | ≦10 | ≦10 | ≦10 |
| 6 | ≦10 | ≦10 | ≦10 | 10 | ≦10 | ≦10 |
| 7 | ≦10 | ≦10 | 14 | 40 | 20 | 10 |
| 8 | ≦10 | ≦10 | 10 | 56 | 56 | 14 |
| Control (EIV-CP) | | | | | | |
| 9 | ≦10 | ≦10 | ≦10 | 10 | 160 | 224 |

[a]Expressed as the reciprocal of the highest dilution that provided >50% protection of the BHK-21cell monolayer.

C. Protection of Horses Immunized with AHSV-CP

Figure 31:
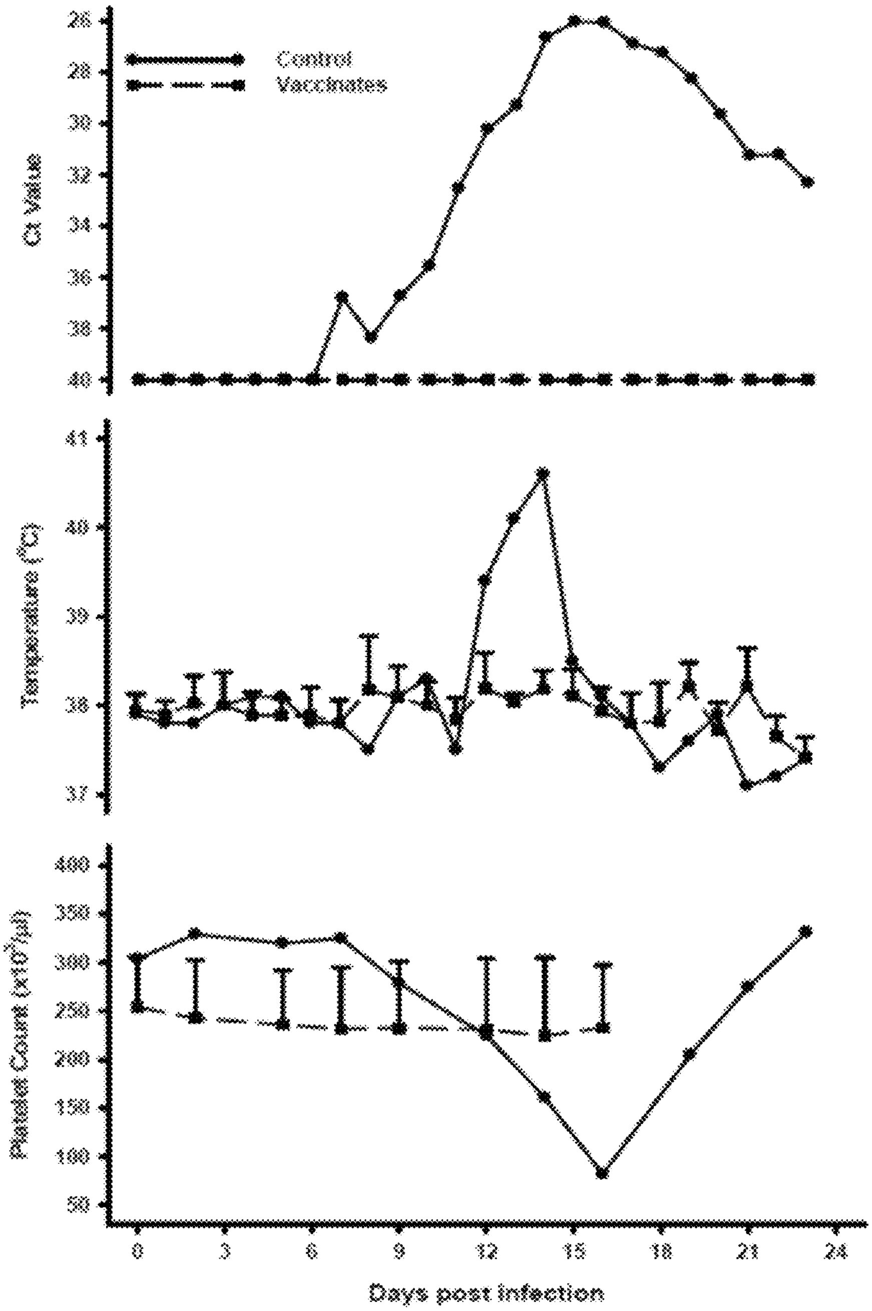
FIG. 31 provides 3 panels with AHSV challenge results from 8 vaccinated with vCP2377 (in part set forth by SEQ ID NO:17) and a control horse immunized with EIV-CP.

The ability of AHSV-CP to protectively immunize horses was evaluated by comparing amounts of AHSV nucleic acid (Ct values) in the blood of AHSV-CP (vaccinates) and EIV-CP (control) immunized horses after challenge infection (FIG. 31, Panel A). Whereas AHSV nucleic acid was detected from 8 days post infection (DPI) of the control horse (EIV-CP), it was never detected in the blood of the vaccinated horses. Similarly, AHSV-4 was repeatedly isolated from the blood of the control horse but never from the vaccinated horses (data not shown).

The control (EIV-CP) horse developed clinical signs consistent with the "dikkop" or cardiac form of African horse sickness, whereas the vaccinated horses all remained normal throughout the study. Specifically, the control horse developed high fever and thrombocytopenia that coincided with increasing viral load in blood (FIG. 31, Panel B and C, respectively). The control horse also developed prominent oedema of the supraorbital fossae at 12 DPI, which persisted until 21 DPI.

D. Serological Responses of AHSV-CP Vaccinated and Control Horses after Challenge Exposure to AHSV-4

The serological responses of vaccinated (AHSV-CP) and control (EIV-CP) horses were determined following challenge infection with AHSV-4 by both SN (Table 2) and ELISA (data not shown) tests. The control horse seroconverted to AHSV by 4 weeks after challenge, as determined by SN assays, whilst none of the vaccinated horses did so. Furthermore, all the vaccinated horses remained negative for antibodies to VP7 by ELISA for the duration of the study. The lack of seroconversion of the vaccinated horses on SN assays and the failure to detect antibody to VP7 by ELISA suggests that virus replication was absent or minimal in the vaccinated horses. Similarly, the AHSV-4 neutralizing antibody after challenge infection in the control (WNV-CP) horse that was seronegative prior to challenge was considerably greater than the titres observed in the vaccinated horses at 4 and 6 weeks after infection.

CITED REFERENCES

1. Andreansky, S. S., He, B. et al., *The application of genetically engineered herpes simplex viruses to the treatment of experimental brain tumors* (1996). *Proc Natl Acad Sci USA* 93(21): 11313-8.
2. Ballay, A., Levrero, M. et al., *In vitro and in vivo synthesis of the hepatitis B virus surface antigen and of the receptor for polymerized human serum albumin from recombinant human adenoviruses* (1985). *Embo J* 4(13B): 3861-5.
3. Bocchia, M. et al., *Specific Binding of Leukemia Oncogene Fusion Protein Peptides to HLA Class I Molecules* (2000). *Blood* 85: 2680-2684.
4. Bonneau, K. R., Zhang, N., Zhu, J., Zhang, F., L1, Z., Zhang, K., Xiao, L., Xiang, W., MacLachlan, N. J., *Sequence comparison of the L2 and S10 genes of bluetongue viruses from the United States and the People's Republic of China* (1999). *Virus Research* 61: 153-160.
5. Bonneau, K. R, Mullens, B. A, MacLachlan, N. J., *Occurrence of genetic drift and founder effect during quasispecies evolution of the VP2 and NS3/NS3A genes of bluetongue virus upon passage between sheep, cattle, and Culicoides sonorensis*; (2001). *Journal of Virology* 75: 8298-8305.
6. Boone, J. D., Balasuriya, U. B., Karaca, K., Audonnet, J. C., Yao, J., He, L., Nordgren, R., Monaco, F., Savini, G., Gardner, I. A., MacLachlan, N. J., *Recombinant canarypox virus vaccine coexpressing genes encoding the VP2 and VP5 outer capsid proteins of bluetongue virus induces high level protection in sheep* (2007). *Vaccine* 25: 672-678.
7. Bourne, N., Stanberry, L. R., Bernstein, D. I. & Lew, D., *DNA immunization against experimental genital herpes simplex virus infection* (1996). *Journal of Infectious Diseases* 173,800-7.
8. Bremer, C. W., *A gel electrophoretic study of the protein and nucleic acid components of African horsesickness virus* (1976). *Onderstepoort Journal of Veterinary Research* 43, 193-199.
9. Bremer, C. W., Huismans, H. & Van Dijk, A. A., *Characterization and cloning of the African horsesickness virus genome* (1990). *Journal of General Virology* 71, 793-799.

10. du Plessis, M., Cloete M., Aitchison, H., Van Dijk, A. A., *Protein aggregation complicates the development of baculovirus-expressed African horsesickness virus serotype 5 VP2 subunit vaccines* (1998). *Onderstepoort Journal of Veterinary Research* 65: 321-329.

11. Englehard, V. H., *Structure of peptides associated with class I and class II MHC molecules* (1994). *Ann. Rev. Immunol.* 12:181.

12. Feigner, J. H., Kumar, R. et al., *Enhanced gene delivery and mechanism studies with a novel series of cationic lipid formulations* (1994). *J Biol Chem* 269(4): 2550-61.

13. Fields, J., et al., *Synthetic polyelectrolytes as tumour inhibitors* (Jun. 4, 1960). *Nature* 186, 778-780.

14. Frolov, I., Hoffman, T. A., et al., *Alphavirus-based expression vectors: strategies and applications* (1996). *Proc Natl Acad Sci USA* 93(21), 11371-7.

15. Furth, Pa, Shamay A, Wall R J, Hennighausen L., Gene transfer into somatic tissues by jet injection (1992). *Analytical Biochemistry,* 205, 365-368.

16. Ganne, V. et al., Enhancement of the efficacy of a replication-defective adenovirus-vectored vaccine by the addition of oil adjuvants (1994). *Vaccine,* 12, 1190-1196.

17. Graham, F. L., *Adenoviruses as expression vectors and recombinant vaccines* (1990). *Trends Biotechnol* 8(4), 85-7.

18. Grubman, M. J. & Lewis, S. A., *Identification and characterization of the structural and nonstructural proteins of African horsesickness virus and determination of the genome coding assignments* (1992). *Virology* 186, 444-451.

19. Hamblin, C., Graham, S. D., Anderson, E. C., Crowther, J. R., *A competitive ELISA for the detection of group-specific antibodies to African horse sickness virus*, (1990). *Epidemiology and Infection* 104(2), 303-312 and an AHS serotype 4 specific serum-virus neutralization test.

20. Howell, P G, *The isolation and identification of further antigenic types of African horsesickness virus*, (1962) *Onderstepoort Journal of Veterinary Research* 29, 139-149.

21. Kuby, Janis (1992). Immunology, p. 81.

22. Kuby, Janis, (1992). Immunology, pp. 79-80.

23. Ju, Q., Edelstein, D., et al., *Transduction of non-dividing adult human pancreatic beta cells by an integrating lentiviral vector* (1998). *Diabetologia* 41(6): 736-9.

24. Kendrew, John, (1995). *The Encyclopedia of Molecular Biology* (Blackwell Science Ltd.)

25. Kitson, J. D., Burke, K. L., et al., *Chimeric polioviruses that include sequences derived from two independent antigenic sites of foot-and-mouth disease virus (FMDV) induce neutralizing antibodies against FMDV in guinea pigs* (1991). *J Virol* 65(6), 3068-75.

26. Lewis, S. A. and Grubman, M. J., *VP2 is the major exposed protein on orbiviruses* (1991). *Archives of Virology* 121, 233-236.

27. Luke, et al., An OspA-based DNA vaccine protects mice against infection with *Borrelia burgdorferi* (1997). *J. Infect. Dis.* 175(1):91-97.

28. Martinez-Torrecuadrada, J. L., Iwata, H, Venteo, A., Casal, I., Roy, P., *Expression and characterization of the two outer capsid proteins of African horsesickness virus: The role of VP2 in virus neutralization* (1994). *Virology* 202: 348-359.

29. McClements, W. L., Armstrong, M. E. et al., *Immunization with DNA vaccines encoding glycoprotein D or glycoprotein B, alone or in combination, induces protective immunity in animal models of herpes simplex virus-2 disease* (1996). *Proc Natl Acad Sci USA* 93(21), 11414-20.

30. Minke, J. M., Siger, L., Karaca, K., Austgen, L., Gordy, P., Bowen, R., Renshaw, R. W., Loosmore, S., Audonnet, J. C., Nordgren, B., *Recombinant canarypoxvirus vaccine carrying the prM/E genes of West Nile virus protects horses against a West Nile virus-mosquito challenge* (2004a). *Arch. Virol. Suppl.* 221-230.

31. Minke, J. M., Audonnet, J. C., Fischer, L., *Equine viral vaccines: the past, present and future* (2004b). *Veterinary Research* 35: 425-443.

32. Minke, J. M., Toulemonde, C. E., Coupie, H., Guigal, P. M., Dinic, S., Sindle, T., Jessett, D., Black, L., Bublot, M., Pardo, M. C., Audonnet, J. C., *Efficacy of a canarypox-vectored recombinant vaccine expressing the hemagglutinin gene of equine influenza H3N8 virus in the protection of ponies from viral challenge* (2007). *American Journal of Veterinary Research* 68: 213-219.

33. Moss, B., *Genetically engineered poxviruses for recombinant gene expression, vaccination, and safety* (1996). *Proc Natl Acad Sci USA* 93(21), 11341-8.

34. Norman, J A, Hobart P, Manthorpe M, Felgner P, Wheeler C., Development of Improvedvectors for DNA-based immunization and other gene therapy applications (1997). *Vaccine,* 15(8):801-803.

35. Oellermann, R. A., Els, H. J. & Erasmus, B. J., *Characterization of African horsesickness virus* (1970). *Archiv für die gesamte Virusforschung* 29, 163-174.

36. Paoletti, E., *Applications of pox virus vectors to vaccination: an update* (1996). *Proc Natl Acad Sci USA* 93(21): 11349-53.

37. Pearson, L. D., Roy, P., *Genetically engineered multi-component virus-like particles as veterinary vaccines* (1993). *Immunol. Cell Biol.* 71 (Pt 5), 381-389.

38. Pennock, G. D., Shoemaker, C. et al., *Strong and regulated expression of Escherichia coli beta-galactosidase in insect cells with a baculovirus vector* (1984). *Mol Cell Biol* 4(3): 399-406.

39. Piccini, A., Perkus, M. E., Paoletti, E., *Vaccinia virus as an expression vector*, (1987) Methods. *Enzymol.* 153: 545-563.

40. Poulet, H., Brunet, S., Boularand, C., Guiot, A. L., Leroy, V., Tartaglia, J., Minke, J., Audonnet, J. C., Desmettre, P., *Efficacy of a canarypox virus-vectored vaccine against feline leukaemia* (2003). *Veterinary Record* 153: 141-145.

41. Prevec, L., Schneider, M. et al., *Use of human adenovirus-based vectors for antigen expression in animals* (1989). *J Gen Virol* 70 (Pt 2), 429-34.

42. Quan M, Van Vuuren M, Howell P G, Groenewald D, Guthrie A J. *Molecular epidemiology of the African horse sickness virus S10 gene* (2008). *J Gen Virol* May; 89(Pt 5):1159-68.

43. Quan M, Guthrie A J., *Development and optimisation of a quantitative duplex real-time RT-PCR assay for African horse sickness virus* (2009) *J Virol Methods.*

44. Richardson, C. D., *Methods in Molecular Biology* (1995). Baculovirus Expression Protocols, *Humana Press Inc. Vol.* 39.

45. Robertson, E. S., Ooka, T., et al., *Epstein-Barr virus vectors for gene delivery to B lymphocytes* (1996). *Proc Natl Acad Sci USA* 93(21), 11334-40.

46. Robinson, H. L. and Tones, C. A., *DNA vaccines* (1997). *Semin Immunol* 9(5), 271-83.

47. Roizman, B., *The function of herpes simplex virus genes: a primer for genetic engineering of novel vectors* (1996). *Proc Natl Acad Sci USA* 93(21), 11307-12.

48. Sambrook, Fritsch and Maniatis, Molecular Cloning, A Laboratory Manual, 2nd Ed., Cold Spring Harbor Laboratory Press, 1982

49. Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986)
50. Scanlen, M., Paweska, J. T., Verschoor, J. A., Van Dijk, A. A., *The protective efficacy of a recombinant VP2-based African horsesickness subunit vaccine candidate is determined by adjuvant* (2002). *Vaccine* 20, 1079-1088.
51. Siger, L., Bowen, R., Karaca, K., Murray, M., Jagannatha, S., Echols, B., Nordgren, R., Minke, J. M., *Evaluation of the efficacy provided by a Recombinant Canarypox-Vectored Equine West Nile Virus vaccine against an experimental West Nile Virus intrathecal challenge in horses* (2006). *Vet. Ther.* 7, 249-256.
52. Smith, G. E., Summers, M. D., et al., *Production of human beta interferon in insect cells infected with a baculovirus expression vector* (1983). *Mol Cell Biol* 3(12), 2156-65.
53. Tang, D. C., DeVit, M. et al., *Genetic immunization is a simple method for eliciting an immune response* (1992). *Nature* 356(6365), 152-4.
54. Ulmer, J. B., Donnelly, J. J., et al., *Heterologous protection against influenza by injection of DNA encoding a viral protein* (1993). *Science* 259(5102): 1745-9.

Having thus described in detail preferred embodiments of the present invention, it is to be understood that the invention defined by the appended paragraphs is not to be limited to particular details set forth in the above description as many apparent variations thereof are possible without departing from the spirit or scope of the present invention.

What is claimed is:

1. An immunogenic composition comprising
a recombinant poxvirus wherein the recombinant poxvirus comprises two nucleic acid molecules encoding polypeptides African Horse Sickness Virus (AHSV) VP2 and AHSV VP5; and wherein the composition is capable of eliciting a protective immune response in an equine animal.

2. The composition of claim 1, wherein the VP2 polypeptide is encoded by the sequence as set forth in SEQ ID NO:4 and the VP5 polypeptide is encoded by the sequence as set forth in SEQ ID NO:5.

3. The composition of claim 1, wherein the nucleic acid molecule comprises a sequence having at least 95% sequence identity to a polynucleotide having the sequence as set forth in SEQ ID NO:17.

4. The composition of claim 1, wherein the poxvirus comprises a nucleic acid sequence as set forth in SEQ ID NO:17.

5. The composition of claim 1 further comprising a carboxypolymethylene adjuvant.

6. An expression vector comprising one or more polynucleotide selected from the sequence as set forth in SEQ ID NO:4, the sequence as set forth in SEQ ID NO:5, and the combination of both.

7. The vector of claim 6, wherein the the vector comprises both SEQ ID NOs: 4 and 5.

8. The vector of claim 7, wherein the vector is a viral vector, and wherein the viral vector is an avipox, a canarypox or a fowlpox vector.

9. The vector of claim 8, wherein the vector comprises both SEQ ID NO:4 and SEQ ID NO:5.

10. The vector of claim 8, wherein the polynucleotide is operably linked to a promoter selected from the group consisting of H6 vaccinia promoter, I3L vaccinia promoter, 42K poxviral promoter, 7.5K vaccinia promoter, and Pi vaccinia promoter.

11. The vector of claim 9, wherein SEQ ID NO:2 is operably linked to the H6 vaccinia promoter and SEQ ID NO:5 is operably linked to the 42K poxviral promoter.

12. An isolated host cell transformed with the vector of claim 6.

13. A method for inducing an immunological response in an animal comprising administering to the host an effective amount of the composition of claim 1.

14. A method of vaccinating an animal susceptible to African Horse Sickness comprising administering at least one dose of the composition of claim 1.

15. The method of claim 14 further comprising administering at least a second dose of the composition of claim 1.

* * * * *

```
                         SEQUENCE LISTING


<160> NUMBER OF SEQ ID NOS: 63

<210> SEQ ID NO 1
<211> LENGTH: 1060
<212> TYPE: PRT
<213> ORGANISM: artificial sequence
<220> FEATURE:
<223> OTHER INFORMATION: AHSV4-VP2 polypeptide encoded by codon-
      optimized synthetic AHSV4-VP2 gene

<400> SEQUENCE: 1

Met Ala Ser Glu Phe Gly Ile Leu Met Thr Asn Glu Lys Phe Asp Pro
1               5                   10                  15

Ser Leu Glu Lys Thr Ile Cys Asp Val Ile Val Thr Lys Lys Gly Arg
            20                  25                  30

Val Lys His Lys Glu Val Asp Gly Val Cys Gly Tyr Glu Trp Asp Glu
        35                  40                  45

Thr Asn His Arg Phe Gly Leu Cys Glu Val Glu His Asp Met Ser Ile
    50                  55                  60

Ser Glu Phe Met Tyr Asn Glu Ile Arg Cys Glu Gly Ala Tyr Pro Ile
65                  70                  75                  80

Phe Pro Arg Tyr Ile Ile Asp Thr Leu Lys Tyr Glu Lys Phe Ile Asp
                85                  90                  95

Arg Asn Asp His Gln Ile Arg Val Asp Arg Asp Asp Asn Glu Met Arg
            100                 105                 110

Lys Ile Leu Ile Gln Pro Tyr Ala Gly Glu Met Tyr Phe Ser Pro Glu
        115                 120                 125

Cys Tyr Pro Ser Val Phe Leu Arg Arg Glu Ala Arg Ser Gln Lys Leu
    130                 135                 140

Asp Arg Ile Arg Asn Tyr Ile Gly Lys Arg Val Glu Phe Tyr Glu Glu
145                 150                 155                 160

Glu Ser Lys Arg Lys Ala Ile Leu Asp Gln Asn Lys Met Ser Lys Val
                165                 170                 175

Glu Gln Trp Arg Asp Ala Val Asn Glu Arg Ile Val Ser Ile Glu Pro
            180                 185                 190

Lys Arg Gly Glu Cys Tyr Asp His Gly Thr Asp Ile Ile Tyr Gln Phe
        195                 200                 205

Ile Lys Lys Leu Arg Phe Gly Met Met Tyr Pro His Tyr Tyr Val Leu
    210                 215                 220

His Ser Asp Tyr Cys Ile Val Pro Asn Lys Gly Gly Thr Ser Ile Gly
225                 230                 235                 240
```

```
Ser Trp His Ile Arg Lys Arg Thr Glu Gly Asp Ala Lys Ala Ser Ala
                245                 250                 255

Met Tyr Ser Gly Lys Gly Pro Leu Asn Asp Leu Arg Val Lys Ile Glu
            260                 265                 270

Arg Asp Asp Leu Ser Arg Glu Thr Ile Ile Gln Ile Ile Glu Tyr Gly
        275                 280                 285

Lys Lys Phe Asn Ser Ser Ala Gly Asp Lys Gln Gly Asn Ile Ser Ile
    290                 295                 300

Glu Lys Leu Val Glu Tyr Cys Asp Phe Leu Thr Thr Phe Val His Ala
305                 310                 315                 320

Lys Lys Lys Glu Glu Gly Glu Asp Asp Thr Ala Arg Gln Glu Ile Arg
                325                 330                 335

Lys Ala Trp Val Lys Gly Met Pro Tyr Met Asp Phe Ser Lys Pro Met
            340                 345                 350

Lys Ile Thr Arg Gly Phe Asn Arg Asn Met Leu Phe Phe Ala Ala Leu
        355                 360                 365

Asp Ser Phe Arg Lys Arg Asn Gly Val Asp Val Asp Pro Asn Lys Gly
    370                 375                 380

Lys Trp Lys Glu His Ile Lys Glu Val Thr Glu Lys Leu Lys Lys Ala
385                 390                 395                 400

Gln Thr Glu Asn Gly Gly Gln Pro Cys Gln Val Ser Ile Asp Gly Val
                405                 410                 415

Asn Val Leu Thr Asn Val Asp Tyr Gly Thr Val Asn His Trp Ile Asp
            420                 425                 430

Trp Val Thr Asp Ile Ile Met Val Val Gln Thr Lys Arg Leu Val Lys
        435                 440                 445

Glu Tyr Ala Phe Lys Lys Leu Lys Ser Glu Asn Leu Leu Ala Gly Met
    450                 455                 460

Asn Ser Leu Val Gly Val Leu Arg Cys Tyr Met Tyr Cys Leu Ala Leu
465                 470                 475                 480

Ala Ile Tyr Asp Phe Tyr Glu Gly Thr Ile Asp Gly Phe Lys Lys Gly
                485                 490                 495

Ser Asn Ala Ser Ala Ile Ile Glu Thr Val Ala Gln Met Phe Pro Asp
            500                 505                 510

Phe Arg Arg Glu Leu Val Glu Lys Phe Gly Ile Asp Leu Arg Met Lys
        515                 520                 525

Glu Ile Thr Arg Glu Leu Phe Val Gly Lys Ser Met Thr Ser Lys Phe
    530                 535                 540

Met Glu Glu Gly Glu Tyr Gly Tyr Lys Phe Ala Tyr Gly Trp Arg Arg
545                 550                 555                 560

Asp Gly Phe Ala Val Met Glu Asp Tyr Gly Glu Ile Leu Thr Glu Lys
                565                 570                 575

Val Glu Asp Leu Tyr Lys Gly Val Leu Leu Gly Arg Lys Trp Glu Asp
            580                 585                 590

Glu Val Asp Asp Pro Glu Ser Tyr Phe Tyr Asp Asp Leu Tyr Thr Asn
        595                 600                 605

Glu Pro His Arg Val Phe Leu Ser Ala Gly Lys Asp Val Asp Asn Asn
    610                 615                 620

Ile Thr Leu Arg Ser Ile Ser Gln Ala Glu Thr Thr Tyr Leu Ser Lys
625                 630                 635                 640

Arg Phe Val Ser Tyr Trp Tyr Arg Ile Ser Gln Val Glu Val Thr Lys
                645                 650                 655

Ala Arg Asn Glu Val Leu Asp Met Asn Glu Lys Gln Lys Pro Tyr Phe
```

```
                660                 665                 670

Glu Phe Glu Tyr Asp Asp Phe Lys Pro Cys Ser Ile Gly Glu Leu Gly
        675                 680                 685

Ile His Ala Ser Thr Tyr Ile Tyr Gln Asn Leu Leu Val Gly Arg Asn
    690                 695                 700

Arg Gly Glu Glu Ile Leu Asp Ser Lys Glu Leu Val Trp Met Asp Met
705                 710                 715                 720

Ser Leu Leu Asn Phe Gly Ala Val Arg Ser His Asp Arg Cys Trp Ile
                725                 730                 735

Ser Ser Ser Val Ala Ile Glu Val Asn Leu Arg His Ala Leu Ile Val
            740                 745                 750

Arg Ile Phe Ser Arg Phe Asp Met Met Ser Glu Arg Glu Thr Phe Ser
        755                 760                 765

Thr Ile Leu Glu Lys Val Met Glu Asp Val Lys Glu Leu Arg Phe Phe
    770                 775                 780

Pro Thr Tyr Arg His Tyr Tyr Leu Glu Thr Leu Gln Arg Val Phe Asn
785                 790                 795                 800

Asp Glu Arg Arg Leu Glu Val Asp Asp Phe Tyr Met Arg Leu Tyr Asp
                805                 810                 815

Val Gln Thr Arg Glu Gln Ala Leu Asn Thr Phe Thr Asp Phe His Arg
            820                 825                 830

Cys Val Glu Ser Glu Leu Leu Leu Pro Thr Leu Lys Leu Asn Phe Leu
        835                 840                 845

Leu Trp Ile Val Phe Glu Met Glu Asn Val Glu Val Asn Ala Ala Tyr
    850                 855                 860

Lys Arg His Pro Leu Leu Ile Ser Thr Ala Lys Gly Leu Arg Val Ile
865                 870                 875                 880

Gly Val Asp Ile Phe Asn Ser Gln Leu Ser Ile Ser Met Ser Gly Trp
                885                 890                 895

Ile Pro Tyr Val Glu Arg Met Cys Ala Glu Ser Lys Val Gln Thr Lys
            900                 905                 910

Leu Thr Ala Asp Glu Leu Lys Leu Lys Arg Trp Phe Ile Ser Tyr Tyr
        915                 920                 925

Thr Thr Leu Lys Leu Asp Arg Arg Ala Glu Pro Arg Met Ser Phe Lys
    930                 935                 940

Phe Glu Gly Leu Ser Thr Trp Ile Gly Ser Asn Cys Gly Gly Val Arg
945                 950                 955                 960

Asp Tyr Val Ile Gln Met Leu Pro Thr Arg Lys Pro Lys Pro Gly Ala
                965                 970                 975

Leu Met Val Val Tyr Ala Arg Asp Ser Arg Ile Glu Trp Ile Glu Ala
            980                 985                 990

Glu Leu Ser Gln Trp Leu Gln Met  Glu Gly Ser Leu Gly  Leu Ile Leu
        995                 1000                1005

Val His  Asp Ser Gly Ile Ile  Asn Lys Ser Val Leu  Arg Ala Arg
    1010                1015                1020

Thr Leu  Lys Ile Tyr Asn Arg  Gly Ser Met Asp Thr  Leu Ile Leu
    1025                1030                1035

Ile Ser  Ser Gly Val Tyr Thr  Phe Gly Asn Lys Phe  Leu Leu Ser
    1040                1045                1050

Lys Leu  Leu Ala Lys Thr Glu
    1055                1060
```

<210> SEQ ID NO 2
<211> LENGTH: 505

<212> TYPE: PRT
<213> ORGANISM: artificial sequence
<220> FEATURE:
<223> OTHER INFORMATION: AHSV4-VP5 polypeptide encoded by codon-
      optimized synthetic AHSV4-VP5 gene

<400> SEQUENCE: 2

```
Met Gly Lys Phe Thr Ser Phe Leu Lys Arg Ala Gly Asn Ala Thr Lys
1               5                   10                  15

Arg Ala Leu Thr Ser Asp Ser Ala Lys Lys Met Tyr Lys Leu Ala Gly
            20                  25                  30

Lys Thr Leu Gln Arg Val Val Glu Ser Glu Val Gly Ser Ala Ala Ile
        35                  40                  45

Asp Gly Val Met Gln Gly Ala Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Ile Glu Lys Met Glu Lys Glu Asp Arg Val Ile
            100                 105                 110

Glu Thr His Asn Ala Lys Ile Glu Glu Lys Phe Gly Lys Asp Leu Leu
        115                 120                 125

Ala Ile Arg Lys Ile Val Lys Gly Glu Val Asp Ala Glu Lys Leu Glu
    130                 135                 140

Gly Asn Glu Ile Lys Tyr Val Glu Lys Ala Leu Ser Gly Leu Leu Glu
145                 150                 155                 160

Ile Gly Lys Asp Gln Ser Glu Arg Ile Thr Lys Leu Tyr Arg Ala Leu
                165                 170                 175

Gln Thr Glu Glu Asp Leu Arg Thr Arg Asp Glu Thr Arg Met Ile Asn
            180                 185                 190

Glu Tyr Arg Glu Lys Phe Asp Ala Leu Lys Glu Ala Ile Glu Ile Glu
        195                 200                 205

Gln Gln Ala Thr His Asp Glu Ala Ile Gln Glu Met Leu Asp Leu Ser
    210                 215                 220

Ala Glu Val Ile Glu Thr Ala Ser Glu Glu Val Pro Ile Phe Gly Ala
225                 230                 235                 240

Gly Ala Ala Asn Val Ile Ala Thr Thr Arg Ala Ile Gln Gly Gly Leu
                245                 250                 255

Lys Leu Lys Glu Ile Val Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Arg Asp Thr Val Thr Asp Lys Asp Leu Ala Met Ala Ile Lys Ser Lys
    290                 295                 300

Val Asp Val Ile Asp Glu Met Asn Val Glu Thr Gln His Val Ile Asp
305                 310                 315                 320

Ala Val Leu Pro Ile Val Lys Gln Glu Tyr Glu Arg His Asp Asn Lys
                325                 330                 335

Tyr His Val Arg Ile Pro Gly Ala Leu Lys Ile His Ser Glu His Thr
            340                 345                 350

Pro Lys Ile His Ile Tyr Thr Thr Pro Trp Asp Ser Asp Ser Val Phe
        355                 360                 365

Met Cys Arg Ala Ile Ala Pro His His Gln Gln Arg Ser Phe Phe Ile
    370                 375                 380
```

Gly Phe Asp Leu Glu Ile Glu Tyr Val His Phe Glu Asp Thr Ser Val
385 390 395 400

Glu Gly His Ile Leu His Gly Gly Ala Ile Thr Val Glu Gly Arg Gly
405 410 415

Phe Arg Gln Ala Tyr Thr Glu Phe Met Asn Ala Ala Trp Gly Met Pro
420 425 430

Thr Thr Pro Glu Leu His Lys Arg Lys Leu Gln Arg Ser Met Gly Thr
435 440 445

His Pro Ile Tyr Met Gly Ser Met Asp Tyr Ala Ile Ser Tyr Glu Gln
450 455 460

Leu Val Ser Asn Ala Met Arg Leu Val Tyr Asp Ser Glu Leu Gln Met
465 470 475 480

His Cys Leu Arg Gly Pro Leu Lys Phe Gln Arg Arg Thr Leu Met Asn
485 490 495

Ala Leu Leu Tyr Gly Val Lys Ile Ala
500 505

<210> SEQ ID NO 3
<211> LENGTH: 8550
<212> TYPE: DNA
<213> ORGANISM: artificial sequence
<220> FEATURE:
<223> OTHER INFORMATION: pLHD3460.4 Plasmid (Left Arm to Right Arm) comprising African Horse Virus 4 VP2 & VP5 coding sequences
<220> FEATURE:
<221> NAME/KEY: misc_feature
<222> LOCATION: (3)..(942)
<223> OTHER INFORMATION: C3 Left Arm of Plasmid pLHD3460.4 (pC3 H6p synthetic AHSV 4-VP2/42Kp synthetic AHSV 4-VP5)
<220> FEATURE:
<221> NAME/KEY: promoter
<222> LOCATION: (967)..(1152)
<223> OTHER INFORMATION: H6 promoter
<220> FEATURE:
<221> NAME/KEY: CDS
<222> LOCATION: (1153)..(4338)
<223> OTHER INFORMATION: VP2 - Nucleic acid sequence that encodes the African Horse Sickness Virus-4 VP2 protein
<220> FEATURE:
<221> NAME/KEY: promoter
<222> LOCATION: (4366)..(4397)
<223> OTHER INFORMATION: 42k
<220> FEATURE:
<221> NAME/KEY: CDS
<222> LOCATION: (4398)..(5918)
<223> OTHER INFORMATION: VP5 - Nucleic acid sequence that encodes the African Horse Sickness Virus-4 VP5 protein
<220> FEATURE:
<221> NAME/KEY: misc_feature
<222> LOCATION: (5947)..(8508)
<223> OTHER INFORMATION: C3 Right Arm of Plasmid pLHD3460.4 (pC3 H6p synthetic AHSV 4-VP2/42Kp synthetic AHSV 4-VP5)

<400> SEQUENCE: 3
tgcggccgcg tcgacatgca ttgttagttc tgtagatcag taacgtatag catacgagta 60
taattatcgt aggtagtagg tatcctaaaa taaatctgat acagataata actttgtaaa 120
tcaattcagc aatttctcta ttatcatgat aatgattaat acacagcgtg tcgttatttt 180
ttgttacgat agtatttcta aagtaaagag caggaatccc tagtataata gaaataatcc 240
atatgaaaaa tatagtaatg tacatatttc taatgttaac atatttatag gtaaatccag 300
gaagggtaat ttttacatat ctatatacgc ttattacagt tattaaaaat atacttgcaa 360
acatgttaga agtaaaaaag aaagaactaa ttttacaaag tgctttacca aaatgccaat 420
ggaaattact tagtatgtat ataatgtata aaggtatgaa tatcacaaac agcaaatcgg 480
ctattcccaa gttgagaaac ggtataatag atatatttct agataccatt aataacctta 540

-continued

```
taagcttgac gtttcctata atgcctacta agaaaactag aagatacata catactaacg    600

ccatacgaga gtaactactc atcgtataac tactgttgct aacagtgaca ctgatgttat    660

aactcatctt tgatgtggta taaatgtata ataactatat tacactggta ttttatttca    720

gttatatact atatagtatt aaaaattata tttgtataat tatattatta tattcagtgt    780

agaaagtaaa atactataaa tatgtatctc ttatttataa cttattagta aagtatgtac    840

tattcagtta tattgtttta taaaagctaa atgctactag attgatataa atgaatatgt    900

aataaattag taatgtagta tactaatatt aactcacatt tgactaatta gctataaaaa    960

cccgggttaa ttaattagtc atcaggcagg gcgagaacga gactatctgc tcgttaatta   1020

attagagctt ctttattcta tacttaaaaa gtgaaaataa atacaaaggt tcttgagggt   1080

tgtgttaaat tgaaagcgag aaataatcat aaattatttc attatcgcga tatccgttaa   1140

gtttgtatcg ta atg gcc agc gag ttc ggc atc ctg atg acc aac gag aag   1191
              Met Ala Ser Glu Phe Gly Ile Leu Met Thr Asn Glu Lys
              1               5                   10

ttc gac ccc agc ctg gaa aag acc atc tgc gac gtg atc gtg acc aag     1239
Phe Asp Pro Ser Leu Glu Lys Thr Ile Cys Asp Val Ile Val Thr Lys
    15                  20                  25

aag ggc cgg gtc aag cac aag gaa gtg gac ggc gtg tgc ggc tac gag     1287
Lys Gly Arg Val Lys His Lys Glu Val Asp Gly Val Cys Gly Tyr Glu
30                  35                  40                  45

tgg gac gag acc aac cac cgg ttc ggc ctg tgc gag gtg gag cac gac     1335
Trp Asp Glu Thr Asn His Arg Phe Gly Leu Cys Glu Val Glu His Asp
                50                  55                  60

atg agc atc agc gag ttc atg tac aac gag atc aga tgc gag ggc gcc     1383
Met Ser Ile Ser Glu Phe Met Tyr Asn Glu Ile Arg Cys Glu Gly Ala
            65                  70                  75

tac ccc atc ttc ccc cgg tac atc atc gac acc ctg aag tat gag aag     1431
Tyr Pro Ile Phe Pro Arg Tyr Ile Ile Asp Thr Leu Lys Tyr Glu Lys
        80                  85                  90

ttc atc gac cgg aac gac cac cag atc cgg gtg gac cgg gac gac aac     1479
Phe Ile Asp Arg Asn Asp His Gln Ile Arg Val Asp Arg Asp Asp Asn
    95                  100                 105

gag atg cgg aag atc ctg atc cag ccc tac gcc ggc gag atg tac ttc     1527
Glu Met Arg Lys Ile Leu Ile Gln Pro Tyr Ala Gly Glu Met Tyr Phe
110                 115                 120                 125

agc ccc gag tgc tac ccc agc gtg ttc ctg cgg cgg gag gcc aga agc     1575
Ser Pro Glu Cys Tyr Pro Ser Val Phe Leu Arg Arg Glu Ala Arg Ser
                130                 135                 140

cag aag ctg gac cgg atc agg aac tac atc ggc aag cgg gtg gag ttc     1623
Gln Lys Leu Asp Arg Ile Arg Asn Tyr Ile Gly Lys Arg Val Glu Phe
            145                 150                 155

tac gag gaa gag agc aag cgg aag gcc atc ctg gac cag aac aag atg     1671
Tyr Glu Glu Glu Ser Lys Arg Lys Ala Ile Leu Asp Gln Asn Lys Met
        160                 165                 170

agc aag gtg gaa cag tgg cgg gac gcc gtg aac gag cgg atc gtg agc     1719
Ser Lys Val Glu Gln Trp Arg Asp Ala Val Asn Glu Arg Ile Val Ser
    175                 180                 185

atc gag ccc aag cgg ggc gag tgc tac gac cac ggc acc gac atc atc     1767
Ile Glu Pro Lys Arg Gly Glu Cys Tyr Asp His Gly Thr Asp Ile Ile
190                 195                 200                 205

tac cag ttc atc aag aag ctg cgg ttc ggc atg atg tac ccc cac tac     1815
Tyr Gln Phe Ile Lys Lys Leu Arg Phe Gly Met Met Tyr Pro His Tyr
                210                 215                 220

tac gtg ctg cac agc gac tac tgc atc gtg ccc aac aag ggc ggc acc     1863
Tyr Val Leu His Ser Asp Tyr Cys Ile Val Pro Asn Lys Gly Gly Thr
            225                 230                 235
```

-continued

```
agc atc ggc agc tgg cac atc cgg aag cgg acc gag ggc gac gcc aag     1911
Ser Ile Gly Ser Trp His Ile Arg Lys Arg Thr Glu Gly Asp Ala Lys
        240                 245                 250

gcc agc gcc atg tac agc ggc aag ggc ccc ctg aac gac ctg cgg gtg     1959
Ala Ser Ala Met Tyr Ser Gly Lys Gly Pro Leu Asn Asp Leu Arg Val
    255                 260                 265

aag atc gag cgg gac gac ctg agc cgg gag acc atc atc cag atc atc     2007
Lys Ile Glu Arg Asp Asp Leu Ser Arg Glu Thr Ile Ile Gln Ile Ile
270                 275                 280                 285

gag tac ggc aag aag ttc aac agc tct gcc ggc gac aag cag ggc aac     2055
Glu Tyr Gly Lys Lys Phe Asn Ser Ser Ala Gly Asp Lys Gln Gly Asn
                290                 295                 300

atc agc atc gag aag ctg gtc gag tac tgc gac ttc ctg acc acc ttc     2103
Ile Ser Ile Glu Lys Leu Val Glu Tyr Cys Asp Phe Leu Thr Thr Phe
            305                 310                 315

gtg cac gcc aag aag aag gaa gag ggc gag gac gac acc gcc agg cag     2151
Val His Ala Lys Lys Lys Glu Glu Gly Glu Asp Asp Thr Ala Arg Gln
        320                 325                 330

gaa atc cgg aag gcc tgg gtg aag gga atg ccc tac atg gac ttc agc     2199
Glu Ile Arg Lys Ala Trp Val Lys Gly Met Pro Tyr Met Asp Phe Ser
    335                 340                 345

aag ccc atg aag atc acc cgg ggc ttc aac cgg aat atg ctg ttc ttc     2247
Lys Pro Met Lys Ile Thr Arg Gly Phe Asn Arg Asn Met Leu Phe Phe
350                 355                 360                 365

gcc gcc ctg gac agc ttc cgg aag agg aac ggc gtg gac gtg gac ccc     2295
Ala Ala Leu Asp Ser Phe Arg Lys Arg Asn Gly Val Asp Val Asp Pro
                370                 375                 380

aat aag ggc aag tgg aaa gag cac atc aaa gag gtc acc gag aag ctg     2343
Asn Lys Gly Lys Trp Lys Glu His Ile Lys Glu Val Thr Glu Lys Leu
            385                 390                 395

aag aag gcc cag acc gag aac ggc ggc cag ccc tgc cag gtg tcc atc     2391
Lys Lys Ala Gln Thr Glu Asn Gly Gly Gln Pro Cys Gln Val Ser Ile
        400                 405                 410

gac ggc gtg aac gtg ctg acc aac gtg gac tac ggc acc gtg aac cac     2439
Asp Gly Val Asn Val Leu Thr Asn Val Asp Tyr Gly Thr Val Asn His
    415                 420                 425

tgg atc gac tgg gtg aca gac atc atc atg gtg gtg cag acc aag cgg     2487
Trp Ile Asp Trp Val Thr Asp Ile Ile Met Val Val Gln Thr Lys Arg
430                 435                 440                 445

ctg gtg aaa gag tac gcc ttt aag aag ctg aaa agc gag aac ctg ctg     2535
Leu Val Lys Glu Tyr Ala Phe Lys Lys Leu Lys Ser Glu Asn Leu Leu
                450                 455                 460

gcc ggc atg aac agc ctg gtc ggc gtg ctg cgg tgc tac atg tac tgc     2583
Ala Gly Met Asn Ser Leu Val Gly Val Leu Arg Cys Tyr Met Tyr Cys
            465                 470                 475

ctg gcc ctg gcc atc tac gac ttc tac gag ggc acc atc gat ggc ttc     2631
Leu Ala Leu Ala Ile Tyr Asp Phe Tyr Glu Gly Thr Ile Asp Gly Phe
        480                 485                 490

aag aag ggc agc aac gcc tcc gcc atc atc gag acc gtg gcc cag atg     2679
Lys Lys Gly Ser Asn Ala Ser Ala Ile Ile Glu Thr Val Ala Gln Met
    495                 500                 505

ttc ccc gac ttc cgg cgg gaa ctg gtg gag aag ttt ggc atc gac ctg     2727
Phe Pro Asp Phe Arg Arg Glu Leu Val Glu Lys Phe Gly Ile Asp Leu
510                 515                 520                 525

cgc atg aaa gag atc acc cgc gag ctg ttc gtg ggc aag agc atg acc     2775
Arg Met Lys Glu Ile Thr Arg Glu Leu Phe Val Gly Lys Ser Met Thr
                530                 535                 540

agc aag ttc atg gaa gag ggg gag tac ggc tac aag ttc gcc tac ggc     2823
Ser Lys Phe Met Glu Glu Gly Glu Tyr Gly Tyr Lys Phe Ala Tyr Gly
            545                 550                 555
```

-continued

```
tgg cgg agg gac ggc ttc gcc gtg atg gaa gat tac ggc gag atc ctg     2871
Trp Arg Arg Asp Gly Phe Ala Val Met Glu Asp Tyr Gly Glu Ile Leu
        560                 565                 570

aca gag aag gtg gag gac ctg tac aag ggg gtg ctg ctg ggc cgg aag     2919
Thr Glu Lys Val Glu Asp Leu Tyr Lys Gly Val Leu Leu Gly Arg Lys
    575                 580                 585

tgg gag gac gag gtg gac gac ccc gag agc tac ttc tac gac gac ctg     2967
Trp Glu Asp Glu Val Asp Asp Pro Glu Ser Tyr Phe Tyr Asp Asp Leu
590                 595                 600                 605

tac acc aac gag ccc cac cgg gtg ttc ctg agc gcc ggc aag gac gtg     3015
Tyr Thr Asn Glu Pro His Arg Val Phe Leu Ser Ala Gly Lys Asp Val
                610                 615                 620

gac aac aac atc acc ctg cgg agc atc agc cag gcc gag acc acc tac     3063
Asp Asn Asn Ile Thr Leu Arg Ser Ile Ser Gln Ala Glu Thr Thr Tyr
            625                 630                 635

ctg agc aag cgg ttc gtg agc tac tgg tac agg atc agc cag gtg gag     3111
Leu Ser Lys Arg Phe Val Ser Tyr Trp Tyr Arg Ile Ser Gln Val Glu
        640                 645                 650

gtg acc aag gcc cgg aac gag gtg ctg gac atg aac gag aag cag aag     3159
Val Thr Lys Ala Arg Asn Glu Val Leu Asp Met Asn Glu Lys Gln Lys
    655                 660                 665

ccc tac ttc gag ttc gag tac gac gac ttc aag ccc tgc tcc atc ggc     3207
Pro Tyr Phe Glu Phe Glu Tyr Asp Asp Phe Lys Pro Cys Ser Ile Gly
670                 675                 680                 685

gag ctg ggc atc cac gcc agc acc tac atc tac cag aat ctg ctg gtc     3255
Glu Leu Gly Ile His Ala Ser Thr Tyr Ile Tyr Gln Asn Leu Leu Val
                690                 695                 700

ggc agg aac cgg ggc gag gaa atc ctg gac agc aaa gaa ctg gtc tgg     3303
Gly Arg Asn Arg Gly Glu Glu Ile Leu Asp Ser Lys Glu Leu Val Trp
            705                 710                 715

atg gac atg agc ctg ctg aac ttc ggc gcc gtg cgg agc cac gac cgg     3351
Met Asp Met Ser Leu Leu Asn Phe Gly Ala Val Arg Ser His Asp Arg
        720                 725                 730

tgc tgg atc tct agc agc gtg gcc atc gag gtg aac ctg cgg cac gcc     3399
Cys Trp Ile Ser Ser Ser Val Ala Ile Glu Val Asn Leu Arg His Ala
    735                 740                 745

ctg atc gtg cgg atc ttc agc aga ttc gac atg atg agc gag aga gag     3447
Leu Ile Val Arg Ile Phe Ser Arg Phe Asp Met Met Ser Glu Arg Glu
750                 755                 760                 765

acc ttc agc acc atc ctg gaa aag gtc atg gaa gat gtg aaa gag ctg     3495
Thr Phe Ser Thr Ile Leu Glu Lys Val Met Glu Asp Val Lys Glu Leu
                770                 775                 780

cgg ttc ttc ccc acc tac cgg cac tac tac ctg gaa acc ctg cag cgg     3543
Arg Phe Phe Pro Thr Tyr Arg His Tyr Tyr Leu Glu Thr Leu Gln Arg
            785                 790                 795

gtg ttc aac gac gag cgg cgg ctg gaa gtg gat gac ttc tac atg cgg     3591
Val Phe Asn Asp Glu Arg Arg Leu Glu Val Asp Asp Phe Tyr Met Arg
        800                 805                 810

ctg tac gac gtg cag acc cgg gag cag gcc ctg aac acc ttc acc gac     3639
Leu Tyr Asp Val Gln Thr Arg Glu Gln Ala Leu Asn Thr Phe Thr Asp
    815                 820                 825

ttc cac aga tgc gtg gag agc gag ctg ctg ctg ccc acc ctg aag ctg     3687
Phe His Arg Cys Val Glu Ser Glu Leu Leu Leu Pro Thr Leu Lys Leu
830                 835                 840                 845

aac ttc ctg ctg tgg atc gtg ttc gag atg gaa aac gtg gag gtg aac     3735
Asn Phe Leu Leu Trp Ile Val Phe Glu Met Glu Asn Val Glu Val Asn
                850                 855                 860

gcc gcc tac aag cgg cac ccc ctg ctg atc tct acc gcc aag ggc ctg     3783
Ala Ala Tyr Lys Arg His Pro Leu Leu Ile Ser Thr Ala Lys Gly Leu
            865                 870                 875
```

-continued

```
agg gtg atc ggc gtg gac atc ttc aac agc cag ctg tcc atc agc atg     3831
Arg Val Ile Gly Val Asp Ile Phe Asn Ser Gln Leu Ser Ile Ser Met
        880                 885                 890

agc ggc tgg att ccc tac gtg gag cgg atg tgc gcc gag agc aaa gtg     3879
Ser Gly Trp Ile Pro Tyr Val Glu Arg Met Cys Ala Glu Ser Lys Val
    895                 900                 905

cag acc aaa ctg acc gcc gac gag ctg aaa ctg aag cgg tgg ttc atc     3927
Gln Thr Lys Leu Thr Ala Asp Glu Leu Lys Leu Lys Arg Trp Phe Ile
910                 915                 920                 925

agc tac tac acc aca ctg aag ctg gac aga aga gcc gag ccc cgg atg     3975
Ser Tyr Tyr Thr Thr Leu Lys Leu Asp Arg Arg Ala Glu Pro Arg Met
                930                 935                 940

agc ttc aag ttc gag ggc ctg agc acc tgg atc ggc agc aac tgt ggc     4023
Ser Phe Lys Phe Glu Gly Leu Ser Thr Trp Ile Gly Ser Asn Cys Gly
            945                 950                 955

ggc gtg cgg gac tac gtg atc cag atg ctg cct acc cgg aag ccc aag     4071
Gly Val Arg Asp Tyr Val Ile Gln Met Leu Pro Thr Arg Lys Pro Lys
        960                 965                 970

cct ggc gcc ctg atg gtg gtg tac gcc cgg gac agc cgg atc gag tgg     4119
Pro Gly Ala Leu Met Val Val Tyr Ala Arg Asp Ser Arg Ile Glu Trp
    975                 980                 985

atc gag gcc gag ctg tcc cag tgg ctg cag atg  gaa ggc agc ctg ggc    4167
Ile Glu Ala Glu Leu Ser Gln Trp Leu Gln Met  Glu Gly Ser Leu Gly
990                 995                 1000                1005

ctg atc ctg gtg cac  gac agc ggc atc atc  aac aag agc gtg ctg       4212
Leu Ile Leu Val His  Asp Ser Gly Ile Ile  Asn Lys Ser Val Leu
                1010                1015                1020

agg gcc cgg acc ctg  aaa atc tac aac cgg  ggc agc atg gac acc       4257
Arg Ala Arg Thr Leu  Lys Ile Tyr Asn Arg  Gly Ser Met Asp Thr
                1025                1030                1035

ctg atc ctg atc agc  tcc ggc gtg tac acc  ttc ggc aac aag ttc       4302
Leu Ile Leu Ile Ser  Ser Gly Val Tyr Thr  Phe Gly Asn Lys Phe
                1040                1045                1050

ctg ctg tcc aag ctg  ctg gcc aag acc gag  tga tga ggatccctcg        4348
Leu Leu Ser Lys Leu  Leu Ala Lys Thr Glu
                1055                1060

agtttttatt gactagttca aaattgaaaa tatataatta caatataaa atg ggc aag   4406
                                                      Met Gly Lys

ttt acc  agc ttc ctg aag agg  gcc ggc aac gcc acc  aag cgg gcc      4451
Phe Thr  Ser Phe Leu Lys Arg  Ala Gly Asn Ala Thr  Lys Arg Ala
    1065                1070                1075

ctg acc  agc gac agc gcc aag  aag atg tac aag ctg  gcc ggc aag     4496
Leu Thr  Ser Asp Ser Ala Lys  Lys Met Tyr Lys Leu  Ala Gly Lys
    1080                1085                1090

acc ctg  cag cgg gtg gtg gag  agc gaa gtg ggc agc  gcc gcc atc     4541
Thr Leu  Gln Arg Val Val Glu  Ser Glu Val Gly Ser  Ala Ala Ile
    1095                1100                1105

gac ggc  gtg atg cag ggc gcc  atc cag agc atc atc  cag ggc gag     4586
Asp Gly  Val Met Gln Gly Ala  Ile Gln Ser Ile Ile  Gln Gly Glu
    1110                1115                1120

aac ctg  ggc gac agc atc aag  cag gcc gtg atc ctg  aac gtg gcc     4631
Asn Leu  Gly Asp Ser Ile Lys  Gln Ala Val Ile Leu  Asn Val Ala
    1125                1130                1135

ggc acc  ctg gaa agc gcc cct  gac ccc ctg agc cct  ggc gag cag     4676
Gly Thr  Leu Glu Ser Ala Pro  Asp Pro Leu Ser Pro  Gly Glu Gln
    1140                1145                1150

ctg ctg  tac aac aag gtg tcc  gag atc gag aag atg  gaa aag gaa     4721
Leu Leu  Tyr Asn Lys Val Ser  Glu Ile Glu Lys Met  Glu Lys Glu
    1155                1160                1165
```

-continued

```
gat cgg  gtg atc gag acc cac  aac gcc aag atc gag  gaa aag ttc      4766
Asp Arg  Val Ile Glu Thr His  Asn Ala Lys Ile Glu  Glu Lys Phe
    1170                 1175                 1180

ggc aag  gac ctg ctg gcc atc  cgg aag atc gtg aag  ggc gag gtg      4811
Gly Lys  Asp Leu Leu Ala Ile  Arg Lys Ile Val Lys  Gly Glu Val
    1185                 1190                 1195

gac gcc  gag aag ctg gaa ggc  aac gag atc aag tac  gtg gag aag      4856
Asp Ala  Glu Lys Leu Glu Gly  Asn Glu Ile Lys Tyr  Val Glu Lys
    1200                 1205                 1210

gcc ctg  agc ggc ctg ctg gaa  atc ggc aag gat cag  agc gag cgg      4901
Ala Leu  Ser Gly Leu Leu Glu  Ile Gly Lys Asp Gln  Ser Glu Arg
    1215                 1220                 1225

atc acc  aag ctg tac cgg gcc  ctg cag acc gaa gag  gac ctg cgg      4946
Ile Thr  Lys Leu Tyr Arg Ala  Leu Gln Thr Glu Glu  Asp Leu Arg
    1230                 1235                 1240

acc cgg  gac gag acc cgg atg  atc aac gag tac cgg  gag aag ttc      4991
Thr Arg  Asp Glu Thr Arg Met  Ile Asn Glu Tyr Arg  Glu Lys Phe
    1245                 1250                 1255

gac gcc  ctg aaa gag gcc atc  gag atc gag cag cag  gcc acc cac      5036
Asp Ala  Leu Lys Glu Ala Ile  Glu Ile Glu Gln Gln  Ala Thr His
    1260                 1265                 1270

gac gag  gcc atc cag gaa atg  ctg gac ctg agc gcc  gag gtg atc      5081
Asp Glu  Ala Ile Gln Glu Met  Leu Asp Leu Ser Ala  Glu Val Ile
    1275                 1280                 1285

gaa acc  gcc agc gag gaa gtg  ccc atc ttt ggc gcc  gga gcc gcc      5126
Glu Thr  Ala Ser Glu Glu Val  Pro Ile Phe Gly Ala  Gly Ala Ala
    1290                 1295                 1300

aac gtg  atc gcc acc acc cgg  gcc att cag ggc ggc  ctg aag ctg      5171
Asn Val  Ile Ala Thr Thr Arg  Ala Ile Gln Gly Gly  Leu Lys Leu
    1305                 1310                 1315

aag gaa  atc gtg gac aag ctg  aca ggc atc gac ctg  agc cac ctg      5216
Lys Glu  Ile Val Asp Lys Leu  Thr Gly Ile Asp Leu  Ser His Leu
    1320                 1325                 1330

aag gtg  gcc gac atc cac ccc  cac atc atc gag aag  gcc atg ctg      5261
Lys Val  Ala Asp Ile His Pro  His Ile Ile Glu Lys  Ala Met Leu
    1335                 1340                 1345

cgg gac  acc gtg acc gac aag  gac ctg gct atg gcc  atc aag agc      5306
Arg Asp  Thr Val Thr Asp Lys  Asp Leu Ala Met Ala  Ile Lys Ser
    1350                 1355                 1360

aag gtg  gac gtg atc gac gag  atg aac gtg gag acc  cag cac gtg      5351
Lys Val  Asp Val Ile Asp Glu  Met Asn Val Glu Thr  Gln His Val
    1365                 1370                 1375

atc gat  gcc gtg ctg ccc atc  gtg aag cag gaa tac  gag cgg cac      5396
Ile Asp  Ala Val Leu Pro Ile  Val Lys Gln Glu Tyr  Glu Arg His
    1380                 1385                 1390

gac aac  aag tac cac gtg aga  atc cct ggc gcc ctg  aag atc cac      5441
Asp Asn  Lys Tyr His Val Arg  Ile Pro Gly Ala Leu  Lys Ile His
    1395                 1400                 1405

agc gag  cac acc ccc aag atc  cac atc tac acc acc  ccc tgg gac      5486
Ser Glu  His Thr Pro Lys Ile  His Ile Tyr Thr Thr  Pro Trp Asp
    1410                 1415                 1420

agc gac  tcc gtg ttc atg tgc  cgg gcc atc gcc ccc  cac cat cag      5531
Ser Asp  Ser Val Phe Met Cys  Arg Ala Ile Ala Pro  His His Gln
    1425                 1430                 1435

cag cgg  agc ttc ttc atc ggc  ttc gac ctg gaa atc  gag tac gtg      5576
Gln Arg  Ser Phe Phe Ile Gly  Phe Asp Leu Glu Ile  Glu Tyr Val
    1440                 1445                 1450

cac ttc  gag gac acc agc gtg  gag ggc cac atc ctg  cac ggc gga      5621
His Phe  Glu Asp Thr Ser Val  Glu Gly His Ile Leu  His Gly Gly
    1455                 1460                 1465
```

-continued

```
gcc atc  acc gtg gag ggc agg  ggc ttc cgg cag gcc  tac acc gag      5666
Ala Ile  Thr Val Glu Gly Arg  Gly Phe Arg Gln Ala  Tyr Thr Glu
    1470                 1475                 1480

ttc atg  aac gcc gcc tgg ggc  atg cct acc acc ccc  gag ctg cac      5711
Phe Met  Asn Ala Ala Trp Gly  Met Pro Thr Thr Pro  Glu Leu His
    1485                 1490                 1495

aag cgg  aag ctg cag cgg agc  atg ggc acc cac ccc  atc tac atg      5756
Lys Arg  Lys Leu Gln Arg Ser  Met Gly Thr His Pro  Ile Tyr Met
    1500                 1505                 1510

ggc agc  atg gac tac gcc atc  agc tac gag cag ctg  gtg tcc aat      5801
Gly Ser  Met Asp Tyr Ala Ile  Ser Tyr Glu Gln Leu  Val Ser Asn
    1515                 1520                 1525

gcc atg  cgg ctg gtg tac gac  agc gag ctg cag atg  cac tgc ctg      5846
Ala Met  Arg Leu Val Tyr Asp  Ser Glu Leu Gln Met  His Cys Leu
    1530                 1535                 1540

aga ggc  ccc ctg aag ttc cag  cgg cgg acc ctg atg  aac gcc ctg      5891
Arg Gly  Pro Leu Lys Phe Gln  Arg Arg Thr Leu Met  Asn Ala Leu
    1545                 1550                 1555

ctg tac  ggc gtg aag atc gcc  tga tga tttttctact agttaatcaa        5938
Leu Tyr  Gly Val Lys Ile Ala
    1560                 1565

ataaaaagca tacaagctat tgcttcgcta tcgttacaaa atggcaggaa ttttgtgtaa   5998

actaagccac atacttgcca atgaaaaaaa tagtagaaag gatactattt taatgggatt   6058

agatgttaag gttccttggg attatagtaa ctgggcatct gttaactttt acgacgttag   6118

gttagatact gatgttacag attataataa tgttacaata aaatacatga caggatgtga   6178

tatttttcct catataactc ttggaatagc aaatatggat caatgtgata gatttgaaaa   6238

tttcaaaaag caaataactg atcaagattt acagactatt tctatagtct gtaaagaaga   6298

gatgtgtttt cctcagagta acgcctctaa acagttggga gcgaaaggat gcgctgtagt   6358

tatgaaactg gaggtatctg atgaacttag agccctaaga aatgttctgc tgaatgcggt   6418

accctgttcg aaggacgtgt ttggtgatat cacagtagat aatccgtgga atcctcacat   6478

aacagtagga tatgttaagg aggacgatgt cgaaaacaag aaacgcctaa tggagtgcat   6538

gtccaagttt agggggcaag aaatacaagt tctaggatgg tattaataag tatctaagta   6598

tttggtataa tttattaaat agtataatta taacaaataa taaataacat gataacggtt   6658

tttattagaa taaaatagag ataatatcat aatgatatat aatacttcat taccagaaat   6718

gagtaatgga agacttataa atgaactgca taaagctata aggtatagag atataaattt   6778

agtaaggtat atacttaaaa aatgcaaata caataacgta aatatactat caacgtcttt   6838

gtatttagcc gtaagtattt ctgatataga aatggtaaaa ttattactag aacacggtgc   6898

cgatatttta aaatgtaaaa atcctcctct tcataaagct gctagtttag ataatacaga   6958

aattgctaaa ctactaatag attctggcgc tgacatagaa cagatacatt ctggaaatag   7018

tccgttatat atttctgtat atagaaacaa taagtcatta actagatatt tattaaaaaa   7078

aggtgttaat tgtaatagat tctttctaaa ttattacgat gtactgtatg ataagatatc   7138

tgatgatatg tataaaatat ttatagattt taatattgat cttaatatac aaactagaaa   7198

ttttgaaact ccgttacatt acgctataaa gtataagaat atagatttaa ttaggatatt   7258

gttagataat agtattaaaa tagataaaag tttatttttg cataaacagt atctcataaa   7318

ggcacttaaa aataattgta gttacgatat aatagcgtta cttataaatc acggagtgcc   7378

tataaacgaa caagatgatt taggtaaaac ccattacat cattcggtaa ttaatagaag    7438

aaaagatgta acagcacttc tgttaaatct aggagctgat ataaacgtaa tagatgactg   7498
```

-continued

```
tatgggcagt cccttacatt acgctgtttc acgtaacgat atcgaaacaa caaagacact   7558

tttagaaaga ggatctaatg ttaatgtggt taataatcat atagataccg ttctaaatat   7618

agctgttgca tctaaaaaca aaactatagt aaacttatta ctgaagtacg gtactgatac   7678

aaagttggta ggattagata aacatgttat tcacatagct atagaaatga aagatattaa   7738

tatactgaat gcgatcttat tatatggttg ctatgtaaac gtctataatc ataaaggttt   7798

cactcctcta tacatggcag ttagttctat gaaaacagaa tttgttaaac tcttacttga   7858

ccacggtgct tacgtaaatg ctaaagctaa gttatctgga aatactcctt tacataaagc   7918

tatgttatct aatagtttta ataatataaa attactttta tcttataacg ccgactataa   7978

ttctctaaat aatcacggta atacgcctct aacttgtgtt agctttttag atgacaagat   8038

agctattatg ataatatcta aaatgatgtt agaaatatct aaaaatcctg aaatagctaa   8098

ttcagaaggt tttatagtaa acatggaaca tataaacagt aataaaagac tactatctat   8158

aaaagaatca tgcgaaaaag aactagatgt tataacacat ataaagttaa attctatata   8218

ttcttttaat atctttcttg acaataacat agatcttatg gtaaagttcg taactaatcc   8278

tagagttaat aagatacctg catgtatacg tatatatagg gaattaatac ggaaaaataa   8338

atcattagct tttcatagac atcagctaat agttaaagct gtaaaagaga gtaagaatct   8398

aggaataata ggtaggttac ctatagatat caaacatata ataatggaac tattaagtaa   8458

taatgattta cattctgtta tcaccagctg ttgtaaccca gtagtataaa gagctcgaat   8518

taattcactg gccgtcgttt tacaacgtcg tg                                 8550
```

<210> SEQ ID NO 4
<211> LENGTH: 3186
<212> TYPE: DNA
<213> ORGANISM: artificial sequence
<220> FEATURE:
<223> OTHER INFORMATION: Codon-optimized synthetic AHSV4-VP2 gene

<400> SEQUENCE: 4

```
atggccagcg agttcggcat cctgatgacc aacgagaagt tcgaccccag cctggaaaag     60

accatctgcg acgtgatcgt gaccaagaag ggccgggtca agcacaagga agtggacggc    120

gtgtgcggct acgagtggga cgagaccaac caccggttcg gcctgtgcga ggtggagcac    180

gacatgagca tcagcgagtt catgtacaac gagatcagat gcgagggcgc ctaccccatc    240

ttcccccggt acatcatcga caccctgaag tatgagaagt tcatcgaccg gaacgaccac    300

cagatccggg tggaccggga cgacaacgag atgcggaaga tcctgatcca gccctacgcc    360

ggcgagatgt acttcagccc cgagtgctac cccagcgtgt tcctgcggcg ggaggccaga    420

agccagaagc tggaccggat caggaactac atcggcaagc gggtggagtt ctacgaggaa    480

gagagcaagc ggaaggccat cctggaccag aacaagatga gcaaggtgga acagtggcgg    540

gacgccgtga acgagcggat cgtgagcatc gagcccaagc ggggcgagtg ctacgaccac    600

ggcaccgaca tcatctacca gttcatcaag aagctgcggt tcggcatgat gtacccccac    660

tactacgtgc tgcacagcga ctactgcatc gtgcccaaca agggcggcac cagcatcggc    720

agctggcaca tccggaagcg gaccgagggc gacgccaagg ccagcgccat gtacagcggc    780

aagggccccc tgaacgacct gcgggtgaag atcgagcggg acgacctgag ccgggagacc    840

atcatccaga tcatcgagta cggcaagaag ttcaacagct ctgccggcga caagcagggc    900

aacatcagca tcgagaagct ggtcgagtac tgcgacttcc tgaccacctt cgtgcacgcc    960

aagaagaagg aagagggcga ggacgacacc gccaggcagg aaatccggaa ggcctgggtg   1020
```

-continued

```
aagggaatgc cctacatgga cttcagcaag cccatgaaga tcacccgggg cttcaaccgg   1080

aatatgctgt tcttcgccgc cctggacagc ttccggaaga ggaacggcgt ggacgtggac   1140

cccaataagg gcaagtggaa agagcacatc aaagaggtca ccgagaagct gaagaaggcc   1200

cagaccgaga acggcggcca gccctgccag gtgtccatcg acggcgtgaa cgtgctgacc   1260

aacgtggact acggcaccgt gaaccactgg atcgactggg tgacagacat catcatggtg   1320

gtgcagacca agcggctggt gaaagagtac gcctttaaga agctgaaaag cgagaacctg   1380

ctggccggca tgaacagcct ggtcggcgtg ctgcggtgct acatgtactg cctggccctg   1440

gccatctacg acttctacga gggcaccatc gatggcttca agaagggcag caacgcctcc   1500

gccatcatcg agaccgtggc ccagatgttc cccgacttcc ggcgggaact ggtggagaag   1560

tttggcatcg acctgcgcat gaaagagatc acccgcgagc tgttcgtggg caagagcatg   1620

accagcaagt tcatggaaga gggggagtac ggctacaagt tcgcctacgg ctggcggagg   1680

gacggcttcg ccgtgatgga agattacggc gagatcctga cagagaaggt ggaggacctg   1740

tacaaggggg tgctgctggg ccggaagtgg gaggacgagg tggacgaccc cgagagctac   1800

ttctacgacg acctgtacac caacgagccc caccgggtgt tcctgagcgc cggcaaggac   1860

gtggacaaca acatcaccct gcggagcatc agccaggccg agaccaccta cctgagcaag   1920

cggttcgtga gctactggta caggatcagc caggtggagg tgaccaaggc ccggaacgag   1980

gtgctggaca tgaacgagaa gcagaagccc tacttcgagt tcgagtacga cgacttcaag   2040

ccctgctcca tcggcgagct gggcatccac gccagcacct acatctacca gaatctgctg   2100

gtcggcagga accggggcga ggaaatcctg gacagcaaag aactggtctg gatggacatg   2160

agcctgctga acttcggcgc cgtgcggagc cacgaccggt gctggatctc tagcagcgtg   2220

gccatcgagg tgaacctgcg gcacgccctg atcgtgcgga tcttcagcag attcgacatg   2280

atgagcgaga gagagacctt cagcaccatc ctggaaaagg tcatggaaga tgtgaaagag   2340

ctgcggttct tccccaccta ccggcactac tacctggaaa ccctgcagcg ggtgttcaac   2400

gacgagcggc ggctggaagt ggatgacttc tacatgcggc tgtacgacgt gcagacccgg   2460

gagcaggccc tgaacacctt caccgacttc cacagatgcg tggagagcga gctgctgctg   2520

cccaccctga agctgaactt cctgctgtgg atcgtgttcg agatggaaaa cgtggaggtg   2580

aacgccgcct acaagcggca ccccctgctg atctctaccg ccaagggcct gagggtgatc   2640

ggcgtggaca tcttcaacag ccagctgtcc atcagcatga gcggctggat tccctacgtg   2700

gagcggatgt gcgccgagag caaagtgcag accaaactga ccgccgacga gctgaaactg   2760

aagcggtggt tcatcagcta ctacaccaca ctgaagctgg acagaagagc cgagccccgg   2820

atgagcttca agttcgaggg cctgagcacc tggatcggca gcaactgtgg cggcgtgcgg   2880

gactacgtga tccagatgct gcctacccgg aagcccaagc ctggcgccct gatggtggtg   2940

tacgcccggg acagccggat cgagtggatc gaggccgagc tgtcccagtg gctgcagatg   3000

gaaggcagcc tgggcctgat cctggtgcac gacagcggca tcatcaacaa gagcgtgctg   3060

agggcccgga ccctgaaaat ctacaaccgg ggcagcatgg acaccctgat cctgatcagc   3120

tccggcgtgt acaccttcgg caacaagttc ctgctgtcca agctgctggc caagaccgag   3180

tgatga                                                              3186
```

<210> SEQ ID NO 5
<211> LENGTH: 1521
<212> TYPE: DNA
<213> ORGANISM: artificial sequence
<220> FEATURE:

<223> OTHER INFORMATION: Codon-optimized synthetic AHSV4-VP5 gene

<400> SEQUENCE: 5

```
atgggcaagt ttaccagctt cctgaagagg gccggcaacg ccaccaagcg ggccctgacc     60

agcgacagcg ccaagaagat gtacaagctg gccggcaaga ccctgcagcg ggtggtggag    120

agcgaagtgg gcagcgccgc catcgacggc gtgatgcagg gcgccatcca gagcatcatc    180

cagggcgaga acctgggcga cagcatcaag caggccgtga tcctgaacgt ggccggcacc    240

ctggaaagcg cccctgaccc cctgagccct ggcgagcagc tgctgtacaa caaggtgtcc    300

gagatcgaga agatggaaaa ggaagatcgg gtgatcgaga cccacaacgc caagatcgag    360

gaaaagttcg gcaaggacct gctggccatc cggaagatcg tgaagggcga ggtggacgcc    420

gagaagctgg aaggcaacga gatcaagtac gtggagaagg ccctgagcgg cctgctggaa    480

atcggcaagg atcagagcga gcggatcacc aagctgtacc gggccctgca gaccgaagag    540

gacctgcgga cccgggacga gacccggatg atcaacgagt accgggagaa gttcgacgcc    600

ctgaaagagg ccatcgagat cgagcagcag gccacccacg acgaggccat ccaggaaatg    660

ctggacctga gcgccgaggt gatcgaaacc gccagcgagg aagtgcccat ctttggcgcc    720

ggagccgcca acgtgatcgc caccacccgg gccattcagg gcggcctgaa gctgaaggaa    780

atcgtggaca agctgacagg catcgacctg agccacctga aggtggccga catccacccc    840

cacatcatcg agaaggccat gctgcgggac accgtgaccg acaaggacct ggctatggcc    900

atcaagagca aggtggacgt gatcgacgag atgaacgtgg agacccagca cgtgatcgat    960

gccgtgctgc ccatcgtgaa gcaggaatac gagcggcacg acaacaagta ccacgtgaga   1020

atccctggcg ccctgaagat ccacagcgag cacaccccca agatccacat ctacaccacc   1080

ccctgggaca gcgactccgt gttcatgtgc cgggccatcg ccccccacca tcagcagcgg   1140

agcttcttca tcggcttcga cctggaaatc gagtacgtgc acttcgagga caccagcgtg   1200

gagggccaca tcctgcacgg cggagccatc accgtggagg gcaggggctt ccggcaggcc   1260

tacaccgagt tcatgaacgc cgcctggggc atgcctacca cccccgagct gcacaagcgg   1320

aagctgcagc ggagcatggg cacccacccc atctacatgg gcagcatgga ctacgccatc   1380

agctacgagc agctggtgtc caatgccatg cggctggtgt acgacagcga gctgcagatg   1440

cactgcctga gaggccccct gaagttccag cggcggaccc tgatgaacgc cctgctgtac   1500

ggcgtgaaga tcgcctgatg a                                             1521
```

<210> SEQ ID NO 6
<211> LENGTH: 11158
<212> TYPE: DNA
<213> ORGANISM: Artificial sequence
<220> FEATURE:
<223> OTHER INFORMATION: Theoretical sequence for pLHD3460.4 (pC3 H6p synthetic AHSV4 VP2/42Kp synthetic AHSV4 VP5) - entire plasmid
<220> FEATURE:
<221> NAME/KEY: misc_feature
<222> LOCATION: (3)..(942)
<223> OTHER INFORMATION: C3L Arm
<220> FEATURE:
<221> NAME/KEY: promoter
<222> LOCATION: (967)..(1152)
<223> OTHER INFORMATION: H6 vaccinia promoter
<220> FEATURE:
<221> NAME/KEY: CDS
<222> LOCATION: (1153)..(4338)
<223> OTHER INFORMATION: African Horse Sickness Virus-4 VP2 gene
<220> FEATURE:
<221> NAME/KEY: promoter
<222> LOCATION: (4366)..(4397)
<223> OTHER INFORMATION: 42k poxviral promoter

```
<220> FEATURE:
<221> NAME/KEY: CDS
<222> LOCATION: (4398)..(5918)
<223> OTHER INFORMATION: African Horse Sickness Virus-4 VP5 gene
<220> FEATURE:
<221> NAME/KEY: misc_feature
<222> LOCATION: (5947)..(8509)
<223> OTHER INFORMATION: C3R Arm

<400> SEQUENCE: 6

tgcggccgcg tcgacatgca ttgttagttc tgtagatcag taacgtatag catacgagta     60

taattatcgt aggtagtagg tatcctaaaa taaatctgat acagataata actttgtaaa    120

tcaattcagc aatttctcta ttatcatgat aatgattaat acacagcgtg tcgttatttt    180

ttgttacgat agtatttcta aagtaaagag caggaatccc tagtataata gaaataatcc    240

atatgaaaaa tatagtaatg tacatatttc taatgttaac atatttatag gtaaatccag    300

gaagggtaat tttacatat ctatatacgc ttattacagt tattaaaaat atacttgcaa     360

acatgttaga agtaaaaaag aaagaactaa ttttacaaag tgctttacca aaatgccaat    420

ggaaattact tagtatgtat ataatgtata aaggtatgaa tatcacaaac agcaaatcgg    480

ctattcccaa gttgagaaac ggtataatag atatatttct agataccatt aataacctta    540

taagcttgac gtttcctata atgcctacta agaaaactag aagatacata catactaacg    600

ccatacgaga gtaactactc atcgtataac tactgttgct aacagtgaca ctgatgttat    660

aactcatctt tgatgtggta taaatgtata ataactatat tacactggta ttttatttca    720

gttatatact atatagtatt aaaaattata tttgtataat tatattatta tattcagtgt    780

agaaagtaaa atactataaa tatgtatctc ttatttataa cttattagta aagtatgtac    840

tattcagtta tattgtttta taaaagctaa atgctactag attgatataa atgaatatgt    900

aataaattag taatgtagta tactaatatt aactcacatt tgactaatta gctataaaaa    960

cccgggttaa ttaattagtc atcaggcagg gcgagaacga gactatctgc tcgttaatta   1020

attagagctt ctttattcta tacttaaaaa gtgaaaataa atacaaaggt tcttgagggt   1080

tgtgttaaat tgaaagcgag aaataatcat aaattatttc attatcgcga tatccgttaa   1140

gtttgtatcg ta atg gcc agc gag ttc ggc atc ctg atg acc aac gag aag   1191
              Met Ala Ser Glu Phe Gly Ile Leu Met Thr Asn Glu Lys
              1               5                   10

ttc gac ccc agc ctg gaa aag acc atc tgc gac gtg atc gtg acc aag     1239
Phe Asp Pro Ser Leu Glu Lys Thr Ile Cys Asp Val Ile Val Thr Lys
    15                  20                  25

aag ggc cgg gtc aag cac aag gaa gtg gac ggc gtg tgc ggc tac gag     1287
Lys Gly Arg Val Lys His Lys Glu Val Asp Gly Val Cys Gly Tyr Glu
30                  35                  40                  45

tgg gac gag acc aac cac cgg ttc ggc ctg tgc gag gtg gag cac gac     1335
Trp Asp Glu Thr Asn His Arg Phe Gly Leu Cys Glu Val Glu His Asp
                50                  55                  60

atg agc atc agc gag ttc atg tac aac gag atc aga tgc gag ggc gcc     1383
Met Ser Ile Ser Glu Phe Met Tyr Asn Glu Ile Arg Cys Glu Gly Ala
            65                  70                  75

tac ccc atc ttc ccc cgg tac atc atc gac acc ctg aag tat gag aag     1431
Tyr Pro Ile Phe Pro Arg Tyr Ile Ile Asp Thr Leu Lys Tyr Glu Lys
        80                  85                  90

ttc atc gac cgg aac gac cac cag atc cgg gtg gac cgg gac gac aac     1479
Phe Ile Asp Arg Asn Asp His Gln Ile Arg Val Asp Arg Asp Asp Asn
    95                  100                 105

gag atg cgg aag atc ctg atc cag ccc tac gcc ggc gag atg tac ttc     1527
Glu Met Arg Lys Ile Leu Ile Gln Pro Tyr Ala Gly Glu Met Tyr Phe
110                 115                 120                 125
```

-continued

```
agc ccc gag tgc tac ccc agc gtg ttc ctg cgg cgg gag gcc aga agc      1575
Ser Pro Glu Cys Tyr Pro Ser Val Phe Leu Arg Arg Glu Ala Arg Ser
                130                 135                 140

cag aag ctg gac cgg atc agg aac tac atc ggc aag cgg gtg gag ttc      1623
Gln Lys Leu Asp Arg Ile Arg Asn Tyr Ile Gly Lys Arg Val Glu Phe
            145                 150                 155

tac gag gaa gag agc aag cgg aag gcc atc ctg gac cag aac aag atg      1671
Tyr Glu Glu Glu Ser Lys Arg Lys Ala Ile Leu Asp Gln Asn Lys Met
        160                 165                 170

agc aag gtg gaa cag tgg cgg gac gcc gtg aac gag cgg atc gtg agc      1719
Ser Lys Val Glu Gln Trp Arg Asp Ala Val Asn Glu Arg Ile Val Ser
    175                 180                 185

atc gag ccc aag cgg ggc gag tgc tac gac cac ggc acc gac atc atc      1767
Ile Glu Pro Lys Arg Gly Glu Cys Tyr Asp His Gly Thr Asp Ile Ile
190                 195                 200                 205

tac cag ttc atc aag aag ctg cgg ttc ggc atg atg tac ccc cac tac      1815
Tyr Gln Phe Ile Lys Lys Leu Arg Phe Gly Met Met Tyr Pro His Tyr
                210                 215                 220

tac gtg ctg cac agc gac tac tgc atc gtg ccc aac aag ggc ggc acc      1863
Tyr Val Leu His Ser Asp Tyr Cys Ile Val Pro Asn Lys Gly Gly Thr
            225                 230                 235

agc atc ggc agc tgg cac atc cgg aag cgg acc gag ggc gac gcc aag      1911
Ser Ile Gly Ser Trp His Ile Arg Lys Arg Thr Glu Gly Asp Ala Lys
        240                 245                 250

gcc agc gcc atg tac agc ggc aag ggc ccc ctg aac gac ctg cgg gtg      1959
Ala Ser Ala Met Tyr Ser Gly Lys Gly Pro Leu Asn Asp Leu Arg Val
    255                 260                 265

aag atc gag cgg gac gac ctg agc cgg gag acc atc atc cag atc atc      2007
Lys Ile Glu Arg Asp Asp Leu Ser Arg Glu Thr Ile Ile Gln Ile Ile
270                 275                 280                 285

gag tac ggc aag aag ttc aac agc tct gcc ggc gac aag cag ggc aac      2055
Glu Tyr Gly Lys Lys Phe Asn Ser Ser Ala Gly Asp Lys Gln Gly Asn
                290                 295                 300

atc agc atc gag aag ctg gtc gag tac tgc gac ttc ctg acc acc ttc      2103
Ile Ser Ile Glu Lys Leu Val Glu Tyr Cys Asp Phe Leu Thr Thr Phe
            305                 310                 315

gtg cac gcc aag aag aag gaa gag ggc gag gac gac acc gcc agg cag      2151
Val His Ala Lys Lys Lys Glu Glu Gly Glu Asp Asp Thr Ala Arg Gln
        320                 325                 330

gaa atc cgg aag gcc tgg gtg aag gga atg ccc tac atg gac ttc agc      2199
Glu Ile Arg Lys Ala Trp Val Lys Gly Met Pro Tyr Met Asp Phe Ser
    335                 340                 345

aag ccc atg aag atc acc cgg ggc ttc aac cgg aat atg ctg ttc ttc      2247
Lys Pro Met Lys Ile Thr Arg Gly Phe Asn Arg Asn Met Leu Phe Phe
350                 355                 360                 365

gcc gcc ctg gac agc ttc cgg aag agg aac ggc gtg gac gtg gac ccc      2295
Ala Ala Leu Asp Ser Phe Arg Lys Arg Asn Gly Val Asp Val Asp Pro
                370                 375                 380

aat aag ggc aag tgg aaa gag cac atc aaa gag gtc acc gag aag ctg      2343
Asn Lys Gly Lys Trp Lys Glu His Ile Lys Glu Val Thr Glu Lys Leu
            385                 390                 395

aag aag gcc cag acc gag aac ggc ggc cag ccc tgc cag gtg tcc atc      2391
Lys Lys Ala Gln Thr Glu Asn Gly Gly Gln Pro Cys Gln Val Ser Ile
        400                 405                 410

gac ggc gtg aac gtg ctg acc aac gtg gac tac ggc acc gtg aac cac      2439
Asp Gly Val Asn Val Leu Thr Asn Val Asp Tyr Gly Thr Val Asn His
    415                 420                 425

tgg atc gac tgg gtg aca gac atc atc atg gtg gtg cag acc aag cgg      2487
Trp Ile Asp Trp Val Thr Asp Ile Ile Met Val Val Gln Thr Lys Arg
430                 435                 440                 445
```

```
ctg gtg aaa gag tac gcc ttt aag aag ctg aaa agc gag aac ctg ctg     2535
Leu Val Lys Glu Tyr Ala Phe Lys Lys Leu Lys Ser Glu Asn Leu Leu
                450                 455                 460

gcc ggc atg aac agc ctg gtc ggc gtg ctg cgg tgc tac atg tac tgc     2583
Ala Gly Met Asn Ser Leu Val Gly Val Leu Arg Cys Tyr Met Tyr Cys
            465                 470                 475

ctg gcc ctg gcc atc tac gac ttc tac gag ggc acc atc gat ggc ttc     2631
Leu Ala Leu Ala Ile Tyr Asp Phe Tyr Glu Gly Thr Ile Asp Gly Phe
        480                 485                 490

aag aag ggc agc aac gcc tcc gcc atc atc gag acc gtg gcc cag atg     2679
Lys Lys Gly Ser Asn Ala Ser Ala Ile Ile Glu Thr Val Ala Gln Met
    495                 500                 505

ttc ccc gac ttc cgg cgg gaa ctg gtg gag aag ttt ggc atc gac ctg     2727
Phe Pro Asp Phe Arg Arg Glu Leu Val Glu Lys Phe Gly Ile Asp Leu
510                 515                 520                 525

cgc atg aaa gag atc acc cgc gag ctg ttc gtg ggc aag agc atg acc     2775
Arg Met Lys Glu Ile Thr Arg Glu Leu Phe Val Gly Lys Ser Met Thr
                530                 535                 540

agc aag ttc atg gaa gag ggg gag tac ggc tac aag ttc gcc tac ggc     2823
Ser Lys Phe Met Glu Glu Gly Glu Tyr Gly Tyr Lys Phe Ala Tyr Gly
            545                 550                 555

tgg cgg agg gac ggc ttc gcc gtg atg gaa gat tac ggc gag atc ctg     2871
Trp Arg Arg Asp Gly Phe Ala Val Met Glu Asp Tyr Gly Glu Ile Leu
        560                 565                 570

aca gag aag gtg gag gac ctg tac aag ggg gtg ctg ctg ggc cgg aag     2919
Thr Glu Lys Val Glu Asp Leu Tyr Lys Gly Val Leu Leu Gly Arg Lys
    575                 580                 585

tgg gag gac gag gtg gac gac ccc gag agc tac ttc tac gac gac ctg     2967
Trp Glu Asp Glu Val Asp Asp Pro Glu Ser Tyr Phe Tyr Asp Asp Leu
590                 595                 600                 605

tac acc aac gag ccc cac cgg gtg ttc ctg agc gcc ggc aag gac gtg     3015
Tyr Thr Asn Glu Pro His Arg Val Phe Leu Ser Ala Gly Lys Asp Val
                610                 615                 620

gac aac aac atc acc ctg cgg agc atc agc cag gcc gag acc acc tac     3063
Asp Asn Asn Ile Thr Leu Arg Ser Ile Ser Gln Ala Glu Thr Thr Tyr
            625                 630                 635

ctg agc aag cgg ttc gtg agc tac tgg tac agg atc agc cag gtg gag     3111
Leu Ser Lys Arg Phe Val Ser Tyr Trp Tyr Arg Ile Ser Gln Val Glu
        640                 645                 650

gtg acc aag gcc cgg aac gag gtg ctg gac atg aac gag aag cag aag     3159
Val Thr Lys Ala Arg Asn Glu Val Leu Asp Met Asn Glu Lys Gln Lys
    655                 660                 665

ccc tac ttc gag ttc gag tac gac gac ttc aag ccc tgc tcc atc ggc     3207
Pro Tyr Phe Glu Phe Glu Tyr Asp Asp Phe Lys Pro Cys Ser Ile Gly
670                 675                 680                 685

gag ctg ggc atc cac gcc agc acc tac atc tac cag aat ctg ctg gtc     3255
Glu Leu Gly Ile His Ala Ser Thr Tyr Ile Tyr Gln Asn Leu Leu Val
                690                 695                 700

ggc agg aac cgg ggc gag gaa atc ctg gac agc aaa gaa ctg gtc tgg     3303
Gly Arg Asn Arg Gly Glu Glu Ile Leu Asp Ser Lys Glu Leu Val Trp
            705                 710                 715

atg gac atg agc ctg ctg aac ttc ggc gcc gtg cgg agc cac gac cgg     3351
Met Asp Met Ser Leu Leu Asn Phe Gly Ala Val Arg Ser His Asp Arg
        720                 725                 730

tgc tgg atc tct agc agc gtg gcc atc gag gtg aac ctg cgg cac gcc     3399
Cys Trp Ile Ser Ser Ser Val Ala Ile Glu Val Asn Leu Arg His Ala
    735                 740                 745

ctg atc gtg cgg atc ttc agc aga ttc gac atg atg agc gag aga gag     3447
Leu Ile Val Arg Ile Phe Ser Arg Phe Asp Met Met Ser Glu Arg Glu
750                 755                 760                 765
```

```
acc ttc agc acc atc ctg gaa aag gtc atg gaa gat gtg aaa gag ctg     3495
Thr Phe Ser Thr Ile Leu Glu Lys Val Met Glu Asp Val Lys Glu Leu
                770                 775                 780

cgg ttc ttc ccc acc tac cgg cac tac tac ctg gaa acc ctg cag cgg     3543
Arg Phe Phe Pro Thr Tyr Arg His Tyr Tyr Leu Glu Thr Leu Gln Arg
            785                 790                 795

gtg ttc aac gac gag cgg cgg ctg gaa gtg gat gac ttc tac atg cgg     3591
Val Phe Asn Asp Glu Arg Arg Leu Glu Val Asp Asp Phe Tyr Met Arg
        800                 805                 810

ctg tac gac gtg cag acc cgg gag cag gcc ctg aac acc ttc acc gac     3639
Leu Tyr Asp Val Gln Thr Arg Glu Gln Ala Leu Asn Thr Phe Thr Asp
    815                 820                 825

ttc cac aga tgc gtg gag agc gag ctg ctg ctg ccc acc ctg aag ctg     3687
Phe His Arg Cys Val Glu Ser Glu Leu Leu Leu Pro Thr Leu Lys Leu
830                 835                 840                 845

aac ttc ctg ctg tgg atc gtg ttc gag atg gaa aac gtg gag gtg aac     3735
Asn Phe Leu Leu Trp Ile Val Phe Glu Met Glu Asn Val Glu Val Asn
                850                 855                 860

gcc gcc tac aag cgg cac ccc ctg ctg atc tct acc gcc aag ggc ctg     3783
Ala Ala Tyr Lys Arg His Pro Leu Leu Ile Ser Thr Ala Lys Gly Leu
            865                 870                 875

agg gtg atc ggc gtg gac atc ttc aac agc cag ctg tcc atc agc atg     3831
Arg Val Ile Gly Val Asp Ile Phe Asn Ser Gln Leu Ser Ile Ser Met
        880                 885                 890

agc ggc tgg att ccc tac gtg gag cgg atg tgc gcc gag agc aaa gtg     3879
Ser Gly Trp Ile Pro Tyr Val Glu Arg Met Cys Ala Glu Ser Lys Val
    895                 900                 905

cag acc aaa ctg acc gcc gac gag ctg aaa ctg aag cgg tgg ttc atc     3927
Gln Thr Lys Leu Thr Ala Asp Glu Leu Lys Leu Lys Arg Trp Phe Ile
910                 915                 920                 925

agc tac tac acc aca ctg aag ctg gac aga aga gcc gag ccc cgg atg     3975
Ser Tyr Tyr Thr Thr Leu Lys Leu Asp Arg Arg Ala Glu Pro Arg Met
                930                 935                 940

agc ttc aag ttc gag ggc ctg agc acc tgg atc ggc agc aac tgt ggc     4023
Ser Phe Lys Phe Glu Gly Leu Ser Thr Trp Ile Gly Ser Asn Cys Gly
            945                 950                 955

ggc gtg cgg gac tac gtg atc cag atg ctg cct acc cgg aag ccc aag     4071
Gly Val Arg Asp Tyr Val Ile Gln Met Leu Pro Thr Arg Lys Pro Lys
        960                 965                 970

cct ggc gcc ctg atg gtg gtg tac gcc cgg gac agc cgg atc gag tgg     4119
Pro Gly Ala Leu Met Val Val Tyr Ala Arg Asp Ser Arg Ile Glu Trp
    975                 980                 985

atc gag gcc gag ctg tcc cag tgg ctg cag atg  gaa ggc agc ctg ggc    4167
Ile Glu Ala Glu Leu Ser Gln Trp Leu Gln Met  Glu Gly Ser Leu Gly
990                 995                 1000                1005

ctg atc ctg gtg cac  gac agc ggc atc atc  aac aag agc gtg ctg       4212
Leu Ile Leu Val His  Asp Ser Gly Ile Ile  Asn Lys Ser Val Leu
                1010                 1015                 1020

agg gcc cgg acc ctg  aaa atc tac aac cgg  ggc agc atg gac acc       4257
Arg Ala Arg Thr Leu  Lys Ile Tyr Asn Arg  Gly Ser Met Asp Thr
                1025                 1030                 1035

ctg atc ctg atc agc  tcc ggc gtg tac acc  ttc ggc aac aag ttc       4302
Leu Ile Leu Ile Ser  Ser Gly Val Tyr Thr  Phe Gly Asn Lys Phe
                1040                 1045                 1050

ctg ctg tcc aag ctg  ctg gcc aag acc gag  tga tga ggatccctcg        4348
Leu Leu Ser Lys Leu  Leu Ala Lys Thr Glu
                1055                 1060

agtttttatt gactagttca aaattgaaaa tatataatta caatataaa atg ggc aag   4406
                                                      Met Gly Lys
```

-continued

```
ttt acc  agc ttc ctg aag agg  gcc ggc aac gcc acc  aag cgg gcc      4451
Phe Thr  Ser Phe Leu Lys Arg  Ala Gly Asn Ala Thr  Lys Arg Ala
    1065                 1070                 1075

ctg acc  agc gac agc gcc aag  aag atg tac aag ctg  gcc ggc aag      4496
Leu Thr  Ser Asp Ser Ala Lys  Lys Met Tyr Lys Leu  Ala Gly Lys
    1080                 1085                 1090

acc ctg  cag cgg gtg gtg gag  agc gaa gtg ggc agc  gcc gcc atc      4541
Thr Leu  Gln Arg Val Val Glu  Ser Glu Val Gly Ser  Ala Ala Ile
    1095                 1100                 1105

gac ggc  gtg atg cag ggc gcc  atc cag agc atc atc  cag ggc gag      4586
Asp Gly  Val Met Gln Gly Ala  Ile Gln Ser Ile Ile  Gln Gly Glu
    1110                 1115                 1120

aac ctg  ggc gac agc atc aag  cag gcc gtg atc ctg  aac gtg gcc      4631
Asn Leu  Gly Asp Ser Ile Lys  Gln Ala Val Ile Leu  Asn Val Ala
    1125                 1130                 1135

ggc acc  ctg gaa agc gcc cct  gac ccc ctg agc cct  ggc gag cag      4676
Gly Thr  Leu Glu Ser Ala Pro  Asp Pro Leu Ser Pro  Gly Glu Gln
    1140                 1145                 1150

ctg ctg  tac aac aag gtg tcc  gag atc gag aag atg  gaa aag gaa      4721
Leu Leu  Tyr Asn Lys Val Ser  Glu Ile Glu Lys Met  Glu Lys Glu
    1155                 1160                 1165

gat cgg  gtg atc gag acc cac  aac gcc aag atc gag  gaa aag ttc      4766
Asp Arg  Val Ile Glu Thr His  Asn Ala Lys Ile Glu  Glu Lys Phe
    1170                 1175                 1180

ggc aag  gac ctg ctg gcc atc  cgg aag atc gtg aag  ggc gag gtg      4811
Gly Lys  Asp Leu Leu Ala Ile  Arg Lys Ile Val Lys  Gly Glu Val
    1185                 1190                 1195

gac gcc  gag aag ctg gaa ggc  aac gag atc aag tac  gtg gag aag      4856
Asp Ala  Glu Lys Leu Glu Gly  Asn Glu Ile Lys Tyr  Val Glu Lys
    1200                 1205                 1210

gcc ctg  agc ggc ctg ctg gaa  atc ggc aag gat cag  agc gag cgg      4901
Ala Leu  Ser Gly Leu Leu Glu  Ile Gly Lys Asp Gln  Ser Glu Arg
    1215                 1220                 1225

atc acc  aag ctg tac cgg gcc  ctg cag acc gaa gag  gac ctg cgg      4946
Ile Thr  Lys Leu Tyr Arg Ala  Leu Gln Thr Glu Glu  Asp Leu Arg
    1230                 1235                 1240

acc cgg  gac gag acc cgg atg  atc aac gag tac cgg  gag aag ttc      4991
Thr Arg  Asp Glu Thr Arg Met  Ile Asn Glu Tyr Arg  Glu Lys Phe
    1245                 1250                 1255

gac gcc  ctg aaa gag gcc atc  gag atc gag cag cag  gcc acc cac      5036
Asp Ala  Leu Lys Glu Ala Ile  Glu Ile Glu Gln Gln  Ala Thr His
    1260                 1265                 1270

gac gag  gcc atc cag gaa atg  ctg gac ctg agc gcc  gag gtg atc      5081
Asp Glu  Ala Ile Gln Glu Met  Leu Asp Leu Ser Ala  Glu Val Ile
    1275                 1280                 1285

gaa acc  gcc agc gag gaa gtg  ccc atc ttt ggc gcc  gga gcc gcc      5126
Glu Thr  Ala Ser Glu Glu Val  Pro Ile Phe Gly Ala  Gly Ala Ala
    1290                 1295                 1300

aac gtg  atc gcc acc acc cgg  gcc att cag ggc ggc  ctg aag ctg      5171
Asn Val  Ile Ala Thr Thr Arg  Ala Ile Gln Gly Gly  Leu Lys Leu
    1305                 1310                 1315

aag gaa  atc gtg gac aag ctg  aca ggc atc gac ctg  agc cac ctg      5216
Lys Glu  Ile Val Asp Lys Leu  Thr Gly Ile Asp Leu  Ser His Leu
    1320                 1325                 1330

aag gtg  gcc gac atc cac ccc  cac atc atc gag aag  gcc atg ctg      5261
Lys Val  Ala Asp Ile His Pro  His Ile Ile Glu Lys  Ala Met Leu
    1335                 1340                 1345

cgg gac  acc gtg acc gac aag  gac ctg gct atg gcc  atc aag agc      5306
Arg Asp  Thr Val Thr Asp Lys  Asp Leu Ala Met Ala  Ile Lys Ser
    1350                 1355                 1360
```

-continued

```
aag gtg  gac gtg atc gac gag  atg aac gtg gag acc  cag cac gtg      5351
Lys Val  Asp Val Ile Asp Glu  Met Asn Val Glu Thr  Gln His Val
    1365                 1370                 1375

atc gat  gcc gtg ctg ccc atc  gtg aag cag gaa tac  gag cgg cac      5396
Ile Asp  Ala Val Leu Pro Ile  Val Lys Gln Glu Tyr  Glu Arg His
    1380                 1385                 1390

gac aac  aag tac cac gtg aga  atc cct ggc gcc ctg  aag atc cac      5441
Asp Asn  Lys Tyr His Val Arg  Ile Pro Gly Ala Leu  Lys Ile His
    1395                 1400                 1405

agc gag  cac acc ccc aag atc  cac atc tac acc acc  ccc tgg gac      5486
Ser Glu  His Thr Pro Lys Ile  His Ile Tyr Thr Thr  Pro Trp Asp
    1410                 1415                 1420

agc gac  tcc gtg ttc atg tgc  cgg gcc atc gcc ccc  cac cat cag      5531
Ser Asp  Ser Val Phe Met Cys  Arg Ala Ile Ala Pro  His His Gln
    1425                 1430                 1435

cag cgg  agc ttc ttc atc ggc  ttc gac ctg gaa atc  gag tac gtg      5576
Gln Arg  Ser Phe Phe Ile Gly  Phe Asp Leu Glu Ile  Glu Tyr Val
    1440                 1445                 1450

cac ttc  gag gac acc agc gtg  gag ggc cac atc ctg  cac ggc gga      5621
His Phe  Glu Asp Thr Ser Val  Glu Gly His Ile Leu  His Gly Gly
    1455                 1460                 1465

gcc atc  acc gtg gag ggc agg  ggc ttc cgg cag gcc  tac acc gag      5666
Ala Ile  Thr Val Glu Gly Arg  Gly Phe Arg Gln Ala  Tyr Thr Glu
    1470                 1475                 1480

ttc atg  aac gcc gcc tgg ggc  atg cct acc acc ccc  gag ctg cac      5711
Phe Met  Asn Ala Ala Trp Gly  Met Pro Thr Thr Pro  Glu Leu His
    1485                 1490                 1495

aag cgg  aag ctg cag cgg agc  atg ggc acc cac ccc  atc tac atg      5756
Lys Arg  Lys Leu Gln Arg Ser  Met Gly Thr His Pro  Ile Tyr Met
    1500                 1505                 1510

ggc agc  atg gac tac gcc atc  agc tac gag cag ctg  gtg tcc aat      5801
Gly Ser  Met Asp Tyr Ala Ile  Ser Tyr Glu Gln Leu  Val Ser Asn
    1515                 1520                 1525

gcc atg  cgg ctg gtg tac gac  agc gag ctg cag atg  cac tgc ctg      5846
Ala Met  Arg Leu Val Tyr Asp  Ser Glu Leu Gln Met  His Cys Leu
    1530                 1535                 1540

aga ggc  ccc ctg aag ttc cag  cgg cgg acc ctg atg  aac gcc ctg      5891
Arg Gly  Pro Leu Lys Phe Gln  Arg Arg Thr Leu Met  Asn Ala Leu
    1545                 1550                 1555

ctg tac  ggc gtg aag atc gcc  tga tga tttttctact agttaatcaa        5938
Leu Tyr  Gly Val Lys Ile Ala
    1560                 1565

ataaaaagca tacaagctat tgcttcgcta tcgttacaaa atggcaggaa ttttgtgtaa   5998

actaagccac atacttgcca atgaaaaaaa tagtagaaag gatactattt taatgggatt   6058

agatgttaag gttccttggg attatagtaa ctgggcatct gttaactttt acgacgttag   6118

gttagatact gatgttacag attataataa tgttacaata aaatacatga caggatgtga   6178

tatttttcct catataactc ttggaatagc aaatatggat caatgtgata gatttgaaaa   6238

tttcaaaaag caaataactg atcaagattt acagactatt tctatagtct gtaaagaaga   6298

gatgtgtttt cctcagagta acgcctctaa acagttggga gcgaaaggat gcgctgtagt   6358

tatgaaactg gaggtatctg atgaacttag agccctaaga aatgttctgc tgaatgcggt   6418

accctgttcg aaggacgtgt ttggtgatat cacagtagat aatccgtgga atcctcacat   6478

aacagtagga tatgttaagg aggacgatgt cgaaaacaag aaacgcctaa tggagtgcat   6538

gtccaagttt agggggcaag aaatacaagt tctaggatgg tattaataag tatctaagta   6598

tttggtataa tttattaaat agtataatta taacaaataa taaataacat gataacggtt   6658
```

-continued

```
tttattagaa taaaatagag ataatatcat aatgatatat aatacttcat taccagaaat   6718
gagtaatgga agacttataa atgaactgca taaagctata aggtatagag atataaattt   6778
agtaaggtat atacttaaaa aatgcaaata caataacgta aatatactat caacgtcttt   6838
gtatttagcc gtaagtattt ctgatataga aatggtaaaa ttattactag aacacggtgc   6898
cgatatttta aaatgtaaaa atcctcctct tcataaagct gctagtttag ataatacaga   6958
aattgctaaa ctactaatag attctggcgc tgacatagaa cagatacatt ctggaaatag   7018
tccgttatat atttctgtat atagaaacaa taagtcatta actagatatt tattaaaaaa   7078
aggtgttaat tgtaatagat tctttctaaa ttattacgat gtactgtatg ataagatatc   7138
tgatgatatg tataaaatat ttatagattt taatattgat cttaatatac aaactagaaa   7198
ttttgaaact ccgttacatt acgctataaa gtataagaat atagatttaa ttaggatatt   7258
gttagataat agtattaaaa tagataaaag tttatttttg cataaacagt atctcataaa   7318
ggcacttaaa aataattgta gttacgatat aatagcgtta cttataaatc acggagtgcc   7378
tataaacgaa caagatgatt taggtaaaac cccattacat cattcggtaa ttaatagaag   7438
aaaagatgta acagcacttc tgttaaatct aggagctgat ataaacgtaa tagatgactg   7498
tatgggcagt cccttacatt acgctgtttc acgtaacgat atcgaaacaa caaagacact   7558
tttagaaaga ggatctaatg ttaatgtggt taataatcat atagataccg ttctaaatat   7618
agctgttgca tctaaaaaca aaactatagt aaacttatta ctgaagtacg gtactgatac   7678
aaagttggta ggattagata aacatgttat tcacatagct atagaaatga aagatattaa   7738
tatactgaat gcgatcttat tatatggttg ctatgtaaac gtctataatc ataaaggttt   7798
cactcctcta tacatggcag ttagttctat gaaaacagaa tttgttaaac tcttacttga   7858
ccacggtgct tacgtaaatg ctaaagctaa gttatctgga aatactcctt tacataaagc   7918
tatgttatct aatagtttta ataatataaa attactttta tcttataacg ccgactataa   7978
ttctctaaat aatcacggta atacgcctct aacttgtgtt agctttttag atgacaagat   8038
agctattatg ataatatcta aaatgatgtt agaaatatct aaaaatcctg aaatagctaa   8098
ttcagaaggt tttatagtaa acatggaaca tataaacagt aataaaagac tactatctat   8158
aaaagaatca tgcgaaaaag aactagatgt tataacacat ataaagttaa attctatata   8218
ttcttttaat atctttcttg acaataacat agatcttatg gtaaagttcg taactaatcc   8278
tagagttaat aagatacctg catgtatacg tatatatagg gaattaatac ggaaaaataa   8338
atcattagct tttcatagac atcagctaat agttaaagct gtaaaagaga gtaagaatct   8398
aggaataata ggtaggttac ctatagatat caaacatata ataatggaac tattaagtaa   8458
taatgattta cattctgtta tcaccagctg ttgtaaccca gtagtataaa gagctcgaat   8518
taattcactg gccgtcgttt tacaacgtcg tgactgggaa aaccctggcg ttacccaact   8578
taatcgcctt gcagcacatc ccccttttcgc cagctggcgt aatagcgaag aggcccgcac   8638
cgatcgccct tcccaacagt tgcgcagcct gaatggcgaa tggcgcctga tgcggtattt   8698
tctccttacg catctgtgcg gtatttcaca ccgcatatgg tgcactctca gtacaatctg   8758
ctctgatgcc gcatagttaa gccagccccg acacccgcca acacccgctg acgcgccctg   8818
acgggcttgt ctgctcccgg catccgctta cagacaagct gtgaccgtct ccgggagctg   8878
catgtgtcag aggttttcac cgtcatcacc gaaacgcgcg agacgaaagg gcctcgtgat   8938
acgcctattt ttataggtta atgtcatgat aataatggtt tcttagacgt caggtggcac   8998
ttttcgggga aatgtgcgcg gaacccctat ttgtttattt ttctaaatac attcaaatat   9058
```

```
gtatccgctc atgagacaat aaccctgata aatgcttcaa taatattgaa aaaggaagag    9118

tatgagtatt caacatttcc gtgtcgccct tattcccttt tttgcggcat tttgccttcc    9178

tgtttttgct cacccagaaa cgctggtgaa agtaaaagat gctgaagatc agttgggtgc    9238

acgagtgggt tacatcgaac tggatctcaa cagcggtaag atccttgaga gttttcgccc    9298

cgaagaacgt tttccaatga tgagcacttt taaagttctg ctatgtggcg cggtattatc    9358

ccgtattgac gccgggcaag agcaactcgg tcgccgcata cactattctc agaatgactt    9418

ggttgagtac tcaccagtca cagaaaagca tcttacggat ggcatgacag taagagaatt    9478

atgcagtgct gccataacca tgagtgataa cactgcggcc aacttacttc tgacaacgat    9538

cggaggaccg aaggagctaa ccgctttttt gcacaacatg ggggatcatg taactcgcct    9598

tgatcgttgg gaaccggagc tgaatgaagc cataccaaac gacgagcgtg acaccacgat    9658

gcctgtagca atggcaacaa cgttgcgcaa actattaact ggcgaactac ttactctagc    9718

ttcccggcaa caattaatag actggatgga ggcggataaa gttgcaggac cacttctgcg    9778

ctcggccctt ccggctggct ggtttattgc tgataaatct ggagccggtg agcgtgggtc    9838

tcgcggtatc attgcagcac tggggccaga tggtaagccc tcccgtatcg tagttatcta    9898

cacgacgggg agtcaggcaa ctatggatga acgaaataga cagatcgctg agataggtgc    9958

ctcactgatt aagcattggt aactgtcaga ccaagtttac tcatatatac tttagattga   10018

tttaaaactt catttttaat ttaaaaggat ctaggtgaag atcctttttg ataatctcat   10078

gaccaaaatc ccttaacgtg agttttcgtt ccactgagcg tcagaccccg tagaaaagat   10138

caaaggatct tcttgagatc ctttttttct gcgcgtaatc tgctgcttgc aaacaaaaaa   10198

accaccgcta ccagcggtgg tttgtttgcc ggatcaagag ctaccaactc tttttccgaa   10258

ggtaactggc ttcagcagag cgcagatacc aaatactgtc cttctagtgt agccgtagtt   10318

aggccaccac ttcaagaact ctgtagcacc gcctacatac ctcgctctgc taatcctgtt   10378

accagtggct gctgccagtg gcgataagtc gtgtcttacc gggttggact caagacgata   10438

gttaccggat aaggcgcagc ggtcgggctg aacggggggt tcgtgcacac agcccagctt   10498

ggagcgaacg acctacaccg aactgagata cctacagcgt gagctatgag aaagcgccac   10558

gcttcccgaa gggagaaagg cggacaggta tccggtaagc ggcagggtcg gaacaggaga   10618

gcgcacgagg gagcttccag ggggaaacgc ctggtatctt tatagtcctg tcgggtttcg   10678

ccacctctga cttgagcgtc gatttttgtg atgctcgtca ggggggcgga gcctatggaa   10738

aaacgccagc aacgcggcct ttttacggtt cctggccttt tgctggcctt ttgctcacat   10798

gttctttcct gcgttatccc ctgattctgt ggataaccgt attaccgcct ttgagtgagc   10858

tgataccgct cgccgcagcc gaacgaccga gcgcagcgag tcagtgagcg aggaagcgga   10918

agagcgccca atacgcaaac cgcctctccc cgcgcgttgg ccgattcatt aatgcagctg   10978

gcacgacagg tttcccgact ggaaagcggg cagtgagcgc aacgcaatta atgtgagtta   11038

gctcactcat taggcacccc aggctttaca ctttatgctt ccggctcgta tgttgtgtgg   11098

aattgtgagc ggataacaat ttcacacagg aaacagctat gaccatgatt acgccaagct   11158
```

<210> SEQ ID NO 7
<211> LENGTH: 67
<212> TYPE: DNA
<213> ORGANISM: Artificial sequence
<220> FEATURE:
<223> OTHER INFORMATION: Primer for amplification of 42Kp-AHSV 4 VP5
      expressing cassette

<400> SEQUENCE: 7
tgactagttc aaaattgaaa atatataatt acaatataaa atgggcaagt ttaccagctt 60
cctgaag 67

<210> SEQ ID NO 8
<211> LENGTH: 43
<212> TYPE: DNA
<213> ORGANISM: Artificial sequence
<220> FEATURE:
<223> OTHER INFORMATION: Primer for amplification of 42Kp-AHSV 4 VP5 expressing cassette

<400> SEQUENCE: 8
ttaactagta gaaaaatcat caggcgatct tcacgccgta cag 43

<210> SEQ ID NO 9
<211> LENGTH: 25
<212> TYPE: DNA
<213> ORGANISM: Artificial Sequence
<220> FEATURE:
<223> OTHER INFORMATION: Primers for amplifying the AHSV-4 VP2 probe for the vCP2377.6.1.1 viral vector

<400> SEQUENCE: 9
tacgaccacg gcaccgacat catct 25

<210> SEQ ID NO 10
<211> LENGTH: 25
<212> TYPE: DNA
<213> ORGANISM: artificial sequence
<220> FEATURE:
<223> OTHER INFORMATION: Primers for amplifying the AHSV-4 VP2 probe for the vCP2377.6.1.1 viral vector

<400> SEQUENCE: 10
ttttcagctt cttaaaggcg tactc 25

<210> SEQ ID NO 11
<211> LENGTH: 25
<212> TYPE: DNA
<213> ORGANISM: artificial sequence
<220> FEATURE:
<223> OTHER INFORMATION: Primers for amplifying the AHSV-4 VP5 probe for the vCP2377.6.1.1 viral vector

<400> SEQUENCE: 11
aagaagatgt acaagctggc cggca 25

<210> SEQ ID NO 12
<211> LENGTH: 25
<212> TYPE: DNA
<213> ORGANISM: artificial sequence
<220> FEATURE:
<223> OTHER INFORMATION: Primers for amplifying the AHSV-4 VP5 probe for the vCP2377.6.1.1 viral vector

<400> SEQUENCE: 12
gccgctcgta ttcctgcttc acgat 25

<210> SEQ ID NO 13
<211> LENGTH: 30
<212> TYPE: DNA
<213> ORGANISM: artificial sequence
<220> FEATURE:
<223> OTHER INFORMATION: 8103.JY Primer for PCR amplification of the vCP2377/vCP2383/vCP2398 C3 arms plus insert

<400> SEQUENCE: 13
gaggcatcca acatataaag aagactaaag 30

<210> SEQ ID NO 14
<211> LENGTH: 27
<212> TYPE: DNA
<213> ORGANISM: artificial sequence
<220> FEATURE:
<223> OTHER INFORMATION: 8104.JY Primer Primer for PCR amplification of the vCP2377/vCP2383/vCP2398 C3 arms plus insert

<400> SEQUENCE: 14
tagttaaata ctcataactc atatctg 27

<210> SEQ ID NO 15
<211> LENGTH: 25
<212> TYPE: DNA
<213> ORGANISM: artificial sequence
<220> FEATURE:
<223> OTHER INFORMATION: 13616.LH Primer for PCR amplification of the vCP2377 C3 arms plus insert

<400> SEQUENCE: 15
tgccggccag cttgtacatc ttctt 25

<210> SEQ ID NO 16
<211> LENGTH: 25
<212> TYPE: DNA
<213> ORGANISM: artificial sequence
<220> FEATURE:
<223> OTHER INFORMATION: 13637.LH Primer for PCR amplification of the vCP2377 C3 arms plus insert

<400> SEQUENCE: 16
caccacactg aagctggaca gaaga 25

<210> SEQ ID NO 17
<211> LENGTH: 8800
<212> TYPE: DNA
<213> ORGANISM: artificial sequence
<220> FEATURE:
<223> OTHER INFORMATION: vCP2377.6.1.1 viral vector sequence from left arm to right arm, including H6p-codon-optimized AHSV4-VP2, 42Kp-codon-optimized AHSV4-VP5
<220> FEATURE:
<221> NAME/KEY: C3 left arm: 265-1205
<222> LOCATION: (265)..(1205)
<223> OTHER INFORMATION: C3 left arm: 265-1205
<220> FEATURE:
<221> NAME/KEY: H6 promoter: 1230-1415
<222> LOCATION: (1230)..(1415)
<223> OTHER INFORMATION: H6 promoter: 1230-1415
<220> FEATURE:
<221> NAME/KEY: AHSV4-VP2: 1416-4601
<222> LOCATION: (1416)..(4601)
<223> OTHER INFORMATION: AHSV4-VP2: 1416-4601
<220> FEATURE:
<221> NAME/KEY: 42K promoter: 4629-4660
<222> LOCATION: (4629)..(4660)
<223> OTHER INFORMATION: 42K promoter: 4629-4660
<220> FEATURE:
<221> NAME/KEY: AHSV4-VP5: 4661-6165
<222> LOCATION: (4661)..(6165)
<223> OTHER INFORMATION: AHSV4-VP5: 4661-6165
<220> FEATURE:
<221> NAME/KEY: C3 right arm: 6209-8772
<222> LOCATION: (6209)..(8772)
<223> OTHER INFORMATION: C3 right arm: 6209-8772

<400> SEQUENCE: 17
atctgtcaac gtttctctaa gagattcata ggtattatta ttacatcgat ctagaagtct 60

-continued

```
aataactgct aagtatatta ttggatttaa cgcgctataa acgcatccaa aacctacaaa    120
tataggagaa gcttctctta tgaaacttct taaagcttta ctcttactat tactactcaa    180
aagagatatt acattaatta tgtgatgagg catccaacat ataaagaaga ctaaagctgt    240
agaagctgtt atgaagaata tcttatcaga tatattagat gcattgttag ttctgtagat    300
cagtaacgta tagcatacga gtataattat cgtaggtagt aggtatccta aaataaatct    360
gatacagata ataactttgt aaatcaattc agcaatttct ctattatcat gataatgatt    420
aatacacagc gtgtcgttat tttttgttac gatagtattt ctaaagtaaa gagcaggaat    480
ccctagtata atagaaataa tccatatgaa aaatatagta atgtacatat ttctaatgtt    540
aacatattta taggtaaatc caggaagggt aatttttaca tatctatata cgcttattac    600
agttattaaa aatatacttg caaacatgtt agaagtaaaa aagaaagaac taattttaca    660
aagtgcttta ccaaaatgcc aatggaaatt acttagtatg tatataatgt ataaaggtat    720
gaatatcaca aacagcaaat cggctattcc caagttgaga aacggtataa tagatatatt    780
tctagatacc attaataacc ttataagctt gacgtttcct ataatgccta ctaagaaaac    840
tagaagatac atacatacta acgccatacg agagtaacta ctcatcgtat aactactgtt    900
gctaacagtg acactgatgt tataactcat ctttgatgtg gtataaatgt ataataacta    960
tattacactg gtattttatt tcagttatat actatatagt attaaaaatt atatttgtat   1020
aattatatta ttatattcag tgtagaaagt aaaatactat aaatatgtat ctcttattta   1080
taacttatta gtaaagtatg tactattcag ttatattgtt ttataaaagc taaatgctac   1140
tagattgata taaatgaata tgtaataaat tagtaatgta gtatactaat attaactcac   1200
atttgactaa ttagctataa aaacccgggt taattaatta gtcatcaggc agggcgagaa   1260
cgagactatc tgctcgttaa ttaattagag cttctttatt ctatacttaa aaagtgaaaa   1320
taaatacaaa ggttcttgag ggttgtgtta aattgaaagc gagaaataat cataaattat   1380
ttcattatcg cgatatccgt taagtttgta tcgtaatggc cagcgagttc ggcatcctga   1440
tgaccaacga gaagttcgac cccagcctgg aaaagaccat ctgcgacgtg atcgtgacca   1500
agaagggccg ggtcaagcac aaggaagtgg acggcgtgtg cggctacgag tgggacgaga   1560
ccaaccaccg gttcggcctg tgcgaggtgg agcacgacat gagcatcagc gagttcatgt   1620
acaacgagat cagatgcgag ggcgcctacc ccatcttccc ccggtacatc atcgacaccc   1680
tgaagtatga gaagttcatc gaccggaacg accaccagat ccgggtggac cgggacgaca   1740
acgagatgcg gaagatcctg atccagccct acgccggcga gatgtacttc agccccgagt   1800
gctaccccag cgtgttcctg cggcgggagg ccagaagcca gaagctggac cggatcagga   1860
actacatcgg caagcgggtg gagttctacg aggaagagag caagcggaag gccatcctgg   1920
accagaacaa gatgagcaag gtggaacagt ggcgggacgc cgtgaacgag cggatcgtga   1980
gcatcgagcc caagcggggc gagtgctacg accacggcac cgacatcatc taccagttca   2040
tcaagaagct gcggttcggc atgatgtacc cccactacta cgtgctgcac agcgactact   2100
gcatcgtgcc caacaagggc ggcaccagca tcggcagctg gcacatccgg aagcggaccg   2160
agggcgacgc caaggccagc gccatgtaca gcggcaaggg cccccctgaac gacctgcggg   2220
tgaagatcga gcgggacgac ctgagccggg agaccatcat ccagatcatc gagtacggca   2280
agaagttcaa cagctctgcc ggcgacaagc agggcaacat cagcatcgag aagctggtcg   2340
agtactgcga cttcctgacc accttcgtgc acgccaagaa gaaggaagag ggcgaggacg   2400
acaccgccag gcaggaaatc cggaaggcct gggtgaaggg aatgccctac atggacttca   2460
```

-continued

```
gcaagcccat gaagatcacc cggggcttca accggaatat gctgttcttc gccgccctgg   2520
acagcttccg gaagaggaac ggcgtggacg tggaccccaa taagggcaag tggaaagagc   2580
acatcaaaga ggtcaccgag aagctgaaga aggcccagac cgagaacggc ggccagccct   2640
gccaggtgtc catcgacggc gtgaacgtgc tgaccaacgt ggactacggc accgtgaacc   2700
actggatcga ctgggtgaca gacatcatca tggtggtgca gaccaagcgg ctggtgaaag   2760
agtacgcctt taagaagctg aaaagcgaga acctgctggc cggcatgaac agcctggtcg   2820
gcgtgctgcg gtgctacatg tactgcctgg ccctggccat ctacgacttc tacgagggca   2880
ccatcgatgg cttcaagaag ggcagcaacg cctccgccat catcgagacc gtggcccaga   2940
tgttccccga cttccggcgg gaactggtgg agaagtttgg catcgacctg cgcatgaaag   3000
agatcacccg cgagctgttc gtgggcaaga gcatgaccag caagttcatg gaagaggggg   3060
agtacggcta caagttcgcc tacggctggc ggagggacgg cttcgccgtg atggaagatt   3120
acggcgagat cctgacagag aaggtggagg acctgtacaa gggggtgctg ctgggccgga   3180
agtgggagga cgaggtggac gaccccgaga gctacttcta cgacgacctg tacaccaacg   3240
agccccaccg ggtgttcctg agcgccggca aggacgtgga caacaacatc accctgcgga   3300
gcatcagcca ggccgagacc acctacctga gcaagcggtt cgtgagctac tggtacagga   3360
tcagccaggt ggaggtgacc aaggcccgga acgaggtgct ggacatgaac gagaagcaga   3420
agccctactt cgagttcgag tacgacgact tcaagccctg ctccatcggc gagctgggca   3480
tccacgccag cacctacatc taccagaatc tgctggtcgg caggaaccgg ggcgaggaaa   3540
tcctggacag caaagaactg gtctggatgg acatgagcct gctgaacttc ggcgccgtgc   3600
ggagccacga ccggtgctgg atctctagca gcgtggccat cgaggtgaac ctgcggcacg   3660
ccctgatcgt gcggatcttc agcagattcg acatgatgag cgagagagag accttcagca   3720
ccatcctgga aaaggtcatg gaagatgtga aagagctgcg gttcttcccc acctaccggc   3780
actactacct ggaaaccctg cagcgggtgt tcaacgacga gcggcggctg gaagtggatg   3840
acttctacat gcggctgtac gacgtgcaga cccgggagca ggccctgaac accttcaccg   3900
acttccacag atgcgtggag agcgagctgc tgctgcccac cctgaagctg aacttcctgc   3960
tgtggatcgt gttcgagatg gaaaacgtgg aggtgaacgc cgcctacaag cggcaccccc   4020
tgctgatctc taccgccaag ggcctgaggg tgatcggcgt ggacatcttc aacagccagc   4080
tgtccatcag catgagcggc tggattccct acgtggagcg gatgtgcgcc gagagcaaag   4140
tgcagaccaa actgaccgcc gacgagctga aactgaagcg gtggttcatc agctactaca   4200
ccacactgaa gctggacaga agagccgagc cccggatgag cttcaagttc gagggcctga   4260
gcacctggat cggcagcaac tgtggcggcg tgcgggacta cgtgatccag atgctgccta   4320
cccggaagcc caagcctggc gccctgatgg tggtgtacgc ccgggacagc cggatcgagt   4380
ggatcgaggc cgagctgtcc cagtggctgc agatggaagg cagcctgggc ctgatcctgg   4440
tgcacgacag cggcatcatc aacaagagcg tgctgagggc ccggaccctg aaaatctaca   4500
accggggcag catggacacc ctgatcctga tcagctccgg cgtgtacacc ttcggcaaca   4560
agttcctgct gtccaagctg ctggccaaga ccgagtgatg aggatccctc gagtttttat   4620
tgactagttc aaaattgaaa atatataatt acaatataaa atgggcaagt ttaccagctt   4680
cctgaagagg gccggcaacg ccaccaagcg ggccctgacc agcgacagcg ccaagaagat   4740
gtacaagctg gccggcaaga ccctgcagcg ggtggtggag agcgaagtgg gcagcgccgc   4800
catcgacggc gtgatgcagg gcgccatcca gagcatcatc cagggcgaga acctgggcga   4860
```

-continued

```
cagcatcaag caggccgtga tcctgaacgt ggccggcacc ctggaaagcg cccctgaccc   4920
cctgagccct ggcgagcagc tgctgtacaa caaggtgtcc gagatcgaga agatggaaaa   4980
ggaagatcgg gtgatcgaga cccacaacgc caagatcgag gaaaagttcg gcaaggacct   5040
gctggccatc cggaagatcg tgaagggcga ggtggacgcc gagaagctgg aaggcaacga   5100
gatcaagtac gtggagaagg ccctgagcgg cctgctggaa atcggcaagg atcagagcga   5160
gcggatcacc aagctgtacc gggccctgca gaccgaagag gacctgcgga cccgggacga   5220
gacccggatg atcaacgagt accgggagaa gttcgacgcc ctgaaagagg ccatcgagat   5280
cgagcagcag gccacccacg acgaggccat ccaggaaatg ctggacctga gcgccgaggt   5340
gatcgaaacc gccagcgagg aagtgcccat ctttggcgcc ggagccgcca acgtgatcgc   5400
caccacccgg gccattcagg gcggcctgaa gctgaaggaa atcgtggaca agctgacagg   5460
catcgacctg agccacctga aggtggccga catccacccc cacatcatcg agaaggccat   5520
gctgcgggac accgtgaccg acaaggacct ggctatggcc atcaagagca aggtggacgt   5580
gatcgacgag atgaacgtgg agacccagca cgtgatcgat gccgtgctgc ccatcgtgaa   5640
gcaggaatac gagcggcacg acaacaagta ccacgtgaga atccctggcg ccctgaagat   5700
ccacagcgag cacaccccca agatccacat ctacaccacc ccctgggaca gcgactccgt   5760
gttcatgtgc cgggccatcg ccccccacca tcagcagcgg agcttcttca tcggcttcga   5820
cctggaaatc gagtacgtgc acttcgagga caccagcgtg gagggccaca tcctgcacgg   5880
cggagccatc accgtggagg gcaggggctt ccggcaggcc tacaccgagt tcatgaacgc   5940
cgcctggggc atgcctacca cccccgagct gcacaagcgg aagctgcagc ggagcatggg   6000
cacccacccc atctacatgg gcagcatgga ctacgccatc agctacgagc agctggtgtc   6060
caatgccatg cggctggtgt acgacagcga gctgcagatg cactgcctga gaggcccccct  6120
gaagttccag cggcggaccc tgatgaacgc cctgctgtac ggcgtgaaga tcgcctgatg   6180
atttttctac tagttaatca aataaaaagc atacaagcta ttgcttcgct atcgttacaa   6240
aatggcagga attttgtgta aactaagcca catacttgcc aatgaaaaaa atagtagaaa   6300
ggatactatt ttaatgggat tagatgttaa ggttccttgg gattatagta actgggcatc   6360
tgttaacttt tacgacgtta ggttagatac tgatgttaca gattataata atgttacaat   6420
aaaatacatg acaggatgtg atatttttcc tcatataact cttggaatag caaatatgga   6480
tcaatgtgat agatttgaaa atttcaaaaa gcaaataact gatcaagatt tacagactat   6540
ttctatagtc tgtaaagaag agatgtgttt tcctcagagt aacgcctcta aacagttggg   6600
agcgaaagga tgcgctgtag ttatgaaact ggaggtatct gatgaactta gagccctaag   6660
aaatgttctg ctgaatgcgg taccctgttc gaaggacgtg tttggtgata tcacagtaga   6720
taatccgtgg aatcctcaca taacagtagg atatgttaag gaggacgatg tcgaaaacaa   6780
gaaacgccta atggagtgca tgtccaagtt taggggggcaa gaaatacaag ttctaggatg  6840
gtattaataa gtatctaagt atttggtata atttattaaa tagtataatt ataacaaata   6900
ataaataaca tgataacggt ttttattaga ataaaataga gataatatca taatgatata   6960
taatacttca ttaccagaaa tgagtaatgg aagacttata aatgaactgc ataaagctat   7020
aaggtataga gatataaatt tagtaaggta tatacttaaa aaatgcaaat acaataacgt   7080
aaatatacta tcaacgtctt tgtatttagc cgtaagtatt tctgatatag aaatggtaaa   7140
attattacta gaacacggtg ccgatatttt aaaatgtaaa aatcctcctc ttcataaagc   7200
tgctagttta gataatacag aaattgctaa actactaata gattctggcg ctgacataga   7260
```

```
acagatacat tctggaaata gtccgttata tatttctgta tatagaaaca ataagtcatt   7320
aactagatat ttattaaaaa aaggtgttaa ttgtaataga ttctttctaa attattacga   7380
tgtactgtat gataagatat ctgatgatat gtataaaata tttatagatt ttaatattga   7440
tcttaatata caaactagaa attttgaaac tccgttacat tacgctataa agtataagaa   7500
tatagattta attaggatat tgttagataa tagtattaaa atagataaaa gtttattttt   7560
gcataaacag tatctcataa aggcacttaa aaataattgt agttacgata taatagcgtt   7620
acttataaat cacggagtgc ctataaacga acaagatgat ttaggtaaaa ccccattaca   7680
tcattcggta attaatagaa gaaaagatgt aacagcactt ctgttaaatc taggagctga   7740
tataaacgta atagatgact gtatgggcag tcccttacat tacgctgttt cacgtaacga   7800
tatcgaaaca acaaagacac ttttagaaag aggatctaat gttaatgtgg ttaataatca   7860
tatagatacc gttctaaata tagctgttgc atctaaaaac aaaactatag taaacttatt   7920
actgaagtac ggtactgata caaagttggt aggattagat aaacatgtta ttcacatagc   7980
tatagaaatg aaagatatta atatactgaa tgcgatctta ttatatggtt gctatgtaaa   8040
cgtctataat cataaaggtt tcactcctct atacatggca gttagttcta tgaaaacaga   8100
atttgttaaa ctcttacttg accacggtgc ttacgtaaat gctaaagcta agttatctgg   8160
aaatactcct ttacataaag ctatgttatc taatagtttt aataatataa aattactttt   8220
atcttataac gccgactata attctctaaa taatcacggt aatacgcctc taacttgtgt   8280
tagcttttta gatgacaaga tagctattat gataatatct aaaatgatgt tagaaatatc   8340
taaaaatcct gaaatagcta attcagaagg ttttatagta aacatggaac atataaacag   8400
taataaaaga ctactatcta taaaagaatc atgcgaaaaa gaactagatg ttataacaca   8460
tataaagtta aattctatat attcttttaa tatctttctt gacaataaca tagatcttat   8520
ggtaaagttc gtaactaatc ctagagttaa taagatacct gcatgtatac gtatatatag   8580
ggaattaata cggaaaaata aatcattagc ttttcataga catcagctaa tagttaaagc   8640
tgtaaaagag agtaagaatc taggaataat aggtaggtta cctatagata tcaaacatat   8700
aataatggaa ctattaagta ataatgattt acattctgtt atcaccagct gttgtaaccc   8760
agtagtataa agtgatttta ttcaattacg aagataaaca                         8800
```

<210> SEQ ID NO 18
<211> LENGTH: 3156
<212> TYPE: DNA
<213> ORGANISM: artificial sequence
<220> FEATURE:
<223> OTHER INFORMATION: AHSV-9 VP2 from pCXL2415.1

<400> SEQUENCE: 18

```
atggccttcg agttcggcat cctgcagacc gacaagatcc gggagaacac cctggaaaag     60
accaactgcg acgtgatcct gacccgggag aaccgcgtgc gggccagaga agtggacggc    120
gtgaagggct actactggga ggacaccgac caccggctgg gcctgtgcga ggtggagcac    180
accgtgagcg tgcgggactt catgtacaag cagaccaagt gcgagggcag ctaccccgtg    240
gtgcccctgt acatgatcga cgccatcaag tacggccgga tgatcgaccg gaacgaccac    300
cagatccggg tggacaagga cgacaagacc ctgttcaaga tccaggtgca gccctacctg    360
ggcgacgcct acttcagccc cgagcactac accgccacat tcttcaagcg ggagcccctg    420
cccatccacg tggacaccat ccgggactac atcggcaagc ggatcaacta cttcgagcgg    480
gagctgggca gcggcgtgag ggacgccaac ctggaaacca tcgtgggcaa gtggaaggac    540
```

-continued

```
aacacctaca agcggatcga gggcgaaaag accaccatgt gcgtgcggca cgagcccgac    600
agcgtgctgc agatcctgaa gaagatgcgg ttcggcatgc tgtaccccaa ctactacatg    660
ctgaacaccg gctacatcgt gaccgagagc agcaaaggcg cccctctgaa ccggtggctg    720
gtgaaagaac ggaccgtggg caaggtgaaa gccgccgagg ccttcgccgg caacagcctg    780
ctgaagaacc tggccagccg gatggaagat gaggaactga gccgggagat catcgtggcc    840
gtgatcaact acggcagcaa gttcggcacc agaagcggca agaagaagga cctgatgacc    900
atcgacaagc tggaaaagta ctgcgagagc ctgaccacct tcgtgcaccg gaagaagcgg    960
gacgagggcg acgacgagac cgccagggcc atcatccgga accagtggat caagggcatg   1020
cccagcatga acctgaagaa ggagatgaag gtctccaggg gccctatcca gaactggtcc   1080
ttcttcatga gcctggaagt gttcaagcgg aacaacaagg tggacatcga ccccaaccac   1140
gacacctgga agaaccacgt gaaagagatc cgcgagcgga tgcagaagga acagagcgcc   1200
aacagcaaca gccccctgaa gattcaggtg gacggggtgt ccctgagcac cagcgagttc   1260
tacggcaccg tggagcactg gatcgactgg gtggtggacc tgatcatgct ggcccaggtc   1320
aagcggctga tcaaagagta caagttcatc cggctggaaa ccaccaacct gatggccggc   1380
atgaacaagc tggtcggcgc cctgcggtgc tacgcctact gcctgatcct ggccctgtac   1440
gacttctacg gcgccgacat cgagggcttc gagaagggca gcaacagcag cgccatcgtg   1500
gagaccgtgg tgcagatgtt ccccaacttc aagcaggaaa tccaggccaa cttcggcatc   1560
aacctgaaca tcaaggacaa gaagcaggtc ctgttcgtcc ggatggacat ggacagcgag   1620
ttcagcgagg acgagcagaa gggctacatg ttcgagtacg gctgggccaa gcgggaggaa   1680
cggatctgga ccaactacgg cgacatcctg accgacctgg tggagcagct gtacaagagc   1740
atcctggacc acgaggaatg ggagaagatc gtggacgacc ccgagcggta cttctacgac   1800
gagctgttca acgccagccc cgagaccgtg ttcatcagca agggctacga cctggacaac   1860
aacatcgtga tcgagggcaa agtgggccag gacgtgacct acttctccaa gcggttcgtg   1920
agctactggt acagagtgcg gcaggtgcag accagcaagg gcatcgagcg gcggagcatc   1980
gaggacgtga agtaccggga gttcgacatc gagtccttca agccctacgc catcggcgag   2040
atcggcatcc acgccagcac ctacaagtac caggacctgc tggccggacg gaaccggggc   2100
gagaaggtga aagacagcca ggccctggtc tggtacgacc tggccctgac caactacacc   2160
ctggtccggc cccaggaccg gtgctggatc atgagctgca ccgacagcga gtacaccctg   2220
cggttcgcca tgatcaccat gatcttcgag agactgagcg aggaaaccga cctgagctac   2280
cacgacatcc tgctgagagt gagagagtac cccatccagt ccttcgccag ctacaagcac   2340
ttctacgtgc gggtgctgca gcatgtgttc agggactacc aggaaatcga cgtcctggaa   2400
ttctgcaccc ggatgctgga cccccggacc agagagagcg gcctgaacaa gttcagccgg   2460
ttcaagcagt ggcgggagag cgagttcctg atcgatgccc tgaagatgaa cttcctgctg   2520
tgggtggtgt tcgagctgga aaacatcgac gtggactaca gcaagaagcg gcacccccctg   2580
ctgatctcca ccgacaaggg cctgagagtg gtgcccgtgg acctgttcaa tagcatgctg   2640
tccgtgagca gcagcggctg gattccctac gtggagagag tgtgcgagcg gagcgagatc   2700
aagcggcggc tgaacgccga cgagctgaag ctgaagaact ggttcatcgc ctactacatc   2760
accctgcccc tgctgcggag agccgagccc cggatgagct tcaagtacga gggcatcacc   2820
acctggatcg gcagcaactg tggcggcgtg agagactacc tgatccagat gctgcccgcc   2880
aggaagccca agcccggcgt cctgattctg gcctatggcg ccgagaccaa cgtggcctgg   2940
```

```
ctgaaccacg ccctgcggga catcctgtcc ctggaaggca gcctgggcat gatcatcatc   3000

agcgacggca gcgtggtgaa caagagcaag ctgagagtgc gggacatgaa aatctacaac   3060

aggggcgagg tggaccggct gatcctgatc agctccggcg actacacctt cggcaacaag   3120

tacctgctgt ccaagctgat ggccaagatc gagcag                             3156


<210> SEQ ID NO 19
<211> LENGTH: 1509
<212> TYPE: DNA
<213> ORGANISM: artificial sequence
<220> FEATURE:
<223> OTHER INFORMATION: AHSV-9 VP5 from pCXL2415.1

<400> SEQUENCE: 19

atgggcaagt ttaccagctt cctgaagagg gccggcagcg ccaccaagaa ggccctgacc     60

agcgacgccg ccaagcggat gtacaagatg gccggcaaga ccctgcagaa ggtcgtcgag    120

agcgaagtgg gcagcgccgc catcgacggc gtgatgcagg gcaccatcca gagcatcatc    180

cagggcgaga acctgggcga cagcatcaag caggccgtga tcctgaacgt ggccggcacc    240

ctggaaagcg cccctgaccc cctgagccct ggcgagcagc tgctgtacaa caaggtgtcc    300

gagatcgagc gggccgagaa ggaagatcgg gtcatcgaga cccacaacaa gaagatcatc    360

gagaagtacg gcgaggacct gctgaagatc cggaagatca tgaagggcga ggccgaggcc    420

gagcagctgg aaggcaaaga gatggaatac gtcgaaaagg ccctgaaggg catgctgcgg    480

atcggcaagg accagagcga gcggatcacc cggctgtacc gggccctgca gaccgaagag    540

gacctgagaa ccagcgacga gacccggatg atcagcgagt accgggagaa gttcgaggcc    600

ctgaaacagg ccatcgagct ggaacagcag gccacccacg aggaagccgt gcaggaaatg    660

ctggacctga gcgccgaggt gatcgaaaca gccgccgagg aagtgcccgt gtttggcgct    720

ggggccgcta acgtggtggc cacaacccgg gccattcagg gcggcctgaa gctgaaagag    780

atcatcgaca agctgaccgg catcgacctg agccacctga aggtggccga catccacccc    840

cacatcatcg aaaaggccat gctgaagaac aagatccccg acaacgagct ggccatggct    900

atcaagagca aggtggaagt gatcgacgag atgaacaccg agaccgagca cgtgatcgag    960

agcatcatgc ccctggtgaa gaaggaatac gagaagcacg acaacaagta ccacgtgaac   1020

atccccagcg ccctgaagat ccacagcgag cacaccccca aggtgcacat ctacaccacc   1080

ccctgggaca gcgacaaggt gttcatctgc cggtgcatcg ccccccacca tcagcagcgg   1140

agcttcatga tcggcttcga cctggaaatc gagttcgtgt tctacgagga caccagcgtg   1200

gagggccaca tcatgcacgg cggagccgtg agcatcgagg gcaggggctt ccggcaggcc   1260

tacagcgagt tcatgaacgc cgcctggtcc atgcccagca cccccgagct gcacaagcgg   1320

cggctgcagc ggagcctggg cagccacccc atctacatgg gcagcatgga ctacaccgtg   1380

agctatgagc agctggtgtc caacgccatg aagctggtgt acgacaccga cctgcagatg   1440

cactgcctga gaggccccct gaagttccag cggcggaccc tgatgaacgc cctgctgttc   1500

ggcgtgaaa                                                           1509


<210> SEQ ID NO 20
<211> LENGTH: 1052
<212> TYPE: PRT
<213> ORGANISM: artificial sequence
<220> FEATURE:
<223> OTHER INFORMATION: Predicted AHSV-9 amino acid seq VP2 in
      pCXL2415.1

<400> SEQUENCE: 20
```

```
Met Ala Phe Glu Phe Gly Ile Leu Gln Thr Asp Lys Ile Arg Glu Asn
1               5                   10                  15

Thr Leu Glu Lys Thr Asn Cys Asp Val Ile Leu Thr Arg Glu Asn Arg
            20                  25                  30

Val Arg Ala Arg Glu Val Asp Gly Val Lys Gly Tyr Tyr Trp Glu Asp
        35                  40                  45

Thr Asp His Arg Leu Gly Leu Cys Glu Val Glu His Thr Val Ser Val
    50                  55                  60

Arg Asp Phe Met Tyr Lys Gln Thr Lys Cys Glu Gly Ser Tyr Pro Val
65                  70                  75                  80

Val Pro Leu Tyr Met Ile Asp Ala Ile Lys Tyr Gly Arg Met Ile Asp
                85                  90                  95

Arg Asn Asp His Gln Ile Arg Val Asp Lys Asp Asp Lys Thr Leu Phe
            100                 105                 110

Lys Ile Gln Val Gln Pro Tyr Leu Gly Asp Ala Tyr Phe Ser Pro Glu
        115                 120                 125

His Tyr Thr Ala Thr Phe Phe Lys Arg Glu Pro Leu Pro Ile His Val
    130                 135                 140

Asp Thr Ile Arg Asp Tyr Ile Gly Lys Arg Ile Asn Tyr Phe Glu Arg
145                 150                 155                 160

Glu Leu Gly Ser Gly Val Arg Asp Ala Asn Leu Glu Thr Ile Val Gly
                165                 170                 175

Lys Trp Lys Asp Asn Thr Tyr Lys Arg Ile Glu Gly Glu Lys Thr Thr
            180                 185                 190

Met Cys Val Arg His Glu Pro Asp Ser Val Leu Gln Ile Leu Lys Lys
        195                 200                 205

Met Arg Phe Gly Met Leu Tyr Pro Asn Tyr Tyr Met Leu Asn Thr Gly
    210                 215                 220

Tyr Ile Val Thr Glu Ser Ser Lys Gly Ala Pro Leu Asn Arg Trp Leu
225                 230                 235                 240

Val Lys Glu Arg Thr Val Gly Lys Val Lys Ala Ala Glu Ala Phe Ala
                245                 250                 255

Gly Asn Ser Leu Leu Lys Asn Leu Ala Ser Arg Met Glu Asp Glu Glu
            260                 265                 270

Leu Ser Arg Glu Ile Ile Val Ala Val Ile Asn Tyr Gly Ser Lys Phe
        275                 280                 285

Gly Thr Arg Ser Gly Lys Lys Lys Asp Leu Met Thr Ile Asp Lys Leu
    290                 295                 300

Glu Lys Tyr Cys Glu Ser Leu Thr Thr Phe Val His Arg Lys Lys Arg
305                 310                 315                 320

Asp Glu Gly Asp Asp Glu Thr Ala Arg Ala Ile Ile Arg Asn Gln Trp
                325                 330                 335

Ile Lys Gly Met Pro Ser Met Asn Leu Lys Lys Glu Met Lys Val Ser
            340                 345                 350

Arg Gly Pro Ile Gln Asn Trp Ser Phe Phe Met Ser Leu Glu Val Phe
        355                 360                 365

Lys Arg Asn Asn Lys Val Asp Ile Asp Pro Asn His Asp Thr Trp Lys
    370                 375                 380

Asn His Val Lys Glu Ile Arg Glu Arg Met Gln Lys Glu Gln Ser Ala
385                 390                 395                 400

Asn Ser Asn Ser Pro Leu Lys Ile Gln Val Asp Gly Val Ser Leu Ser
                405                 410                 415

Thr Ser Glu Phe Tyr Gly Thr Val Glu His Trp Ile Asp Trp Val Val
```

-continued

```
            420                 425                 430

Asp Leu Ile Met Leu Ala Gln Val Lys Arg Leu Ile Lys Glu Tyr Lys
        435                 440                 445

Phe Ile Arg Leu Glu Thr Thr Asn Leu Met Ala Gly Met Asn Lys Leu
    450                 455                 460

Val Gly Ala Leu Arg Cys Tyr Ala Tyr Cys Leu Ile Leu Ala Leu Tyr
465                 470                 475                 480

Asp Phe Tyr Gly Ala Asp Ile Glu Gly Phe Glu Lys Gly Ser Asn Ser
                485                 490                 495

Ser Ala Ile Val Glu Thr Val Val Gln Met Phe Pro Asn Phe Lys Gln
            500                 505                 510

Glu Ile Gln Ala Asn Phe Gly Ile Asn Leu Asn Ile Lys Asp Lys Lys
        515                 520                 525

Gln Val Leu Phe Val Arg Met Asp Met Asp Ser Glu Phe Ser Glu Asp
    530                 535                 540

Glu Gln Lys Gly Tyr Met Phe Glu Tyr Gly Trp Ala Lys Arg Glu Glu
545                 550                 555                 560

Arg Ile Trp Thr Asn Tyr Gly Asp Ile Leu Thr Asp Leu Val Glu Gln
                565                 570                 575

Leu Tyr Lys Ser Ile Leu Asp His Glu Glu Trp Glu Lys Ile Val Asp
            580                 585                 590

Asp Pro Glu Arg Tyr Phe Tyr Asp Glu Leu Phe Asn Ala Ser Pro Glu
        595                 600                 605

Thr Val Phe Ile Ser Lys Gly Tyr Asp Leu Asp Asn Asn Ile Val Ile
    610                 615                 620

Glu Gly Lys Val Gly Gln Asp Val Thr Tyr Phe Ser Lys Arg Phe Val
625                 630                 635                 640

Ser Tyr Trp Tyr Arg Val Arg Gln Val Gln Thr Ser Lys Gly Ile Glu
                645                 650                 655

Arg Arg Ser Ile Glu Asp Val Lys Tyr Arg Glu Phe Asp Ile Glu Ser
            660                 665                 670

Phe Lys Pro Tyr Ala Ile Gly Glu Ile Gly Ile His Ala Ser Thr Tyr
        675                 680                 685

Lys Tyr Gln Asp Leu Leu Ala Gly Arg Asn Arg Gly Glu Lys Val Lys
    690                 695                 700

Asp Ser Gln Ala Leu Val Trp Tyr Asp Leu Ala Leu Thr Asn Tyr Thr
705                 710                 715                 720

Leu Val Arg Pro Gln Asp Arg Cys Trp Ile Met Ser Cys Thr Asp Ser
                725                 730                 735

Glu Tyr Thr Leu Arg Phe Ala Met Ile Thr Met Ile Phe Glu Arg Leu
            740                 745                 750

Ser Glu Glu Thr Asp Leu Ser Tyr His Asp Ile Leu Leu Arg Val Arg
        755                 760                 765

Glu Tyr Pro Ile Gln Ser Phe Ala Ser Tyr Lys His Phe Tyr Val Arg
    770                 775                 780

Val Leu Gln His Val Phe Arg Asp Tyr Gln Glu Ile Asp Val Leu Glu
785                 790                 795                 800

Phe Cys Thr Arg Met Leu Asp Pro Arg Thr Arg Glu Ser Gly Leu Asn
                805                 810                 815

Lys Phe Ser Arg Phe Lys Gln Trp Arg Glu Ser Glu Phe Leu Ile Asp
            820                 825                 830

Ala Leu Lys Met Asn Phe Leu Leu Trp Val Val Phe Glu Leu Glu Asn
        835                 840                 845
```

```
Ile Asp Val Asp Tyr Ser Lys Lys Arg His Pro Leu Leu Ile Ser Thr
    850                 855                 860

Asp Lys Gly Leu Arg Val Val Pro Val Asp Leu Phe Asn Ser Met Leu
865                 870                 875                 880

Ser Val Ser Ser Ser Gly Trp Ile Pro Tyr Val Glu Arg Val Cys Glu
                885                 890                 895

Arg Ser Glu Ile Lys Arg Arg Leu Asn Ala Asp Glu Leu Lys Leu Lys
            900                 905                 910

Asn Trp Phe Ile Ala Tyr Tyr Ile Thr Leu Pro Leu Leu Arg Arg Ala
        915                 920                 925

Glu Pro Arg Met Ser Phe Lys Tyr Glu Gly Ile Thr Thr Trp Ile Gly
    930                 935                 940

Ser Asn Cys Gly Gly Val Arg Asp Tyr Leu Ile Gln Met Leu Pro Ala
945                 950                 955                 960

Arg Lys Pro Lys Pro Gly Val Leu Ile Leu Ala Tyr Gly Ala Glu Thr
                965                 970                 975

Asn Val Ala Trp Leu Asn His Ala Leu Arg Asp Ile Leu Ser Leu Glu
            980                 985                 990

Gly Ser Leu Gly Met Ile Ile Ile  Ser Asp Gly Ser Val  Val Asn Lys
        995                 1000                1005

Ser Lys  Leu Arg Val Arg Asp  Met Lys Ile Tyr Asn  Arg Gly Glu
    1010                1015                1020

Val Asp  Arg Leu Ile Leu Ile  Ser Ser Gly Asp Tyr  Thr Phe Gly
    1025                1030                1035

Asn Lys  Tyr Leu Leu Ser Lys  Leu Met Ala Lys Ile  Glu Gln
    1040                1045                1050


<210> SEQ ID NO 21
<211> LENGTH: 503
<212> TYPE: PRT
<213> ORGANISM: artificial sequence
<220> FEATURE:
<223> OTHER INFORMATION: Predicted AHSV-9 amino acid seq VP5 in
      pCXL2415.1

<400> SEQUENCE: 21

Met Gly Lys Phe Thr Ser Phe Leu Lys Arg Ala Gly Ser Ala Thr Lys
1               5                   10                  15

Lys Ala Leu Thr Ser Asp Ala Ala Lys Arg Met Tyr Lys Met Ala Gly
            20                  25                  30

Lys Thr Leu Gln Lys Val Val Glu Ser Glu Val Gly Ser Ala Ala Ile
        35                  40                  45

Asp Gly Val Met Gln Gly Thr Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Ile Glu Arg Ala Glu Lys Glu Asp Arg Val Ile
            100                 105                 110

Glu Thr His Asn Lys Lys Ile Ile Glu Lys Tyr Gly Glu Asp Leu Leu
        115                 120                 125

Lys Ile Arg Lys Ile Met Lys Gly Glu Ala Glu Ala Glu Gln Leu Glu
    130                 135                 140

Gly Lys Glu Met Glu Tyr Val Glu Lys Ala Leu Lys Gly Met Leu Arg
145                 150                 155                 160
```

-continued

```
Ile Gly Lys Asp Gln Ser Glu Arg Ile Thr Arg Leu Tyr Arg Ala Leu
                165                 170                 175

Gln Thr Glu Glu Asp Leu Arg Thr Ser Asp Glu Thr Arg Met Ile Ser
            180                 185                 190

Glu Tyr Arg Glu Lys Phe Glu Ala Leu Lys Gln Ala Ile Glu Leu Glu
        195                 200                 205

Gln Gln Ala Thr His Glu Glu Ala Val Gln Glu Met Leu Asp Leu Ser
    210                 215                 220

Ala Glu Val Ile Glu Thr Ala Ala Glu Glu Val Pro Val Phe Gly Ala
225                 230                 235                 240

Gly Ala Ala Asn Val Val Ala Thr Thr Arg Ala Ile Gln Gly Gly Leu
                245                 250                 255

Lys Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Lys Asn Lys Ile Pro Asp Asn Glu Leu Ala Met Ala Ile Lys Ser Lys
    290                 295                 300

Val Glu Val Ile Asp Glu Met Asn Thr Glu Thr Glu His Val Ile Glu
305                 310                 315                 320

Ser Ile Met Pro Leu Val Lys Lys Glu Tyr Glu Lys His Asp Asn Lys
                325                 330                 335

Tyr His Val Asn Ile Pro Ser Ala Leu Lys Ile His Ser Glu His Thr
            340                 345                 350

Pro Lys Val His Ile Tyr Thr Thr Pro Trp Asp Ser Asp Lys Val Phe
        355                 360                 365

Ile Cys Arg Cys Ile Ala Pro His His Gln Gln Arg Ser Phe Met Ile
    370                 375                 380

Gly Phe Asp Leu Glu Ile Glu Phe Val Phe Tyr Glu Asp Thr Ser Val
385                 390                 395                 400

Glu Gly His Ile Met His Gly Gly Ala Val Ser Ile Glu Gly Arg Gly
                405                 410                 415

Phe Arg Gln Ala Tyr Ser Glu Phe Met Asn Ala Ala Trp Ser Met Pro
            420                 425                 430

Ser Thr Pro Glu Leu His Lys Arg Arg Leu Gln Arg Ser Leu Gly Ser
        435                 440                 445

His Pro Ile Tyr Met Gly Ser Met Asp Tyr Thr Val Ser Tyr Glu Gln
    450                 455                 460

Leu Val Ser Asn Ala Met Lys Leu Val Tyr Asp Thr Asp Leu Gln Met
465                 470                 475                 480

His Cys Leu Arg Gly Pro Leu Lys Phe Gln Arg Arg Thr Leu Met Asn
                485                 490                 495

Ala Leu Leu Phe Gly Val Lys
            500
```

<210> SEQ ID NO 22
<211> LENGTH: 11131
<212> TYPE: DNA
<213> ORGANISM: artificial sequence
<220> FEATURE:
<223> OTHER INFORMATION: Entire plasmid pCXL2415.1
<220> FEATURE:
<221> NAME/KEY: misc_feature
<222> LOCATION: (48)..(972)
<223> OTHER INFORMATION: C3L
<220> FEATURE:
<221> NAME/KEY: primer
<222> LOCATION: (665)..(688)

```
<220> FEATURE:
<221> NAME/KEY: primer
<222> LOCATION: (695)..(718)
<220> FEATURE:
<221> NAME/KEY: promoter
<222> LOCATION: (1061)..(1184)
<223> OTHER INFORMATION: H6 vaccinia promoter
<220> FEATURE:
<221> NAME/KEY: CDS
<222> LOCATION: (1185)..(4346)
<223> OTHER INFORMATION: AHSV-9 VP2
<220> FEATURE:
<221> NAME/KEY: primer
<222> LOCATION: (1198)..(1222)
<220> FEATURE:
<221> NAME/KEY: primer
<222> LOCATION: (1285)..(1320)
<220> FEATURE:
<221> NAME/KEY: primer
<222> LOCATION: (1821)..(1846)
<220> FEATURE:
<221> NAME/KEY: primer
<222> LOCATION: (1942)..(1966)
<220> FEATURE:
<221> NAME/KEY: primer
<222> LOCATION: (2451)..(2476)
<220> FEATURE:
<221> NAME/KEY: primer
<222> LOCATION: (2590)..(2614)
<220> FEATURE:
<221> NAME/KEY: primer
<222> LOCATION: (3065)..(3090)
<220> FEATURE:
<221> NAME/KEY: primer
<222> LOCATION: (3211)..(3235)
<220> FEATURE:
<221> NAME/KEY: primer
<222> LOCATION: (3661)..(3685)
<220> FEATURE:
<221> NAME/KEY: primer
<222> LOCATION: (3844)..(3867)
<220> FEATURE:
<221> NAME/KEY: primer
<222> LOCATION: (4290)..(4314)
<220> FEATURE:
<221> NAME/KEY: promoter
<222> LOCATION: (4374)..(4405)
<223> OTHER INFORMATION: 42K poxviral promoter
<220> FEATURE:
<221> NAME/KEY: CDS
<222> LOCATION: (4406)..(5917)
<223> OTHER INFORMATION: AHSV-9 VP5
<220> FEATURE:
<221> NAME/KEY: primer
<222> LOCATION: (4872)..(4897)
<220> FEATURE:
<221> NAME/KEY: primer
<222> LOCATION: (4890)..(4913)
<220> FEATURE:
<221> NAME/KEY: primer
<222> LOCATION: (5389)..(5412)
<220> FEATURE:
<221> NAME/KEY: primer
<222> LOCATION: (5394)..(5417)
<220> FEATURE:
<221> NAME/KEY: misc_feature
<222> LOCATION: (5943)..(8514)
<223> OTHER INFORMATION: C3R
<220> FEATURE:
<221> NAME/KEY: primer
<222> LOCATION: (5950)..(5973)
<220> FEATURE:
<221> NAME/KEY: primer
<222> LOCATION: (6057)..(6080)
<220> FEATURE:
<221> NAME/KEY: primer
<222> LOCATION: (6376)..(6399)
<220> FEATURE:
<221> NAME/KEY: primer
<222> LOCATION: (6830)..(6854)
```

<220> FEATURE:
<221> NAME/KEY: primer
<222> LOCATION: (6887)..(6910)
<220> FEATURE:
<221> NAME/KEY: primer
<222> LOCATION: (7672)..(7695)
<220> FEATURE:
<221> NAME/KEY: primer
<222> LOCATION: (7748)..(7771)
<220> FEATURE:
<221> NAME/KEY: primer
<222> LOCATION: (8531)..(8546)
<220> FEATURE:
<221> NAME/KEY: CDS
<222> LOCATION: (9125)..(9982)
<223> OTHER INFORMATION: Amp R

<400> SEQUENCE: 22
ggaaacagct atgaccatga ttacgccaag cttgcggccg cgtcgacatg cattgttagt 60
tctgtagatc agtaacgtat agcatacgag tataattatc gtaggtagta ggtatcctaa 120
aataaatctg atacagataa taactttgta aatcaattca gcaatttctc tattatcatg 180
ataatgatta atacacagcg tgtcgttatt ttttgttacg atagtatttc taaagtaaag 240
agcaggaatc cctagtataa tagaaataat ccatatgaaa aatatagtaa tgtacatatt 300
tctaatgtta acatatttat aggtaaatcc aggaagggta atttttacat atctatatac 360
gcttattaca gttattaaaa atatacttgc aaacatgtta gaagtaaaaa agaaagaact 420
aattttacaa agtgctttac caaaatgcca atggaaatta cttagtatgt atataatgta 480
taaaggtatg aatatcacaa acagcaaatc ggctattccc aagttgagaa acggtataat 540
agatatattt ctagatacca ttaataacct tataagcttg acgtttccta taatgcctac 600
taagaaaact agaagataca tacatactaa cgccatacga gagtaactac tcatcgtata 660
actactgttg ctaacagtga cactgatgtt ataactcatc tttgatgtgg tataaatgta 720
taataactat attacactgg tattttattt cagttatata ctatatagta ttaaaaatta 780
tatttgtata attatattat tatattcagt gtagaaagta aaatactata aatatgtatc 840
tcttatttat aacttattag taaagtatgt actattcagt tatattgttt tataaaagct 900
aaatgctact agattgatat aaatgaatat gtaataaatt agtaatgtag tatactaata 960
ttaactcaca tttgactaat tagctataaa aacccgggtt aattaattag tcatcaggca 1020
gggcgagaac gagactatct gctcgttaat taattagagc ttctttattc tatacttaaa 1080
aagtgaaaat aaatacaaag gttcttgagg gttgtgttaa attgaaagcg agaaataatc 1140
ataaattatt tcattatcgc gatatccgtt aagtttgtat cgta atg gcc ttc gag 1196
Met Ala Phe Glu
1 ttc ggc atc ctg cag acc gac aag atc cgg gag aac acc ctg gaa aag 1244
Phe Gly Ile Leu Gln Thr Asp Lys Ile Arg Glu Asn Thr Leu Glu Lys
5 10 15 20 acc aac tgc gac gtg atc ctg acc cgg gag aac cgc gtg cgg gcc aga 1292
Thr Asn Cys Asp Val Ile Leu Thr Arg Glu Asn Arg Val Arg Ala Arg
25 30 35 gaa gtg gac ggc gtg aag ggc tac tac tgg gag gac acc gac cac cgg 1340
Glu Val Asp Gly Val Lys Gly Tyr Tyr Trp Glu Asp Thr Asp His Arg
40 45 50 ctg ggc ctg tgc gag gtg gag cac acc gtg agc gtg cgg gac ttc atg 1388
Leu Gly Leu Cys Glu Val Glu His Thr Val Ser Val Arg Asp Phe Met
55 60 65 tac aag cag acc aag tgc gag ggc agc tac ccc gtg gtg ccc ctg tac 1436
Tyr Lys Gln Thr Lys Cys Glu Gly Ser Tyr Pro Val Val Pro Leu Tyr
70 75 80

```
atg atc gac gcc atc aag tac ggc cgg atg atc gac cgg aac gac cac     1484
Met Ile Asp Ala Ile Lys Tyr Gly Arg Met Ile Asp Arg Asn Asp His
85                  90                  95                  100

cag atc cgg gtg gac aag gac gac aag acc ctg ttc aag atc cag gtg     1532
Gln Ile Arg Val Asp Lys Asp Asp Lys Thr Leu Phe Lys Ile Gln Val
                105                 110                 115

cag ccc tac ctg ggc gac gcc tac ttc agc ccc gag cac tac acc gcc     1580
Gln Pro Tyr Leu Gly Asp Ala Tyr Phe Ser Pro Glu His Tyr Thr Ala
            120                 125                 130

aca ttc ttc aag cgg gag ccc ctg ccc atc cac gtg gac acc atc cgg     1628
Thr Phe Phe Lys Arg Glu Pro Leu Pro Ile His Val Asp Thr Ile Arg
        135                 140                 145

gac tac atc ggc aag cgg atc aac tac ttc gag cgg gag ctg ggc agc     1676
Asp Tyr Ile Gly Lys Arg Ile Asn Tyr Phe Glu Arg Glu Leu Gly Ser
    150                 155                 160

ggc gtg agg gac gcc aac ctg gaa acc atc gtg ggc aag tgg aag gac     1724
Gly Val Arg Asp Ala Asn Leu Glu Thr Ile Val Gly Lys Trp Lys Asp
165                 170                 175                 180

aac acc tac aag cgg atc gag ggc gaa aag acc acc atg tgc gtg cgg     1772
Asn Thr Tyr Lys Arg Ile Glu Gly Glu Lys Thr Thr Met Cys Val Arg
                185                 190                 195

cac gag ccc gac agc gtg ctg cag atc ctg aag aag atg cgg ttc ggc     1820
His Glu Pro Asp Ser Val Leu Gln Ile Leu Lys Lys Met Arg Phe Gly
            200                 205                 210

atg ctg tac ccc aac tac tac atg ctg aac acc ggc tac atc gtg acc     1868
Met Leu Tyr Pro Asn Tyr Tyr Met Leu Asn Thr Gly Tyr Ile Val Thr
        215                 220                 225

gag agc agc aaa ggc gcc cct ctg aac cgg tgg ctg gtg aaa gaa cgg     1916
Glu Ser Ser Lys Gly Ala Pro Leu Asn Arg Trp Leu Val Lys Glu Arg
    230                 235                 240

acc gtg ggc aag gtg aaa gcc gcc gag gcc ttc gcc ggc aac agc ctg     1964
Thr Val Gly Lys Val Lys Ala Ala Glu Ala Phe Ala Gly Asn Ser Leu
245                 250                 255                 260

ctg aag aac ctg gcc agc cgg atg gaa gat gag gaa ctg agc cgg gag     2012
Leu Lys Asn Leu Ala Ser Arg Met Glu Asp Glu Glu Leu Ser Arg Glu
                265                 270                 275

atc atc gtg gcc gtg atc aac tac ggc agc aag ttc ggc acc aga agc     2060
Ile Ile Val Ala Val Ile Asn Tyr Gly Ser Lys Phe Gly Thr Arg Ser
            280                 285                 290

ggc aag aag aag gac ctg atg acc atc gac aag ctg gaa aag tac tgc     2108
Gly Lys Lys Lys Asp Leu Met Thr Ile Asp Lys Leu Glu Lys Tyr Cys
        295                 300                 305

gag agc ctg acc acc ttc gtg cac cgg aag aag cgg gac gag ggc gac     2156
Glu Ser Leu Thr Thr Phe Val His Arg Lys Lys Arg Asp Glu Gly Asp
    310                 315                 320

gac gag acc gcc agg gcc atc atc cgg aac cag tgg atc aag ggc atg     2204
Asp Glu Thr Ala Arg Ala Ile Ile Arg Asn Gln Trp Ile Lys Gly Met
325                 330                 335                 340

ccc agc atg aac ctg aag aag gag atg aag gtc tcc agg ggc cct atc     2252
Pro Ser Met Asn Leu Lys Lys Glu Met Lys Val Ser Arg Gly Pro Ile
                345                 350                 355

cag aac tgg tcc ttc ttc atg agc ctg gaa gtg ttc aag cgg aac aac     2300
Gln Asn Trp Ser Phe Phe Met Ser Leu Glu Val Phe Lys Arg Asn Asn
            360                 365                 370

aag gtg gac atc gac ccc aac cac gac acc tgg aag aac cac gtg aaa     2348
Lys Val Asp Ile Asp Pro Asn His Asp Thr Trp Lys Asn His Val Lys
        375                 380                 385

gag atc cgc gag cgg atg cag aag gaa cag agc gcc aac agc aac agc     2396
Glu Ile Arg Glu Arg Met Gln Lys Glu Gln Ser Ala Asn Ser Asn Ser
    390                 395                 400
```

```
ccc ctg aag att cag gtg gac ggg gtg tcc ctg agc acc agc gag ttc      2444
Pro Leu Lys Ile Gln Val Asp Gly Val Ser Leu Ser Thr Ser Glu Phe
405                 410                 415                 420

tac ggc acc gtg gag cac tgg atc gac tgg gtg gtg gac ctg atc atg      2492
Tyr Gly Thr Val Glu His Trp Ile Asp Trp Val Val Asp Leu Ile Met
                425                 430                 435

ctg gcc cag gtc aag cgg ctg atc aaa gag tac aag ttc atc cgg ctg      2540
Leu Ala Gln Val Lys Arg Leu Ile Lys Glu Tyr Lys Phe Ile Arg Leu
            440                 445                 450

gaa acc acc aac ctg atg gcc ggc atg aac aag ctg gtc ggc gcc ctg      2588
Glu Thr Thr Asn Leu Met Ala Gly Met Asn Lys Leu Val Gly Ala Leu
        455                 460                 465

cgg tgc tac gcc tac tgc ctg atc ctg gcc ctg tac gac ttc tac ggc      2636
Arg Cys Tyr Ala Tyr Cys Leu Ile Leu Ala Leu Tyr Asp Phe Tyr Gly
    470                 475                 480

gcc gac atc gag ggc ttc gag aag ggc agc aac agc agc gcc atc gtg      2684
Ala Asp Ile Glu Gly Phe Glu Lys Gly Ser Asn Ser Ser Ala Ile Val
485                 490                 495                 500

gag acc gtg gtg cag atg ttc ccc aac ttc aag cag gaa atc cag gcc      2732
Glu Thr Val Val Gln Met Phe Pro Asn Phe Lys Gln Glu Ile Gln Ala
                505                 510                 515

aac ttc ggc atc aac ctg aac atc aag gac aag aag cag gtc ctg ttc      2780
Asn Phe Gly Ile Asn Leu Asn Ile Lys Asp Lys Lys Gln Val Leu Phe
            520                 525                 530

gtc cgg atg gac atg gac agc gag ttc agc gag gac gag cag aag ggc      2828
Val Arg Met Asp Met Asp Ser Glu Phe Ser Glu Asp Glu Gln Lys Gly
        535                 540                 545

tac atg ttc gag tac ggc tgg gcc aag cgg gag gaa cgg atc tgg acc      2876
Tyr Met Phe Glu Tyr Gly Trp Ala Lys Arg Glu Glu Arg Ile Trp Thr
    550                 555                 560

aac tac ggc gac atc ctg acc gac ctg gtg gag cag ctg tac aag agc      2924
Asn Tyr Gly Asp Ile Leu Thr Asp Leu Val Glu Gln Leu Tyr Lys Ser
565                 570                 575                 580

atc ctg gac cac gag gaa tgg gag aag atc gtg gac gac ccc gag cgg      2972
Ile Leu Asp His Glu Glu Trp Glu Lys Ile Val Asp Asp Pro Glu Arg
                585                 590                 595

tac ttc tac gac gag ctg ttc aac gcc agc ccc gag acc gtg ttc atc      3020
Tyr Phe Tyr Asp Glu Leu Phe Asn Ala Ser Pro Glu Thr Val Phe Ile
            600                 605                 610

agc aag ggc tac gac ctg gac aac aac atc gtg atc gag ggc aaa gtg      3068
Ser Lys Gly Tyr Asp Leu Asp Asn Asn Ile Val Ile Glu Gly Lys Val
        615                 620                 625

ggc cag gac gtg acc tac ttc tcc aag cgg ttc gtg agc tac tgg tac      3116
Gly Gln Asp Val Thr Tyr Phe Ser Lys Arg Phe Val Ser Tyr Trp Tyr
    630                 635                 640

aga gtg cgg cag gtg cag acc agc aag ggc atc gag cgg cgg agc atc      3164
Arg Val Arg Gln Val Gln Thr Ser Lys Gly Ile Glu Arg Arg Ser Ile
645                 650                 655                 660

gag gac gtg aag tac cgg gag ttc gac atc gag tcc ttc aag ccc tac      3212
Glu Asp Val Lys Tyr Arg Glu Phe Asp Ile Glu Ser Phe Lys Pro Tyr
                665                 670                 675

gcc atc ggc gag atc ggc atc cac gcc agc acc tac aag tac cag gac      3260
Ala Ile Gly Glu Ile Gly Ile His Ala Ser Thr Tyr Lys Tyr Gln Asp
            680                 685                 690

ctg ctg gcc gga cgg aac cgg ggc gag aag gtg aaa gac agc cag gcc      3308
Leu Leu Ala Gly Arg Asn Arg Gly Glu Lys Val Lys Asp Ser Gln Ala
        695                 700                 705

ctg gtc tgg tac gac ctg gcc ctg acc aac tac acc ctg gtc cgg ccc      3356
Leu Val Trp Tyr Asp Leu Ala Leu Thr Asn Tyr Thr Leu Val Arg Pro
    710                 715                 720
```

-continued

```
cag gac cgg tgc tgg atc atg agc tgc acc gac agc gag tac acc ctg      3404
Gln Asp Arg Cys Trp Ile Met Ser Cys Thr Asp Ser Glu Tyr Thr Leu
725                 730                 735                 740

cgg ttc gcc atg atc acc atg atc ttc gag aga ctg agc gag gaa acc      3452
Arg Phe Ala Met Ile Thr Met Ile Phe Glu Arg Leu Ser Glu Glu Thr
                745                 750                 755

gac ctg agc tac cac gac atc ctg ctg aga gtg aga gag tac ccc atc      3500
Asp Leu Ser Tyr His Asp Ile Leu Leu Arg Val Arg Glu Tyr Pro Ile
            760                 765                 770

cag tcc ttc gcc agc tac aag cac ttc tac gtg cgg gtg ctg cag cat      3548
Gln Ser Phe Ala Ser Tyr Lys His Phe Tyr Val Arg Val Leu Gln His
        775                 780                 785

gtg ttc agg gac tac cag gaa atc gac gtc ctg gaa ttc tgc acc cgg      3596
Val Phe Arg Asp Tyr Gln Glu Ile Asp Val Leu Glu Phe Cys Thr Arg
    790                 795                 800

atg ctg gac ccc cgg acc aga gag agc ggc ctg aac aag ttc agc cgg      3644
Met Leu Asp Pro Arg Thr Arg Glu Ser Gly Leu Asn Lys Phe Ser Arg
805                 810                 815                 820

ttc aag cag tgg cgg gag agc gag ttc ctg atc gat gcc ctg aag atg      3692
Phe Lys Gln Trp Arg Glu Ser Glu Phe Leu Ile Asp Ala Leu Lys Met
                825                 830                 835

aac ttc ctg ctg tgg gtg gtg ttc gag ctg gaa aac atc gac gtg gac      3740
Asn Phe Leu Leu Trp Val Val Phe Glu Leu Glu Asn Ile Asp Val Asp
            840                 845                 850

tac agc aag aag cgg cac ccc ctg ctg atc tcc acc gac aag ggc ctg      3788
Tyr Ser Lys Lys Arg His Pro Leu Leu Ile Ser Thr Asp Lys Gly Leu
        855                 860                 865

aga gtg gtg ccc gtg gac ctg ttc aat agc atg ctg tcc gtg agc agc      3836
Arg Val Val Pro Val Asp Leu Phe Asn Ser Met Leu Ser Val Ser Ser
    870                 875                 880

agc ggc tgg att ccc tac gtg gag aga gtg tgc gag cgg agc gag atc      3884
Ser Gly Trp Ile Pro Tyr Val Glu Arg Val Cys Glu Arg Ser Glu Ile
885                 890                 895                 900

aag cgg cgg ctg aac gcc gac gag ctg aag ctg aag aac tgg ttc atc      3932
Lys Arg Arg Leu Asn Ala Asp Glu Leu Lys Leu Lys Asn Trp Phe Ile
                905                 910                 915

gcc tac tac atc acc ctg ccc ctg ctg cgg aga gcc gag ccc cgg atg      3980
Ala Tyr Tyr Ile Thr Leu Pro Leu Leu Arg Arg Ala Glu Pro Arg Met
            920                 925                 930

agc ttc aag tac gag ggc atc acc acc tgg atc ggc agc aac tgt ggc      4028
Ser Phe Lys Tyr Glu Gly Ile Thr Thr Trp Ile Gly Ser Asn Cys Gly
        935                 940                 945

ggc gtg aga gac tac ctg atc cag atg ctg ccc gcc agg aag ccc aag      4076
Gly Val Arg Asp Tyr Leu Ile Gln Met Leu Pro Ala Arg Lys Pro Lys
    950                 955                 960

ccc ggc gtc ctg att ctg gcc tat ggc gcc gag acc aac gtg gcc tgg      4124
Pro Gly Val Leu Ile Leu Ala Tyr Gly Ala Glu Thr Asn Val Ala Trp
965                 970                 975                 980

ctg aac cac gcc ctg cgg gac atc ctg tcc ctg gaa ggc agc ctg ggc      4172
Leu Asn His Ala Leu Arg Asp Ile Leu Ser Leu Glu Gly Ser Leu Gly
                985                 990                 995

atg atc atc atc  agc gac ggc agc gtg  gtg aac aag agc aag  ctg      4217
Met Ile Ile Ile  Ser Asp Gly Ser Val  Val Asn Lys Ser Lys  Leu
            1000                 1005                 1010

aga gtg cgg gac  atg aaa atc tac aac  agg ggc gag gtg gac  cgg      4262
Arg Val Arg Asp  Met Lys Ile Tyr Asn  Arg Gly Glu Val Asp  Arg
            1015                 1020                 1025

ctg atc ctg atc  agc tcc ggc gac tac  acc ttc ggc aac aag  tac      4307
Leu Ile Leu Ile  Ser Ser Gly Asp Tyr  Thr Phe Gly Asn Lys  Tyr
            1030                 1035                 1040
```

```
ctg ctg tcc aag  ctg atg gcc aag atc  gag cag tga tga ggatccctcg    4356
Leu Leu Ser Lys  Leu Met Ala Lys Ile  Glu Gln
            1045                 1050

agtttttatt gactagttca aaattgaaaa tatataatta caatataaa atg ggc      4411
                                                      Met Gly

aag  ttt acc agc ttc ctg  aag agg gcc ggc agc  gcc acc aag aag      4456
Lys  Phe Thr Ser Phe Leu  Lys Arg Ala Gly Ser  Ala Thr Lys Lys
1055                 1060                 1065

gcc  ctg acc agc gac gcc  gcc aag cgg atg tac  aag atg gcc ggc      4501
Ala  Leu Thr Ser Asp Ala  Ala Lys Arg Met Tyr  Lys Met Ala Gly
1070                 1075                 1080

aag  acc ctg cag aag gtc  gtc gag agc gaa gtg  ggc agc gcc gcc      4546
Lys  Thr Leu Gln Lys Val  Val Glu Ser Glu Val  Gly Ser Ala Ala
1085                 1090                 1095

atc  gac ggc gtg atg cag  ggc acc atc cag agc  atc atc cag ggc      4591
Ile  Asp Gly Val Met Gln  Gly Thr Ile Gln Ser  Ile Ile Gln Gly
1100                 1105                 1110

gag  aac ctg ggc gac agc  atc aag cag gcc gtg  atc ctg aac gtg      4636
Glu  Asn Leu Gly Asp Ser  Ile Lys Gln Ala Val  Ile Leu Asn Val
1115                 1120                 1125

gcc  ggc acc ctg gaa agc  gcc cct gac ccc ctg  agc cct ggc gag      4681
Ala  Gly Thr Leu Glu Ser  Ala Pro Asp Pro Leu  Ser Pro Gly Glu
1130                 1135                 1140

cag  ctg ctg tac aac aag  gtg tcc gag atc gag  cgg gcc gag aag      4726
Gln  Leu Leu Tyr Asn Lys  Val Ser Glu Ile Glu  Arg Ala Glu Lys
1145                 1150                 1155

gaa  gat cgg gtc atc gag  acc cac aac aag aag  atc atc gag aag      4771
Glu  Asp Arg Val Ile Glu  Thr His Asn Lys Lys  Ile Ile Glu Lys
1160                 1165                 1170

tac  ggc gag gac ctg ctg  aag atc cgg aag atc  atg aag ggc gag      4816
Tyr  Gly Glu Asp Leu Leu  Lys Ile Arg Lys Ile  Met Lys Gly Glu
1175                 1180                 1185

gcc  gag gcc gag cag ctg  gaa ggc aaa gag atg  gaa tac gtc gaa      4861
Ala  Glu Ala Glu Gln Leu  Glu Gly Lys Glu Met  Glu Tyr Val Glu
1190                 1195                 1200

aag  gcc ctg aag ggc atg  ctg cgg atc ggc aag  gac cag agc gag      4906
Lys  Ala Leu Lys Gly Met  Leu Arg Ile Gly Lys  Asp Gln Ser Glu
1205                 1210                 1215

cgg  atc acc cgg ctg tac  cgg gcc ctg cag acc  gaa gag gac ctg      4951
Arg  Ile Thr Arg Leu Tyr  Arg Ala Leu Gln Thr  Glu Glu Asp Leu
1220                 1225                 1230

aga  acc agc gac gag acc  cgg atg atc agc gag  tac cgg gag aag      4996
Arg  Thr Ser Asp Glu Thr  Arg Met Ile Ser Glu  Tyr Arg Glu Lys
1235                 1240                 1245

ttc  gag gcc ctg aaa cag  gcc atc gag ctg gaa  cag cag gcc acc      5041
Phe  Glu Ala Leu Lys Gln  Ala Ile Glu Leu Glu  Gln Gln Ala Thr
1250                 1255                 1260

cac  gag gaa gcc gtg cag  gaa atg ctg gac ctg  agc gcc gag gtg      5086
His  Glu Glu Ala Val Gln  Glu Met Leu Asp Leu  Ser Ala Glu Val
1265                 1270                 1275

atc  gaa aca gcc gcc gag  gaa gtg ccc gtg ttt  ggc gct ggg gcc      5131
Ile  Glu Thr Ala Ala Glu  Glu Val Pro Val Phe  Gly Ala Gly Ala
1280                 1285                 1290

gct  aac gtg gtg gcc aca  acc cgg gcc att cag  ggc ggc ctg aag      5176
Ala  Asn Val Val Ala Thr  Thr Arg Ala Ile Gln  Gly Gly Leu Lys
1295                 1300                 1305

ctg  aaa gag atc atc gac  aag ctg acc ggc atc  gac ctg agc cac      5221
Leu  Lys Glu Ile Ile Asp  Lys Leu Thr Gly Ile  Asp Leu Ser His
1310                 1315                 1320
```

-continued

```
ctg  aag gtg gcc gac atc  cac ccc cac atc atc  gaa aag gcc atg      5266
Leu  Lys Val Ala Asp Ile  His Pro His Ile Ile  Glu Lys Ala Met
1325                 1330                 1335

ctg  aag aac aag atc ccc  gac aac gag ctg gcc  atg gct atc aag      5311
Leu  Lys Asn Lys Ile Pro  Asp Asn Glu Leu Ala  Met Ala Ile Lys
1340                 1345                 1350

agc  aag gtg gaa gtg atc  gac gag atg aac acc  gag acc gag cac      5356
Ser  Lys Val Glu Val Ile  Asp Glu Met Asn Thr  Glu Thr Glu His
1355                 1360                 1365

gtg  atc gag agc atc atg  ccc ctg gtg aag aag  gaa tac gag aag      5401
Val  Ile Glu Ser Ile Met  Pro Leu Val Lys Lys  Glu Tyr Glu Lys
1370                 1375                 1380

cac  gac aac aag tac cac  gtg aac atc ccc agc  gcc ctg aag atc      5446
His  Asp Asn Lys Tyr His  Val Asn Ile Pro Ser  Ala Leu Lys Ile
1385                 1390                 1395

cac  agc gag cac acc ccc  aag gtg cac atc tac  acc acc ccc tgg      5491
His  Ser Glu His Thr Pro  Lys Val His Ile Tyr  Thr Thr Pro Trp
1400                 1405                 1410

gac  agc gac aag gtg ttc  atc tgc cgg tgc atc  gcc ccc cac cat      5536
Asp  Ser Asp Lys Val Phe  Ile Cys Arg Cys Ile  Ala Pro His His
1415                 1420                 1425

cag  cag cgg agc ttc atg  atc ggc ttc gac ctg  gaa atc gag ttc      5581
Gln  Gln Arg Ser Phe Met  Ile Gly Phe Asp Leu  Glu Ile Glu Phe
1430                 1435                 1440

gtg  ttc tac gag gac acc  agc gtg gag ggc cac  atc atg cac ggc      5626
Val  Phe Tyr Glu Asp Thr  Ser Val Glu Gly His  Ile Met His Gly
1445                 1450                 1455

gga  gcc gtg agc atc gag  ggc agg ggc ttc cgg  cag gcc tac agc      5671
Gly  Ala Val Ser Ile Glu  Gly Arg Gly Phe Arg  Gln Ala Tyr Ser
1460                 1465                 1470

gag  ttc atg aac gcc gcc  tgg tcc atg ccc agc  acc ccc gag ctg      5716
Glu  Phe Met Asn Ala Ala  Trp Ser Met Pro Ser  Thr Pro Glu Leu
1475                 1480                 1485

cac  aag cgg cgg ctg cag  cgg agc ctg ggc agc  cac ccc atc tac      5761
His  Lys Arg Arg Leu Gln  Arg Ser Leu Gly Ser  His Pro Ile Tyr
1490                 1495                 1500

atg  ggc agc atg gac tac  acc gtg agc tat gag  cag ctg gtg tcc      5806
Met  Gly Ser Met Asp Tyr  Thr Val Ser Tyr Glu  Gln Leu Val Ser
1505                 1510                 1515

aac  gcc atg aag ctg gtg  tac gac acc gac ctg  cag atg cac tgc      5851
Asn  Ala Met Lys Leu Val  Tyr Asp Thr Asp Leu  Gln Met His Cys
1520                 1525                 1530

ctg  aga ggc ccc ctg aag  ttc cag cgg cgg acc  ctg atg aac gcc      5896
Leu  Arg Gly Pro Leu Lys  Phe Gln Arg Arg Thr  Leu Met Asn Ala
1535                 1540                 1545

ctg  ctg ttc ggc gtg aaa  tga tagtaatttt tctactagtt aatcaaataa      5947
Leu  Leu Phe Gly Val Lys
1550                 1555

aaagcataca agctattgct tcgctatcgt tacaaaatgg caggaatttt gtgtaaacta   6007

agccacatac ttgccaatga aaaaaatagt agaaaggata ctattttaat gggattagat   6067

gttaaggttc cttgggatta tagtaactgg gcatctgtta acttttacga cgttaggtta   6127

gatactgatg ttacagatta taataatgtt acaataaaat acatgacagg atgtgatatt   6187

tttcctcata taactcttgg aatagcaaat atggatcaat gtgatagatt tgaaaatttc   6247

aaaaagcaaa taactgatca agatttacag actatttcta tagtctgtaa agaagagatg   6307

tgttttcctc agagtaacgc ctctaaacag ttgggagcga aaggatgcgc tgtagttatg   6367

aaactggagg tatctgatga acttagagcc ctaagaaatg ttctgctgaa tgcggtaccc   6427
```

-continued

```
tgttcgaagg acgtgtttgg tgatatcaca gtagataatc cgtggaatcc tcacataaca   6487

gtaggatatg ttaaggagga cgatgtcgaa aacaagaaac gcctaatgga gtgcatgtcc   6547

aagtttaggg ggcaagaaat acaagttcta ggatggtatt aataagtatc taagtatttg   6607

gtataattta ttaaatagta taattataac aaataataaa taacatgata acggttttta   6667

ttagaataaa atagagataa tatcataatg atatataata cttcattacc agaaatgagt   6727

aatggaagac ttataaatga actgcataaa gctataaggt atagagatat aaatttagta   6787

aggtatatac ttaaaaaatg caaatacaat aacgtaaata tactatcaac gtctttgtat   6847

ttagccgtaa gtatttctga tatagaaatg gtaaaattat tactagaaca cggtgccgat   6907

attttaaaat gtaaaaatcc tcctcttcat aaagctgcta gtttagataa tacagaaatt   6967

gctaaactac taatagattc tggcgctgac atagaacaga tacattctgg aaatagtccg   7027

ttatatattt ctgtatatag aaacaataag tcattaacta gatatttatt aaaaaaaggt   7087

gttaattgta atagattctt tctaaattat tacgatgtac tgtatgataa gatatctgat   7147

gatatgtata aaatatttat agattttaat attgatctta atatacaaac tagaaatttt   7207

gaaactccgt tacattacgc tataaagtat aagaatatag atttaattag gatattgtta   7267

gataatagta ttaaaataga taaaagttta tttttgcata aacagtatct cataaaggca   7327

cttaaaaata attgtagtta cgatataata gcgttactta taaatcacgg agtgcctata   7387

aacgaacaag atgatttagg taaaacccca ttacatcatt cggtaattaa tagaagaaaa   7447

gatgtaacag cacttctgtt aaatctagga gctgatataa acgtaataga tgactgtatg   7507

ggcagtccct tacattacgc tgtttcacgt aacgatatcg aaacaacaaa gacactttta   7567

gaaagaggat ctaatgttaa tgtggttaat aatcatatag ataccgttct aaatatagct   7627

gttgcatcta aaaacaaaac tatagtaaac ttattactga agtacggtac tgatacaaag   7687

ttggtaggat tagataaaca tgttattcac atagctatag aaatgaaaga tattaatata   7747

ctgaatgcga tcttattata tggttgctat gtaaacgtct ataatcataa aggtttcact   7807

cctctataca tggcagttag ttctatgaaa acagaatttg ttaaactctt acttgaccac   7867

ggtgcttacg taaatgctaa agctaagtta tctggaaata ctcctttaca taaagctatg   7927

ttatctaata gttttaataa tataaaatta cttttatctt ataacgccga ctataattct   7987

ctaaataatc acggtaatac gcctctaact tgtgttagct tttagatga caagatagct   8047

attatgataa tatctaaaat gatgttagaa atatctaaaa atcctgaaat agctaattca   8107

gaaggtttta tagtaaacat ggaacatata aacagtaata aaagactact atctataaaa   8167

gaatcatgcg aaaaagaact agatgttata acacatataa agttaaattc tatatattct   8227

tttaatatct ttcttgacaa taacatagat cttatggtaa agttcgtaac taatcctaga   8287

gttaataaga tacctgcatg tatacgtata tatagggaat taatacggaa aaataaatca   8347

ttagcttttc atagacatca gctaatagtt aaagctgtaa aagagagtaa gaatctagga   8407

ataataggta ggttacctat agatatcaaa catataataa tggaactatt aagtaataat   8467

gatttacatt ctgttatcac cagctgttgt aacccagtag tataaagagc tcgaattaat   8527

tcactggccg tcgttttaca acgtcgtgac tgggaaaacc ctggcgttac ccaacttaat   8587

cgccttgcag cacatccccc tttcgccagc tggcgtaata gcgaagaggc ccgcaccgat   8647

cgcccttccc aacagttgcg cagcctgaat ggcgaatggc gcctgatgcg gtattttctc   8707

cttacgcatc tgtgcggtat ttcacaccgc atatggtgca ctctcagtac aatctgctct   8767

gatgccgcat agttaagcca gccccgacac ccgccaacac ccgctgacgc gccctgacgg   8827
```

-continued

```
gcttgtctgc tcccggcatc cgcttacaga caagctgtga ccgtctccgg gagctgcatg   8887

tgtcagaggt tttcaccgtc atcaccgaaa cgcgcgagac gaaagggcct cgtgatacgc   8947

ctatttttat aggttaatgt catgataata atggtttctt agacgtcagg tggcactttt   9007

cggggaaatg tgcgcggaac ccctatttgt ttatttttct aaatacattc aaatatgtat   9067

ccgctcatga gacaataacc ctgataaatg cttcaataat attgaaaaag gaagagt      9124

atg agt att caa cat  ttc cgt gtc gcc ctt  att ccc ttt ttt gcg      9169
Met Ser Ile Gln His  Phe Arg Val Ala Leu  Ile Pro Phe Phe Ala
                1560                 1565                 1570

gca ttt tgc ctt cct  gtt ttt gct cac cca  gaa acg ctg gtg aaa      9214
Ala Phe Cys Leu Pro  Val Phe Ala His Pro  Glu Thr Leu Val Lys
                1575                 1580                 1585

gta aaa gat gct gaa  gat cag ttg ggt gca  cga gtg ggt tac atc      9259
Val Lys Asp Ala Glu  Asp Gln Leu Gly Ala  Arg Val Gly Tyr Ile
                1590                 1595                 1600

gaa ctg gat ctc aac  agc ggt aag atc ctt  gag agt ttt cgc ccc      9304
Glu Leu Asp Leu Asn  Ser Gly Lys Ile Leu  Glu Ser Phe Arg Pro
                1605                 1610                 1615

gaa gaa cgt ttt cca  atg atg agc act ttt  aaa gtt ctg cta tgt      9349
Glu Glu Arg Phe Pro  Met Met Ser Thr Phe  Lys Val Leu Leu Cys
                1620                 1625                 1630

ggc gcg gta tta tcc  cgt att gac gcc ggg  caa gag caa ctc ggt      9394
Gly Ala Val Leu Ser  Arg Ile Asp Ala Gly  Gln Glu Gln Leu Gly
                1635                 1640                 1645

cgc cgc ata cac tat  tct cag aat gac ttg  gtt gag tac tca cca      9439
Arg Arg Ile His Tyr  Ser Gln Asn Asp Leu  Val Glu Tyr Ser Pro
                1650                 1655                 1660

gtc aca gaa aag cat  ctt acg gat ggc atg  aca gta aga gaa tta      9484
Val Thr Glu Lys His  Leu Thr Asp Gly Met  Thr Val Arg Glu Leu
                1665                 1670                 1675

tgc agt gct gcc ata  acc atg agt gat aac  act gcg gcc aac tta      9529
Cys Ser Ala Ala Ile  Thr Met Ser Asp Asn  Thr Ala Ala Asn Leu
                1680                 1685                 1690

ctt ctg aca acg atc  gga gga ccg aag gag  cta acc gct ttt ttg      9574
Leu Leu Thr Thr Ile  Gly Gly Pro Lys Glu  Leu Thr Ala Phe Leu
                1695                 1700                 1705

cac aac atg ggg gat  cat gta act cgc ctt  gat cgt tgg gaa ccg      9619
His Asn Met Gly Asp  His Val Thr Arg Leu  Asp Arg Trp Glu Pro
                1710                 1715                 1720

gag ctg aat gaa gcc  ata cca aac gac gag  cgt gac acc acg atg      9664
Glu Leu Asn Glu Ala  Ile Pro Asn Asp Glu  Arg Asp Thr Thr Met
                1725                 1730                 1735

cct gta gca atg gca  aca acg ttg cgc aaa  cta tta act ggc gaa      9709
Pro Val Ala Met Ala  Thr Thr Leu Arg Lys  Leu Leu Thr Gly Glu
                1740                 1745                 1750

cta ctt act cta gct  tcc cgg caa caa tta  ata gac tgg atg gag      9754
Leu Leu Thr Leu Ala  Ser Arg Gln Gln Leu  Ile Asp Trp Met Glu
                1755                 1760                 1765

gcg gat aaa gtt gca  gga cca ctt ctg cgc  tcg gcc ctt ccg gct      9799
Ala Asp Lys Val Ala  Gly Pro Leu Leu Arg  Ser Ala Leu Pro Ala
                1770                 1775                 1780

ggc tgg ttt att gct  gat aaa tct gga gcc  ggt gag cgt ggg tct      9844
Gly Trp Phe Ile Ala  Asp Lys Ser Gly Ala  Gly Glu Arg Gly Ser
                1785                 1790                 1795

cgc ggt atc att gca  gca ctg ggg cca gat  ggt aag ccc tcc cgt      9889
Arg Gly Ile Ile Ala  Ala Leu Gly Pro Asp  Gly Lys Pro Ser Arg
                1800                 1805                 1810

atc gta gtt atc tac  acg acg ggg agt cag  gca act atg gat gaa      9934
Ile Val Val Ile Tyr  Thr Thr Gly Ser Gln  Ala Thr Met Asp Glu
```

```
              1815                1820                1825

cga aat aga cag atc  gct gag ata ggt gcc  tca ctg att aag cat       9979
Arg Asn Arg Gln Ile  Ala Glu Ile Gly Ala  Ser Leu Ile Lys His
              1830                1835                1840

tgg taactgtcag accaagttta ctcatatata ctttagattg atttaaaact         10032
Trp

tcatttttaa tttaaaagga tctaggtgaa gatccttttt gataatctca tgaccaaaat  10092

cccttaacgt gagttttcgt tccactgagc gtcagacccc gtagaaaaga tcaaaggatc  10152

ttcttgagat cctttttttc tgcgcgtaat ctgctgcttg caaacaaaaa aaccaccgct  10212

accagcggtg gtttgtttgc cggatcaaga gctaccaact ctttttccga aggtaactgg  10272

cttcagcaga gcgcagatac caaatactgt ccttctagtg tagccgtagt taggccacca  10332

cttcaagaac tctgtagcac cgcctacata cctcgctctg ctaatcctgt taccagtggc  10392

tgctgccagt ggcgataagt cgtgtcttac cgggttggac tcaagacgat agttaccgga  10452

taaggcgcag cggtcgggct gaacgggggg ttcgtgcaca cagcccagct tggagcgaac  10512

gacctacacc gaactgagat acctacagcg tgagctatga gaaagcgcca cgcttcccga  10572

agggagaaag gcggacaggt atccggtaag cggcagggtc ggaacaggag agcgcacgag  10632

ggagcttcca gggggaaacg cctggtatct ttatagtcct gtcgggtttc gccacctctg  10692

acttgagcgt cgatttttgt gatgctcgtc aggggggcgg agcctatgga aaaacgccag  10752

caacgcggcc tttttacggt tcctggcctt ttgctggcct tttgctcaca tgttctttcc  10812

tgcgttatcc cctgattctg tggataaccg tattaccgcc tttgagtgag ctgataccgc  10872

tcgccgcagc cgaacgaccg agcgcagcga gtcagtgagc gaggaagcgg aagagcgccc  10932

aatacgcaaa ccgcctctcc ccgcgcgttg gccgattcat taatgcagct ggcacgacag  10992

gtttcccgac tggaaagcgg gcagtgagcg caacgcaatt aatgtgagtt agctcactca  11052

ttaggcaccc caggctttac actttatgct tccggctcgt atgttgtgtg gaattgtgag  11112

cggataacaa tttcacaca                                               11131
```

<210> SEQ ID NO 23
<211> LENGTH: 36
<212> TYPE: DNA
<213> ORGANISM: artificial sequence
<220> FEATURE:
<223> OTHER INFORMATION: 18020CXL Primer for amplifying the AHSV-9 VP5 probe for the vCP2383.3.1.1.1 viral vector

<400> SEQUENCE: 23

```
ctagactagt ttactatcat ttcacgccga acagca                               36
```

<210> SEQ ID NO 24
<211> LENGTH: 24
<212> TYPE: DNA
<213> ORGANISM: artificial sequence
<220> FEATURE:
<223> OTHER INFORMATION: 18021CXL Primer for amplifying the AHSV-9 VP5 probe for the vCP2383.3.1.1.1 viral vector

<400> SEQUENCE: 24

```
gcaaggacca gagcgagcgg atca                                            24
```

<210> SEQ ID NO 25
<211> LENGTH: 25
<212> TYPE: DNA
<213> ORGANISM: artificial sequence
<220> FEATURE:
<223> OTHER INFORMATION: 13660CXL Primer for amplifying the AHSV-9 VP2 probe for the vCP2383.3.1.1.1 viral vector

<400> SEQUENCE: 25
aggccttcgc cggcaacagc ctgct 25

<210> SEQ ID NO 26
<211> LENGTH: 25
<212> TYPE: DNA
<213> ORGANISM: artificial sequence
<220> FEATURE:
<223> OTHER INFORMATION: 13665CXL Primer for amplifying the AHSV-9 VP2 probe for the vCP2383.3.1.1.1 viral vector

<400> SEQUENCE: 26
agggcatcga tcaggaactc gctct 25

<210> SEQ ID NO 27
<211> LENGTH: 8607
<212> TYPE: DNA
<213> ORGANISM: artificial sequence
<220> FEATURE:
<223> OTHER INFORMATION: vCP2383 viral vector sequence from left arm to right arm

<400> SEQUENCE: 27
gaggcatcca acatataaag aagactaaag ctgtagaagc tgttatgaag aatatcttat 60
cagatatatt agatgcattg ttagttctgt agatcagtaa cgtatagcat acgagtataa 120
ttatcgtagg tagtaggtat cctaaaataa atctgataca gataataact ttgtaaatca 180
attcagcaat ttctctatta tcatgataat gattaataca cagcgtgtcg ttattttttg 240
ttacgatagt atttctaaag taaagagcag gaatccctag tataatagaa ataatccata 300
tgaaaaatat agtaatgtac atatttctaa tgttaacata tttataggta aatccaggaa 360
gggtaatttt tacatatcta tatacgctta ttacagttat taaaaatata cttgcaaaca 420
tgttagaagt aaaaaagaaa gaactaattt tacaaagtgc tttaccaaaa tgccaatgga 480
aattacttag tatgtatata atgtataaag gtatgaatat cacaaacagc aaatcggcta 540
ttcccaagtt gagaaacggt ataatagata tatttctaga taccattaat aaccttataa 600
gcttgacgtt tcctataatg cctactaaga aaactagaag atacatacat actaacgcca 660
tacgagagta actactcatc gtataactac tgttgctaac agtgacactg atgttataac 720
tcatctttga tgtggtataa atgtataata actatattac actggtattt tatttcagtt 780
atatactata tagtattaaa aattatattt gtataattat attattatat tcagtgtaga 840
aagtaaaata ctataaatat gtatctctta tttataactt attagtaaag tatgtactat 900
tcagttatat tgttttataa aagctaaatg ctactagatt gatataaatg aatatgtaat 960
aaattagtaa tgtagtatac taatattaac tcacatttga ctaattagct ataaaaaccc 1020
gggttaatta attagtcatc aggcagggcg agaacgagac tatctgctcg ttaattaatt 1080
agagcttctt tattctatac ttaaaaagtg aaaataaata caaaggttct tgagggttgt 1140
gttaaattga aagcgagaaa taatcataaa ttatttcatt atcgcgatat ccgttaagtt 1200
tgtatcgtaa tggccttcga gttcggcatc ctgcagaccg acaagatccg ggagaacacc 1260
ctggaaaaga ccaactgcga cgtgatcctg acccgggaga accgcgtgcg ggccagagaa 1320
gtggacggcg tgaagggcta ctactgggag gacaccgacc accggctggg cctgtgcgag 1380
gtggagcaca ccgtgagcgt gcgggacttc atgtacaagc agaccaagtg cgagggcagc 1440
taccccgtgg tgcccctgta catgatcgac gccatcaagt acggccggat gatcgaccgg 1500

-continued

```
aacgaccacc agatccgggt ggacaaggac gacaagaccc tgttcaagat ccaggtgcag   1560
ccctacctgg gcgacgccta cttcagcccc gagcactaca ccgccacatt cttcaagcgg   1620
gagcccctgc ccatccacgt ggacaccatc cgggactaca tcggcaagcg gatcaactac   1680
ttcgagcggg agctgggcag cggcgtgagg gacgccaacc tggaaaccat cgtgggcaag   1740
tggaaggaca acacctacaa gcggatcgag ggcgaaaaga ccaccatgtg cgtgcggcac   1800
gagcccgaca gcgtgctgca gatcctgaag aagatgcggt tcggcatgct gtaccccaac   1860
tactacatgc tgaacaccgg ctacatcgtg accgagagca gcaaaggcgc ccctctgaac   1920
cggtggctgg tgaaagaacg gaccgtgggc aaggtgaaag ccgccgaggc cttcgccggc   1980
aacagcctgc tgaagaacct ggccagccgg atggaagatg aggaactgag ccgggagatc   2040
atcgtggccg tgatcaacta cggcagcaag ttcggcacca gaagcggcaa gaagaaggac   2100
ctgatgacca tcgacaagct ggaaaagtac tgcgagagcc tgaccacctt cgtgcaccgg   2160
aagaagcggg acgagggcga cgacgagacc gccagggcca tcatccggaa ccagtggatc   2220
aagggcatgc ccagcatgaa cctgaagaag gagatgaagg tctccagggg ccctatccag   2280
aactggtcct tcttcatgag cctggaagtg ttcaagcgga acaacaaggt ggacatcgac   2340
cccaaccacg acacctggaa gaaccacgtg aaagagatcc gcgagcggat gcagaaggaa   2400
cagagcgcca acagcaacag ccccctgaag attcaggtgg acggggtgtc cctgagcacc   2460
agcgagttct acggcaccgt ggagcactgg atcgactggg tggtggacct gatcatgctg   2520
gcccaggtca agcggctgat caaagagtac aagttcatcc ggctggaaac caccaacctg   2580
atggccggca tgaacaagct ggtcggcgcc ctgcggtgct acgcctactg cctgatcctg   2640
gccctgtacg acttctacgg cgccgacatc gagggcttcg agaagggcag caacagcagc   2700
gccatcgtgg agaccgtggt gcagatgttc cccaacttca agcaggaaat ccaggccaac   2760
ttcggcatca acctgaacat caaggacaag aagcaggtcc tgttcgtccg gatggacatg   2820
gacagcgagt tcagcgagga cgagcagaag ggctacatgt tcgagtacgg ctgggccaag   2880
cgggaggaac ggatctggac caactacggc gacatcctga ccgacctggt ggagcagctg   2940
tacaagagca tcctggacca cgaggaatgg gagaagatcg tggacgaccc cgagcggtac   3000
ttctacgacg agctgttcaa cgccagcccc gagaccgtgt tcatcagcaa gggctacgac   3060
ctggacaaca acatcgtgat cgagggcaaa gtgggccagg acgtgaccta cttctccaag   3120
cggttcgtga gctactggta cagagtgcgg caggtgcaga ccagcaaggg catcgagcgg   3180
cggagcatcg aggacgtgaa gtaccgggag ttcgacatcg agtccttcaa gccctacgcc   3240
atcggcgaga tcggcatcca cgccagcacc tacaagtacc aggacctgct ggccggacgg   3300
aaccggggcg agaaggtgaa agacagccag gccctggtct ggtacgacct ggccctgacc   3360
aactacaccc tggtccggcc ccaggaccgg tgctggatca tgagctgcac cgacagcgag   3420
tacaccctgc ggttcgccat gatcaccatg atcttcgaga gactgagcga ggaaaccgac   3480
ctgagctacc acgacatcct gctgagagtg agagagtacc ccatccagtc cttcgccagc   3540
tacaagcact tctacgtgcg ggtgctgcag catgtgttca gggactacca ggaaatcgac   3600
gtcctggaat tctgcacccg gatgctggac ccccggacca gagagagcgg cctgaacaag   3660
ttcagccggt tcaagcagtg gcgggagagc gagttcctga tcgatgccct gaagatgaac   3720
ttcctgctgt gggtggtgtt cgagctggaa aacatcgacg tggactacag caagaagcgg   3780
cacccccctgc tgatctccac cgacaagggc ctgagagtgg tgcccgtgga cctgttcaat   3840
agcatgctgt ccgtgagcag cagcggctgg attccctacg tggagagagt gtgcgagcgg   3900
```

-continued

```
agcgagatca agcggcggct gaacgccgac gagctgaagc tgaagaactg gttcatcgcc   3960
tactacatca ccctgcccct gctgcggaga gccgagcccc ggatgagctt caagtacgag   4020
ggcatcacca cctggatcgg cagcaactgt ggcggcgtga gagactacct gatccagatg   4080
ctgcccgcca ggaagcccaa gcccggcgtc ctgattctgg cctatggcgc cgagaccaac   4140
gtggcctggc tgaaccacgc cctgcgggac atcctgtccc tggaaggcag cctgggcatg   4200
atcatcatca gcgacggcag cgtggtgaac aagagcaagc tgagagtgcg ggacatgaaa   4260
atctacaaca ggggcgaggt ggaccggctg atcctgatca gctccggcga ctacaccttc   4320
ggcaacaagt acctgctgtc caagctgatg gccaagatcg agcagtgatg aggatccctc   4380
gagtttttat tgactagttc aaaattgaaa atatataatt acaatataaa atgggcaagt   4440
ttaccagctt cctgaagagg gccggcagcg ccaccaagaa ggccctgacc agcgacgccg   4500
ccaagcggat gtacaagatg gccggcaaga ccctgcagaa ggtcgtcgag agcgaagtgg   4560
gcagcgccgc catcgacggc gtgatgcagg gcaccatcca gagcatcatc cagggcgaga   4620
acctgggcga cagcatcaag caggccgtga tcctgaacgt ggccggcacc ctggaaagcg   4680
cccctgaccc cctgagccct ggcgagcagc tgctgtacaa caaggtgtcc gagatcgagc   4740
gggccgagaa ggaagatcgg gtcatcgaga cccacaacaa gaagatcatc gagaagtacg   4800
gcgaggacct gctgaagatc cggaagatca tgaagggcga ggccgaggcc gagcagctgg   4860
aaggcaaaga gatggaatac gtcgaaaagg ccctgaaggg catgctgcgg atcggcaagg   4920
accagagcga gcggatcacc cggctgtacc gggccctgca gaccgaagag gacctgagaa   4980
ccagcgacga gacccggatg atcagcgagt accgggagaa gttcgaggcc ctgaaacagg   5040
ccatcgagct ggaacagcag gccacccacg aggaagccgt gcaggaaatg ctggacctga   5100
gcgccgaggt gatcgaaaca gccgccgagg aagtgcccgt gtttggcgct ggggccgcta   5160
acgtggtggc cacaacccgg gccattcagg gcggcctgaa gctgaaagag atcatcgaca   5220
agctgaccgg catcgacctg agccacctga aggtggccga catccacccc cacatcatcg   5280
aaaaggccat gctgaagaac aagatccccg acaacgagct ggccatggct atcaagagca   5340
aggtggaagt gatcgacgag atgaacaccg agaccgagca cgtgatcgag agcatcatgc   5400
ccctggtgaa gaaggaatac gagaagcacg acaacaagta ccacgtgaac atccccagcg   5460
ccctgaagat ccacagcgag cacacccca aggtgcacat ctacaccacc ccctgggaca   5520
gcgacaaggt gttcatctgc cggtgcatcg cccccacca tcagcagcgg agcttcatga   5580
tcggcttcga cctggaaatc gagttcgtgt tctacgagga caccagcgtg gagggccaca   5640
tcatgcacgg cggagccgtg agcatcgagg gcaggggctt ccggcaggcc tacagcgagt   5700
tcatgaacgc cgcctggtcc atgcccagca cccccgagct gcacaagcgg cggctgcagc   5760
ggagcctggg cagccacccc atctacatgg gcagcatgga ctacaccgtg agctatgagc   5820
agctggtgtc caacgccatg aagctggtgt acgacaccga cctgcagatg cactgcctga   5880
gaggcccccct gaagttccag cggcggaccc tgatgaacgc cctgctgttc ggcgtgaaat   5940
gatagtaatt tttctactag ttaatcaaat aaaaagcata caagctattg cttcgctatc   6000
gttacaaaat ggcaggaatt ttgtgtaaac taagccacat acttgccaat gaaaaaaata   6060
gtagaaagga tactatttta atgggattag atgttaaggt tccttgggat tatagtaact   6120
gggcatctgt taacttttac gacgttaggt tagatactga tgttacagat tataataatg   6180
ttacaataaa atacatgaca ggatgtgata tttttcctca tataactctt ggaatagcaa   6240
atatggatca atgtgataga tttgaaaatt tcaaaaagca aataactgat caagatttac   6300
```

agactatttc tatagtctgt aaagaagaga tgtgttttcc tcagagtaac gcctctaaac 6360
agttgggagc gaaaggatgc gctgtagtta tgaaactgga ggtatctgat gaacttagag 6420
ccctaagaaa tgttctgctg aatgcggtac cctgttcgaa ggacgtgttt ggtgatatca 6480
cagtagataa tccgtggaat cctcacataa cagtaggata tgttaaggag gacgatgtcg 6540
aaaacaagaa acgcctaatg gagtgcatgt ccaagtttag ggggcaagaa atacaagttc 6600
taggatggta ttaataagta tctaagtatt tggtataatt tattaaatag tataattata 6660
acaaataata aataacatga taacggtttt tattagaata aaatagagat aatatcataa 6720
tgatatataa tacttcatta ccagaaatga gtaatggaag acttataaat gaactgcata 6780
aagctataag gtatagagat ataaatttag taaggtatat acttaaaaaa tgcaaataca 6840
ataacgtaaa tatactatca acgtctttgt atttagccgt aagtatttct gatatagaaa 6900
tggtaaaatt attactagaa cacggtgccg atattttaaa atgtaaaaat cctcctcttc 6960
ataaagctgc tagtttagat aatacagaaa ttgctaaact actaatagat tctggcgctg 7020
acatagaaca gatacattct ggaaatagtc cgttatatat ttctgtatat agaaacaata 7080
agtcattaac tagatattta ttaaaaaaag gtgttaattg taatagattc tttctaaatt 7140
attacgatgt actgtatgat aagatatctg atgatatgta taaaatattt atagatttta 7200
atattgatct taatatacaa actagaaatt ttgaaactcc gttacattac gctataaagt 7260
ataagaatat agatttaatt aggatattgt tagataatag tattaaaata gataaaagtt 7320
tatttttgca taaacagtat ctcataaagg cacttaaaaa taattgtagt tacgatataa 7380
tagcgttact tataaatcac ggagtgccta taaacgaaca agatgattta ggtaaaaccc 7440
cattacatca ttcggtaatt aatagaagaa aagatgtaac agcacttctg ttaaatctag 7500
gagctgatat aaacgtaata gatgactgta tgggcagtcc cttacattac gctgtttcac 7560
gtaacgatat cgaaacaaca aagacacttt tagaaagagg atctaatgtt aatgtggtta 7620
ataatcatat agataccgtt ctaaatatag ctgttgcatc taaaaacaaa actatagtaa 7680
acttattact gaagtacggt actgatacaa agttggtagg attagataaa catgttattc 7740
acatagctat agaaatgaaa gatattaata tactgaatgc gatcttatta tatggttgct 7800
atgtaaacgt ctataatcat aaaggtttca ctcctctata catggcagtt agttctatga 7860
aaacagaatt tgttaaactc ttacttgacc acggtgctta cgtaaatgct aaagctaagt 7920
tatctggaaa tactccttta cataaagcta tgttatctaa tagttttaat aatataaaat 7980
tacttttatc ttataacgcc gactataatt ctctaaataa tcacggtaat acgcctctaa 8040
cttgtgttag ctttttagat gacaagatag ctattatgat aatatctaaa atgatgttag 8100
aaatatctaa aaatcctgaa atagctaatt cagaaggttt tatagtaaac atggaacata 8160
taaacagtaa taaaagacta ctatctataa aagaatcatg cgaaaaagaa ctagatgtta 8220
taacacatat aaagttaaat tctatatatt cttttaatat ctttcttgac aataacatag 8280
atcttatggt aaagttcgta actaatccta gagttaataa gatacctgca tgtatacgta 8340
tatataggga attaatacgg aaaaataaat cattagcttt tcatagacat cagctaatag 8400
ttaaagctgt aaaagagagt aagaatctag gaataatagg taggttacct atagatatca 8460
aacatataat aatggaacta ttaagtaata atgatttaca ttctgttatc accagctgtt 8520
gtaacccagt agtataaagt gattttattc aattacgaag ataaacatta aatttgttaa 8580
cagatatgag ttatgagtat ttaacta 8607

<210> SEQ ID NO 28

<211> LENGTH: 3154
<212> TYPE: DNA
<213> ORGANISM: artificial sequence
<220> FEATURE:
<223> OTHER INFORMATION: AHSV-9 VP2 of vCP2383

<400> SEQUENCE: 28
atggccttcg agttcggcat cctgcagacc gacaagatcc gggagaacac cctggaaaag 60
accaactgcg acgtgatcct gacccgggag aaccgcgtgc gggccagaga agtggacggc 120
gtgaagggct actactggga ggacaccgac caccggctgg gcctgtgcga ggtggagcac 180
accgtgagcg tgcgggactt catgtacaag cagaccaagt gcgagggcag ctaccccgtg 240
gtgcccctgt acatgatcga cgccatcaag tacggccgga tgatcgaccg gaacgaccac 300
cagatccggg tggacaagga cgacaagacc ctgttcaaga tccaggtgca gccctacctg 360
ggcgacgcct acttcagccc cgagcactac accgccacat tcttcaagcg ggagcccctg 420
cccatccacg tggacaccat ccgggactac atcggcaagc ggatcaacta cttcgagcgg 480
gagctgggca gcggcgtgag ggacgccaac ctggaaacca tcgtgggcaa gtggaaggac 540
aacacctaca agcggatcga gggcgaaaag accaccatgt gcgtgcggca cgagcccgac 600
agcgtgctgc agatcctgaa gaagatgcgg ttcggcatgc tgtaccccaa ctactacatg 660
ctgaacaccg gctacatcgt gaccgagagc agcaaaggcg cccctctgaa ccggtggctg 720
gtgaaagaac ggaccgtggg caaggtgaaa gccgccgagg ccttcgccgg caacagcctg 780
ctgaagaacc tggccagccg gatggaagat gaggaactga gccgggagat catcgtggcc 840
gtgatcaact acggcagcaa gttcggcacc agaagcggca agaagaagga cctgatgacc 900
atcgacaagc tggaaaagta ctgcgagagc ctgaccacct tcgtgcaccg gaagaagcgg 960
gacgagggcg acgacgagac cgccagggcc atcatccgga accagtggat caagggcatg 1020
cccagcatga acctgaagaa ggagatgaag gtctccaggg gccctatcca gaactggtcc 1080
ttcttcatga gcctggaagt gttcaagcgg aacaacaagg tggacatcga ccccaaccac 1140
gacacctgga agaaccacgt gaaagagatc cgcgagcgga tgcagaagga acagagcgcc 1200
aacagcaaca gcccccctgaa gattcaggtg gacggggtgt ccctgagcac cagcgagttc 1260
tacggcaccg tggagcactg gatcgactgg gtggtggacc tgatcatgct ggcccaggtc 1320
aagcggctga tcaaagagta caagttcatc cggctggaaa ccaccaacct gatggccggc 1380
atgaacaagc tggtcggcgc cctgcggtgc tacgcctact gcctgatcct ggccctgtac 1440
gacttctacg gcgccgacat cgagggcttc gagaagggca gcaacagcag cgccatcgtg 1500
gagaccgtgg tgcagatgtt ccccaacttc aagcaggaaa tccaggccaa cttcggcatc 1560
aacctgaaca tcaaggacaa gaagcaggtc ctgttcgtcc ggatggacat ggacagcgag 1620
ttcagcgagg acgagcagaa gggctacatg ttcgagtacg gctgggccaa gcgggaggaa 1680
cggatctgga ccaactacgg cgacatcctg accgacctgg tggagcagct gtacaagagc 1740
atcctggacc acgaggaatg ggagaagatc gtggacgacc ccgagcggta cttctacgac 1800
gagctgttca acgccagccc cgagaccgtg ttcatcagca agggctacga cctggacaac 1860
aacatcgtga tcgagggcaa agtgggccag gacgtgacct acttctccaa gcggttcgtg 1920
agctactggt acagagtgcg gcaggtgcag accagcaagg gcatcgagcg gcggagcatc 1980
gaggacgtga agtaccggga gttcgacatc gagtccttca agccctacgc catcggcgag 2040
atcggcatcc acgccagcac ctacaagtac caggacctgc tggccggacg gaaccggggc 2100
gagaaggtga aagacagcca ggccctggtc tggtacgacc tggccctgac caactacacc 2160

-continued

```
ctggtccggc cccaggaccg gtgctggatc atgagctgca ccgacagcga gtacaccctg   2220

cggttcgcca tgatcaccat gatcttcgag agactgagcg aggaaaccga cctgagctac   2280

cacgacatcc tgctgagagt gagagagtac cccatccagt ccttcgccag ctacaagcac   2340

ttctacgtgc gggtgctgca gcatgtgttc agggactacc aggaaatcga cgtcctggaa   2400

ttctgcaccc ggatgctgga cccccggacc agagagagcg gcctgaacaa gttcagccgg   2460

ttcaagcagt ggcgggagag cgagttcctg atcgatgccc tgaagatgaa cttcctgctg   2520

tgggtggtgt tcgagctgga aaacatcgac gtggactaca gcaagaagcg gcaccccctg   2580

ctgatctcca ccgacaaggg cctgagagtg gtgcccgtgg acctgttcaa tagcatgctg   2640

tccgtgagca gcagcggctg gattccctac gtggagagag tgtgcgagcg gagcgagatc   2700

aagcggcggc tgaacgccga cgagctgaag ctgaagaact ggttcatcgc ctactacatc   2760

accctgcccc tgctgcggag agccgagccc cggatgagct tcaagtacga gggcatcacc   2820

acctggatcg gcagcaactg tggcggcgtg agagactacc tgatccagat gctgcccgcc   2880

aggaagccca agcccggcgt cctgattctg gcctatggcg ccgagaccaa cgtggcctgg   2940

ctgaaccacg ccctgcggga catcctgtcc ctggaaggca gcctgggcat gatcatcatc   3000

agcgacggca gcgtggtgaa caagagcaag ctgagagtgc gggacatgaa aatctacaac   3060

aggggcgagg tggaccggct gatcctgatc agctccggcg actacacctt cggcaacaag   3120

tacctgctgt ccaagctgat ggccaagatc gagc                             3154
```

```
<210> SEQ ID NO 29
<211> LENGTH: 1509
<212> TYPE: DNA
<213> ORGANISM: artificial sequence
<220> FEATURE:
<223> OTHER INFORMATION: AHSV-9 VP5 of vCP2383

<400> SEQUENCE: 29

atgggcaagt ttaccagctt cctgaagagg gccggcagcg ccaccaagaa ggccctgacc     60

agcgacgccg ccaagcggat gtacaagatg gccggcaaga ccctgcagaa ggtcgtcgag    120

agcgaagtgg gcagcgccgc catcgacggc gtgatgcagg gcaccatcca gagcatcatc    180

cagggcgaga acctgggcga cagcatcaag caggccgtga tcctgaacgt ggccggcacc    240

ctggaaagcg cccctgaccc cctgagccct ggcgagcagc tgctgtacaa caaggtgtcc    300

gagatcgagc gggccgagaa ggaagatcgg gtcatcgaga cccacaacaa gaagatcatc    360

gagaagtacg gcgaggacct gctgaagatc cggaagatca tgaagggcga ggccgaggcc    420

gagcagctgg aaggcaaaga gatggaatac gtcgaaaagg ccctgaaggg catgctgcgg    480

atcggcaagg accagagcga gcggatcacc cggctgtacc gggccctgca gaccgaagag    540

gacctgagaa ccagcgacga gacccggatg atcagcgagt accgggagaa gttcgaggcc    600

ctgaaacagg ccatcgagct ggaacagcag gccacccacg aggaagccgt gcaggaaatg    660

ctggacctga gcgccgaggt gatcgaaaca gccgccgagg aagtgcccgt gtttggcgct    720

ggggccgcta acgtggtggc cacaacccgg gccattcagg gcggcctgaa gctgaaagag    780

atcatcgaca agctgaccgg catcgacctg agccacctga aggtggccga catccacccc    840

cacatcatcg aaaaggccat gctgaagaac aagatccccg acaacgagct ggccatggct    900

atcaagagca aggtggaagt gatcgacgag atgaacaccg agaccgagca cgtgatcgag    960

agcatcatgc ccctggtgaa gaaggaatac gagaagcacg acaacaagta ccacgtgaac   1020

atccccagcg ccctgaagat ccacagcgag cacaccccca aggtgcacat ctacaccacc   1080
```

-continued ccctgggaca gcgacaaggt gttcatctgc cggtgcatcg ccccccacca tcagcagcgg 1140
agcttcatga tcggcttcga cctggaaatc gagttcgtgt tctacgagga caccagcgtg 1200
gagggccaca tcatgcacgg cggagccgtg agcatcgagg gcaggggctt ccggcaggcc 1260
tacagcgagt tcatgaacgc cgcctggtcc atgcccagca cccccgagct gcacaagcgg 1320
cggctgcagc ggagcctggg cagccacccc atctacatgg gcagcatgga ctacaccgtg 1380
agctatgagc agctggtgtc caacgccatg aagctggtgt acgacaccga cctgcagatg 1440
cactgcctga gaggcccct gaagttccag cggcggaccc tgatgaacgc cctgctgttc 1500
ggcgtgaaa 1509

<210> SEQ ID NO 30
<211> LENGTH: 1051
<212> TYPE: PRT
<213> ORGANISM: artificial sequence
<220> FEATURE:
<223> OTHER INFORMATION: AHSV-9 VP2 amino acid seq of vCP2383

<400> SEQUENCE: 30

Met Ala Phe Glu Phe Gly Ile Leu Gln Thr Asp Lys Ile Arg Glu Asn
1 5 10 15

Thr Leu Glu Lys Thr Asn Cys Asp Val Ile Leu Thr Arg Glu Asn Arg
20 25 30

Val Arg Ala Arg Glu Val Asp Gly Val Lys Gly Tyr Tyr Trp Glu Asp
35 40 45

Thr Asp His Arg Leu Gly Leu Cys Glu Val Glu His Thr Val Ser Val
50 55 60

Arg Asp Phe Met Tyr Lys Gln Thr Lys Cys Glu Gly Ser Tyr Pro Val
65 70 75 80

Val Pro Leu Tyr Met Ile Asp Ala Ile Lys Tyr Gly Arg Met Ile Asp
85 90 95

Arg Asn Asp His Gln Ile Arg Val Asp Lys Asp Asp Lys Thr Leu Phe
100 105 110

Lys Ile Gln Val Gln Pro Tyr Leu Gly Asp Ala Tyr Phe Ser Pro Glu
115 120 125

His Tyr Thr Ala Thr Phe Phe Lys Arg Glu Pro Leu Pro Ile His Val
130 135 140

Asp Thr Ile Arg Asp Tyr Ile Gly Lys Arg Ile Asn Tyr Phe Glu Arg
145 150 155 160

Glu Leu Gly Ser Gly Val Arg Asp Ala Asn Leu Glu Thr Ile Val Gly
165 170 175

Lys Trp Lys Asp Asn Thr Tyr Lys Arg Ile Glu Gly Glu Lys Thr Thr
180 185 190

Met Cys Val Arg His Glu Pro Asp Ser Val Leu Gln Ile Leu Lys Lys
195 200 205

Met Arg Phe Gly Met Leu Tyr Pro Asn Tyr Tyr Met Leu Asn Thr Gly
210 215 220

Tyr Ile Val Thr Glu Ser Ser Lys Gly Ala Pro Leu Asn Arg Trp Leu
225 230 235 240

Val Lys Glu Arg Thr Val Gly Lys Val Lys Ala Ala Glu Ala Phe Ala
245 250 255

Gly Asn Ser Leu Leu Lys Asn Leu Ala Ser Arg Met Glu Asp Glu Glu
260 265 270

Leu Ser Arg Glu Ile Ile Val Ala Val Ile Asn Tyr Gly Ser Lys Phe
275 280 285

```
Gly Thr Arg Ser Gly Lys Lys Lys Asp Leu Met Thr Ile Asp Lys Leu
    290                 295                 300

Glu Lys Tyr Cys Glu Ser Leu Thr Thr Phe Val His Arg Lys Lys Arg
305                 310                 315                 320

Asp Glu Gly Asp Asp Glu Thr Ala Arg Ala Ile Ile Arg Asn Gln Trp
                325                 330                 335

Ile Lys Gly Met Pro Ser Met Asn Leu Lys Lys Glu Met Lys Val Ser
            340                 345                 350

Arg Gly Pro Ile Gln Asn Trp Ser Phe Phe Met Ser Leu Glu Val Phe
        355                 360                 365

Lys Arg Asn Asn Lys Val Asp Ile Asp Pro Asn His Asp Thr Trp Lys
    370                 375                 380

Asn His Val Lys Glu Ile Arg Glu Arg Met Gln Lys Glu Gln Ser Ala
385                 390                 395                 400

Asn Ser Asn Ser Pro Leu Lys Ile Gln Val Asp Gly Val Ser Leu Ser
                405                 410                 415

Thr Ser Glu Phe Tyr Gly Thr Val Glu His Trp Ile Asp Trp Val Val
            420                 425                 430

Asp Leu Ile Met Leu Ala Gln Val Lys Arg Leu Ile Lys Glu Tyr Lys
        435                 440                 445

Phe Ile Arg Leu Glu Thr Thr Asn Leu Met Ala Gly Met Asn Lys Leu
    450                 455                 460

Val Gly Ala Leu Arg Cys Tyr Ala Tyr Cys Leu Ile Leu Ala Leu Tyr
465                 470                 475                 480

Asp Phe Tyr Gly Ala Asp Ile Glu Gly Phe Glu Lys Gly Ser Asn Ser
                485                 490                 495

Ser Ala Ile Val Glu Thr Val Val Gln Met Phe Pro Asn Phe Lys Gln
            500                 505                 510

Glu Ile Gln Ala Asn Phe Gly Ile Asn Leu Asn Ile Lys Asp Lys Lys
        515                 520                 525

Gln Val Leu Phe Val Arg Met Asp Met Asp Ser Glu Phe Ser Glu Asp
    530                 535                 540

Glu Gln Lys Gly Tyr Met Phe Glu Tyr Gly Trp Ala Lys Arg Glu Glu
545                 550                 555                 560

Arg Ile Trp Thr Asn Tyr Gly Asp Ile Leu Thr Asp Leu Val Glu Gln
                565                 570                 575

Leu Tyr Lys Ser Ile Leu Asp His Glu Glu Trp Glu Lys Ile Val Asp
            580                 585                 590

Asp Pro Glu Arg Tyr Phe Tyr Asp Glu Leu Phe Asn Ala Ser Pro Glu
        595                 600                 605

Thr Val Phe Ile Ser Lys Gly Tyr Asp Leu Asp Asn Asn Ile Val Ile
    610                 615                 620

Glu Gly Lys Val Gly Gln Asp Val Thr Tyr Phe Ser Lys Arg Phe Val
625                 630                 635                 640

Ser Tyr Trp Tyr Arg Val Arg Gln Val Gln Thr Ser Lys Gly Ile Glu
                645                 650                 655

Arg Arg Ser Ile Glu Asp Val Lys Tyr Arg Glu Phe Asp Ile Glu Ser
            660                 665                 670

Phe Lys Pro Tyr Ala Ile Gly Glu Ile Gly Ile His Ala Ser Thr Tyr
        675                 680                 685

Lys Tyr Gln Asp Leu Leu Ala Gly Arg Asn Arg Gly Glu Lys Val Lys
    690                 695                 700

Asp Ser Gln Ala Leu Val Trp Tyr Asp Leu Ala Leu Thr Asn Tyr Thr
705                 710                 715                 720
```

-continued

```
Leu Val Arg Pro Gln Asp Arg Cys Trp Ile Met Ser Cys Thr Asp Ser
                725                 730                 735

Glu Tyr Thr Leu Arg Phe Ala Met Ile Thr Met Ile Phe Glu Arg Leu
            740                 745                 750

Ser Glu Glu Thr Asp Leu Ser Tyr His Asp Ile Leu Leu Arg Val Arg
        755                 760                 765

Glu Tyr Pro Ile Gln Ser Phe Ala Ser Tyr Lys His Phe Tyr Val Arg
    770                 775                 780

Val Leu Gln His Val Phe Arg Asp Tyr Gln Glu Ile Asp Val Leu Glu
785                 790                 795                 800

Phe Cys Thr Arg Met Leu Asp Pro Arg Thr Arg Glu Ser Gly Leu Asn
                805                 810                 815

Lys Phe Ser Arg Phe Lys Gln Trp Arg Glu Ser Glu Phe Leu Ile Asp
            820                 825                 830

Ala Leu Lys Met Asn Phe Leu Leu Trp Val Val Phe Glu Leu Glu Asn
        835                 840                 845

Ile Asp Val Asp Tyr Ser Lys Lys Arg His Pro Leu Leu Ile Ser Thr
    850                 855                 860

Asp Lys Gly Leu Arg Val Val Pro Val Asp Leu Phe Asn Ser Met Leu
865                 870                 875                 880

Ser Val Ser Ser Ser Gly Trp Ile Pro Tyr Val Glu Arg Val Cys Glu
                885                 890                 895

Arg Ser Glu Ile Lys Arg Arg Leu Asn Ala Asp Glu Leu Lys Leu Lys
            900                 905                 910

Asn Trp Phe Ile Ala Tyr Tyr Ile Thr Leu Pro Leu Leu Arg Arg Ala
        915                 920                 925

Glu Pro Arg Met Ser Phe Lys Tyr Glu Gly Ile Thr Thr Trp Ile Gly
    930                 935                 940

Ser Asn Cys Gly Gly Val Arg Asp Tyr Leu Ile Gln Met Leu Pro Ala
945                 950                 955                 960

Arg Lys Pro Lys Pro Gly Val Leu Ile Leu Ala Tyr Gly Ala Glu Thr
                965                 970                 975

Asn Val Ala Trp Leu Asn His Ala Leu Arg Asp Ile Leu Ser Leu Glu
            980                 985                 990

Gly Ser Leu Gly Met Ile Ile Ile  Ser Asp Gly Ser Val  Val Asn Lys
        995                 1000                1005

Ser Lys  Leu Arg Val Arg Asp  Met Lys Ile Tyr Asn  Arg Gly Glu
    1010                1015                1020

Val Asp  Arg Leu Ile Leu Ile  Ser Ser Gly Asp Tyr  Thr Phe Gly
    1025                1030                1035

Asn Lys  Tyr Leu Leu Ser Lys  Leu Met Ala Lys Ile  Glu
    1040                1045                1050


<210> SEQ ID NO 31
<211> LENGTH: 503
<212> TYPE: PRT
<213> ORGANISM: artificial sequence
<220> FEATURE:
<223> OTHER INFORMATION: AHSV-9 VP5 amino acid seq of vCP2383

<400> SEQUENCE: 31

Met Gly Lys Phe Thr Ser Phe Leu Lys Arg Ala Gly Ser Ala Thr Lys
1               5                   10                  15

Lys Ala Leu Thr Ser Asp Ala Ala Lys Arg Met Tyr Lys Met Ala Gly
            20                  25                  30
```

-continued

```
Lys Thr Leu Gln Lys Val Val Glu Ser Glu Val Gly Ser Ala Ala Ile
        35                  40                  45

Asp Gly Val Met Gln Gly Thr Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Ile Glu Arg Ala Glu Lys Glu Asp Arg Val Ile
            100                 105                 110

Glu Thr His Asn Lys Lys Ile Ile Glu Lys Tyr Gly Glu Asp Leu Leu
        115                 120                 125

Lys Ile Arg Lys Ile Met Lys Gly Glu Ala Glu Ala Glu Gln Leu Glu
    130                 135                 140

Gly Lys Glu Met Glu Tyr Val Glu Lys Ala Leu Lys Gly Met Leu Arg
145                 150                 155                 160

Ile Gly Lys Asp Gln Ser Glu Arg Ile Thr Arg Leu Tyr Arg Ala Leu
                165                 170                 175

Gln Thr Glu Glu Asp Leu Arg Thr Ser Asp Glu Thr Arg Met Ile Ser
            180                 185                 190

Glu Tyr Arg Glu Lys Phe Glu Ala Leu Lys Gln Ala Ile Glu Leu Glu
        195                 200                 205

Gln Gln Ala Thr His Glu Glu Ala Val Gln Glu Met Leu Asp Leu Ser
    210                 215                 220

Ala Glu Val Ile Glu Thr Ala Ala Glu Glu Val Pro Val Phe Gly Ala
225                 230                 235                 240

Gly Ala Ala Asn Val Val Ala Thr Thr Arg Ala Ile Gln Gly Gly Leu
                245                 250                 255

Lys Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Lys Asn Lys Ile Pro Asp Asn Glu Leu Ala Met Ala Ile Lys Ser Lys
    290                 295                 300

Val Glu Val Ile Asp Glu Met Asn Thr Glu Thr Glu His Val Ile Glu
305                 310                 315                 320

Ser Ile Met Pro Leu Val Lys Lys Glu Tyr Glu Lys His Asp Asn Lys
                325                 330                 335

Tyr His Val Asn Ile Pro Ser Ala Leu Lys Ile His Ser Glu His Thr
            340                 345                 350

Pro Lys Val His Ile Tyr Thr Thr Pro Trp Asp Ser Asp Lys Val Phe
        355                 360                 365

Ile Cys Arg Cys Ile Ala Pro His His Gln Gln Arg Ser Phe Met Ile
    370                 375                 380

Gly Phe Asp Leu Glu Ile Glu Phe Val Phe Tyr Glu Asp Thr Ser Val
385                 390                 395                 400

Glu Gly His Ile Met His Gly Gly Ala Val Ser Ile Glu Gly Arg Gly
                405                 410                 415

Phe Arg Gln Ala Tyr Ser Glu Phe Met Asn Ala Ala Trp Ser Met Pro
            420                 425                 430

Ser Thr Pro Glu Leu His Lys Arg Arg Leu Gln Arg Ser Leu Gly Ser
        435                 440                 445

His Pro Ile Tyr Met Gly Ser Met Asp Tyr Thr Val Ser Tyr Glu Gln
    450                 455                 460
```

```
Leu Val Ser Asn Ala Met Lys Leu Val Tyr Asp Thr Asp Leu Gln Met
465                 470                 475                 480

His Cys Leu Arg Gly Pro Leu Lys Phe Gln Arg Arg Thr Leu Met Asn
                485                 490                 495

Ala Leu Leu Phe Gly Val Lys
            500


<210> SEQ ID NO 32
<211> LENGTH: 11143
<212> TYPE: DNA
<213> ORGANISM: artificial sequence
<220> FEATURE:
<223> OTHER INFORMATION: pJSY2247.2 plasmid DNA sequence

<400> SEQUENCE: 32

tgcggccgcg tcgacatgca ttgttagttc tgtagatcag taacgtatag catacgagta     60

taattatcgt aggtagtagg tatcctaaaa taaatctgat acagataata actttgtaaa    120

tcaattcagc aatttctcta ttatcatgat aatgattaat acacagcgtg tcgttatttt    180

ttgttacgat agtatttcta aagtaaagag caggaatccc tagtataata gaaataatcc    240

atatgaaaaa tatagtaatg tacatatttc taatgttaac atatttatag gtaaatccag    300

gaagggtaat ttttacatat ctatatacgc ttattacagt tattaaaaat atacttgcaa    360

acatgttaga agtaaaaaag aaagaactaa ttttacaaag tgctttacca aaatgccaat    420

ggaaattact tagtatgtat ataatgtata aaggtatgaa tatcacaaac agcaaatcgg    480

ctattcccaa gttgagaaac ggtataatag atatatttct agataccatt aataacctta    540

taagcttgac gtttcctata atgcctacta agaaaactag aagatacata catactaacg    600

ccatacgaga gtaactactc atcgtataac tactgttgct aacagtgaca ctgatgttat    660

aactcatctt tgatgtggta taaatgtata ataactatat tacactggta ttttatttca    720

gttatatact atatagtatt aaaaattata tttgtataat tatattatta tattcagtgt    780

agaaagtaaa atactataaa tatgtatctc ttatttataa cttattagta aagtatgtac    840

tattcagtta tattgtttta taaaagctaa atgctactag attgatataa atgaatatgt    900

aataaattag taatgtagta tactaatatt aactcacatt tgactaatta gctataaaaa    960

cccgggttaa ttaattagtc atcaggcagg gcgagaacga gactatctgc tcgttaatta   1020

attagagctt ctttattcta tacttaaaaa gtgaaaataa atacaaaggt tcttgagggt   1080

tgtgttaaat tgaaagcgag aaataatcat aaattatttc attatcgcga tatccgttaa   1140

gtttgtatcg taatggccag cgagttcggc gtgctgctga ccgacaaggt ggaaggcgac   1200

gccctggaaa agaccaactg cgaggtgatc ctgacccggt ccggcagagt gcggcggaga   1260

gaagtggacg gcgtgaaggg ctacgagtgg gagttcaccg accaccggct gggcctgtgc   1320

gagatcgagc acaccatgag catggccgat ttcttctaca accagatcaa gtgcgagggc   1380

gcctacccca tcttccccca ctacatcacc gacgtgctga agtacggcaa gatggtggac   1440

cggaacgacc accagatccg ggtggaccgg gacgtgaaag agctgtccaa gatcctgatc   1500

cagccctact tcggcgaggc ctacttcagc cccgagttct acaccagcac cttcagcaag   1560

cggcaggcca tccagatgaa cgtggagatg ctgcgggcct tcgtgcccaa gcgggtggcc   1620

ttctacgagg acgacatgcg gaggggcggc accatcgacg gcaactggat cggcgccctg   1680

caggcctgga agaagaaggc cgacctgcag atgagccggg agggcaacag ccagaccaat   1740

tgcgtggacc acaacgccga cgtgatctac cagcacatga agaagctgcg gttcggcctg   1800
```

-continued

```
ctgtaccccc actactacat gctgaacagc gagtacaccg tggaggaaaa gagcaagggc   1860
ggcctgatcg ccaactggct ggtgaaagag aaagccgccg gacgggccga gaacagcccc   1920
atgtacagcg gcgtgggccc cctgaacacc ctgcgggagc ggatcgagcg ggacgagctg   1980
gacgagaagg tgatccagga aatcatcgcc tacggcagca agttcagcac ctacgccggc   2040
acccggaccg gcgacctgac cctgaacgag ctggtgaagt actgcgagag cctgaccacc   2100
ttcgtgcaca agaagaagaa agagggcgag gacgagaccg ccagagagtt cttcaagagc   2160
aagtggattc agggcatgcc caagatgaac ttcgagaacg agatgatcat gagccggaag   2220
agctgggcca acaccaagtt cttttggagc atcgacatgt tcaagcggaa caacggcgtg   2280
gacatcgacc ccaacggcaa gaactggaag gactataaga agaagatcca ggaacagctg   2340
gacgaagccc agaagaagaa caacaacgag ccctacaaag tgatggtgga cggggtgaac   2400
atcatgacca acaagaaata cggcagcgtg gagaactggg tggactgggt cgtgaactac   2460
atcatgctgt cccacgtgaa gcggctggtg aaggactaca agttcaagcg gctgaagccc   2520
gacaacctga tgagcggcat gaacaaactg gtcggcgctc tcaggtgcta cgcctactgc   2580
ctgatcctgg ccctgtacga ccactttggc gaggatattg agggcttcaa gaagggcacc   2640
aacgccgcca gcatcgtgga gaccgtgagc cagatgttcc cccagttccg gaaagaggtg   2700
tccgagacct tcggcatcac cctgaatacc aaggacgtga agtacgagct gttcatcgcc   2760
cgggacatga gcgccaaaga ggcccagagc ggcgaagtgg gctacaagtt ccagtacggc   2820
tggcgcaaga ccgaccagaa agtgatgagc gactacgccg acatcctgag cgagaaggtg   2880
gaggccctgt accaggccct gctgtccggc cggaagtgga gcgacatcgc cgacgacacc   2940
gaggaatact tcatcgacga cctgtacgtg aacaagcccg accgggtgtt cgagagagcc   3000
ggcctggacc ccgagcggca catcaaggtg aaaggcgtga tgaatgagct gaccacctac   3060
ttctccaagc ggttcgtgag ctactggtac aagatcacca aagtggaggc ccggaacctg   3120
ctgaccctga ccgacatcgg cggcgacgcc aagaagtaca cccagttcga ccccgacgac   3180
ttcaagccca tggccgtggc cgagctggga gcccacgcct ccacctacgt gtaccagaat   3240
ctgatcctgg gccggaaccg gggcgagaag atcgacgacg ccaaagaaat cgtgtggtac   3300
gacctgtccc tgaccaactt tggctgctct cgcagcctgg acagctgctg ggtgggcagc   3360
gtggccagaa gcgagctgaa cctgcggttc cacctgatca gcgccatctt cgagagatac   3420
cagcacgacg ccaggcggag cagcttctac gagatcatct tcgacctgcc cagcaagaaa   3480
gagaagattt tccccagcta caagcactac tacgtggccc tgctgcagaa catcttcaac   3540
gacacccagc ggctggaagt gatggactac tgcgagcggc tgatgaaccc cgagacccgg   3600
atgagcgccc tgctgtctct gcaaggcttt aagaactgcg tggagagcga gttcgtggcc   3660
cccaccctga agatgaatgc cctgctgtgg gtgctggccg acatggaaaa catcgacatc   3720
aactacagca acaagcggat gcccctgctg ctgtccaccg agaagggcct gcgggtgatc   3780
tccatcgata tgtttaacgg catgctgggc gtgagctata gcggctggat tccctacctg   3840
gaacggatct gctccgaggt gaacctgcag cggcggctga gggccgacga gctgaagctg   3900
aagaagtggt tcatcagcta ctacgccacc tacgaggtgg agcggagagc cgagcccagg   3960
atgagcttca agatggaagg catcagcacc tggatcggca gcaactgtgg cggcgtgcag   4020
gactacgtgc tgcacctgat ccccagcagg cggcccaagc ctggcctgct gttcctgatc   4080
tacgccgacg acggcgacgt ggattgggtg gccaacatgc tgtccgatgt gatcggcagc   4140
gagggcagcc tgggcttcat cttcatcaac gaccggacct tcgtgaataa gagccagctg   4200
```

-continued

```
aaagtgcgga ccctgaaaat ctacaaccgg ggcatgctgg atcggctcat cctgatttcc   4260
ggcggcaact acaccttcgg caacaagttt ctgctgtcca agctgctggc caagacagag   4320
aaatgatgac tcgagttttt attgactagt tcaaaattga aaatatataa ttacaatata   4380
aaatgggcaa gttcaccagc tttctgaaga gggccggcag cgccaccaag aaggccctga   4440
ccagcgacac cgccaagcgg atgtacaaga tggccggcaa gaccctgcag aaagtggtgg   4500
agaacgaagt gggcagcgcc gccatcgacg gcgtgatgca gggcaccatc cagagcatca   4560
tccagggcga gaacctgggc gacagcatcc ggcaggccgt gatcctgaac gtggccggca   4620
ccctggaaag cgcccctgac cccctgagcc ctggcgagca gctgctgtac aacaaggtgt   4680
ccgagctgga acgggccgag aaagaagatc gggtcatcga gacccacaac gagaagatca   4740
tcgagaagta cggcgaggac ctgctgaaga tccggaagat catgaagggc gaggccaagg   4800
ccgagcagct ggaaggcaaa gaaatcgagt acgtggagat ggccctgaag ggcatgctga   4860
agattggcaa ggaccagagc gagcggatca cccagctgta ccgggccctg cagaccgaag   4920
aggacctgcg gaccagcgac gagacccgga tgatcaacga gtaccgggag aagttcgacg   4980
ccctgaagca ggccatcgaa ctggaacagc aggccaccca cgaggaagcc gtgcaggaaa   5040
tgctggacct gagcgccgag gtgatcgaaa cagccgccga ggaagtgccc atctttggcg   5100
ctggggctgc caacgtggtg gctactacca gggccgtgca gggcggcctg aagctgaaag   5160
agatcatcga caagctgacc ggcatcgacc tgagccacct gaaggtggcc gacatccacc   5220
cccacatcat cgaaaaggcc atgctgaaag acaagatccc cgacaacgag ctggctatgg   5280
ccatcaagag caaggtggaa gtgatcgacg agatgaacac cgagaccgag cacgtgatcg   5340
agagcatcat gcccctggtg aagaaagagt acgagaagca cgacaacaag taccacgtga   5400
acatccccag cgtgctgaaa atccacagcg agcacacccc caaggtgcac atctacacca   5460
ccccctggga cagcgacaag gtgttcatct gccggtgcat cgccccccac catcagcaga   5520
aaagcttcat gatcggcttc gacctggaaa tcgagtttgt gttctacgag gacaccagcg   5580
tggagggcca catcatgcac ggcggagccg tgctgatcga gggcaggggc ttcaggcagg   5640
cctacagcga gttcatgaac gccgcctggt ccatgcccag cacccccgag ctgcacaagc   5700
ggcggctgca gcggagcctg ggcagccacc ccatctacat gggcagcatg gactacaccg   5760
tgagctacga ccagctggtg tccaacgcca tgaagctggt gtacgacacc gagctgcaga   5820
tgcactgcct gagaggcccc ctgaagttcc agcggcggac cctgatgaac gccctgctgt   5880
tcggcgtgaa gatcgcctga tgatttttct actagttaat caaataaaaa gcatacaagc   5940
tattgcttcg ctatcgttac aaaatggcag gaattttgtg taaactaagc cacatacttg   6000
ccaatgaaaa aaatagtaga aaggatacta ttttaatggg attagatgtt aaggttcctt   6060
gggattatag taactgggca tctgttaact tttacgacgt taggttagat actgatgtta   6120
cagattataa taatgttaca ataaaataca tgacaggatg tgatattttt cctcatataa   6180
ctcttggaat agcaaatatg gatcaatgtg atagatttga aaatttcaaa aagcaaataa   6240
ctgatcaaga tttacagact atttctatag tctgtaaaga agagatgtgt tttcctcaga   6300
gtaacgcctc taaacagttg ggagcgaaag gatgcgctgt agttatgaaa ctggaggtat   6360
ctgatgaact tagagcccta agaaatgttc tgctgaatgc ggtaccctgt tcgaaggacg   6420
tgtttggtga tatcacagta gataatccgt ggaatcctca cataacagta ggatatgtta   6480
aggaggacga tgtcgaaaac aagaaacgcc taatggagtg catgtccaag tttagggggc   6540
aagaaataca agttctagga tggtattaat aagtatctaa gtatttggta taatttatta   6600
```

-continued

```
aatagtataa ttataacaaa taataaataa catgataacg gtttttatta gaataaaata   6660
gagataatat cataatgata tataatactt cattaccaga aatgagtaat ggaagactta   6720
taaatgaact gcataaagct ataaggtata gagatataaa tttagtaagg tatatactta   6780
aaaaatgcaa atacaataac gtaaatatac tatcaacgtc tttgtattta gccgtaagta   6840
tttctgatat agaaatggta aaattattac tagaacacgg tgccgatatt ttaaaatgta   6900
aaaatcctcc tcttcataaa gctgctagtt tagataatac agaaattgct aaactactaa   6960
tagattctgg cgctgacata gaacagatac attctggaaa tagtccgtta tatatttctg   7020
tatatagaaa caataagtca ttaactagat atttattaaa aaaaggtgtt aattgtaata   7080
gattctttct aaattattac gatgtactgt atgataagat atctgatgat atgtataaaa   7140
tatttataga ttttaatatt gatcttaata tacaaactag aaattttgaa actccgttac   7200
attacgctat aaagtataag aatatagatt taattaggat attgttagat aatagtatta   7260
aaatagataa aagtttattt ttgcataaac agtatctcat aaaggcactt aaaaataatt   7320
gtagttacga tataatagcg ttacttataa atcacggagt gcctataaac gaacaagatg   7380
atttaggtaa aaccccatta catcattcgg taattaatag aagaaaagat gtaacagcac   7440
ttctgttaaa tctaggagct gatataaacg taatagatga ctgtatgggc agtcccttac   7500
attacgctgt ttcacgtaac gatatcgaaa caacaaagac acttttagaa agaggatcta   7560
atgttaatgt ggttaataat catatagata ccgttctaaa tatagctgtt gcatctaaaa   7620
acaaaactat agtaaactta ttactgaagt acggtactga tacaaagttg gtaggattag   7680
ataaacatgt tattcacata gctatagaaa tgaaagatat taatatactg aatgcgatct   7740
tattatatgg ttgctatgta aacgtctata atcataaagg tttcactcct ctatacatgg   7800
cagttagttc tatgaaaaca gaatttgtta aactcttact tgaccacggt gcttacgtaa   7860
atgctaaagc taagttatct ggaaatactc ctttacataa agctatgtta tctaatagtt   7920
ttaataatat aaaattactt ttatcttata acgccgacta taattctcta aataatcacg   7980
gtaatacgcc tctaacttgt gttagctttt tagatgacaa gatagctatt atgataaatat   8040
ctaaaatgat gttagaaata tctaaaaatc ctgaaatagc taattcagaa ggttttatag   8100
taaacatgga acatataaac agtaataaaa gactactatc tataaaagaa tcatgcgaaa   8160
aagaactaga tgttataaca catataaagt taaattctat atattctttt aatatctttc   8220
ttgacaataa catagatctt atggtaaagt tcgtaactaa tcctagagtt aataagatac   8280
ctgcatgtat acgtatatat agggaattaa tacggaaaaa taaatcatta gcttttcata   8340
gacatcagct aatagttaaa gctgtaaaag agagtaagaa tctaggaata ataggtaggt   8400
tacctataga tatcaaacat ataataatgg aactattaag taataatgat ttacattctg   8460
ttatcaccag ctgttgtaac ccagtagtat aaagagctcg aattaattca ctggccgtcg   8520
ttttacaacg tcgtgactgg gaaaaccctg gcgttaccca acttaatcgc cttgcagcac   8580
atccccctttt cgccagctgg cgtaatagcg aagaggcccg caccgatcgc ccttcccaac   8640
agttgcgcag cctgaatggc gaatggcgcc tgatgcggta ttttctcctt acgcatctgt   8700
gcggtatttc acaccgcata tggtgcactc tcagtacaat ctgctctgat gccgcatagt   8760
taagccagcc ccgacacccg ccaacacccg ctgacgcgcc ctgacgggct tgtctgctcc   8820
cggcatccgc ttacagacaa gctgtgaccg tctccgggag ctgcatgtgt cagaggtttt   8880
caccgtcatc accgaaacgc gcgagacgaa agggcctcgt gatacgccta tttttatagg   8940
ttaatgtcat gataataatg gtttcttaga cgtcaggtgg cacttttcgg ggaaatgtgc   9000
```

```
gcggaacccc tatttgttta tttttctaaa tacattcaaa tatgtatccg ctcatgagac   9060

aataaccctg ataaatgctt caataatatt gaaaaaggaa gagtatgagt attcaacatt   9120

tccgtgtcgc ccttattccc ttttttgcgg cattttgcct tcctgttttt gctcacccag   9180

aaacgctggt gaaagtaaaa gatgctgaag atcagttggg tgcacgagtg ggttacatcg   9240

aactggatct caacagcggt aagatccttg agagttttcg ccccgaagaa cgttttccaa   9300

tgatgagcac ttttaaagtt ctgctatgtg gcgcggtatt atcccgtatt gacgccgggc   9360

aagagcaact cggtcgccgc atacactatt ctcagaatga cttggttgag tactcaccag   9420

tcacagaaaa gcatcttacg gatggcatga cagtaagaga attatgcagt gctgccataa   9480

ccatgagtga taacactgcg gccaacttac ttctgacaac gatcggagga ccgaaggagc   9540

taaccgcttt tttgcacaac atgggggatc atgtaactcg ccttgatcgt tgggaaccgg   9600

agctgaatga agccatacca aacgacgagc gtgacaccac gatgcctgta gcaatggcaa   9660

caacgttgcg caaactatta actggcgaac tacttactct agcttcccgg caacaattaa   9720

tagactggat ggaggcggat aaagttgcag gaccacttct gcgctcggcc cttccggctg   9780

gctggtttat tgctgataaa tctggagccg gtgagcgtgg gtctcgcggt atcattgcag   9840

cactggggcc agatggtaag ccctcccgta tcgtagttat ctacacgacg gggagtcagg   9900

caactatgga tgaacgaaat agacagatcg ctgagatagg tgcctcactg attaagcatt   9960

ggtaactgtc agaccaagtt tactcatata tactttagat tgatttaaaa cttcattttt  10020

aatttaaaag gatctaggtg aagatccttt ttgataatct catgaccaaa atcccttaac  10080

gtgagttttc gttccactga gcgtcagacc ccgtagaaaa gatcaaagga tcttcttgag  10140

atcctttttt tctgcgcgta atctgctgct tgcaaacaaa aaaaccaccg ctaccagcgg  10200

tggtttgttt gccggatcaa gagctaccaa ctctttttcc gaaggtaact ggcttcagca  10260

gagcgcagat accaaatact gtccttctag tgtagccgta gttaggccac cacttcaaga  10320

actctgtagc accgcctaca tacctcgctc tgctaatcct gttaccagtg gctgctgcca  10380

gtggcgataa gtcgtgtctt accgggttgg actcaagacg atagttaccg gataaggcgc  10440

agcggtcggg ctgaacgggg ggttcgtgca cacagcccag cttggagcga acgacctaca  10500

ccgaactgag atacctacag cgtgagctat gagaaagcgc cacgcttccc gaagggagaa  10560

aggcggacag gtatccggta agcggcaggg tcggaacagg agagcgcacg agggagcttc  10620

caggggggaaa cgcctggtat ctttatagtc ctgtcgggtt tcgccacctc tgacttgagc  10680

gtcgattttt gtgatgctcg tcaggggggc ggagcctatg gaaaaacgcc agcaacgcgg  10740

cctttttacg gttcctggcc ttttgctggc cttttgctca catgttcttt cctgcgttat  10800

cccctgattc tgtggataac cgtattaccg cctttgagtg agctgatacc gctcgccgca  10860

gccgaacgac cgagcgcagc gagtcagtga gcgaggaagc ggaagagcgc ccaatacgca  10920

aaccgcctct ccccgcgcgt tggccgattc attaatgcag ctggcacgac aggtttcccg  10980

actggaaagc gggcagtgag cgcaacgcaa ttaatgtgag ttagctcact cattaggcac  11040

cccaggcttt acactttatg cttccggctc gtatgttgtg tggaattgtg agcggataac  11100

aatttcacac aggaaacagc tatgaccatg attacgccaa gct                    11143
```

```
<210> SEQ ID NO 33
<211> LENGTH: 3171
<212> TYPE: DNA
<213> ORGANISM: artificial sequence
<220> FEATURE:
<223> OTHER INFORMATION: AHSV-5 VP2 in pJSY2247.2
```

<400> SEQUENCE: 33
atggccagcg agttcggcgt gctgctgacc gacaaggtgg aaggcgacgc cctggaaaag 60
accaactgcg aggtgatcct gacccggtcc ggcagagtgc ggcggagaga agtggacggc 120
gtgaagggct acgagtggga gttcaccgac caccggctgg gcctgtgcga gatcgagcac 180
accatgagca tggccgattt cttctacaac cagatcaagt gcgagggcgc ctaccccatc 240
ttcccccact acatcaccga cgtgctgaag tacggcaaga tggtggaccg gaacgaccac 300
cagatccggg tggaccggga cgtgaaagag ctgtccaaga tcctgatcca gccctacttc 360
ggcgaggcct acttcagccc cgagttctac accagcacct tcagcaagcg gcaggccatc 420
cagatgaacg tggagatgct gcgggccttc gtgcccaagc gggtggcctt ctacgaggac 480
gacatgcgga ggggcggcac catcgacggc aactggatcg gcgccctgca ggcctggaag 540
aagaaggccg acctgcagat gagccgggag ggcaacagcc agaccaattg cgtggaccac 600
aacgccgacg tgatctacca gcacatgaag aagctgcggt tcggcctgct gtacccccac 660
tactacatgc tgaacagcga gtacaccgtg gaggaaaaga gcaagggcgg cctgatcgcc 720
aactggctgg tgaaagagaa agccgccgga cgggccgaga acagccccat gtacagcggc 780
gtgggccccc tgaacaccct gcgggagcgg atcgagcggg acgagctgga cgagaaggtg 840
atccaggaaa tcatcgccta cggcagcaag ttcagcacct acgccggcac ccggaccggc 900
gacctgaccc tgaacgagct ggtgaagtac tgcgagagcc tgaccacctt cgtgcacaag 960
aagaagaaag agggcgagga cgagaccgcc agagagttct tcaagagcaa gtggattcag 1020
ggcatgccca agatgaactt cgagaacgag atgatcatga gccggaagag ctgggccaac 1080
accaagttct tttggagcat cgacatgttc aagcggaaca acggcgtgga catcgacccc 1140
aacggcaaga actggaagga ctataagaag aagatccagg aacagctgga cgaagcccag 1200
aagaagaaca acaacgagcc ctacaaagtg atggtggacg gggtgaacat catgaccaac 1260
aagaaatacg gcagcgtgga gaactgggtg gactgggtcg tgaactacat catgctgtcc 1320
cacgtgaagc ggctggtgaa ggactacaag ttcaagcggc tgaagcccga caacctgatg 1380
agcggcatga acaaactggt cggcgctctc aggtgctacg cctactgcct gatcctggcc 1440
ctgtacgacc actttggcga ggatattgag ggcttcaaga agggcaccaa cgccgccagc 1500
atcgtggaga ccgtgagcca gatgttcccc cagttccgga aagaggtgtc cgagaccttc 1560
ggcatcaccc tgaataccaa ggacgtgaag tacgagctgt tcatcgcccg ggacatgagc 1620
gccaaagagg cccagagcgg cgaagtgggc tacaagttcc agtacggctg gcgcaagacc 1680
gaccagaaag tgatgagcga ctacgccgac atcctgagcg agaaggtgga ggccctgtac 1740
caggccctgc tgtccggccg gaagtggagc gacatcgccg acgacaccga ggaatacttc 1800
atcgacgacc tgtacgtgaa caagcccgac cgggtgttcg agagagccgg cctggacccc 1860
gagcggcaca tcaaggtgaa aggcgtgatg aatgagctga ccacctactt ctccaagcgg 1920
ttcgtgagct actggtacaa gatcaccaaa gtggaggccc ggaacctgct gaccctgacc 1980
gacatcggcg gcgacgccaa gaagtacacc cagttcgacc ccgacgactt caagcccatg 2040
gccgtggccg agctgggagc ccacgcctcc acctacgtgt accagaatct gatcctgggc 2100
cggaaccggg gcgagaagat cgacgacgcc aaagaaatcg tgtggtacga cctgtccctg 2160
accaactttg gctgctctcg cagcctggac agctgctggg tgggcagcgt ggccagaagc 2220
gagctgaacc tgcggttcca cctgatcagc gccatcttcg agagatacca gcacgacgcc 2280
aggcggagca gcttctacga gatcatcttc gacctgccca gcaagaaaga gaagatttc 2340

-continued

```
cccagctaca agcactacta cgtggccctg ctgcagaaca tcttcaacga cacccagcgg   2400

ctggaagtga tggactactg cgagcggctg atgaaccccg agacccggat gagcgccctg   2460

ctgtctctgc aaggctttaa gaactgcgtg gagagcgagt tcgtggcccc caccctgaag   2520

atgaatgccc tgctgtgggt gctggccgac atggaaaaca tcgacatcaa ctacagcaac   2580

aagcggatgc ccctgctgct gtccaccgag aagggcctgc gggtgatctc catcgatatg   2640

tttaacggca tgctgggcgt gagctatagc ggctggattc cctacctgga acggatctgc   2700

tccgaggtga acctgcagcg gcggctgagg gccgacgagc tgaagctgaa gaagtggttc   2760

atcagctact acgccaccta cgaggtggag cggagagccg agcccaggat gagcttcaag   2820

atggaaggca tcagcacctg gatcggcagc aactgtggcg gcgtgcagga ctacgtgctg   2880

cacctgatcc ccagcaggcg gcccaagcct ggcctgctgt tcctgatcta cgccgacgac   2940

ggcgacgtgg attgggtggc caacatgctg tccgatgtga tcggcagcga gggcagcctg   3000

ggcttcatct tcatcaacga ccggaccttc gtgaataaga gccagctgaa agtgcggacc   3060

ctgaaaatct acaaccgggg catgctggat cggctcatcc tgatttccgg cggcaactac   3120

accttcggca acaagtttct gctgtccaag ctgctggcca agacagagaa a            3171
```

<210> SEQ ID NO 34
<211> LENGTH: 1515
<212> TYPE: DNA
<213> ORGANISM: artificial sequence
<220> FEATURE:
<223> OTHER INFORMATION: AHSV-5 VP5 of pJSY2247.2

<400> SEQUENCE: 34

```
atgggcaagt tcaccagctt tctgaagagg gccggcagcg ccaccaagaa ggccctgacc     60

agcgacaccg ccaagcggat gtacaagatg gccggcaaga ccctgcagaa agtggtggag    120

aacgaagtgg gcagcgccgc catcgacggc gtgatgcagg gcaccatcca gagcatcatc    180

cagggcgaga acctgggcga cagcatccgg caggccgtga tcctgaacgt ggccggcacc    240

ctggaaagcg cccctgaccc cctgagccct ggcgagcagc tgctgtacaa caaggtgtcc    300

gagctggaac gggccgagaa agaagatcgg gtcatcgaga cccacaacga gaagatcatc    360

gagaagtacg gcgaggacct gctgaagatc cggaagatca tgaagggcga ggccaaggcc    420

gagcagctgg aaggcaaaga aatcgagtac gtggagatgg ccctgaaggg catgctgaag    480

attggcaagg accagagcga gcggatcacc cagctgtacc gggccctgca gaccgaagag    540

gacctgcgga ccagcgacga gacccggatg atcaacgagt accgggagaa gttcgacgcc    600

ctgaagcagg ccatcgaact ggaacagcag gccacccacg aggaagccgt gcaggaaatg    660

ctggacctga gcgccgaggt gatcgaaaca gccgccgagg aagtgcccat ctttggcgct    720

ggggctgcca acgtggtggc tactaccagg gccgtgcagg gcggcctgaa gctgaaagag    780

atcatcgaca agctgaccgg catcgacctg agccacctga aggtggccga catccacccc    840

cacatcatcg aaaaggccat gctgaaagac aagatccccg acaacgagct ggctatggcc    900

atcaagagca aggtggaagt gatcgacgag atgaacaccg agaccgagca cgtgatcgag    960

agcatcatgc ccctggtgaa gaaagagtac gagaagcacg acaacaagta ccacgtgaac   1020

atccccagcg tgctgaaaat ccacagcgag cacaccccca aggtgcacat ctacaccacc   1080

ccctgggaca gcgacaaggt gttcatctgc cggtgcatcg ccccccacca tcagcagaaa   1140

agcttcatga tcggcttcga cctggaaatc gagtttgtgt tctacgagga caccagcgtg   1200

gagggccaca tcatgcacgg cggagccgtg ctgatcgagg gcaggggctt caggcaggcc   1260
```

```
tacagcgagt tcatgaacgc cgcctggtcc atgcccagca cccccgagct gcacaagcgg   1320

cggctgcagc ggagcctggg cagccacccc atctacatgg gcagcatgga ctacaccgtg   1380

agctacgacc agctggtgtc caacgccatg aagctggtgt acgacaccga gctgcagatg   1440

cactgcctga gaggccccct gaagttccag cggcggaccc tgatgaacgc cctgctgttc   1500

ggcgtgaaga tcgcc                                                    1515


<210> SEQ ID NO 35
<211> LENGTH: 1057
<212> TYPE: PRT
<213> ORGANISM: artificial sequence
<220> FEATURE:
<223> OTHER INFORMATION: AHSV-5 VP2 in pC3 H6p-AHSV 5-VP2/42Kp-VP5
      (pJSY2247.2)

<400> SEQUENCE: 35

Met Ala Ser Glu Phe Gly Val Leu Leu Thr Asp Lys Val Glu Gly Asp
1               5                   10                  15

Ala Leu Glu Lys Thr Asn Cys Glu Val Ile Leu Thr Arg Ser Gly Arg
            20                  25                  30

Val Arg Arg Arg Glu Val Asp Gly Val Lys Gly Tyr Glu Trp Glu Phe
        35                  40                  45

Thr Asp His Arg Leu Gly Leu Cys Glu Ile Glu His Thr Met Ser Met
    50                  55                  60

Ala Asp Phe Phe Tyr Asn Gln Ile Lys Cys Glu Gly Ala Tyr Pro Ile
65                  70                  75                  80

Phe Pro His Tyr Ile Thr Asp Val Leu Lys Tyr Gly Lys Met Val Asp
                85                  90                  95

Arg Asn Asp His Gln Ile Arg Val Asp Arg Asp Val Lys Glu Leu Ser
            100                 105                 110

Lys Ile Leu Ile Gln Pro Tyr Phe Gly Glu Ala Tyr Phe Ser Pro Glu
        115                 120                 125

Phe Tyr Thr Ser Thr Phe Ser Lys Arg Gln Ala Ile Gln Met Asn Val
    130                 135                 140

Glu Met Leu Arg Ala Phe Val Pro Lys Arg Val Ala Phe Tyr Glu Asp
145                 150                 155                 160

Asp Met Arg Arg Gly Gly Thr Ile Asp Gly Asn Trp Ile Gly Ala Leu
                165                 170                 175

Gln Ala Trp Lys Lys Lys Ala Asp Leu Gln Met Ser Arg Glu Gly Asn
            180                 185                 190

Ser Gln Thr Asn Cys Val Asp His Asn Ala Asp Val Ile Tyr Gln His
        195                 200                 205

Met Lys Lys Leu Arg Phe Gly Leu Leu Tyr Pro His Tyr Tyr Met Leu
    210                 215                 220

Asn Ser Glu Tyr Thr Val Glu Glu Lys Ser Lys Gly Gly Leu Ile Ala
225                 230                 235                 240

Asn Trp Leu Val Lys Glu Lys Ala Ala Gly Arg Ala Glu Asn Ser Pro
                245                 250                 255

Met Tyr Ser Gly Val Gly Pro Leu Asn Thr Leu Arg Glu Arg Ile Glu
            260                 265                 270

Arg Asp Glu Leu Asp Glu Lys Val Ile Gln Glu Ile Ile Ala Tyr Gly
        275                 280                 285

Ser Lys Phe Ser Thr Tyr Ala Gly Thr Arg Thr Gly Asp Leu Thr Leu
    290                 295                 300

Asn Glu Leu Val Lys Tyr Cys Glu Ser Leu Thr Thr Phe Val His Lys
305                 310                 315                 320
```

-continued

```
Lys Lys Lys Glu Gly Glu Asp Glu Thr Ala Arg Glu Phe Phe Lys Ser
                325                 330                 335

Lys Trp Ile Gln Gly Met Pro Lys Met Asn Phe Glu Asn Glu Met Ile
            340                 345                 350

Met Ser Arg Lys Ser Trp Ala Asn Thr Lys Phe Phe Trp Ser Ile Asp
        355                 360                 365

Met Phe Lys Arg Asn Asn Gly Val Asp Ile Asp Pro Asn Gly Lys Asn
    370                 375                 380

Trp Lys Asp Tyr Lys Lys Lys Ile Gln Glu Gln Leu Asp Glu Ala Gln
385                 390                 395                 400

Lys Lys Asn Asn Asn Glu Pro Tyr Lys Val Met Val Asp Gly Val Asn
                405                 410                 415

Ile Met Thr Asn Lys Lys Tyr Gly Ser Val Glu Asn Trp Val Asp Trp
            420                 425                 430

Val Val Asn Tyr Ile Met Leu Ser His Val Lys Arg Leu Val Lys Asp
        435                 440                 445

Tyr Lys Phe Lys Arg Leu Lys Pro Asp Asn Leu Met Ser Gly Met Asn
    450                 455                 460

Lys Leu Val Gly Ala Leu Arg Cys Tyr Ala Tyr Cys Leu Ile Leu Ala
465                 470                 475                 480

Leu Tyr Asp His Phe Gly Glu Asp Ile Glu Gly Phe Lys Lys Gly Thr
                485                 490                 495

Asn Ala Ala Ser Ile Val Glu Thr Val Ser Gln Met Phe Pro Gln Phe
            500                 505                 510

Arg Lys Glu Val Ser Glu Thr Phe Gly Ile Thr Leu Asn Thr Lys Asp
        515                 520                 525

Val Lys Tyr Glu Leu Phe Ile Ala Arg Asp Met Ser Ala Lys Glu Ala
    530                 535                 540

Gln Ser Gly Glu Val Gly Tyr Lys Phe Gln Tyr Gly Trp Arg Lys Thr
545                 550                 555                 560

Asp Gln Lys Val Met Ser Asp Tyr Ala Asp Ile Leu Ser Glu Lys Val
                565                 570                 575

Glu Ala Leu Tyr Gln Ala Leu Leu Ser Gly Arg Lys Trp Ser Asp Ile
            580                 585                 590

Ala Asp Asp Thr Glu Glu Tyr Phe Ile Asp Asp Leu Tyr Val Asn Lys
        595                 600                 605

Pro Asp Arg Val Phe Glu Arg Ala Gly Leu Asp Pro Glu Arg His Ile
    610                 615                 620

Lys Val Lys Gly Val Met Asn Glu Leu Thr Thr Tyr Phe Ser Lys Arg
625                 630                 635                 640

Phe Val Ser Tyr Trp Tyr Lys Ile Thr Lys Val Glu Ala Arg Asn Leu
                645                 650                 655

Leu Thr Leu Thr Asp Ile Gly Gly Asp Ala Lys Lys Tyr Thr Gln Phe
            660                 665                 670

Asp Pro Asp Asp Phe Lys Pro Met Ala Val Ala Glu Leu Gly Ala His
        675                 680                 685

Ala Ser Thr Tyr Val Tyr Gln Asn Leu Ile Leu Gly Arg Asn Arg Gly
    690                 695                 700

Glu Lys Ile Asp Asp Ala Lys Glu Ile Val Trp Tyr Asp Leu Ser Leu
705                 710                 715                 720

Thr Asn Phe Gly Cys Ser Arg Ser Leu Asp Ser Cys Trp Val Gly Ser
                725                 730                 735

Val Ala Arg Ser Glu Leu Asn Leu Arg Phe His Leu Ile Ser Ala Ile
```

```
        740                 745                 750

Phe Glu Arg Tyr Gln His Asp Ala Arg Arg Ser Ser Phe Tyr Glu Ile
    755                 760                 765

Ile Phe Asp Leu Pro Ser Lys Lys Glu Lys Ile Phe Pro Ser Tyr Lys
    770                 775                 780

His Tyr Tyr Val Ala Leu Leu Gln Asn Ile Phe Asn Asp Thr Gln Arg
785                 790                 795                 800

Leu Glu Val Met Asp Tyr Cys Glu Arg Leu Met Asn Pro Glu Thr Arg
                805                 810                 815

Met Ser Ala Leu Leu Ser Leu Gln Gly Phe Lys Asn Cys Val Glu Ser
            820                 825                 830

Glu Phe Val Ala Pro Thr Leu Lys Met Asn Ala Leu Leu Trp Val Leu
        835                 840                 845

Ala Asp Met Glu Asn Ile Asp Ile Asn Tyr Ser Asn Lys Arg Met Pro
    850                 855                 860

Leu Leu Leu Ser Thr Glu Lys Gly Leu Arg Val Ile Ser Ile Asp Met
865                 870                 875                 880

Phe Asn Gly Met Leu Gly Val Ser Tyr Ser Gly Trp Ile Pro Tyr Leu
                885                 890                 895

Glu Arg Ile Cys Ser Glu Val Asn Leu Gln Arg Arg Leu Arg Ala Asp
            900                 905                 910

Glu Leu Lys Leu Lys Lys Trp Phe Ile Ser Tyr Tyr Ala Thr Tyr Glu
        915                 920                 925

Val Glu Arg Arg Ala Glu Pro Arg Met Ser Phe Lys Met Glu Gly Ile
    930                 935                 940

Ser Thr Trp Ile Gly Ser Asn Cys Gly Gly Val Gln Asp Tyr Val Leu
945                 950                 955                 960

His Leu Ile Pro Ser Arg Arg Pro Lys Pro Gly Leu Leu Phe Leu Ile
                965                 970                 975

Tyr Ala Asp Asp Gly Asp Val Asp Trp Val Ala Asn Met Leu Ser Asp
            980                 985                 990

Val Ile Gly Ser Glu Gly Ser Leu  Gly Phe Ile Phe Ile  Asn Asp Arg
        995                 1000                1005

Thr Phe  Val Asn Lys Ser Gln  Leu Lys Val Arg Thr  Leu Lys Ile
    1010                1015                1020

Tyr Asn  Arg Gly Met Leu Asp  Arg Leu Ile Leu Ile  Ser Gly Gly
    1025                1030                1035

Asn Tyr  Thr Phe Gly Asn Lys  Phe Leu Leu Ser Lys  Leu Leu Ala
    1040                1045                1050

Lys Thr  Glu Lys
    1055


<210> SEQ ID NO 36
<211> LENGTH: 505
<212> TYPE: PRT
<213> ORGANISM: artificial sequence
<220> FEATURE:
<223> OTHER INFORMATION: AHSV-5 VP5 in pC3 H6p-AHSV 5-VP2/42Kp-VP5
      (pJSY2247.2)

<400> SEQUENCE: 36

Met Gly Lys Phe Thr Ser Phe Leu Lys Arg Ala Gly Ser Ala Thr Lys
1               5                   10                  15

Lys Ala Leu Thr Ser Asp Thr Ala Lys Arg Met Tyr Lys Met Ala Gly
            20                  25                  30

Lys Thr Leu Gln Lys Val Val Glu Asn Glu Val Gly Ser Ala Ala Ile
```

-continued

```
        35                  40                  45

Asp Gly Val Met Gln Gly Thr Ile Gln Ser Ile Ile Gln Gly Glu Asn
    50                  55                  60

Leu Gly Asp Ser Ile Arg Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Leu Glu Arg Ala Glu Lys Glu Asp Arg Val Ile
            100                 105                 110

Glu Thr His Asn Glu Lys Ile Ile Glu Lys Tyr Gly Glu Asp Leu Leu
        115                 120                 125

Lys Ile Arg Lys Ile Met Lys Gly Glu Ala Lys Ala Glu Gln Leu Glu
    130                 135                 140

Gly Lys Glu Ile Glu Tyr Val Glu Met Ala Leu Lys Gly Met Leu Lys
145                 150                 155                 160

Ile Gly Lys Asp Gln Ser Glu Arg Ile Thr Gln Leu Tyr Arg Ala Leu
                165                 170                 175

Gln Thr Glu Glu Asp Leu Arg Thr Ser Asp Glu Thr Arg Met Ile Asn
            180                 185                 190

Glu Tyr Arg Glu Lys Phe Asp Ala Leu Lys Gln Ala Ile Glu Leu Glu
        195                 200                 205

Gln Gln Ala Thr His Glu Glu Ala Val Gln Glu Met Leu Asp Leu Ser
    210                 215                 220

Ala Glu Val Ile Glu Thr Ala Ala Glu Glu Val Pro Ile Phe Gly Ala
225                 230                 235                 240

Gly Ala Ala Asn Val Val Ala Thr Thr Arg Ala Val Gln Gly Gly Leu
                245                 250                 255

Lys Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Lys Asp Lys Ile Pro Asp Asn Glu Leu Ala Met Ala Ile Lys Ser Lys
    290                 295                 300

Val Glu Val Ile Asp Glu Met Asn Thr Glu Thr Glu His Val Ile Glu
305                 310                 315                 320

Ser Ile Met Pro Leu Val Lys Lys Glu Tyr Glu Lys His Asp Asn Lys
                325                 330                 335

Tyr His Val Asn Ile Pro Ser Val Leu Lys Ile His Ser Glu His Thr
            340                 345                 350

Pro Lys Val His Ile Tyr Thr Thr Pro Trp Asp Ser Asp Lys Val Phe
        355                 360                 365

Ile Cys Arg Cys Ile Ala Pro His His Gln Gln Lys Ser Phe Met Ile
    370                 375                 380

Gly Phe Asp Leu Glu Ile Glu Phe Val Phe Tyr Glu Asp Thr Ser Val
385                 390                 395                 400

Glu Gly His Ile Met His Gly Gly Ala Val Leu Ile Glu Gly Arg Gly
                405                 410                 415

Phe Arg Gln Ala Tyr Ser Glu Phe Met Asn Ala Ala Trp Ser Met Pro
            420                 425                 430

Ser Thr Pro Glu Leu His Lys Arg Arg Leu Gln Arg Ser Leu Gly Ser
        435                 440                 445

His Pro Ile Tyr Met Gly Ser Met Asp Tyr Thr Val Ser Tyr Asp Gln
    450                 455                 460
```

-continued

```
Leu Val Ser Asn Ala Met Lys Leu Val Tyr Asp Thr Glu Leu Gln Met
465                 470                 475                 480

His Cys Leu Arg Gly Pro Leu Lys Phe Gln Arg Arg Thr Leu Met Asn
                485                 490                 495

Ala Leu Leu Phe Gly Val Lys Ile Ala
            500                 505


<210> SEQ ID NO 37
<211> LENGTH: 24
<212> TYPE: DNA
<213> ORGANISM: artificial sequence
<220> FEATURE:
<223> OTHER INFORMATION: 18098.JY Primer for amplifying the AHSV-5 VP2
      probe for the vCP2398.2.1.1 viral vector

<400> SEQUENCE: 37

ggatcgagcg ggacgagctg gacg                                            24


<210> SEQ ID NO 38
<211> LENGTH: 24
<212> TYPE: DNA
<213> ORGANISM: artificial sequence
<220> FEATURE:
<223> OTHER INFORMATION: 18103.JY Primer for amplifying the AHSV-5 VP2
      probe for the vCP2398.2.1.1 viral vector

<400> SEQUENCE: 38

gccagccgta ctggaacttg tagc                                            24


<210> SEQ ID NO 39
<211> LENGTH: 24
<212> TYPE: DNA
<213> ORGANISM: artificial sequence
<220> FEATURE:
<223> OTHER INFORMATION: 18115.JY Primer for amplifying the AHSV-5 VP5
      probe for the vCP2398.2.1.1 viral vector

<400> SEQUENCE: 39

tgctggacct gagcgccgag gtga                                            24


<210> SEQ ID NO 40
<211> LENGTH: 24
<212> TYPE: DNA
<213> ORGANISM: artificial sequence
<220> FEATURE:
<223> OTHER INFORMATION: 18120.JY Primer for amplifying the AHSV-5 VP5
      probe for the vCP2398.2.1.1 viral vector

<400> SEQUENCE: 40

tcaggcgatc ttcacgccga acag                                            24


<210> SEQ ID NO 41
<211> LENGTH: 8936
<212> TYPE: DNA
<213> ORGANISM: artificial sequence
<220> FEATURE:
<223> OTHER INFORMATION: vCP2398 viral vector sequence
<220> FEATURE:
<221> NAME/KEY: C3 left arm:  211-1137
<222> LOCATION: (211)..(1137)
<223> OTHER INFORMATION: C3 left arm:  211-1137
<220> FEATURE:
<221> NAME/KEY: H6 promoter: 1162-1347
<222> LOCATION: (1162)..(1347)
<223> OTHER INFORMATION: H6 promoter: 1162-1347
<220> FEATURE:
<221> NAME/KEY: AHSV5-VP2: 1348-4524
<222> LOCATION: (1348)..(4524)
<223> OTHER INFORMATION: AHSV5-VP2: 1348-4524
```

<220> FEATURE:
<221> NAME/KEY: 42K promoter: 4542-4573
<222> LOCATION: (4542)..(4573)
<223> OTHER INFORMATION: 42K promoter: 4542-4573
<220> FEATURE:
<221> NAME/KEY: AHSV5-VP5: 4574-6094
<222> LOCATION: (4574)..(6094)
<223> OTHER INFORMATION: AHSV5-VP5: 4574-6094
<220> FEATURE:
<221> NAME/KEY: C3 right arm: 6123-8685
<222> LOCATION: (6123)..(8685)
<223> OTHER INFORMATION: C3 right arm: 6123-8685

<400> SEQUENCE: 41

```
ctaagtatat tattggattt aacgcgctat aaacgcatcc aaaacctaca aatataggag     60

aagcttctct tatgaaactt cttaaagctt tactcttact attactactc aaaagagata    120

ttacattaat tatgtgatga ggcatccaac atataaagaa gactaaagct gtagaagctg    180

ttatgaagaa tatcttatca gatatattag atgcattgtt agttctgtag atcagtaacg    240

tatagcatac gagtataatt atcgtaggta gtaggtatcc taaaataaat ctgatacaga    300

taataacttt gtaaatcaat tcagcaattt ctctattatc atgataatga ttaatacaca    360

gcgtgtcgtt attttttgtt acgatagtat ttctaaagta aagagcagga atccctagta    420

taatagaaat aatccatatg aaaaatatag taatgtacat atttctaatg ttaacatatt    480

tataggtaaa tccaggaagg gtaattttta catatctata tacgcttatt acagttatta    540

aaaatatact tgcaaacatg ttagaagtaa aaaagaaaga actaatttta caaagtgctt    600

taccaaaatg ccaatggaaa ttacttagta tgtatataat gtataaaggt atgaatatca    660

caaacagcaa atcggctatt cccaagttga gaaacggtat aatagatata tttctagata    720

ccattaataa ccttataagc ttgacgtttc ctataatgcc tactaagaaa actagaagat    780

acatacatac taacgccata cgagagtaac tactcatcgt ataactactg ttgctaacag    840

tgacactgat gttataactc atctttgatg tggtataaat gtataataac tatattacac    900

tggtatttta tttcagttat atactatata gtattaaaaa ttatatttgt ataattatat    960

tattatattc agtgtagaaa gtaaaatact ataaatatgt atctcttatt tataacttat   1020

tagtaaagta tgtactattc agttatattg ttttataaaa gctaaatgct actagattga   1080

tataaatgaa tatgtaataa attagtaatg tagtatacta atattaactc acatttgact   1140

aattagctat aaaaacccgg gttaattaat tagtcatcag gcagggcgag aacgagacta   1200

tctgctcgtt aattaattag agcttcttta ttctatactt aaaaagtgaa aataaataca   1260

aaggttcttg agggttgtgt taaattgaaa gcgagaaata atcataaatt atttcattat   1320

cgcgatatcc gttaagtttg tatcgtaatg gccagcgagt tcggcgtgct gctgaccgac   1380

aaggtggaag gcgacgccct ggaaaagacc aactgcgagg tgatcctgac ccggtccggc   1440

agagtgcggc ggagagaagt ggacggcgtg aagggctacg agtgggagtt caccgaccac   1500

cggctgggcc tgtgcgagat cgagcacacc atgagcatgg ccgatttctt ctacaaccag   1560

atcaagtgcg agggcgccta ccccatcttc ccccactaca tcaccgacgt gctgaagtac   1620

ggcaagatgg tggaccggaa cgaccaccag atccgggtgg accgggacgt gaaagagctg   1680

tccaagatcc tgatccagcc ctacttcggc gaggcctact tcagccccga gttctacacc   1740

agcaccttca gcaagcggca ggccatccag atgaacgtgg agatgctgcg ggccttcgtg   1800

cccaagcggg tggccttcta cgaggacgac atgcggaggg gcggcaccat cgacggcaac   1860

tggatcggcg ccctgcaggc ctggaagaag aaggccgacc tgcagatgag ccgggagggc   1920

aacagccaga ccaattgcgt ggaccacaac gccgacgtga tctaccagca catgaagaag   1980
```

ctgcggttcg gcctgctgta cccccactac tacatgctga acagcgagta caccgtggag 2040
gaaaagagca agggcggcct gatcgccaac tggctggtga aagagaaagc cgccggacgg 2100
gccgagaaca gccccatgta cagcggcgtg ggcccccctga acaccctgcg ggagcggatc 2160
gagcgggacg agctggacga gaaggtgatc caggaaatca tcgcctacgg cagcaagttc 2220
agcacctacg ccggcacccg gaccggcgac ctgaccctga acgagctggt gaagtactgc 2280
gagagcctga ccaccttcgt gcacaagaag aagaaagagg gcgaggacga gaccgccaga 2340
gagttcttca agagcaagtg gattcagggc atgcccaaga tgaacttcga gaacgagatg 2400
atcatgagcc ggaagagctg ggccaacacc aagttctttt ggagcatcga catgttcaag 2460
cggaacaacg gcgtggacat cgaccccaac ggcaagaact ggaaggacta taagaagaag 2520
atccaggaac agctggacga agcccagaag aagaacaaca acgagcccta caaagtgatg 2580
gtggacgggg tgaacatcat gaccaacaag aaatacggca gcgtggagaa ctgggtggac 2640
tgggtcgtga actacatcat gctgtcccac gtgaagcggc tggtgaagga ctacaagttc 2700
aagcggctga agcccgacaa cctgatgagc ggcatgaaca aactggtcgg cgctctcagg 2760
tgctacgcct actgcctgat cctggccctg tacgaccact ttggcgagga tattgagggc 2820
ttcaagaagg gcaccaacgc cgccagcatc gtggagaccg tgagccagat gttcccccag 2880
ttccggaaag aggtgtccga gaccttcggc atcaccctga ataccaagga cgtgaagtac 2940
gagctgttca tcgcccggga catgagcgcc aaagaggccc agagcggcga agtgggctac 3000
aagttccagt acggctggcg caagaccgac cagaaagtga tgagcgacta cgccgacatc 3060
ctgagcgaga aggtggaggc cctgtaccag gccctgctgt ccggccggaa gtggagcgac 3120
atcgccgacg acaccgagga atacttcatc gacgacctgt acgtgaacaa gcccgaccgg 3180
gtgttcgaga gagccggcct ggaccccgag cggcacatca aggtgaaagg cgtgatgaat 3240
gagctgacca cctacttctc caagcggttc gtgagctact ggtacaagat caccaaagtg 3300
gaggcccgga acctgctgac cctgaccgac atcggcggcg acgccaagaa gtacacccag 3360
ttcgaccccg acgacttcaa gcccatggcc gtggccgagc tgggagccca cgcctccacc 3420
tacgtgtacc agaatctgat cctgggccgg aaccggggcg agaagatcga cgacgccaaa 3480
gaaatcgtgt ggtacgacct gtccctgacc aactttggct gctctcgcag cctggacagc 3540
tgctgggtgg gcagcgtggc cagaagcgag ctgaacctgc ggttccacct gatcagcgcc 3600
atcttcgaga gataccagca cgacgccagg cggagcagct tctacgagat catcttcgac 3660
ctgcccagca agaaagagaa gattttcccc agctacaagc actactacgt ggccctgctg 3720
cagaacatct tcaacgacac ccagcggctg gaagtgatgg actactgcga gcggctgatg 3780
aaccccgaga cccggatgag cgccctgctg tctctgcaag gctttaagaa ctgcgtggag 3840
agcgagttcg tggcccccac cctgaagatg aatgccctgc tgtgggtgct ggccgacatg 3900
gaaaacatcg acatcaacta cagcaacaag cggatgcccc tgctgctgtc caccgagaag 3960
ggcctgcggg tgatctccat cgatatgttt aacggcatgc tgggcgtgag ctatagcggc 4020
tggattccct acctggaacg gatctgctcc gaggtgaacc tgcagcggcg gctgagggcc 4080
gacgagctga agctgaagaa gtggttcatc agctactacg ccacctacga ggtggagcgg 4140
agagccgagc ccaggatgag cttcaagatg gaaggcatca gcacctggat cggcagcaac 4200
tgtggcggcg tgcaggacta cgtgctgcac ctgatcccca gcaggcggcc caagcctggc 4260
ctgctgttcc tgatctacgc cgacgacggc gacgtggatt gggtggccaa catgctgtcc 4320
gatgtgatcg gcagcgaggg cagcctgggc ttcatcttca tcaacgaccg gaccttcgtg 4380

```
aataagagcc agctgaaagt gcggaccctg aaaatctaca accggggcat gctggatcgg   4440
ctcatcctga tttccggcgg caactacacc ttcggcaaca agtttctgct gtccaagctg   4500
ctggccaaga cagagaaatg atgactcgag tttttattga ttcaaaattg aaaatatata   4560
attacaatat aaaatgggca agttcaccag ctttctgaag agggccggca gcgccaccaa   4620
gaaggccctg accagcgaca ccgccaagcg gatgtacaag atggccggca agaccctgca   4680
gaaagtggtg gagaacgaag tgggcagcgc cgccatcgac ggcgtgatgc agggcaccat   4740
ccagagcatc atccagggcg agaacctggg cgacagcatc cggcaggccg tgatcctgaa   4800
cgtggccggc accctggaaa gcgcccctga ccccctgagc cctggcgagc agctgctgta   4860
caacaaggtg tccgagctgg aacgggccga gaaagaagat cgggtcatcg agacccacaa   4920
cgagaagatc atcgagaagt acggcgagga cctgctgaag atccggaaga tcatgaaggg   4980
cgaggccaag gccgagcagc tggaaggcaa agaaatcgag tacgtggaga tggccctgaa   5040
gggcatgctg aagattggca aggaccagag cgagcggatc acccagctgt accgggccct   5100
gcagaccgaa gaggacctgc ggaccagcga cgagacccgg atgatcaacg agtaccggga   5160
gaagttcgac gccctgaagc aggccatcga actggaacag caggccaccc acgaggaagc   5220
cgtgcaggaa atgctggacc tgagcgccga ggtgatcgaa acagccgccg aggaagtgcc   5280
catctttggc gctggggctg ccaacgtggt ggctactacc agggccgtgc agggcggcct   5340
gaagctgaaa gagatcatcg acaagctgac cggcatcgac ctgagccacc tgaaggtggc   5400
cgacatccac ccccacatca tcgaaaaggc catgctgaaa gacaagatcc ccgacaacga   5460
gctggctatg gccatcaaga gcaaggtgga agtgatcgac gagatgaaca ccgagaccga   5520
gcacgtgatc gagagcatca tgcccctggt gaagaaagag tacgagaagc acgacaacaa   5580
gtaccacgtg aacatcccca gcgtgctgaa aatccacagc gagcacaccc ccaaggtgca   5640
catctacacc accccctggg acagcgacaa ggtgttcatc tgccggtgca tcgcccccca   5700
ccatcagcag aaaagcttca tgatcggctt cgacctggaa atcgagtttg tgttctacga   5760
ggacaccagc gtggagggcc acatcatgca cggcggagcc gtgctgatcg agggcagggg   5820
cttcaggcag gcctacagcg agttcatgaa cgccgcctgg tccatgccca gcacccccga   5880
gctgcacaag cggcggctgc agcggagcct gggcagccac cccatctaca tgggcagcat   5940
ggactacacc gtgagctacg accagctggt gtccaacgcc atgaagctgg tgtacgacac   6000
cgagctgcag atgcactgcc tgagaggccc cctgaagttc cagcggcgga ccctgatgaa   6060
cgccctgctg ttcggcgtga agatcgcctg atgatttttc tactagttaa tcaaataaaa   6120
agcatacaag ctattgcttc gctatcgtta caaaatggca ggaattttgt gtaaactaag   6180
ccacatactt gccaatgaaa aaaatagtag aaaggatact attttaatgg gattagatgt   6240
taaggttcct tgggattata gtaactgggc atctgttaac ttttacgacg ttaggttaga   6300
tactgatgtt acagattata ataatgttac aataaaatac atgacaggat gtgatatttt   6360
tcctcatata actcttggaa tagcaaatat ggatcaatgt gatagatttg aaaatttcaa   6420
aaagcaaata actgatcaag atttacagac tatttctata gtctgtaaag aagagatgtg   6480
ttttcctcag agtaacgcct ctaaacagtt gggagcgaaa ggatgcgctg tagttatgaa   6540
actggaggta tctgatgaac ttagagccct aagaaatgtt ctgctgaatg cggtaccctg   6600
ttcgaaggac gtgtttggtg atatcacagt agataatccg tggaatcctc acataacagt   6660
aggatatgtt aaggaggacg atgtcgaaaa caagaaacgc ctaatggagt gcatgtccaa   6720
gtttaggggg caagaaatac aagttctagg atggtattaa taagtatcta agtatttggt   6780
```

ataatttatt aaatagtata attataacaa ataataaata acatgataac ggtttttatt 6840
agaataaaat agagataata tcataatgat atataatact tcattaccag aaatgagtaa 6900
tggaagactt ataaatgaac tgcataaagc tataaggtat agagatataa atttagtaag 6960
gtatatactt aaaaaatgca aatacaataa cgtaaatata ctatcaacgt ctttgtattt 7020
agccgtaagt atttctgata tagaaatggt aaaattatta ctagaacacg gtgccgatat 7080
tttaaaatgt aaaaatcctc ctcttcataa agctgctagt ttagataata cagaaattgc 7140
taaactacta atagattctg gcgctgacat agaacagata cattctggaa atagtccgtt 7200
atatatttct gtatatagaa acaataagtc attaactaga tatttattaa aaaaaggtgt 7260
taattgtaat agattctttc taaattatta cgatgtactg tatgataaga tatctgatga 7320
tatgtataaa atatttatag attttaatat tgatcttaat atacaaacta gaaattttga 7380
aactccgtta cattacgcta taaagtataa gaatatagat ttaattagga tattgttaga 7440
taatagtatt aaaaatagata aaagtttatt tttgcataaa cagtatctca taaaggcact 7500
taaaaataat tgtagttacg atataatagc gttacttata aatcacggag tgcctataaa 7560
cgaacaagat gatttaggta aaaccccatt acatcattcg gtaattaata gaagaaaaga 7620
tgtaacagca cttctgttaa atctaggagc tgatataaac gtaatagatg actgtatggg 7680
cagtccctta cattacgctg tttcacgtaa cgatatcgaa acaacaaaga cacttttaga 7740
aagaggatct aatgttaatg tggttaataa tcatatagat accgttctaa atatagctgt 7800
tgcatctaaa aacaaaacta tagtaaactt attactgaag tacggtactg atacaaagtt 7860
ggtaggatta gataaacatg ttattcacat agctatagaa atgaaagata ttaatatact 7920
gaatgcgatc ttattatatg gttgctatgt aaacgtctat aatcataaag gtttcactcc 7980
tctatacatg gcagttagtt ctatgaaaac agaatttgtt aaactcttac ttgaccacgg 8040
tgcttacgta aatgctaaag ctaagttatc tggaaatact cctttacata aagctatgtt 8100
atctaatagt tttaataata taaaattact tttatcttat aacgccgact ataattctct 8160
aaataatcac ggtaatacgc ctctaacttg tgttagcttt ttagatgaca agatagctat 8220
tatgataata tctaaaatga tgttagaaat atctaaaaat cctgaaatag ctaattcaga 8280
aggttttata gtaaacatgg aacatataaa cagtaataaa agactactat ctataaaaga 8340
atcatgcgaa aaagaactag atgttataac acatataaag ttaaattcta tatattcttt 8400
taatatcttt cttgacaata acatagatct tatggtaaag ttcgtaacta atcctagagt 8460
taataagata cctgcatgta tacgtatata tagggaatta atacggaaaa ataaatcatt 8520
agcttttcat agacatcagc taatagttaa agctgtaaaa gagagtaaga atctaggaat 8580
aataggtagg ttacctatag atatcaaaca tataataatg gaactattaa gtaataatga 8640
tttacattct gttatcacca gctgttgtaa cccagtagta taaagtgatt ttattcaatt 8700
acgaagataa acattaaatt tgttaacaga tatgagttat gagtatttaa ctaaagttac 8760
tttaggtaca aataaaatat tatgtaatat aatagaaaat tatcttgagt cttcatttcc 8820
atcaccgtct aaatttatta ttaaaacctt attatataag gctgttgagt ttagaaatgt 8880
aaatgctgta aaaaaaatat tacagaatga tattgaatat gttaaagtag atagtc 8936

<210> SEQ ID NO 42
<211> LENGTH: 3171
<212> TYPE: DNA
<213> ORGANISM: artificial sequence
<220> FEATURE:
<223> OTHER INFORMATION: AHSV-5 VP2 of vCP2398

<400> SEQUENCE: 42
atggccagcg agttcggcgt gctgctgacc gacaaggtgg aaggcgacgc cctggaaaag 60
accaactgcg aggtgatcct gacccggtcc ggcagagtgc ggcggagaga agtggacggc 120
gtgaagggct acgagtggga gttcaccgac caccggctgg gcctgtgcga gatcgagcac 180
accatgagca tggccgattt cttctacaac cagatcaagt gcgagggcgc ctaccccatc 240
ttcccccact acatcaccga cgtgctgaag tacggcaaga tggtggaccg gaacgaccac 300
cagatccggg tggaccggga cgtgaaagag ctgtccaaga tcctgatcca gccctacttc 360
ggcgaggcct acttcagccc cgagttctac accagcacct tcagcaagcg gcaggccatc 420
cagatgaacg tggagatgct gcgggccttc gtgcccaagc gggtggcctt ctacgaggac 480
gacatgcgga ggggcggcac catcgacggc aactggatcg gcgccctgca ggcctggaag 540
aagaaggccg acctgcagat gagccgggag ggcaacagcc agaccaattg cgtggaccac 600
aacgccgacg tgatctacca gcacatgaag aagctgcggt tcggcctgct gtacccccac 660
tactacatgc tgaacagcga gtacaccgtg gaggaaaaga gcaagggcgg cctgatcgcc 720
aactggctgg tgaaagagaa agccgccgga cgggccgaga acagccccat gtacagcggc 780
gtgggccccc tgaacaccct gcgggagcgg atcgagcggg acgagctgga cgagaaggtg 840
atccaggaaa tcatcgccta cggcagcaag ttcagcacct acgccggcac ccggaccggc 900
gacctgaccc tgaacgagct ggtgaagtac tgcgagagcc tgaccacctt cgtgcacaag 960
aagaagaaag agggcgagga cgagaccgcc agagagttct tcaagagcaa gtggattcag 1020
ggcatgccca agatgaactt cgagaacgag atgatcatga gccggaagag ctgggccaac 1080
accaagttct tttggagcat cgacatgttc aagcggaaca acggcgtgga catcgacccc 1140
aacggcaaga actggaagga ctataagaag aagatccagg aacagctgga cgaagcccag 1200
aagaagaaca acaacgagcc ctacaaagtg atggtggacg gggtgaacat catgaccaac 1260
aagaaatacg gcagcgtgga gaactgggtg gactgggtcg tgaactacat catgctgtcc 1320
cacgtgaagc ggctggtgaa ggactacaag ttcaagcggc tgaagcccga caacctgatg 1380
agcggcatga acaaactggt cggcgctctc aggtgctacg cctactgcct gatcctggcc 1440
ctgtacgacc actttggcga ggatattgag ggcttcaaga agggcaccaa cgccgccagc 1500
atcgtggaga ccgtgagcca gatgttcccc cagttccgga aagaggtgtc cgagaccttc 1560
ggcatcaccc tgaataccaa ggacgtgaag tacgagctgt tcatcgcccg ggacatgagc 1620
gccaaagagg cccagagcgg cgaagtgggc tacaagttcc agtacggctg gcgcaagacc 1680
gaccagaaag tgatgagcga ctacgccgac atcctgagcg agaaggtgga ggccctgtac 1740
caggccctgc tgtccggccg gaagtggagc gacatcgccg acgacaccga ggaatacttc 1800
atcgacgacc tgtacgtgaa caagcccgac cgggtgttcg agagagccgg cctggacccc 1860
gagcggcaca tcaaggtgaa aggcgtgatg aatgagctga ccacctactt ctccaagcgg 1920
ttcgtgagct actggtacaa gatcaccaaa gtggaggccc ggaacctgct gaccctgacc 1980
gacatcggcg gcgacgccaa gaagtacacc cagttcgacc ccgacgactt caagcccatg 2040
gccgtggccg agctgggagc ccacgcctcc acctacgtgt accagaatct gatcctgggc 2100
cggaaccggg gcgagaagat cgacgacgcc aaagaaatcg tgtggtacga cctgtccctg 2160
accaactttg gctgctctcg cagcctggac agctgctggg tgggcagcgt ggccagaagc 2220
gagctgaacc tgcggttcca cctgatcagc gccatcttcg agagatacca gcacgacgcc 2280
aggcggagca gcttctacga gatcatcttc gacctgccca gcaagaaaga gaagattttc 2340

```
cccagctaca agcactacta cgtggccctg ctgcagaaca tcttcaacga cacccagcgg   2400

ctggaagtga tggactactg cgagcggctg atgaaccccg agacccggat gagcgccctg   2460

ctgtctctgc aaggctttaa gaactgcgtg gagagcgagt tcgtggcccc caccctgaag   2520

atgaatgccc tgctgtgggt gctggccgac atggaaaaca tcgacatcaa ctacagcaac   2580

aagcggatgc ccctgctgct gtccaccgag aagggcctgc gggtgatctc catcgatatg   2640

tttaacggca tgctgggcgt gagctatagc ggctggattc cctacctgga acggatctgc   2700

tccgaggtga acctgcagcg gcggctgagg gccgacgagc tgaagctgaa gaagtggttc   2760

atcagctact acgccaccta cgaggtggag cggagagccg agcccaggat gagcttcaag   2820

atggaaggca tcagcacctg gatcggcagc aactgtggcg gcgtgcagga ctacgtgctg   2880

cacctgatcc ccagcaggcg gcccaagcct ggcctgctgt tcctgatcta cgccgacgac   2940

ggcgacgtgg attgggtggc caacatgctg tccgatgtga tcggcagcga gggcagcctg   3000

ggcttcatct tcatcaacga ccggaccttc gtgaataaga gccagctgaa agtgcggacc   3060

ctgaaaatct acaaccgggg catgctggat cggctcatcc tgatttccgg cggcaactac   3120

accttcggca acaagtttct gctgtccaag ctgctggcca agacagagaa a             3171
```

```
<210> SEQ ID NO 43
<211> LENGTH: 1515
<212> TYPE: DNA
<213> ORGANISM: artificial sequence
<220> FEATURE:
<223> OTHER INFORMATION: AHSV-5 VP5 of vCP2398

<400> SEQUENCE: 43

atgggcaagt tcaccagctt tctgaagagg gccggcagcg ccaccaagaa ggccctgacc     60

agcgacaccg ccaagcggat gtacaagatg gccggcaaga ccctgcagaa agtggtggag    120

aacgaagtgg gcagcgccgc catcgacggc gtgatgcagg gcaccatcca gagcatcatc    180

cagggcgaga acctgggcga cagcatccgg caggccgtga tcctgaacgt ggccggcacc    240

ctggaaagcg cccctgaccc cctgagccct ggcgagcagc tgctgtacaa caaggtgtcc    300

gagctggaac gggccgagaa agaagatcgg gtcatcgaga cccacaacga gaagatcatc    360

gagaagtacg gcgaggacct gctgaagatc cggaagatca tgaagggcga ggccaaggcc    420

gagcagctgg aaggcaaaga aatcgagtac gtggagatgg ccctgaaggg catgctgaag    480

attggcaagg accagagcga gcggatcacc cagctgtacc gggccctgca gaccgaagag    540

gacctgcgga ccagcgacga gacccggatg atcaacgagt accgggagaa gttcgacgcc    600

ctgaagcagg ccatcgaact ggaacagcag gccacccacg aggaagccgt gcaggaaatg    660

ctggacctga gcgccgaggt gatcgaaaca gccgccgagg aagtgcccat ctttggcgct    720

ggggctgcca acgtggtggc tactaccagg gccgtgcagg gcggcctgaa gctgaaagag    780

atcatcgaca agctgaccgg catcgacctg agccacctga aggtggccga catccacccc    840

cacatcatcg aaaaggccat gctgaaagac aagatccccg acaacgagct ggctatggcc    900

atcaagagca aggtggaagt gatcgacgag atgaacaccg agaccgagca cgtgatcgag    960

agcatcatgc ccctggtgaa gaaagagtac gagaagcacg acaacaagta ccacgtgaac   1020

atccccagcg tgctgaaaat ccacagcgag cacaccccca aggtgcacat ctacaccacc   1080

ccctgggaca gcgacaaggt gttcatctgc cggtgcatcg ccccccacca tcagcagaaa   1140

agcttcatga tcggcttcga cctggaaatc gagtttgtgt tctacgagga caccagcgtg   1200

gagggccaca tcatgcacgg cggagccgtg ctgatcgagg gcaggggctt caggcaggcc   1260
```

-continued tacagcgagt tcatgaacgc cgcctggtcc atgcccagca cccccgagct gcacaagcgg 1320
cggctgcagc ggagcctggg cagccacccc atctacatgg gcagcatgga ctacaccgtg 1380
agctacgacc agctggtgtc caacgccatg aagctggtgt acgacaccga gctgcagatg 1440
cactgcctga gaggcccccct gaagttccag cggcggaccc tgatgaacgc cctgctgttc 1500
ggcgtgaaga tcgcc 1515

<210> SEQ ID NO 44
<211> LENGTH: 1057
<212> TYPE: PRT
<213> ORGANISM: artificial sequence
<220> FEATURE:
<223> OTHER INFORMATION: Predicted Amino Acid Sequence for AHSV-5 VP2 of vCP2398

<400> SEQUENCE: 44

Met Ala Ser Glu Phe Gly Val Leu Leu Thr Asp Lys Val Glu Gly Asp
1 5 10 15

Ala Leu Glu Lys Thr Asn Cys Glu Val Ile Leu Thr Arg Ser Gly Arg
20 25 30

Val Arg Arg Arg Glu Val Asp Gly Val Lys Gly Tyr Glu Trp Glu Phe
35 40 45

Thr Asp His Arg Leu Gly Leu Cys Glu Ile Glu His Thr Met Ser Met
50 55 60

Ala Asp Phe Phe Tyr Asn Gln Ile Lys Cys Glu Gly Ala Tyr Pro Ile
65 70 75 80

Phe Pro His Tyr Ile Thr Asp Val Leu Lys Tyr Gly Lys Met Val Asp
85 90 95

Arg Asn Asp His Gln Ile Arg Val Asp Arg Asp Val Lys Glu Leu Ser
100 105 110

Lys Ile Leu Ile Gln Pro Tyr Phe Gly Glu Ala Tyr Phe Ser Pro Glu
115 120 125

Phe Tyr Thr Ser Thr Phe Ser Lys Arg Gln Ala Ile Gln Met Asn Val
130 135 140

Glu Met Leu Arg Ala Phe Val Pro Lys Arg Val Ala Phe Tyr Glu Asp
145 150 155 160

Asp Met Arg Arg Gly Gly Thr Ile Asp Gly Asn Trp Ile Gly Ala Leu
165 170 175

Gln Ala Trp Lys Lys Lys Ala Asp Leu Gln Met Ser Arg Glu Gly Asn
180 185 190

Ser Gln Thr Asn Cys Val Asp His Asn Ala Asp Val Ile Tyr Gln His
195 200 205

Met Lys Lys Leu Arg Phe Gly Leu Leu Tyr Pro His Tyr Tyr Met Leu
210 215 220

Asn Ser Glu Tyr Thr Val Glu Glu Lys Ser Lys Gly Gly Leu Ile Ala
225 230 235 240

Asn Trp Leu Val Lys Glu Lys Ala Ala Gly Arg Ala Glu Asn Ser Pro
245 250 255

Met Tyr Ser Gly Val Gly Pro Leu Asn Thr Leu Arg Glu Arg Ile Glu
260 265 270

Arg Asp Glu Leu Asp Glu Lys Val Ile Gln Glu Ile Ile Ala Tyr Gly
275 280 285

Ser Lys Phe Ser Thr Tyr Ala Gly Thr Arg Thr Gly Asp Leu Thr Leu
290 295 300

Asn Glu Leu Val Lys Tyr Cys Glu Ser Leu Thr Thr Phe Val His Lys

-continued

```
305                 310                 315                 320

Lys Lys Lys Glu Gly Glu Asp Glu Thr Ala Arg Glu Phe Phe Lys Ser
                325                 330                 335

Lys Trp Ile Gln Gly Met Pro Lys Met Asn Phe Glu Asn Glu Met Ile
            340                 345                 350

Met Ser Arg Lys Ser Trp Ala Asn Thr Lys Phe Phe Trp Ser Ile Asp
        355                 360                 365

Met Phe Lys Arg Asn Asn Gly Val Asp Ile Asp Pro Asn Gly Lys Asn
    370                 375                 380

Trp Lys Asp Tyr Lys Lys Lys Ile Gln Glu Gln Leu Asp Glu Ala Gln
385                 390                 395                 400

Lys Lys Asn Asn Asn Glu Pro Tyr Lys Val Met Val Asp Gly Val Asn
                405                 410                 415

Ile Met Thr Asn Lys Lys Tyr Gly Ser Val Glu Asn Trp Val Asp Trp
            420                 425                 430

Val Val Asn Tyr Ile Met Leu Ser His Val Lys Arg Leu Val Lys Asp
        435                 440                 445

Tyr Lys Phe Lys Arg Leu Lys Pro Asp Asn Leu Met Ser Gly Met Asn
    450                 455                 460

Lys Leu Val Gly Ala Leu Arg Cys Tyr Ala Tyr Cys Leu Ile Leu Ala
465                 470                 475                 480

Leu Tyr Asp His Phe Gly Glu Asp Ile Glu Gly Phe Lys Lys Gly Thr
                485                 490                 495

Asn Ala Ala Ser Ile Val Glu Thr Val Ser Gln Met Phe Pro Gln Phe
            500                 505                 510

Arg Lys Glu Val Ser Glu Thr Phe Gly Ile Thr Leu Asn Thr Lys Asp
        515                 520                 525

Val Lys Tyr Glu Leu Phe Ile Ala Arg Asp Met Ser Ala Lys Glu Ala
    530                 535                 540

Gln Ser Gly Glu Val Gly Tyr Lys Phe Gln Tyr Gly Trp Arg Lys Thr
545                 550                 555                 560

Asp Gln Lys Val Met Ser Asp Tyr Ala Asp Ile Leu Ser Glu Lys Val
                565                 570                 575

Glu Ala Leu Tyr Gln Ala Leu Leu Ser Gly Arg Lys Trp Ser Asp Ile
            580                 585                 590

Ala Asp Asp Thr Glu Glu Tyr Phe Ile Asp Asp Leu Tyr Val Asn Lys
        595                 600                 605

Pro Asp Arg Val Phe Glu Arg Ala Gly Leu Asp Pro Glu Arg His Ile
    610                 615                 620

Lys Val Lys Gly Val Met Asn Glu Leu Thr Thr Tyr Phe Ser Lys Arg
625                 630                 635                 640

Phe Val Ser Tyr Trp Tyr Lys Ile Thr Lys Val Glu Ala Arg Asn Leu
                645                 650                 655

Leu Thr Leu Thr Asp Ile Gly Gly Asp Ala Lys Lys Tyr Thr Gln Phe
            660                 665                 670

Asp Pro Asp Asp Phe Lys Pro Met Ala Val Ala Glu Leu Gly Ala His
        675                 680                 685

Ala Ser Thr Tyr Val Tyr Gln Asn Leu Ile Leu Gly Arg Asn Arg Gly
    690                 695                 700

Glu Lys Ile Asp Asp Ala Lys Glu Ile Val Trp Tyr Asp Leu Ser Leu
705                 710                 715                 720

Thr Asn Phe Gly Cys Ser Arg Ser Leu Asp Ser Cys Trp Val Gly Ser
                725                 730                 735
```

-continued

```
Val Ala Arg Ser Glu Leu Asn Leu Arg Phe His Leu Ile Ser Ala Ile
            740                 745                 750

Phe Glu Arg Tyr Gln His Asp Ala Arg Arg Ser Ser Phe Tyr Glu Ile
        755                 760                 765

Ile Phe Asp Leu Pro Ser Lys Lys Glu Lys Ile Phe Pro Ser Tyr Lys
    770                 775                 780

His Tyr Tyr Val Ala Leu Leu Gln Asn Ile Phe Asn Asp Thr Gln Arg
785                 790                 795                 800

Leu Glu Val Met Asp Tyr Cys Glu Arg Leu Met Asn Pro Glu Thr Arg
                805                 810                 815

Met Ser Ala Leu Leu Ser Leu Gln Gly Phe Lys Asn Cys Val Glu Ser
            820                 825                 830

Glu Phe Val Ala Pro Thr Leu Lys Met Asn Ala Leu Leu Trp Val Leu
        835                 840                 845

Ala Asp Met Glu Asn Ile Asp Ile Asn Tyr Ser Asn Lys Arg Met Pro
    850                 855                 860

Leu Leu Leu Ser Thr Glu Lys Gly Leu Arg Val Ile Ser Ile Asp Met
865                 870                 875                 880

Phe Asn Gly Met Leu Gly Val Ser Tyr Ser Gly Trp Ile Pro Tyr Leu
                885                 890                 895

Glu Arg Ile Cys Ser Glu Val Asn Leu Gln Arg Arg Leu Arg Ala Asp
            900                 905                 910

Glu Leu Lys Leu Lys Lys Trp Phe Ile Ser Tyr Tyr Ala Thr Tyr Glu
        915                 920                 925

Val Glu Arg Arg Ala Glu Pro Arg Met Ser Phe Lys Met Glu Gly Ile
    930                 935                 940

Ser Thr Trp Ile Gly Ser Asn Cys Gly Gly Val Gln Asp Tyr Val Leu
945                 950                 955                 960

His Leu Ile Pro Ser Arg Arg Pro Lys Pro Gly Leu Leu Phe Leu Ile
                965                 970                 975

Tyr Ala Asp Asp Gly Asp Val Asp Trp Val Ala Asn Met Leu Ser Asp
            980                 985                 990

Val Ile Gly Ser Glu Gly Ser Leu  Gly Phe Ile Phe Ile  Asn Asp Arg
        995                 1000                 1005

Thr Phe  Val Asn Lys Ser Gln  Leu Lys Val Arg Thr  Leu Lys Ile
    1010                 1015                 1020

Tyr Asn  Arg Gly Met Leu Asp  Arg Leu Ile Leu Ile  Ser Gly Gly
    1025                 1030                 1035

Asn Tyr  Thr Phe Gly Asn Lys  Phe Leu Leu Ser Lys  Leu Leu Ala
    1040                 1045                 1050

Lys Thr  Glu Lys
    1055
```

<210> SEQ ID NO 45
<211> LENGTH: 505
<212> TYPE: PRT
<213> ORGANISM: artificial sequence
<220> FEATURE:
<223> OTHER INFORMATION: Predicted Amino Acid Sequence for AHSV-5 VP5 of vCP2398

<400> SEQUENCE: 45

```
Met Gly Lys Phe Thr Ser Phe Leu Lys Arg Ala Gly Ser Ala Thr Lys
1               5                   10                  15

Lys Ala Leu Thr Ser Asp Thr Ala Lys Arg Met Tyr Lys Met Ala Gly
            20                  25                  30
```

-continued

```
Lys Thr Leu Gln Lys Val Val Glu Asn Glu Val Gly Ser Ala Ala Ile
        35                  40                  45

Asp Gly Val Met Gln Gly Thr Ile Gln Ser Ile Ile Gln Gly Glu Asn
    50                  55                  60

Leu Gly Asp Ser Ile Arg Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Leu Glu Arg Ala Glu Lys Glu Asp Arg Val Ile
            100                 105                 110

Glu Thr His Asn Glu Lys Ile Ile Glu Lys Tyr Gly Glu Asp Leu Leu
        115                 120                 125

Lys Ile Arg Lys Ile Met Lys Gly Glu Ala Lys Ala Glu Gln Leu Glu
    130                 135                 140

Gly Lys Glu Ile Glu Tyr Val Glu Met Ala Leu Lys Gly Met Leu Lys
145                 150                 155                 160

Ile Gly Lys Asp Gln Ser Glu Arg Ile Thr Gln Leu Tyr Arg Ala Leu
                165                 170                 175

Gln Thr Glu Glu Asp Leu Arg Thr Ser Asp Glu Thr Arg Met Ile Asn
            180                 185                 190

Glu Tyr Arg Glu Lys Phe Asp Ala Leu Lys Gln Ala Ile Glu Leu Glu
        195                 200                 205

Gln Gln Ala Thr His Glu Glu Ala Val Gln Glu Met Leu Asp Leu Ser
    210                 215                 220

Ala Glu Val Ile Glu Thr Ala Ala Glu Glu Val Pro Ile Phe Gly Ala
225                 230                 235                 240

Gly Ala Ala Asn Val Val Ala Thr Thr Arg Ala Val Gln Gly Gly Leu
                245                 250                 255

Lys Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Lys Asp Lys Ile Pro Asp Asn Glu Leu Ala Met Ala Ile Lys Ser Lys
    290                 295                 300

Val Glu Val Ile Asp Glu Met Asn Thr Glu Thr Glu His Val Ile Glu
305                 310                 315                 320

Ser Ile Met Pro Leu Val Lys Lys Glu Tyr Glu Lys His Asp Asn Lys
                325                 330                 335

Tyr His Val Asn Ile Pro Ser Val Leu Lys Ile His Ser Glu His Thr
            340                 345                 350

Pro Lys Val His Ile Tyr Thr Thr Pro Trp Asp Ser Asp Lys Val Phe
        355                 360                 365

Ile Cys Arg Cys Ile Ala Pro His His Gln Gln Lys Ser Phe Met Ile
    370                 375                 380

Gly Phe Asp Leu Glu Ile Glu Phe Val Phe Tyr Glu Asp Thr Ser Val
385                 390                 395                 400

Glu Gly His Ile Met His Gly Gly Ala Val Leu Ile Glu Gly Arg Gly
                405                 410                 415

Phe Arg Gln Ala Tyr Ser Glu Phe Met Asn Ala Ala Trp Ser Met Pro
            420                 425                 430

Ser Thr Pro Glu Leu His Lys Arg Arg Leu Gln Arg Ser Leu Gly Ser
        435                 440                 445

His Pro Ile Tyr Met Gly Ser Met Asp Tyr Thr Val Ser Tyr Asp Gln
    450                 455                 460
```

```
Leu Val Ser Asn Ala Met Lys Leu Val Tyr Asp Thr Glu Leu Gln Met
465                 470                 475                 480

His Cys Leu Arg Gly Pro Leu Lys Phe Gln Arg Arg Thr Leu Met Asn
                485                 490                 495

Ala Leu Leu Phe Gly Val Lys Ile Ala
            500                 505


<210> SEQ ID NO 46
<211> LENGTH: 43
<212> TYPE: DNA
<213> ORGANISM: artificial sequence
<220> FEATURE:
<223> OTHER INFORMATION: 18041 CXL mutagenesis primer

<400> SEQUENCE: 46

cggcgtgaaa tgatagtaat ttttctacta gtctagaagg gcg                      43


<210> SEQ ID NO 47
<211> LENGTH: 43
<212> TYPE: DNA
<213> ORGANISM: artificial sequence
<220> FEATURE:
<223> OTHER INFORMATION: 18042 CXL mutagenesis primer

<400> SEQUENCE: 47

cgcccttcta gactagtaga aaaattacta tcatttcacg ccg                      43


<210> SEQ ID NO 48
<211> LENGTH: 3183
<212> TYPE: DNA
<213> ORGANISM: artificial sequence
<220> FEATURE:
<223> OTHER INFORMATION: AHSV4-Jane Strain-L2/VP2 gene

<400> SEQUENCE: 48

atggcgtccg agtttggaat attgatgaca aatgaaaaat ttgacccaag cttagagaaa     60

accatttgcg atgttatagt tacgaagaag ggaagagtga agcataaaga ggtggatggc    120

gtatgtggat acgagtggga tgaaacgaat caccgattcg gattgtgtaa ggtggaacac    180

gacatgtcta tatcggaatt tatgtacaat gagatcagat gtgagggggc atatccaatt    240

tttccgcgtt atataattga tacgttaaaa tacgagaaat ttattgatag gaatgaccat    300

caaattagag tggatagaga tgataacgaa atgaggaaaa tattgataca gccgtatgca    360

ggtgagatgt acttttcgcc ggaatgttat ccgagcgttt ttcttcggag ggaagcgcga    420

agtcaaaagc ttgatcggat tcggaattat attggaaaga gagtcgaatt ttatgaagag    480

gagagtaaga gaaaagcaat ccttgatcag aataagatgt ctaaggttga acaatggaga    540

gatgcggtta atgaaaggat tgtgagtatc gaaccaaagc gaggtgagtg ctatgatcac    600

ggaaccgaca ttatctacca attcataaaa aagctgagat ttggaatgat gtacccacac    660

tattatgttt tgcatagtga ttactgtatt gtaccaaata aggggggaac tagtattgga    720

tcatggcata taagaaaacg tactgagggt gatgcgaaag cttctgctat gtattctgga    780

aaaggtccac tgaatgactt acgagttaaa attgagcggg atgatttatc tcgagagaca    840

attattcaga tcattgagta cggtaagaaa tttaattcat cagcaggtga taagcagggg    900

aacatttcaa ttgaaaaatt ggtagagtat tgtgattttt tgacaacatt cgttcatgcg    960

aagaagaaag aagagggtga ggatgatact gctcgacagg agataagaaa agcatgggtt   1020

aaggggatgc cttatatgga tttctcaaaa ccgatgaaaa tcacgcgtgg attcaacaga   1080
```

-continued

```
aatatgcttt tccttgcggc gctcgattca ttcagaaaga ggaacggtgt agatgttgat   1140
ccgaataagg gtaagtggaa agaacatata aaggaggtaa ccgaaaaatt gaagaaagcg   1200
caaaccgaaa atggaggaca accatgccaa gtgtcgatcg atggagtaaa cgtcttgact   1260
aacgtagatt acggtacggt taatcattgg atagattggg taacagatat aattatggtt   1320
gtacaaacta aacgtttggt gaaagagtat gcatttaaaa aactaaagag cgaaaactta   1380
cttgctggaa tgaatagttt agttggggta ttaagatgtt atatgtattg cttagcttta   1440
gcgatctatg atttttatga agggactatt gatggtttta agaaaggctc gaatgcttcc   1500
gctatcattg aaactgtcgc gcagatgttt ccggactttc gcagagagct tgtcgaaaaa   1560
ttcggtatag atttaaggat gaaggaaatc acgcgtgagt tgtttgttgg taagagcatg   1620
acgtcaaaat ttatggagga aggtgaatat ggatataagt tcgcctatgg atggcgtagg   1680
gatggcttcg cggtgatgga agattacgga gaaattttga cagaaaaagt ggaggaccta   1740
tataagggtg tacttttagg acgaaagtgg gaggatgagg ttgatgatcc agagagttat   1800
ttttatgatg atctttatac taatgagccc cacagagtgt ttctaagcgc aggaaaggat   1860
gtggataata atatcacgct tcgatcgatt tcgcaggcgg aaaccacgta tctatcgaaa   1920
cgtttcgtat catattggta tagaatatca caagttgaag taacgaaggc gcgtaatgaa   1980
gttctggaca tgaatgagaa acagaagccg tattttgaat ttgaatatga tgatttcaaa   2040
ccctgttcaa ttggagagtt ggggatccat gcatccacat atatatatca gaacctactg   2100
gtcggacgta atagaggtga ggaaatactt gattcgaaag agctcgtctg gatggatatg   2160
tcacttttaa attttggagc ggtcagatct cacgataggt gctggatctc ctcaagcgtc   2220
gcgattgagg tgaatttacg tcatgcacta atagttagga ttttttcacg ctttgacatg   2280
atgtcggaaa gagaaacgtt ttcaaccatt ttagaaaaag tcatggagga tgtgaaagag   2340
ttgagatttt tcccgacata tcgtcattat tatttggaaa ctctccaacg tgtctttaac   2400
gatgagagac gcttagaagt tgatgacttt tatatgaggt tatatgatgt gcagacaagg   2460
gagcaggcac taaatacttt cacggatttt cacaggtgtg ttgagtcgga actgctctta   2520
ccgacactta aacttaactt tctgctgtgg attgtttttg aaatggaaaa tgttgaagtg   2580
aacgcggcgt acaagcgtca tccgctttta atctcaactg ccaaagggtt aagggttatc   2640
ggcgttgata ttttcaactc acagctttcg atatcaatga gcggatggat tccgtatgtc   2700
gaacggatgt gcgcggagag taaagttcaa acaaaattga cggctgatga gctgaaattg   2760
aagaggtggt tcatctcata ttatacgacg ttgaaattgg accgcagagc ggagccacgt   2820
atgagtttca aatttgaggg gttgagtaca tggatcggtt cgaactgcgg aggtgttagg   2880
gattacgtaa tacagatgct tcctaccaga aaacctaaac cgggagcttt gatggtggta   2940
tacgcgcggg attcgagaat cgagtggatc gaagcagagc tatcacagtg gctgcaaatg   3000
gaaggttcgc ttggtttgat cctcgttcat gattcaggta taataaataa gagcgtattg   3060
agagcgagaa ctctgaaaat ttacaatagg ggttcgatgg atactttaat tctaatttcg   3120
agtggagttt acactttcgg aaataaattc ttgttgtcga agttactcgc aaaaacagaa   3180
tag                                                                 3183
```

<210> SEQ ID NO 49
<211> LENGTH: 1060
<212> TYPE: PRT
<213> ORGANISM: artificial sequence
<220> FEATURE:
<223> OTHER INFORMATION: AHSV4-Jane Strain-VP2 predicted AA sequence -continued

<400> SEQUENCE: 49

```
Met Ala Ser Glu Phe Gly Ile Leu Met Thr Asn Glu Lys Phe Asp Pro
1               5                   10                  15

Ser Leu Glu Lys Thr Ile Cys Asp Val Ile Val Thr Lys Lys Gly Arg
            20                  25                  30

Val Lys His Lys Glu Val Asp Gly Val Cys Gly Tyr Glu Trp Asp Glu
        35                  40                  45

Thr Asn His Arg Phe Gly Leu Cys Lys Val Glu His Asp Met Ser Ile
    50                  55                  60

Ser Glu Phe Met Tyr Asn Glu Ile Arg Cys Glu Gly Ala Tyr Pro Ile
65                  70                  75                  80

Phe Pro Arg Tyr Ile Ile Asp Thr Leu Lys Tyr Glu Lys Phe Ile Asp
                85                  90                  95

Arg Asn Asp His Gln Ile Arg Val Asp Arg Asp Asp Asn Glu Met Arg
            100                 105                 110

Lys Ile Leu Ile Gln Pro Tyr Ala Gly Glu Met Tyr Phe Ser Pro Glu
        115                 120                 125

Cys Tyr Pro Ser Val Phe Leu Arg Arg Glu Ala Arg Ser Gln Lys Leu
    130                 135                 140

Asp Arg Ile Arg Asn Tyr Ile Gly Lys Arg Val Glu Phe Tyr Glu Glu
145                 150                 155                 160

Glu Ser Lys Arg Lys Ala Ile Leu Asp Gln Asn Lys Met Ser Lys Val
                165                 170                 175

Glu Gln Trp Arg Asp Ala Val Asn Glu Arg Ile Val Ser Ile Glu Pro
            180                 185                 190

Lys Arg Gly Glu Cys Tyr Asp His Gly Thr Asp Ile Ile Tyr Gln Phe
        195                 200                 205

Ile Lys Lys Leu Arg Phe Gly Met Met Tyr Pro His Tyr Tyr Val Leu
    210                 215                 220

His Ser Asp Tyr Cys Ile Val Pro Asn Lys Gly Gly Thr Ser Ile Gly
225                 230                 235                 240

Ser Trp His Ile Arg Lys Arg Thr Glu Gly Asp Ala Lys Ala Ser Ala
                245                 250                 255

Met Tyr Ser Gly Lys Gly Pro Leu Asn Asp Leu Arg Val Lys Ile Glu
            260                 265                 270

Arg Asp Asp Leu Ser Arg Glu Thr Ile Ile Gln Ile Ile Glu Tyr Gly
        275                 280                 285

Lys Lys Phe Asn Ser Ser Ala Gly Asp Lys Gln Gly Asn Ile Ser Ile
    290                 295                 300

Glu Lys Leu Val Glu Tyr Cys Asp Phe Leu Thr Thr Phe Val His Ala
305                 310                 315                 320

Lys Lys Lys Glu Glu Gly Glu Asp Asp Thr Ala Arg Gln Glu Ile Arg
                325                 330                 335

Lys Ala Trp Val Lys Gly Met Pro Tyr Met Asp Phe Ser Lys Pro Met
            340                 345                 350

Lys Ile Thr Arg Gly Phe Asn Arg Asn Met Leu Phe Leu Ala Ala Leu
        355                 360                 365

Asp Ser Phe Arg Lys Arg Asn Gly Val Asp Val Asp Pro Asn Lys Gly
    370                 375                 380

Lys Trp Lys Glu His Ile Lys Glu Val Thr Glu Lys Leu Lys Lys Ala
385                 390                 395                 400

Gln Thr Glu Asn Gly Gly Gln Pro Cys Gln Val Ser Ile Asp Gly Val
                405                 410                 415
```

-continued

Asn Val Leu Thr Asn Val Asp Tyr Gly Thr Val Asn His Trp Ile Asp
420 425 430

Trp Val Thr Asp Ile Ile Met Val Val Gln Thr Lys Arg Leu Val Lys
435 440 445

Glu Tyr Ala Phe Lys Lys Leu Lys Ser Glu Asn Leu Leu Ala Gly Met
450 455 460

Asn Ser Leu Val Gly Val Leu Arg Cys Tyr Met Tyr Cys Leu Ala Leu
465 470 475 480

Ala Ile Tyr Asp Phe Tyr Glu Gly Thr Ile Asp Gly Phe Lys Lys Gly
485 490 495

Ser Asn Ala Ser Ala Ile Ile Glu Thr Val Ala Gln Met Phe Pro Asp
500 505 510

Phe Arg Arg Glu Leu Val Glu Lys Phe Gly Ile Asp Leu Arg Met Lys
515 520 525

Glu Ile Thr Arg Glu Leu Phe Val Gly Lys Ser Met Thr Ser Lys Phe
530 535 540

Met Glu Glu Gly Glu Tyr Gly Tyr Lys Phe Ala Tyr Gly Trp Arg Arg
545 550 555 560

Asp Gly Phe Ala Val Met Glu Asp Tyr Gly Glu Ile Leu Thr Glu Lys
565 570 575

Val Glu Asp Leu Tyr Lys Gly Val Leu Leu Gly Arg Lys Trp Glu Asp
580 585 590

Glu Val Asp Asp Pro Glu Ser Tyr Phe Tyr Asp Asp Leu Tyr Thr Asn
595 600 605

Glu Pro His Arg Val Phe Leu Ser Ala Gly Lys Asp Val Asp Asn Asn
610 615 620

Ile Thr Leu Arg Ser Ile Ser Gln Ala Glu Thr Thr Tyr Leu Ser Lys
625 630 635 640

Arg Phe Val Ser Tyr Trp Tyr Arg Ile Ser Gln Val Glu Val Thr Lys
645 650 655

Ala Arg Asn Glu Val Leu Asp Met Asn Glu Lys Gln Lys Pro Tyr Phe
660 665 670

Glu Phe Glu Tyr Asp Asp Phe Lys Pro Cys Ser Ile Gly Glu Leu Gly
675 680 685

Ile His Ala Ser Thr Tyr Ile Tyr Gln Asn Leu Leu Val Gly Arg Asn
690 695 700

Arg Gly Glu Glu Ile Leu Asp Ser Lys Glu Leu Val Trp Met Asp Met
705 710 715 720

Ser Leu Leu Asn Phe Gly Ala Val Arg Ser His Asp Arg Cys Trp Ile
725 730 735

Ser Ser Ser Val Ala Ile Glu Val Asn Leu Arg His Ala Leu Ile Val
740 745 750

Arg Ile Phe Ser Arg Phe Asp Met Met Ser Glu Arg Glu Thr Phe Ser
755 760 765

Thr Ile Leu Glu Lys Val Met Glu Asp Val Lys Glu Leu Arg Phe Phe
770 775 780

Pro Thr Tyr Arg His Tyr Tyr Leu Glu Thr Leu Gln Arg Val Phe Asn
785 790 795 800

Asp Glu Arg Arg Leu Glu Val Asp Asp Phe Tyr Met Arg Leu Tyr Asp
805 810 815

Val Gln Thr Arg Glu Gln Ala Leu Asn Thr Phe Thr Asp Phe His Arg
820 825 830

Cys Val Glu Ser Glu Leu Leu Leu Pro Thr Leu Lys Leu Asn Phe Leu
835 840 845

```
Leu Trp Ile Val Phe Glu Met Glu Asn Val Glu Val Asn Ala Ala Tyr
    850                 855                 860

Lys Arg His Pro Leu Leu Ile Ser Thr Ala Lys Gly Leu Arg Val Ile
865                 870                 875                 880

Gly Val Asp Ile Phe Asn Ser Gln Leu Ser Ile Ser Met Ser Gly Trp
                885                 890                 895

Ile Pro Tyr Val Glu Arg Met Cys Ala Glu Ser Lys Val Gln Thr Lys
            900                 905                 910

Leu Thr Ala Asp Glu Leu Lys Leu Lys Arg Trp Phe Ile Ser Tyr Tyr
        915                 920                 925

Thr Thr Leu Lys Leu Asp Arg Arg Ala Glu Pro Arg Met Ser Phe Lys
    930                 935                 940

Phe Glu Gly Leu Ser Thr Trp Ile Gly Ser Asn Cys Gly Gly Val Arg
945                 950                 955                 960

Asp Tyr Val Ile Gln Met Leu Pro Thr Arg Lys Pro Lys Pro Gly Ala
                965                 970                 975

Leu Met Val Val Tyr Ala Arg Asp Ser Arg Ile Glu Trp Ile Glu Ala
            980                 985                 990

Glu Leu Ser Gln Trp Leu Gln Met  Glu Gly Ser Leu Gly  Leu Ile Leu
        995                 1000                1005

Val His  Asp Ser Gly Ile Ile  Asn Lys Ser Val Leu  Arg Ala Arg
    1010                1015                1020

Thr Leu  Lys Ile Tyr Asn Arg  Gly Ser Met Asp Thr  Leu Ile Leu
    1025                1030                1035

Ile Ser  Ser Gly Val Tyr Thr  Phe Gly Asn Lys Phe  Leu Leu Ser
    1040                1045                1050

Lys Leu  Leu Ala Lys Thr Glu
    1055                1060


<210> SEQ ID NO 50
<211> LENGTH: 1566
<212> TYPE: DNA
<213> ORGANISM: artificial sequence
<220> FEATURE:
<223> OTHER INFORMATION: AHSV4-Jane Strain-L2/VP5 gene

<400> SEQUENCE: 50

gttaattttt ccagaagcca tgggaaagtt cacatctttt ttgaagcgcg cgggcaatgc      60

gaccaagagg gcgctgacgt cggattcagc aaagaagatg tataagttgg cggggaaaac     120

gttacagaga gtggtagaaa gtgaagttgg aagtgcagcg atcgatggcg tgatgcaggg     180

ggcgatacaa agcataatac aaggcgaaaa ccttggtgat tcaattaagc aggcggttat     240

tttaaatgtt gcggggacat tggaatcggc gccagacccg ttgagcccag gggagcagct     300

cctttacaat aaggtttctg aaatcgagaa aatggaaaaa gaggatcgag tgattgaaac     360

acacaatgcg aaaatagaag aaaaatttgg taaagattta ttagcgattc gaaagattgt     420

gaaaggcgag gttgatgcag aaaagctgga aggtaacgaa attaagtacg tagaaaaagc     480

gcttagcggt ttgctggaga tagggaaaga tcagtcagaa cgcattacaa agctatatcg     540

cgcgttacaa acagaggaag atttgcggac acgagatgag actagaatga taaacgaata     600

tagagaaaaa tttgacgcgt tgaaagaagc gattgaaatc gagcagcaag cgacacatga     660

tgaggcgatt caagagatgc tcgacttaag cgcggaagta attgagactg cgtcggagga     720

ggtaccaatc ttcggcgctg gggcggcgaa cgttatcgcc acaacccgcg caatacaggg     780

ggggttaaaa ctaaaggaaa ttgttgataa gcttacgggc atagatttga gccatttgaa     840
```

```
ggtggccgac attcatccac acatcattga aaaggcaatg ctacgtgata ctgtaacgga    900

caaagatttg gcgatggcaa ttaagtcaaa agtggatgta attgacgaga tgaacgtaga    960

aacgcagcac gtaatcgatg ccgttctacc gatagttaaa caagaatatg agagacatga   1020

taacaaatat catgttagga tcccaggtgc attgaagata cattcagagc acacgcctaa   1080

gatacatata tatacgaccc catgggattc ggatagcgtc ttcatgtgta gagccattgc   1140

accgcatcat caacaacgaa gctttttcat tggatttgat ctagaaattg aatatgtcca   1200

ttttgaagat acttcagttg agggacatat attacatgga ggggcaataa ccgttgaggg   1260

tagaggattt cgacaggcgt atactgagtt catgaatgca gcgtggggga tgccaacaac   1320

cccagagctc cataaacgta agctacaaag gagtatggga actcatccga tctatatggg   1380

atcgatggat tacgctataa gctacgaaca gctggtttct aacgcgatga gattagttta   1440

tgattccgag ttacaaatgc attgtctccg tgggcctcta aaatttcaac gccgcacgct   1500

aatgaacgcg cttctatatg gtgtgaaaat agcttgaaag cctcacggcg cggagaaaac   1560

acatac                                                              1566
```

<210> SEQ ID NO 51
<211> LENGTH: 505
<212> TYPE: PRT
<213> ORGANISM: artificial sequence
<220> FEATURE:
<223> OTHER INFORMATION: AHSV4-Jane Strain-VP5 predicted AA sequence

<400> SEQUENCE: 51

```
Met Gly Lys Phe Thr Ser Phe Leu Lys Arg Ala Gly Asn Ala Thr Lys
1               5                   10                  15

Arg Ala Leu Thr Ser Asp Ser Ala Lys Lys Met Tyr Lys Leu Ala Gly
            20                  25                  30

Lys Thr Leu Gln Arg Val Val Glu Ser Glu Val Gly Ser Ala Ala Ile
        35                  40                  45

Asp Gly Val Met Gln Gly Ala Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Ile Glu Lys Met Glu Lys Glu Asp Arg Val Ile
            100                 105                 110

Glu Thr His Asn Ala Lys Ile Glu Glu Lys Phe Gly Lys Asp Leu Leu
        115                 120                 125

Ala Ile Arg Lys Ile Val Lys Gly Glu Val Asp Ala Glu Lys Leu Glu
    130                 135                 140

Gly Asn Glu Ile Lys Tyr Val Glu Lys Ala Leu Ser Gly Leu Leu Glu
145                 150                 155                 160

Ile Gly Lys Asp Gln Ser Glu Arg Ile Thr Lys Leu Tyr Arg Ala Leu
                165                 170                 175

Gln Thr Glu Glu Asp Leu Arg Thr Arg Asp Glu Thr Arg Met Ile Asn
            180                 185                 190

Glu Tyr Arg Glu Lys Phe Asp Ala Leu Lys Glu Ala Ile Glu Ile Glu
        195                 200                 205

Gln Gln Ala Thr His Asp Glu Ala Ile Gln Glu Met Leu Asp Leu Ser
    210                 215                 220

Ala Glu Val Ile Glu Thr Ala Ser Glu Glu Val Pro Ile Phe Gly Ala
```

```
225                 230                 235                 240

Gly Ala Ala Asn Val Ile Ala Thr Thr Arg Ala Ile Gln Gly Gly Leu
                245                 250                 255

Lys Leu Lys Glu Ile Val Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Arg Asp Thr Val Thr Asp Lys Asp Leu Ala Met Ala Ile Lys Ser Lys
    290                 295                 300

Val Asp Val Ile Asp Glu Met Asn Val Glu Thr Gln His Val Ile Asp
305                 310                 315                 320

Ala Val Leu Pro Ile Val Lys Gln Glu Tyr Glu Arg His Asp Asn Lys
                325                 330                 335

Tyr His Val Arg Ile Pro Gly Ala Leu Lys Ile His Ser Glu His Thr
            340                 345                 350

Pro Lys Ile His Ile Tyr Thr Thr Pro Trp Asp Ser Asp Ser Val Phe
        355                 360                 365

Met Cys Arg Ala Ile Ala Pro His His Gln Gln Arg Ser Phe Phe Ile
    370                 375                 380

Gly Phe Asp Leu Glu Ile Glu Tyr Val His Phe Glu Asp Thr Ser Val
385                 390                 395                 400

Glu Gly His Ile Leu His Gly Gly Ala Ile Thr Val Glu Gly Arg Gly
                405                 410                 415

Phe Arg Gln Ala Tyr Thr Glu Phe Met Asn Ala Ala Trp Gly Met Pro
            420                 425                 430

Thr Thr Pro Glu Leu His Lys Arg Lys Leu Gln Arg Ser Met Gly Thr
        435                 440                 445

His Pro Ile Tyr Met Gly Ser Met Asp Tyr Ala Ile Ser Tyr Glu Gln
    450                 455                 460

Leu Val Ser Asn Ala Met Arg Leu Val Tyr Asp Ser Glu Leu Gln Met
465                 470                 475                 480

His Cys Leu Arg Gly Pro Leu Lys Phe Gln Arg Arg Thr Leu Met Asn
                485                 490                 495

Ala Leu Leu Tyr Gly Val Lys Ile Ala
            500                 505
```

<210> SEQ ID NO 52
<211> LENGTH: 505
<212> TYPE: PRT
<213> ORGANISM: artificial sequence
<220> FEATURE:
<223> OTHER INFORMATION: AHSV4-VP5 - B4UUP0

<400> SEQUENCE: 52

```
Met Gly Lys Phe Thr Ser Phe Leu Lys Arg Ala Gly Asn Ala Thr Lys
1               5                   10                  15

Arg Ala Leu Thr Ser Asp Ser Ala Lys Lys Met Tyr Lys Leu Ala Gly
            20                  25                  30

Lys Thr Leu Gln Arg Val Val Glu Ser Glu Val Gly Ser Ala Ala Ile
        35                  40                  45

Asp Gly Val Met Gln Gly Ala Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95
```

```
Asn Lys Val Ser Glu Ile Glu Lys Met Glu Lys Glu Asp Arg Val Ile
            100                 105                 110

Glu Thr His Asn Ala Lys Ile Glu Glu Lys Phe Gly Lys Asp Leu Leu
        115                 120                 125

Ala Ile Arg Lys Ile Val Lys Gly Glu Val Asp Ala Glu Lys Leu Glu
    130                 135                 140

Gly Asn Glu Ile Lys Tyr Val Glu Lys Ala Leu Ser Gly Leu Leu Glu
145                 150                 155                 160

Ile Gly Lys Asp Gln Ser Glu Arg Ile Thr Lys Leu Tyr Arg Ala Leu
                165                 170                 175

Gln Thr Glu Glu Asp Leu Arg Thr Arg Asp Glu Thr Arg Met Ile Asn
            180                 185                 190

Glu Tyr Arg Glu Lys Phe Asp Ala Leu Lys Glu Ala Ile Glu Ile Glu
        195                 200                 205

Gln Gln Ala Thr His Asp Glu Ala Ile Gln Glu Met Leu Asp Leu Ser
    210                 215                 220

Ala Glu Val Ile Glu Thr Ala Ser Glu Glu Val Pro Ile Phe Gly Ala
225                 230                 235                 240

Gly Ala Ala Asn Val Ile Ala Thr Thr Arg Ala Ile Gln Gly Gly Leu
                245                 250                 255

Lys Leu Lys Glu Ile Val Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Arg Asp Thr Val Thr Asp Lys Asp Leu Ala Met Ala Ile Lys Ser Lys
    290                 295                 300

Val Asp Val Ile Asp Glu Met Asn Val Glu Thr Gln His Val Ile Asp
305                 310                 315                 320

Ala Val Leu Pro Ile Val Lys Gln Glu Tyr Glu Lys His Asp Asn Lys
                325                 330                 335

Tyr His Val Arg Ile Pro Gly Ala Leu Lys Ile His Ser Glu His Thr
            340                 345                 350

Pro Lys Ile His Ile Tyr Thr Thr Pro Trp Asp Ser Asp Ser Val Phe
        355                 360                 365

Met Cys Arg Ala Ile Ala Pro His His Gln Gln Arg Ser Phe Phe Ile
    370                 375                 380

Gly Phe Asp Leu Glu Ile Glu Tyr Val His Phe Glu Asp Thr Ser Val
385                 390                 395                 400

Glu Gly His Ile Leu His Gly Gly Ala Ile Thr Val Glu Gly Arg Gly
                405                 410                 415

Phe Arg Gln Ala Tyr Thr Glu Phe Met Asn Ala Ala Trp Gly Met Pro
            420                 425                 430

Thr Thr Pro Glu Leu His Lys Arg Lys Leu Gln Arg Ser Met Gly Thr
        435                 440                 445

His Pro Ile Tyr Met Gly Ser Met Asp Tyr Ala Ile Ser Tyr Glu Gln
    450                 455                 460

Leu Val Ser Asn Ala Met Arg Leu Val Tyr Asp Ser Glu Leu Gln Met
465                 470                 475                 480

His Cys Leu Arg Gly Pro Leu Lys Phe Gln Arg Arg Thr Leu Met Asn
                485                 490                 495

Ala Leu Leu Tyr Gly Val Lys Ile Ala
            500                 505
```

<210> SEQ ID NO 53
<211> LENGTH: 505
<212> TYPE: PRT
<213> ORGANISM: artificial sequence
<220> FEATURE:
<223> OTHER INFORMATION: AHSV4-VP5 - B4UUP1

<400> SEQUENCE: 53

Met Gly Lys Phe Thr Ser Phe Leu Lys Arg Thr Gly Ser Ala Thr Lys
1 5 10 15

Lys Ala Leu Thr Ser Asp Ala Ala Lys Arg Met Tyr Lys Met Ala Gly
20 25 30

Lys Thr Leu Gln Lys Val Val Glu Ser Glu Val Gly Ser Ala Ala Ile
35 40 45

Asp Gly Val Met Gln Gly Thr Ile Gln Ser Ile Ile Gln Gly Glu Asn
50 55 60

Leu Gly Asp Ser Ile Lys Gln Ala Val Ile Leu Asn Val Ala Gly Thr
65 70 75 80

Leu Glu Ser Ala Pro Asp Pro Leu Ser Pro Gly Glu Gln Leu Leu Tyr
85 90 95

Asn Lys Val Ser Glu Ile Glu Arg Ala Glu Lys Glu Asp Arg Val Ile
100 105 110

Glu Ile His Asn Lys Lys Ile Val Glu Lys Tyr Gly Glu Asp Leu Leu
115 120 125

Lys Ile Arg Lys Ile Met Lys Gly Glu Ala Glu Ala Glu Gln Leu Glu
130 135 140

Gly Lys Glu Met Glu Tyr Val Glu Lys Ala Leu Arg Gly Met Leu Lys
145 150 155 160

Ile Gly Lys Asp Gln Ser Glu Arg Ile Thr Arg Leu Tyr Arg Ala Leu
165 170 175

Gln Thr Glu Glu Asp Leu Arg Thr Ser Asp Glu Thr Arg Ile Ile Ser
180 185 190

Glu Tyr Arg Glu Lys Phe Asp Ala Leu Lys Gln Ala Ile Glu Leu Glu
195 200 205

Gln Gln Ala Thr His Glu Glu Ala Val Gln Glu Met Leu Asp Leu Ser
210 215 220

Ala Glu Val Ile Glu Thr Ala Ala Glu Glu Val Pro Val Phe Gly Ala
225 230 235 240

Gly Ala Ala Asn Val Val Ala Thr Thr Arg Ala Ile Gln Gly Gly Leu
245 250 255

Lys Leu Lys Glu Ile Ile Asp Lys Leu Thr Gly Ile Asp Leu Ser His
260 265 270

Leu Lys Val Ala Asp Ile His Pro His Ile Ile Glu Lys Ala Met Leu
275 280 285

Lys Val Lys Ile Pro Asp Asn Glu Leu Ala Met Ala Ile Lys Ser Lys
290 295 300

Val Glu Val Val Asp Glu Met Asn Thr Glu Thr Glu His Val Ile Glu
305 310 315 320

Ser Ile Met Pro Leu Val Lys Lys Glu Tyr Glu Lys His Asp Asn Lys
325 330 335

Tyr His Val Asn Ile Pro Ser Ala Leu Lys Ile His Ser Glu Gln Thr
340 345 350

Pro Lys Val His Ile Tyr Thr Thr Pro Trp Asp Ser Asp Lys Val Phe
355 360 365

Ile Cys Arg Cys Ile Ala Pro His His Gln Gln Lys Ser Phe Met Ile
370 375 380

Gly Phe Asp Leu Glu Ile Glu Phe Val Phe Tyr Glu Asp Thr Ser Val
385 390 395 400

Glu Gly His Ile Met His Gly Gly Ala Val Ser Ile Glu Gly Arg Gly
405 410 415

Phe Arg Gln Ala Tyr Ser Glu Phe Met Asn Ala Ala Trp Ser Met Pro
420 425 430

Leu Thr Pro Glu Leu His Lys Arg Arg Leu Gln Arg Ser Leu Gly Ser
435 440 445

His Pro Ile Tyr Met Gly Ser Met Asp Tyr Thr Ile Ser Tyr Glu Gln
450 455 460

Leu Val Ser Asn Ala Met Lys Leu Val Tyr Asp Thr Asp Leu Gln Met
465 470 475 480

His Cys Leu Arg Gly Pro Leu Lys Phe Gln Arg Arg Thr Leu Met Asn
485 490 495

Ala Leu Leu Phe Gly Val Lys Val Ala
500 505

<210> SEQ ID NO 54
<211> LENGTH: 505
<212> TYPE: PRT
<213> ORGANISM: Artificial Sequence
<220> FEATURE:
<223> OTHER INFORMATION: AHSV4-VP5 - B4UUP2

<400> SEQUENCE: 54

Met Gly Lys Phe Thr Ser Phe Leu Lys Arg Ala Gly Ser Ala Thr Lys
1 5 10 15

Lys Ala Leu Thr Ser Asp Thr Ala Lys Arg Met Tyr Lys Met Ala Gly
20 25 30

Lys Thr Leu Gln Lys Val Val Glu Ser Glu Val Gly Ser Ala Ala Ile
35 40 45

Asp Gly Val Met Gln Gly Thr Ile Gln Ser Ile Ile Gln Gly Glu Asn
50 55 60

Leu Gly Asp Ser Ile Arg Gln Ala Val Ile Leu Asn Val Ala Gly Thr
65 70 75 80

Leu Glu Ser Ala Pro Asp Pro Leu Ser Pro Gly Glu Gln Leu Leu Tyr
85 90 95

Asn Lys Val Ala Glu Leu Glu Arg Ala Glu Lys Glu Asp Arg Val Ile
100 105 110

Glu Thr His Asn Glu Lys Ile Ile Gln Glu Tyr Gly Lys Asp Leu Leu
115 120 125

Lys Ile Arg Lys Ile Met Lys Gly Glu Ala Lys Ala Glu Gln Leu Glu
130 135 140

Gly Lys Glu Ile Glu Tyr Val Glu Met Ala Leu Lys Gly Met Leu Lys
145 150 155 160

Ile Gly Lys Asp Gln Ser Glu Arg Ile Thr Gln Leu Tyr Arg Ala Leu
165 170 175

Gln Thr Glu Glu Asp Leu Arg Thr Ser Asp Glu Thr Arg Met Ile Asn
180 185 190

Glu Tyr Arg Glu Lys Phe Asp Ala Leu Lys Gln Ala Ile Glu Leu Glu
195 200 205

Gln Gln Ala Thr His Glu Glu Ala Val Gln Glu Met Leu Asp Leu Ser
210 215 220

Ala Glu Val Ile Glu Thr Ala Ala Glu Glu Val Pro Ile Phe Gly Ala
225 230 235 240

```
Gly Ala Ala Asn Val Val Ala Thr Thr Arg Ala Val Gln Gly Gly Leu
                245                 250                 255

Lys Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Ile Leu
        275                 280                 285

Lys Asp Lys Ile Pro Asp Ser Glu Leu Ala Met Ala Ile Lys Ser Lys
    290                 295                 300

Val Glu Val Ile Asp Glu Met Asn Thr Glu Thr Glu His Val Ile Lys
305                 310                 315                 320

Ser Ile Met Pro Leu Val Lys Lys Glu Tyr Glu Lys His Asp Asn Lys
                325                 330                 335

Tyr His Val Asn Ile Pro Ser Val Leu Lys Ile His Ser Glu His Thr
            340                 345                 350

Pro Lys Val His Ile Tyr Thr Thr Pro Trp Asp Ser Asp Lys Val Phe
        355                 360                 365

Ile Cys Arg Cys Ile Ala Pro His His Gln Gln Lys Ser Phe Met Ile
    370                 375                 380

Gly Phe Asp Leu Glu Ile Glu Phe Val Phe Tyr Glu Asp Thr Ser Val
385                 390                 395                 400

Glu Gly His Ile Met His Gly Gly Ala Val Ser Ile Glu Gly Arg Gly
                405                 410                 415

Phe Arg Gln Ala Tyr Ser Glu Phe Met Asn Ala Ala Trp Ser Met Pro
            420                 425                 430

Ser Thr Pro Glu Leu His Lys Arg Arg Leu Gln Arg Ser Leu Gly Ser
        435                 440                 445

His Pro Ile Tyr Met Gly Ser Met Asp Tyr Thr Val Ser Tyr Asp Gln
    450                 455                 460

Leu Val Ser Asn Ala Met Lys Leu Val Tyr Asp Thr Glu Leu Gln Met
465                 470                 475                 480

His Cys Leu Arg Gly Pro Leu Lys Phe Gln Arg Arg Thr Leu Met Asn
                485                 490                 495

Ala Leu Leu Phe Gly Val Lys Ile Ala
            500                 505
```

<210> SEQ ID NO 55
<211> LENGTH: 505
<212> TYPE: PRT
<213> ORGANISM: Artificial Sequence
<220> FEATURE:
<223> OTHER INFORMATION: AHSV4-VP5 - B4UUP3

<400> SEQUENCE: 55

```
Met Gly Lys Phe Thr Ser Phe Leu Lys Arg Ala Gly Ser Ala Thr Lys
1               5                   10                  15

Lys Ala Leu Thr Ser Asp Ala Ala Lys Arg Met Tyr Lys Met Ala Gly
            20                  25                  30

Lys Ala Leu Gln Lys Val Val Glu Ser Glu Val Gly Ser Ala Ala Ile
        35                  40                  45

Asp Gly Val Met Gln Gly Thr Phe Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Ile Glu Arg Ala Glu Lys Glu Asp Arg Val Ile
```

```
            100                 105                 110

Glu Thr His Asn Lys Lys Ile Val Glu Lys Tyr Gly Glu Asp Leu Leu
        115                 120                 125

Lys Ile Arg Lys Ile Met Lys Gly Glu Ala Glu Ala Glu Gln Leu Glu
    130                 135                 140

Gly Lys Glu Met Glu Tyr Val Glu Lys Ala Leu Arg Gly Met Leu Lys
145                 150                 155                 160

Ile Gly Lys Asp Gln Ser Glu Arg Ile Thr Arg Leu Tyr Arg Ala Leu
                165                 170                 175

Gln Thr Glu Glu Asp Leu Arg Thr Ser Asp Glu Thr Arg Ile Ile Ser
            180                 185                 190

Glu Tyr Arg Glu Lys Phe Asp Ala Leu Lys Gln Ala Ile Glu Leu Glu
        195                 200                 205

Gln Gln Ala Thr His Glu Glu Ala Val Gln Glu Met Leu Asp Leu Ser
    210                 215                 220

Ala Glu Val Ile Glu Thr Ala Ala Glu Glu Val Pro Val Phe Gly Ala
225                 230                 235                 240

Gly Ala Ala Asn Val Val Ala Thr Thr Arg Ala Ile Gln Gly Gly Leu
                245                 250                 255

Lys Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Lys Asp Lys Ile Pro Asp Asn Glu Leu Ala Met Ala Ile Lys Ser Lys
    290                 295                 300

Val Glu Val Val Asp Glu Met Asn Thr Glu Met Glu His Val Ile Glu
305                 310                 315                 320

Ser Ile Met Pro Leu Val Lys Lys Glu Tyr Glu Lys His Asp Asn Lys
                325                 330                 335

Tyr His Val Asn Ile Pro Ser Ala Leu Lys Ile His Ser Glu His Thr
            340                 345                 350

Pro Lys Val His Ile Tyr Thr Thr Pro Trp Asp Ser Asp Lys Val Phe
        355                 360                 365

Ile Cys Arg Cys Ile Ala Pro His His Gln Gln Arg Ser Phe Met Ile
    370                 375                 380

Gly Phe Asp Leu Gly Ile Glu Phe Val Phe Tyr Glu Asp Thr Ser Val
385                 390                 395                 400

Glu Gly His Ile Met His Gly Gly Ala Val Ser Ile Glu Gly Arg Gly
                405                 410                 415

Phe Arg Gln Ala Tyr Ser Glu Phe Met Asn Ala Ala Trp Ser Met Pro
            420                 425                 430

Ser Thr Pro Glu Leu His Lys Arg Arg Leu Gln Arg Ser Leu Gly Ser
        435                 440                 445

His Pro Ile Tyr Met Gly Ser Met Asp Tyr Thr Ile Ser Tyr Glu Gln
    450                 455                 460

Leu Val Ser Asn Ala Met Lys Leu Val Tyr Asp Thr Asp Leu Gln Met
465                 470                 475                 480

His Cys Leu Arg Gly Pro Leu Lys Leu Gln Arg Arg Thr Leu Met Asn
                485                 490                 495

Ala Leu Leu Phe Gly Val Lys Val Ala
            500                 505
```

<210> SEQ ID NO 56
<211> LENGTH: 505

```
<212> TYPE: PRT
<213> ORGANISM: Artificial Sequence
<220> FEATURE:
<223> OTHER INFORMATION: AHSV4-VP5 - B4XIE4

<400> SEQUENCE: 56

Met Gly Lys Phe Thr Ser Phe Leu Lys Arg Ala Gly Ser Ala Thr Lys
1               5                   10                  15

Lys Ala Leu Thr Ser Asp Ala Ala Lys Arg Met Tyr Lys Met Ala Gly
            20                  25                  30

Lys Thr Leu Gln Lys Val Val Asp Ser Glu Val Gly Ser Ala Ala Ile
        35                  40                  45

Asp Gly Val Met Gln Gly Thr Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Pro Pro Asp Pro Leu Ser Pro Gly Glu Gln Leu Leu Tyr
                85                  90                  95

Asn Lys Val Ser Lys Ile Glu Arg Ala Glu Lys Glu Asp Arg Val Ile
            100                 105                 110

Glu Thr His Asn Glu Lys Ile Ile Glu Lys Tyr Gly Glu Asp Leu Leu
        115                 120                 125

Lys Ile Arg Lys Ile Met Lys Gly Glu Ala Glu Ala Glu Gln Leu Glu
    130                 135                 140

Gly Lys Glu Met Glu Tyr Val Glu Lys Ala Leu Lys Gly Met Leu Lys
145                 150                 155                 160

Ile Gly Lys Asp Gln Ser Glu Arg Ile Thr Arg Leu Tyr Arg Ala Leu
                165                 170                 175

Gln Thr Glu Glu Asp Leu Arg Thr Ser Asp Glu Thr Arg Met Ile Ser
            180                 185                 190

Glu Tyr Arg Glu Lys Phe Asp Ala Leu Lys Gln Ala Ile Glu Leu Glu
        195                 200                 205

Gln Gln Ala Thr His Glu Glu Ala Val Gln Glu Met Leu Asp Leu Ser
    210                 215                 220

Ala Glu Val Ile Glu Thr Ala Ala Glu Asp Leu Pro Ile Phe Gly Ala
225                 230                 235                 240

Gly Ala Ala Asn Val Val Ala Thr Thr Arg Ala Ile Gln Gly Gly Leu
                245                 250                 255

Lys Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Lys Asp Lys Ile Pro Asp Asn Glu Leu Ala Met Ala Ile Lys Ser Lys
    290                 295                 300

Val Glu Val Ile Asp Glu Met Asn Thr Glu Thr Glu His Val Ile Glu
305                 310                 315                 320

Ser Ile Met Pro Leu Val Lys Lys Glu Tyr Glu Lys His Asp Asn Lys
                325                 330                 335

Tyr His Val Asn Ile Pro Ser Ala Leu Lys Ile His Ser Glu His Thr
            340                 345                 350

Pro Lys Val His Ile Tyr Thr Thr Pro Trp Asp Ser Asp Lys Val Phe
        355                 360                 365

Ile Cys Arg Cys Ile Ala Pro His His Gln Gln Arg Ser Phe Met Ile
    370                 375                 380

Gly Phe Asp Leu Glu Ile Glu Phe Val Phe Tyr Glu Asp Thr Ser Val
```

```
385                 390                 395                 400

Glu Gly His Ile Met His Gly Gly Ala Val Ser Ile Glu Gly Arg Gly
                405                 410                 415

Phe Arg Gln Ala Tyr Ser Glu Phe Met Asn Ala Ala Trp Ser Met Pro
            420                 425                 430

Ser Thr Pro Glu Leu His Lys Arg Arg Leu Gln Arg Ser Leu Gly Ser
        435                 440                 445

His Pro Ile Tyr Met Gly Ser Met Asp Tyr Thr Val Ser Tyr Glu Gln
    450                 455                 460

Leu Val Ser Asn Ala Met Lys Leu Val Tyr Asp Thr Asp Leu Gln Met
465                 470                 475                 480

His Cys Leu Arg Gly Pro Leu Lys Phe Gln Arg Arg Thr Leu Met Asn
                485                 490                 495

Ala Leu Leu Phe Gly Val Lys Val Ala
            500                 505


<210> SEQ ID NO 57
<211> LENGTH: 505
<212> TYPE: PRT
<213> ORGANISM: Artificial Sequence
<220> FEATURE:
<223> OTHER INFORMATION: AHSV4-VP5 - B4XIE5

<400> SEQUENCE: 57

Met Gly Lys Phe Thr Ser Phe Leu Lys Arg Ala Gly Ser Ala Thr Lys
1               5                   10                  15

Lys Ala Leu Thr Ser Asp Ala Ala Lys Arg Met Tyr Lys Met Ala Gly
            20                  25                  30

Lys Thr Leu Gln Lys Val Val Glu Ser Glu Val Gly Ser Ala Ala Ile
        35                  40                  45

Asp Gly Val Met Gln Gly Thr Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Ile Glu Arg Ala Glu Lys Glu Asp Arg Val Ile
            100                 105                 110

Glu Thr His Asn Lys Lys Ile Val Glu Lys Tyr Gly Glu Asp Leu Leu
        115                 120                 125

Lys Ile Arg Lys Ile Met Lys Gly Glu Ala Glu Ala Glu Gln Leu Glu
    130                 135                 140

Gly Lys Glu Met Glu Tyr Val Glu Lys Ala Leu Arg Gly Met Leu Lys
145                 150                 155                 160

Ile Gly Lys Asp Gln Ser Glu Arg Ile Thr Arg Leu Tyr Arg Ala Leu
                165                 170                 175

Gln Thr Glu Glu Asp Leu Arg Thr Ser Asp Glu Thr Arg Ile Ile Ser
            180                 185                 190

Glu Tyr Arg Glu Lys Phe Asp Ala Leu Lys Gln Ala Ile Glu Leu Glu
        195                 200                 205

Gln Gln Ala Thr His Glu Glu Ala Val Gln Glu Met Leu Asp Leu Ser
    210                 215                 220

Ala Glu Val Ile Glu Thr Ala Ala Glu Glu Val Pro Val Phe Gly Ala
225                 230                 235                 240

Gly Ala Ala Asn Val Val Ala Thr Thr Arg Ala Ile Gln Gly Gly Leu
                245                 250                 255
```

Lys Leu Lys Glu Ile Ile Asp Lys Leu Thr Gly Ile Asp Leu Ser His
260 265 270

Leu Lys Val Ala Asp Ile His Pro His Ile Ile Glu Lys Ala Met Leu
275 280 285

Lys Asp Lys Ile Pro Asp Asn Glu Leu Ala Met Ala Ile Lys Ser Lys
290 295 300

Val Glu Val Val Asp Glu Met Asn Thr Glu Thr Glu His Val Ile Glu
305 310 315 320

Ser Ile Met Pro Leu Val Lys Lys Glu Tyr Glu Lys His Asp Asn Lys
325 330 335

Tyr His Val Asn Ile Pro Ser Ala Leu Lys Ile His Ser Glu His Thr
340 345 350

Pro Lys Val His Ile Tyr Thr Thr Pro Trp Asp Ser Asp Lys Val Phe
355 360 365

Ile Cys Arg Cys Ile Ala Pro His His Gln Gln Arg Ser Phe Met Ile
370 375 380

Gly Phe Asp Leu Glu Ile Glu Phe Val Phe Tyr Glu Asp Thr Ser Val
385 390 395 400

Glu Gly His Ile Met His Gly Gly Ala Val Ser Ile Glu Gly Arg Gly
405 410 415

Phe Arg Gln Ala Tyr Ser Glu Phe Met Asn Ala Ala Trp Ser Met Pro
420 425 430

Ser Thr Pro Glu Leu His Lys Arg Arg Leu Gln Arg Ser Leu Gly Ser
435 440 445

His Pro Ile Tyr Met Gly Ser Met Asp Tyr Thr Ile Ser Tyr Glu Gln
450 455 460

Leu Val Ser Asn Ala Met Lys Leu Val Tyr Asp Thr Asp Leu Gln Met
465 470 475 480

His Cys Leu Arg Gly Pro Leu Lys Phe Gln Arg Arg Thr Leu Met Asn
485 490 495

Ala Leu Leu Phe Gly Val Lys Val Ala
500 505

<210> SEQ ID NO 58
<211> LENGTH: 505
<212> TYPE: PRT
<213> ORGANISM: Artificial Sequence
<220> FEATURE:
<223> OTHER INFORMATION: AHSV4-VP5 - B4XIE7

<400> SEQUENCE: 58

Met Gly Lys Phe Thr Ser Phe Leu Lys Arg Ala Gly Asn Ala Thr Lys
1 5 10 15

Arg Ala Leu Thr Ser Asp Ser Ala Lys Lys Met Tyr Lys Leu Ala Gly
20 25 30

Lys Thr Leu Gln Arg Val Val Glu Ser Glu Val Gly Ser Ala Ala Ile
35 40 45

Asp Gly Val Met Gln Gly Ala Ile Gln Ser Ile Ile Gln Gly Glu Asn
50 55 60

Leu Gly Asp Ser Ile Lys Gln Ala Val Ile Leu Asn Val Ala Gly Thr
65 70 75 80

Leu Glu Ser Ala Pro Asp Pro Leu Ser Pro Gly Glu Arg Leu Leu Tyr
85 90 95

Asn Lys Val Ser Glu Ile Glu Lys Met Glu Lys Glu Asp Arg Val Ile
100 105 110

```
Glu Thr His Asn Ala Lys Ile Glu Glu Lys Phe Gly Lys Asp Leu Leu
        115                 120                 125

Ala Ile Arg Lys Ile Val Lys Gly Glu Val Asp Ala Glu Lys Leu Glu
    130                 135                 140

Gly Asn Glu Ile Lys Tyr Val Glu Lys Ala Leu Ser Gly Leu Leu Glu
145                 150                 155                 160

Ile Gly Lys Asp Gln Ser Glu Arg Ile Thr Lys Leu Tyr Arg Ala Leu
                165                 170                 175

Gln Thr Glu Glu Asp Leu Arg Thr Arg Asp Glu Thr Arg Met Ile Asn
            180                 185                 190

Glu Tyr Arg Glu Lys Phe Asp Ala Leu Lys Glu Ala Ile Glu Ile Glu
        195                 200                 205

Gln Gln Ala Thr His Asp Glu Ala Ile Gln Glu Met Leu Asp Leu Ser
    210                 215                 220

Ala Glu Val Ile Glu Thr Ala Ser Glu Glu Val Pro Ile Phe Gly Ala
225                 230                 235                 240

Gly Ala Ala Asn Val Ile Ala Thr Thr Arg Ala Ile Gln Gly Gly Leu
                245                 250                 255

Lys Leu Lys Glu Ile Val Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Arg Asp Thr Val Thr Asp Lys Asp Leu Ala Met Ala Ile Lys Ser Lys
    290                 295                 300

Val Asp Val Ile Asp Glu Met Asn Val Glu Thr Gln His Val Ile Asp
305                 310                 315                 320

Ala Val Leu Pro Ile Val Lys Gln Glu Tyr Glu Lys His Asp Asn Lys
                325                 330                 335

Tyr His Val Arg Ile Pro Gly Ala Leu Lys Ile His Ser Glu His Thr
            340                 345                 350

Pro Lys Ile His Ile Tyr Thr Thr Pro Trp Asp Ser Asp Ser Val Phe
        355                 360                 365

Met Cys Arg Ala Ile Ala Pro His His Gln Gln Arg Ser Phe Phe Ile
    370                 375                 380

Gly Phe Asp Leu Glu Ile Glu Tyr Val His Phe Glu Asp Thr Ser Val
385                 390                 395                 400

Glu Gly His Ile Leu His Gly Gly Ala Ile Thr Val Glu Gly Arg Gly
                405                 410                 415

Phe Arg Gln Ala Tyr Thr Glu Phe Met Asn Ala Ala Trp Gly Met Pro
            420                 425                 430

Thr Thr Pro Glu Leu His Lys Arg Lys Leu Gln Arg Ser Met Gly Thr
        435                 440                 445

His Pro Ile Tyr Met Gly Ser Met Asp Tyr Ala Ile Ser Tyr Glu Gln
    450                 455                 460

Leu Val Ser Asn Ala Met Arg Leu Val Tyr Asp Ser Glu Leu Gln Met
465                 470                 475                 480

His Cys Leu Arg Gly Pro Leu Lys Phe Gln Arg Arg Thr Leu Met Asn
                485                 490                 495

Ala Leu Leu Tyr Gly Val Lys Ile Ala
            500                 505
```

<210> SEQ ID NO 59
<211> LENGTH: 1057
<212> TYPE: PRT
<213> ORGANISM: Artificial Sequence

<220> FEATURE:
<223> OTHER INFORMATION: AHSV4-VP2 - B4UUN4_9REOV

<400> SEQUENCE: 59

```
Met Ala Ser Glu Phe Gly Ile Leu Leu Thr Ile Gln Ile Tyr Asp Gln
1               5                   10                  15

Thr Tyr Glu Lys Glu Lys Cys Asp Val Ile Ile Thr Ala Glu Asn Ala
            20                  25                  30

Val Arg Arg Val Glu Val Ala Gly Val Tyr Gly Tyr Glu Trp Gly Ala
        35                  40                  45

Thr Asn His Arg Leu Gly Leu Cys Glu Ile Glu Asn Thr Lys Ser Ile
    50                  55                  60

Gly Arg Met Ile Tyr Glu Gln Ile Arg Cys Glu Gly Ala Tyr Pro Ile
65                  70                  75                  80

Phe Pro His Tyr Ile Thr Asp Thr Leu Lys Tyr Gly Lys Ser Ile Asp
                85                  90                  95

Arg Asn Asp Asn Gln Ile Arg Val Asp Arg Asp Asp Glu Arg Leu Arg
            100                 105                 110

Lys Ile Lys Ile Gln Pro Tyr Phe Gly Glu Met Tyr Phe Ser Pro Glu
        115                 120                 125

Asn Tyr Ile Thr Val Phe Cys Lys Arg Gln Ala Ile Ser Gly Gln Ile
    130                 135                 140

Glu Val Ser Arg Ser Ile Ile Gly Arg Arg Met Lys Tyr Glu Glu Ser
145                 150                 155                 160

Ala Glu Gln Thr Lys Gly Thr Ile Asn Ala Asn Lys Tyr Arg Leu Leu
                165                 170                 175

Glu Lys Trp Arg Asp Leu Ala Tyr Glu Gln Ile Glu Met Glu Gly Ser
            180                 185                 190

Ser Glu Arg Cys Leu Thr His Asn Thr Asp Pro Ile Tyr Gln Leu Ile
        195                 200                 205

Lys Lys Met Arg Phe Gly Met Met Tyr Pro Val His Tyr Ile Leu Asn
    210                 215                 220

Asp Lys Tyr Lys Val Val Gln Glu Arg Ala Asp Met Gly Ile Glu Lys
225                 230                 235                 240

Trp Leu Leu Gln Lys Ile Gly Arg Gly Thr Gln Arg Arg Lys Ala Asp
                245                 250                 255

Asp Gly Asp Asn Asp Thr Leu Leu Gln Leu Glu Arg Met Met Ser Ser
            260                 265                 270

Glu Glu Leu Glu Arg Pro Val Ile Glu Ser Val Ile Arg Phe Gly Ser
        275                 280                 285

Leu Tyr Asn Ala His Ala Gly Lys Lys Thr Gly Asp Ile Pro Leu Glu
    290                 295                 300

Val Leu Ile Lys Tyr Cys Asp Ser Leu Thr Thr Phe Val His Lys Lys
305                 310                 315                 320

Asn Arg Glu Gly Gly Asp Asn Gln Thr Ala Arg Asp Glu Ile Arg Arg
                325                 330                 335

Ala Met Val Lys Asn Ile Pro Ser Met Lys Gln Glu Asn Gln Met Lys
            340                 345                 350

Val Thr Pro Asn Ile Arg Asn Phe Leu Phe Phe Ala Tyr Leu Asn Gly
        355                 360                 365

Phe Lys Arg Asn Asn Gly Val Asp Ile Asp Pro Asn Asn Gly Thr Trp
    370                 375                 380

Ser Lys His Lys Thr Glu Val Lys Lys Ile Leu Asp Glu Glu Gln Lys
385                 390                 395                 400
```

```
Lys Asn Glu Asn Lys Pro Leu Lys Val Leu Ile Asp Gly Ala Tyr Ile
                405                 410                 415

Ser Thr Asp Ala Glu Tyr Gly Thr Val Ala His Trp Val Asp Trp Val
            420                 425                 430

Val Asp Ile Ile Met Thr Thr Gln Val Ser Arg Met Ile Lys Glu Tyr
        435                 440                 445

Asn Phe Ile Arg Leu Lys Lys Asp Gln Leu Ile Ser Gly Met Asn Lys
    450                 455                 460

Leu Glu Asp Gly Val Lys Cys Tyr Ala Tyr Cys Leu Ile Leu Ala Leu
465                 470                 475                 480

Tyr Asp Phe His Gly Arg Glu Leu Asp Gly Phe Ala Gln Gly Thr Arg
                485                 490                 495

Thr Ala Ala Ile Val Glu Thr Val Ala Arg Met Phe Pro Asp Phe Arg
            500                 505                 510

Ser Glu Val Ser Glu Lys Phe Gly Ile Asp Leu Ala Val Ser Glu Glu
        515                 520                 525

Ser Asp Glu Leu Phe Val Lys Lys Thr Met Val Ser Ser Phe Ser Asp
    530                 535                 540

Ser Gly Glu Met Gly Tyr Lys Phe Ile Phe Gly Trp Arg Lys Thr Asp
545                 550                 555                 560

Phe Lys Val Glu Thr Asp Tyr Gly Glu Ile Val Ser Asp Glu Val His
                565                 570                 575

Arg Leu Tyr Gln Ala Ile Leu Asp Gly Lys Glu Trp Ser Lys Glu Val
            580                 585                 590

Asp Asp Pro Glu Lys Tyr Phe Val Asp Asp Leu Tyr Asn Arg Cys Pro
        595                 600                 605

Glu Ser Ile Tyr Val Arg Asn Gly Val Asp Pro Asp Asn Lys Ile Met
    610                 615                 620

Ile Lys Lys Arg Gly Leu Val Gly Glu Gly Gln Arg His Phe Ser Ala
625                 630                 635                 640

Arg Phe Val Ser Tyr Trp Tyr Glu Phe Gln Lys Val Thr Ile Lys Ala
                645                 650                 655

Asp Ser Lys Arg Leu Asp Ala Arg Gly Glu His Thr Gln Tyr His Glu
            660                 665                 670

Ile Asp Val Glu Asp Phe Lys Pro Cys Ala Ile Ala Glu Leu Gly Leu
        675                 680                 685

His Cys Ser Thr Tyr Ile Tyr Gln Asp Leu Leu Val Gly Ala Asn Arg
    690                 695                 700

Gly Glu Tyr Val Lys Asp Ala Lys Glu Leu Val Trp Phe Asp Ile Ala
705                 710                 715                 720

Asn Thr Asn Tyr Asn Ile Thr Arg Pro Phe Asp Arg Cys Trp Pro Ser
                725                 730                 735

Ser Cys Ala Glu Ala Glu Leu Ser Leu Arg Phe His Leu Ile Thr Lys
            740                 745                 750

Ile Phe Thr Arg Tyr Arg Gly Glu Arg Thr Ser Phe Val Asp Ile Ile
        755                 760                 765

Asn Glu Leu Ser Glu Arg Gly Tyr Val Lys His Asn Phe Pro Ser Tyr
    770                 775                 780

Lys His Tyr Tyr Leu Ser Val Ile Gln Thr Val Phe Glu Asp Gln Arg
785                 790                 795                 800

Ala Ile Asp Pro Leu Asp Phe Cys Ala Met Ile Ser Arg Asn Glu Thr
                805                 810                 815

Arg Glu Ser Thr Leu Lys Gly Phe Ser Met Phe Ala Ala Ile Val Lys
            820                 825                 830
```

```
Ser Glu Arg Leu Ile Asp Thr Leu Phe Leu Asn Phe Leu Leu Trp Ile
        835                 840                 845

Val Phe Glu Met Glu Asn Val Asp Val Ser Ala Ala Asn Lys Arg His
    850                 855                 860

Pro Leu Leu Ile Ser His Glu Lys Gly Leu Arg Leu Ile Gly Val Asp
865                 870                 875                 880

Leu Phe Asn Gly Ala Leu Ser Ile Ser Thr Gly Gly Trp Ile Pro Tyr
                885                 890                 895

Leu Glu Arg Ile Cys Ser Glu Glu Lys Ala Gln Arg Arg Leu Asn Ala
            900                 905                 910

Asp Glu Leu Lys Ile Lys Ser Trp Phe Leu Thr Tyr Tyr Met Asn Leu
        915                 920                 925

Ser Leu Glu Arg Arg Ala Glu Pro Arg Met Ser Phe Lys Phe Glu Gly
    930                 935                 940

Leu Thr Thr Trp Ile Gly Ser Asn Cys Gly Gly Val Arg Asp Tyr Val
945                 950                 955                 960

Val Gln Ala Leu Pro Met Arg Lys Pro Lys Pro Gly Leu Leu Met Val
                965                 970                 975

Ile Tyr Gly Asp Asp Gly Asp Ala Arg Trp Val Glu Trp Ala Met Lys
            980                 985                 990

Asn Phe Thr Ala Val Asp Gly Ser  Leu Gly Phe Ile Tyr  Ile Asp Arg
        995                 1000                1005

His Lys  Leu Val Asn Lys Ser  Asp Phe Arg Val Arg  Glu Met Lys
    1010                 1015                 1020

Ile Tyr  Asn Arg Gly Arg Leu  Asp Arg Leu Ile Leu  Ile Ser Ser
    1025                 1030                 1035

Gly His  Tyr Thr Phe Gly Asn  Lys Phe Leu Met Ser  Lys Leu Leu
    1040                 1045                 1050

Ala Lys  Thr Glu
    1055


<210> SEQ ID NO 60
<211> LENGTH: 1060
<212> TYPE: PRT
<213> ORGANISM: Artificial Sequence
<220> FEATURE:
<223> OTHER INFORMATION: AHSV4-VP2 - B4UUN5_9REOV

<400> SEQUENCE: 60

Met Ala Ser Glu Phe Gly Ile Leu Met Thr Asn Glu Lys Phe Asp Pro
1               5                   10                  15

Ser Leu Glu Lys Thr Ile Cys Asp Val Ile Val Thr Lys Lys Gly Arg
            20                  25                  30

Val Lys His Lys Glu Val Asp Gly Val Cys Gly Tyr Glu Trp Asp Glu
        35                  40                  45

Thr Asn His Arg Phe Gly Leu Cys Glu Val Glu His Asp Met Ser Ile
    50                  55                  60

Ser Glu Phe Met Tyr Asn Glu Ile Arg Cys Glu Gly Ala Tyr Pro Ile
65                  70                  75                  80

Phe Pro Arg Tyr Ile Ile Asp Thr Leu Lys Tyr Glu Lys Phe Ile Asp
                85                  90                  95

Arg Asn Asp His Gln Ile Arg Val Asp Arg Asp Asp Asn Glu Met Arg
            100                 105                 110

Lys Ile Leu Ile Gln Pro Tyr Ala Gly Glu Met Tyr Phe Ser Pro Glu
        115                 120                 125
```

```
Cys Tyr Pro Ser Val Phe Leu Arg Arg Glu Ala Arg Ser Gln Lys Leu
    130                 135                 140

Asp Arg Ile Arg Asn Tyr Ile Gly Lys Arg Val Glu Phe Tyr Glu Glu
145                 150                 155                 160

Glu Ser Lys Arg Lys Ala Ile Leu Asp Gln Asn Lys Met Ser Lys Val
                165                 170                 175

Glu Gln Trp Arg Asp Ala Val Asn Glu Arg Ile Val Ser Ile Glu Pro
            180                 185                 190

Lys Arg Gly Glu Cys Tyr Asp His Gly Thr Asp Ile Ile Tyr Gln Phe
        195                 200                 205

Ile Lys Lys Leu Arg Phe Gly Met Met Tyr Pro His Tyr Tyr Val Leu
    210                 215                 220

Pro Ser Asp Tyr Cys Ile Val Pro Asn Lys Gly Gly Thr Ser Ile Gly
225                 230                 235                 240

Ser Trp His Ile Arg Lys Arg Thr Glu Gly Asp Ala Lys Val Ser Ala
                245                 250                 255

Met Tyr Ser Gly Lys Gly Pro Leu Asn Asp Leu Arg Val Lys Ile Glu
            260                 265                 270

Arg Asp Asp Leu Ser Arg Glu Thr Ile Ile Gln Ile Ile Glu Tyr Gly
        275                 280                 285

Lys Lys Phe Asn Ser Ser Ala Gly Asp Lys Gln Gly Asn Ile Ser Ile
    290                 295                 300

Glu Lys Leu Val Glu Tyr Phe Asp Phe Leu Thr Thr Phe Val His Ala
305                 310                 315                 320

Lys Lys Lys Glu Glu Gly Glu Asp Asp Thr Ala Arg Gln Glu Ile Arg
                325                 330                 335

Lys Ala Trp Val Lys Gly Met Pro Tyr Met Asp Phe Ser Lys Pro Met
            340                 345                 350

Lys Ile Thr Arg Gly Phe Asn Arg Asn Met Leu Phe Leu Ala Ala Leu
        355                 360                 365

Asp Ser Phe Arg Lys Arg Asn Gly Val Asp Val Asp Pro Asn Lys Gly
    370                 375                 380

Lys Trp Lys Glu His Ile Lys Glu Val Thr Glu Lys Leu Lys Lys Ala
385                 390                 395                 400

Leu Thr Glu Asn Gly Gly Gln Pro Cys Gln Val Ser Ile Asp Gly Val
                405                 410                 415

Asn Val Leu Thr Asn Val Asp Tyr Gly Thr Val Asn His Trp Ile Asp
            420                 425                 430

Trp Val Thr Asp Ile Ile Met Val Val Gln Thr Lys Arg Leu Val Lys
        435                 440                 445

Glu Tyr Ala Phe Lys Lys Leu Lys Ser Glu Asn Leu Leu Ala Gly Met
    450                 455                 460

Asn Ser Leu Val Gly Val Leu Arg Cys Tyr Met Tyr Cys Leu Ala Leu
465                 470                 475                 480

Ala Ile Tyr Asp Phe Tyr Glu Gly Thr Ile Asp Gly Phe Lys Lys Gly
                485                 490                 495

Ser Asn Ala Ser Ala Ile Ile Glu Thr Val Ala Gln Met Phe Pro Asp
            500                 505                 510

Phe Arg Arg Glu Leu Val Glu Lys Phe Gly Ile Asp Leu Arg Met Lys
        515                 520                 525

Glu Ile Thr Arg Glu Leu Phe Val Gly Lys Ser Met Thr Ser Lys Phe
    530                 535                 540

Met Glu Glu Gly Glu Tyr Gly Tyr Lys Phe Ala Tyr Gly Trp Arg Arg
545                 550                 555                 560
```

-continued

```
Asp Gly Phe Ala Val Met Glu Asp Tyr Gly Glu Ile Leu Thr Glu Lys
                565                 570                 575

Val Glu Asp Leu Tyr Lys Gly Val Leu Leu Gly Arg Lys Trp Glu Asp
            580                 585                 590

Glu Val Asp Asp Pro Glu Ser Tyr Phe Tyr Asp Asp Leu Tyr Thr Asn
        595                 600                 605

Glu Pro His Arg Val Phe Leu Ser Ala Gly Lys Asp Val Asp Asn Asn
    610                 615                 620

Ile Thr Leu Arg Ser Ile Ser Gln Ala Glu Thr Thr Tyr Leu Ser Lys
625                 630                 635                 640

Arg Phe Val Ser Tyr Trp Tyr Arg Ile Ser Gln Val Glu Val Thr Lys
                645                 650                 655

Ala Arg Asn Glu Val Leu Asp Met Asn Glu Lys Gln Lys Pro Tyr Phe
            660                 665                 670

Glu Phe Glu Tyr Asp Asp Phe Lys Pro Cys Ser Ile Gly Glu Leu Gly
        675                 680                 685

Ile His Ala Ser Thr Tyr Ile Tyr Gln Asn Leu Leu Val Gly Arg Asn
    690                 695                 700

Arg Gly Glu Glu Ile Leu Asp Ser Lys Glu Leu Val Trp Met Asp Met
705                 710                 715                 720

Ser Leu Leu Asn Phe Gly Ala Val Arg Ser His Asp Arg Cys Trp Ile
                725                 730                 735

Ser Ser Ser Val Ala Ile Glu Val Asn Leu Arg His Ala Leu Ile Val
            740                 745                 750

Arg Ile Phe Ser Arg Phe Asp Met Met Ser Glu Arg Glu Thr Phe Ser
        755                 760                 765

Thr Ile Leu Glu Lys Val Met Glu Asp Val Lys Glu Leu Arg Phe Phe
    770                 775                 780

Pro Thr Tyr Arg His Tyr Tyr Leu Glu Thr Leu Gln Arg Val Phe Asn
785                 790                 795                 800

Asp Glu Arg Arg Leu Glu Val Asp Asp Phe Tyr Met Arg Leu Tyr Asp
                805                 810                 815

Val Gln Thr Arg Glu Gln Ala Leu Asn Thr Phe Thr Asp Phe His Arg
            820                 825                 830

Cys Val Glu Ser Glu Leu Leu Leu Pro Thr Leu Lys Leu Asn Phe Leu
        835                 840                 845

Leu Trp Ile Val Phe Glu Met Glu Asn Val Glu Val Asn Ala Ala Tyr
    850                 855                 860

Lys Arg His Pro Leu Leu Ile Ser Thr Ala Lys Gly Leu Arg Val Ile
865                 870                 875                 880

Gly Val Asp Ile Phe Asn Ser Gln Leu Ser Ile Ser Met Ser Gly Trp
                885                 890                 895

Ile Pro Tyr Val Glu Arg Met Cys Ala Glu Ser Lys Val Gln Thr Lys
            900                 905                 910

Leu Thr Ala Asp Glu Leu Lys Leu Lys Arg Trp Phe Ile Ser Tyr Tyr
        915                 920                 925

Thr Thr Leu Lys Leu Asp Arg Arg Ala Glu Pro Arg Met Ser Phe Lys
    930                 935                 940

Phe Glu Gly Leu Ser Thr Trp Ile Gly Ser Asn Cys Gly Gly Val Arg
945                 950                 955                 960

Asp Tyr Val Ile Gln Met Leu Pro Thr Arg Lys Pro Lys Pro Gly Ala
                965                 970                 975

Leu Met Val Val Tyr Ala Arg Asp Ser Arg Ile Glu Trp Ile Glu Ala
```

-continued

```
            980                 985                 990

Glu Leu Ser Gln Trp Leu Gln Met  Glu Gly Ser Leu Gly  Leu Ile Leu
        995                 1000                1005

Val His  Asp Ser Gly Ile Ile  Asn Lys Ser Val Leu  Arg Ala Arg
    1010                 1015                 1020

Thr Leu  Lys Ile Tyr Asn Arg  Gly Ser Met Asp Thr  Leu Ile Leu
    1025                 1030                 1035

Ile Ser  Ser Gly Val Tyr Thr  Phe Gly Asn Lys Phe  Leu Leu Ser
    1040                 1045                 1050

Lys Leu  Leu Ala Lys Thr Glu
    1055                 1060
```

<210> SEQ ID NO 61
<211> LENGTH: 1051
<212> TYPE: PRT
<213> ORGANISM: Artificial Sequence
<220> FEATURE:
<223> OTHER INFORMATION: AHSV4-VP2 - B4UUN6_9REOV

<400> SEQUENCE: 61

```
Met Ala Ser Glu Phe Gly Ile Leu Ile Cys Asp Lys Leu Lys Glu Asn
1               5                   10                  15

Thr Leu Glu Lys Thr Asn Cys Asp Val Ile Ile Thr Gly Val Gly Lys
            20                  25                  30

Val Ser Val Arg Glu Glu Asp Gly Ile Leu Gly Tyr Glu Trp Glu Glu
        35                  40                  45

Thr Asn His Arg Leu Gly Leu Cys Glu Ile Glu Asn Thr Val Ser Ile
    50                  55                  60

Ser Asp Phe Val Tyr Lys Gln Ile Arg Cys Glu Gly Ala Tyr Pro Ile
65                  70                  75                  80

Leu Pro His Tyr Val Thr Asp Val Ile Lys Tyr Gly Met Val Ile Asp
                85                  90                  95

Arg Asn Asp His Gln Ile Arg Val Asp Arg Asp Glu Lys Ser Ile Gly
            100                 105                 110

Lys Ile Gln Ile Gln Pro Tyr Phe Gly Asp Met Tyr Phe Ser Pro Glu
        115                 120                 125

Tyr Tyr Pro Ala Thr Phe Val Lys Arg Glu Pro Leu Pro Ile Ser Val
    130                 135                 140

Asp Met Ile Arg Asp Tyr Ile Gly Ala Arg Met Arg Lys Ile Glu Ala
145                 150                 155                 160

Arg Ala Gly Arg Ile Lys Glu Gly Gly Gly Asn Leu Leu Glu Cys Ala
                165                 170                 175

Arg Arg Trp Glu Lys Ala Ala Tyr Glu Arg Ile Glu Asn Glu Arg Ala
            180                 185                 190

Leu Arg Cys Val Val His Glu Thr Asp Pro Thr Tyr Gln Ile Leu Lys
        195                 200                 205

Lys Leu Arg Phe Gly Phe Ile Tyr Pro His Tyr Tyr Val Leu Asn Thr
    210                 215                 220

Asp Tyr Asn Pro Thr Thr Val Thr Arg Thr Ser Arg Ile Asn Asp Trp
225                 230                 235                 240

Leu Leu Lys Glu Lys Thr Gln Gly Val Val Lys Ala Ala Glu Ala Tyr
                245                 250                 255

Ser Asp Asn Ala Glu Leu Lys Thr Leu Ala Glu Arg Met Glu Glu Glu
            260                 265                 270

Glu Leu Thr Val Asp Ile Ile Arg Ala Val Ile Arg Tyr Gly Ala Lys
        275                 280                 285
```

```
Tyr Ala Thr Arg Ser Gly Met Arg Glu Asp Thr Leu Ser Leu Gln Glu
    290                 295                 300

Leu Asp Arg Tyr Cys Asp Ser Leu Thr Thr Phe Val His Lys Lys Lys
305                 310                 315                 320

Lys Asp Glu Gly Asp Asp Glu Thr Ala Arg Thr Ile Ile Arg Asn Gln
                325                 330                 335

Trp Ile Lys Gly Met Pro Arg Met Asp Phe Lys Lys Glu Met Lys Ile
            340                 345                 350

Thr Arg Gly Pro Ile Ala Asn Trp Ser Phe Phe Met Ser Ile Asp Ala
        355                 360                 365

Phe Lys Arg Asn Asn Lys Val Asp Ile Asn Pro Asn His Gln Thr Trp
    370                 375                 380

Lys Asp His Ile Lys Glu Val Thr Asp Gln Met Asn Arg Ala Gln Gln
385                 390                 395                 400

Gly Asn Asn Asn Lys Pro Leu Lys Ile Gln Ile Asp Gly Val Ser Ile
                405                 410                 415

Leu Thr Asn Glu Lys Tyr Gly Thr Val Gly His Trp Val Asp Trp Val
            420                 425                 430

Val Asp Leu Ile Met Leu Ala Gln Val Lys Met Leu Ile Lys Glu Tyr
        435                 440                 445

Lys Phe Lys Arg Leu Asn Ser Gln Asn Leu Met Ser Gly Met Asn Lys
    450                 455                 460

Leu Val Gly Ala Leu Arg Cys Tyr Ala Tyr Cys Leu Ile Leu Ala Leu
465                 470                 475                 480

Tyr Asp Tyr Tyr Gly Gln Asp Ile Glu Gly Phe Lys Lys Gly Ser Asn
                485                 490                 495

Ser Ser Ala Ile Leu Glu Thr Val Ile Gln Met Phe Pro Asn Phe Lys
            500                 505                 510

Gln Glu Ile Gln Ala Asn Phe Gly Ile Asn Leu Asn Ile Lys Asp Lys
        515                 520                 525

Lys Gln Ser Leu Phe Val Glu Arg Thr Met His Ser Asp Phe Ser Ser
    530                 535                 540

Asn Glu Glu Tyr Gly Tyr Lys Phe Val Phe Gly Trp Ala Ala Arg Gly
545                 550                 555                 560

Glu Glu Val Leu Ser Asn Tyr Gly Asp Ile Leu Ser Asp Glu Val Glu
                565                 570                 575

Glu Leu Phe Thr Lys Leu Arg Lys Lys Glu His Trp Asp Lys Val Val
            580                 585                 590

Glu Asp Pro Glu Ser Tyr Phe Val Asp Glu Leu Tyr Gln Lys Asn Pro
        595                 600                 605

Ala Glu Val Phe Phe Ser Ala Gly Tyr Asp Thr Asp Gln Asn Val Val
    610                 615                 620

Ile Asp Gly Lys Met Thr Glu Gly Val Thr Tyr Phe Ser Lys Arg Phe
625                 630                 635                 640

Val Ser Tyr Trp Tyr Arg Val Glu Lys Ile Thr Thr Lys His Leu Glu
                645                 650                 655

Phe Leu Asn Glu Glu Gly Arg Lys Val Ala Gln Phe Asp Phe Glu Asp
            660                 665                 670

Tyr Lys Pro Met Ala Ile Gly Glu Met Gly Ile His Ala Ser Thr Tyr
        675                 680                 685

Lys Tyr Glu Ser Leu Leu Leu Gly Lys Asn Arg Gly Gln Lys Val Lys
    690                 695                 700

Asp Ser Ile Ala Leu Cys Asn Tyr Asp Leu Ala Leu Thr Asn Phe Glu
```

705 710 715 720

Val Ser Arg Arg Gln Asp Cys Cys Trp Ile Ser Ser Cys Ser Ala Ile
725 730 735

Glu Leu Ser Met Arg Ala Asn Ile Thr Ile Ala Ile Phe Arg Arg Ile
740 745 750

Glu Asp Arg Arg Tyr Glu Ser Phe Ala Lys Ile Leu Ser Gly Leu Ser
755 760 765

Gln Gln Gln Asp Leu Tyr Phe Pro Thr Tyr Lys His Tyr Tyr Leu Phe
770 775 780

Val Leu Gln Lys Val Leu Arg Asp Glu Arg Arg Ile Asp Gln Asn Arg
785 790 795 800

Met Cys Thr Glu Leu Phe Asp Ile Gln Arg Arg Arg Gly Ile Leu Leu
805 810 815

Ser Phe Thr Thr Leu Arg Phe Trp Asn Asp Ser Glu Phe Leu Gly Asp
820 825 830

Thr Leu Met Met Asn Phe Leu Leu Trp Val Val Phe Glu Met Glu Asn
835 840 845

Ile Asp Val Asp Tyr Gly Lys Lys Trp His Pro Leu Leu Val Ser Ser
850 855 860

Glu Lys Gly Leu Arg Val Ile Ala Val Asp Val Phe Asn Ser Met Met
865 870 875 880

Gly Val Ser Thr Ser Gly Trp Leu Pro Tyr Val Glu Arg Ile Cys Ser
885 890 895

Glu Ser Asp Met Arg Arg Arg Leu Asn Ala Asp Glu Leu Glu Leu Lys
900 905 910

Arg Trp Phe Phe Asp Tyr Tyr Ala Thr Leu Leu Leu Glu Arg Arg Gly
915 920 925

Glu Pro Arg Leu Ser Phe Lys Tyr Glu Gly Leu Thr Thr Trp Ile Gly
930 935 940

Ser Asn Cys Gly Gly Val Arg Asp Tyr Val Val Gln Leu Leu Pro Met
945 950 955 960

Arg Lys Pro Lys Pro Gly Leu Leu Cys Ile Ala Tyr Gly Asp Asp Val
965 970 975

Asn Val Gln Trp Val Glu His Glu Leu Arg Asp Phe Leu Thr His Glu
980 985 990

Gly Ser Leu Gly Leu Val Val Ile Ser Gly Lys Met Leu Val Asn Lys
995 1000 1005

Ser Lys Leu Arg Val Arg Asn Leu Lys Ile Tyr Asn Arg Gly Thr
1010 1015 1020

Leu Asp Ser Leu Phe Leu Ile Ser Gly Gly Ser Tyr Thr Phe Gly
1025 1030 1035

Asn Lys Phe Leu Leu Ser Lys Leu Met Ala Lys Ala Glu
1040 1045 1050

<210> SEQ ID NO 62
<211> LENGTH: 1057
<212> TYPE: PRT
<213> ORGANISM: artificial sequence
<220> FEATURE:
<223> OTHER INFORMATION: AHSV4-VP2 - B4UUN7_9REOV

<400> SEQUENCE: 62

Met Ala Phe Glu Phe Gly Ile Leu Leu Thr Glu Lys Val Glu Gly Asp
1 5 10 15

Ala Leu Glu Lys Thr Asn Cys Glu Val Ile Ile Thr Lys Asn Gly Arg
20 25 30

-continued

```
Val Lys His Lys Glu Val Asp Gly Val Lys Gly Tyr Glu Trp Glu Phe
        35                  40                  45

Thr Asp His Arg Leu Gly Leu Cys Glu Glu Ser Tyr Leu Met Lys Met
    50                  55                  60

Ala Glu Tyr Val Tyr Thr Gln Thr Lys Cys Glu Gly Ala Tyr Pro Val
65                  70                  75                  80

Phe Pro His Tyr Ile Thr Asp Val Leu Lys Tyr Gly Val Met Val Asp
                85                  90                  95

Arg Asn Asp His Gln Ile Arg Val Asp Arg Asp Val Lys Glu Leu Gly
            100                 105                 110

Lys Ile Leu Ile Gln Pro Tyr Phe Gly Glu Val Phe Phe Ser Pro Glu
        115                 120                 125

Phe Tyr Thr Ser Thr Phe Leu Lys Arg Gln Ala Ile Asn Ser Asp Val
    130                 135                 140

Glu Met Leu Arg Arg Ser Ile Pro Lys Arg Ile Lys Tyr Phe Glu Asp
145                 150                 155                 160

Gln Met Glu Leu Arg Lys Ser Val Asn Gly Asn Trp Ile Gly Thr Leu
                165                 170                 175

His Lys Trp Lys Glu Ser Val Asp Ala Arg Met Leu Glu Glu Gly Val
            180                 185                 190

Gly Lys Lys Val Cys Val Ser His Glu Thr Asp Val Val Tyr Gln Leu
        195                 200                 205

Met Lys Lys Met Arg Phe Gly Leu Leu Tyr Pro His Tyr Tyr Met Leu
    210                 215                 220

Asn Asn Glu Tyr Val Val Lys Lys Glu Asn Val Asp Ala Leu Ile Gly
225                 230                 235                 240

Ser Trp Leu Ile Lys Glu Arg Ser Ser Gly Lys Ala Glu Tyr Ser Gln
                245                 250                 255

Met Tyr Ser Gly Val Gly Pro Leu Ser Gly Leu Arg Glu Arg Ile Glu
            260                 265                 270

Lys Asp Glu Leu Asp Glu Lys Val Ile Gln Glu Ile Ile Ala Tyr Gly
        275                 280                 285

Ser Lys Phe Ser Thr Tyr Thr Gly Ala Lys His Gly Asp Ile Ser Leu
    290                 295                 300

Lys Asp Leu Val Glu Tyr Cys Glu Ser Leu Thr Thr Phe Val His Lys
305                 310                 315                 320

Lys Lys Lys Asp Gly Glu Glu Glu Thr Ala Arg Gln Phe Phe Lys Asn
                325                 330                 335

Lys Trp Ile Gln Gly Met Pro Lys Met Asn Phe Glu Ser Glu Met Lys
            340                 345                 350

Val Ser Arg Gly Pro Trp Ala Asn Ile Gln Phe Phe Trp Ser Ile Asp
        355                 360                 365

Met Phe Lys Arg Asn Asn Gly Val Asp Ile Asp Pro Asn Gly Glu Asn
    370                 375                 380

Trp Lys Lys Tyr Lys Ala Glu Val Gln Glu Arg Leu Asn Glu Ala Gln
385                 390                 395                 400

Lys Lys Asn Arg Asn Val Pro His Leu Met Leu Val Asp Gly Val Asn
                405                 410                 415

Ile Met Thr Asp Lys Lys Tyr Gly Thr Val Gln Asn Trp Val Asp Trp
            420                 425                 430

Val Val Asn Tyr Ile Met Leu Ser His Val Lys Arg Leu Val Lys Asp
        435                 440                 445

Tyr Lys Phe Lys Arg Leu Gln Pro Asp Asn Leu Met Ser Gly Met Asn
```

```
    450                 455                 460

Lys Leu Val Gly Ala Leu Arg Cys Tyr Ala Tyr Cys Leu Ile Leu Ala
465                 470                 475                 480

Leu Tyr Asp His Phe Gly Ala Glu Ile Glu Gly Phe Arg Lys Gly Thr
                485                 490                 495

Asn Ala Ala Ser Ile Val Glu Thr Val Ser Gln Met Phe Pro Asn Phe
            500                 505                 510

Arg Lys Glu Val Ser Glu Thr Phe Gly Ile Asp Leu Lys Thr Lys Glu
        515                 520                 525

Ile Lys His Glu Leu Phe Lys Ala Gln Asn Met Asn Val Lys Ala Ala
    530                 535                 540

Asp Val Gly Asp Tyr Gly Tyr Lys Phe Gln Tyr Gly Trp Thr Arg Thr
545                 550                 555                 560

Ala Glu Gln Val Met Ser Asp Tyr Gly Glu Ile Leu Thr Glu Glu Ile
                565                 570                 575

Glu Thr Leu Tyr Gln Ser Ile Leu Ala Gly Lys Glu Trp Glu Lys Val
            580                 585                 590

Ser Asp Glu Thr Asp Val Tyr Phe Ile Asp Asp Leu Phe Ser Ser Thr
        595                 600                 605

Pro Asp Lys Val Phe Arg Arg Val Gly Leu Asp Ser Gln Asn Asn Ile
    610                 615                 620

Lys Ile Glu Gly Lys Met Asn Glu Leu Thr Thr Tyr Phe Ser Lys Arg
625                 630                 635                 640

Phe Val Thr Tyr Trp Tyr Lys Ile Thr Lys Val Glu Lys Lys Asp Leu
                645                 650                 655

Leu Ile Val Asn Asp Ile Tyr Asp Glu Lys Thr Glu Tyr Gln Gln Phe
            660                 665                 670

Asp Pro Asp Asp Phe Lys Pro Met Val Ile Gly Glu Met Gly Val His
        675                 680                 685

Ala Ser Thr Tyr Ile Tyr Gln Asn Leu Ile Leu Gly Arg Asn Arg Gly
    690                 695                 700

Glu Arg Ile Val Asp Ser Lys Glu Ile Val Trp Tyr Asp Leu Ser Leu
705                 710                 715                 720

Thr Asn Phe Gly Leu Val Arg Ser Gln Asn Gln Cys Trp Ile Gly Ser
                725                 730                 735

Ile Ser Asn Phe Glu Leu Ser Met Arg Tyr His Ile Ile Thr Glu Ile
            740                 745                 750

Phe Gln Arg Tyr Arg Val Asp Ser Ala His Lys Ser Tyr His Glu Ile
        755                 760                 765

Ile Ser Gly Leu Thr Lys Lys Asp Val Ile Leu Phe Pro Ser Tyr Lys
    770                 775                 780

His Tyr Tyr Val Arg Val Ile Gln Asp Val Phe Gln Asp Ser Gln Lys
785                 790                 795                 800

Val Asp Val Leu Asp Phe Cys Leu Arg Ile Ala Asn Pro Glu Thr Arg
                805                 810                 815

Leu Ser Thr Leu Leu Lys Ile Gln Gly Phe Arg Ala Cys Val Glu Ser
            820                 825                 830

Glu Phe Leu Leu Pro Thr Leu His Leu Asn Phe Leu Ile Trp Leu Leu
        835                 840                 845

Ile Asp Met Glu Asn Gly Asp Ile Asn Tyr Ser Lys Lys Arg Leu Pro
    850                 855                 860

Leu Leu Ile Ser Thr Thr Asn Gly Leu Arg Val Met Ala Val Asp Ala
865                 870                 875                 880
```

```
Phe Asn Asn Met Ile Ala Met Ser Tyr Ser Gly Trp Leu Pro Tyr Leu
                885                 890                 895

Glu Arg Ile Cys His Glu Thr Lys Gln Arg Thr Arg Leu Asn Ala Asp
            900                 905                 910

Glu Leu Lys Leu Lys Lys Trp Phe Leu Asn Tyr Val Thr Lys Tyr Glu
        915                 920                 925

Val Glu Arg Arg Ala Glu Pro Arg Met Ser Phe Lys Met Glu Gly Ile
    930                 935                 940

Thr Thr Trp Ile Gly Ser Asn Cys Gly Gly Val Gln Asp Tyr Ile Leu
945                 950                 955                 960

His Leu Ile Pro Ser Arg Lys Pro Lys Pro Gly Leu Leu Phe Leu Ile
                965                 970                 975

Tyr Thr Asp Ala Gly Asp Val Asp Trp Val Thr Arg Met Leu Tyr Asp
            980                 985                 990

Val Cys Arg Leu Glu Gly Ser Leu  Gly Phe Ile Leu Ile  Asp Asp Arg
        995                 1000                1005

Val Met  Val Asn Lys Ser Gln  Leu Arg Ala Arg Ile  Leu Lys Ile
    1010                 1015                 1020

Tyr Asn  Arg Gly Lys Leu Asp  Lys Leu Ile Leu Ile  Ser Gly Gly
    1025                 1030                 1035

Asn Tyr  Thr Phe Gly Asn Lys  Phe Leu Leu Ser Lys  Leu Leu Ala
    1040                 1045                 1050

Lys Thr  Glu Lys
    1055


<210> SEQ ID NO 63
<211> LENGTH: 1052
<212> TYPE: PRT
<213> ORGANISM: Artificial Sequence
<220> FEATURE:
<223> OTHER INFORMATION: AHSV4-VP2 - B4UUN8_9REOV

<400> SEQUENCE: 63

Met Ala Phe Glu Phe Gly Ile Leu Gln Thr Asp Lys Ile Arg Glu Asn
1               5                   10                  15

Thr Leu Glu Lys Thr Asn Cys Asp Val Ile Leu Thr Lys Glu Asn Arg
            20                  25                  30

Val Arg Met Lys Glu Val Glu Gly Val Lys Gly Tyr Tyr Trp Glu Asp
        35                  40                  45

Thr Asp His Arg Leu Gly Leu Cys Glu Val Glu His Thr Val Ser Val
    50                  55                  60

Arg Asp Phe Val Tyr Lys Gln Thr Lys Cys Glu Gly Ser Tyr Pro Val
65                  70                  75                  80

Val Pro Leu Tyr Met Ile Asp Ala Ile Lys Tyr Gly Arg Met Ile Asp
                85                  90                  95

Arg Asn Asp His Gln Ile Arg Val Asp Lys Asp Asp Lys Ile Leu Ser
            100                 105                 110

Lys Ile Gln Val Gln Pro Tyr Leu Gly Asp Ala Tyr Phe Ser Pro Glu
        115                 120                 125

Tyr Tyr Thr Ala Thr Phe Phe Lys Arg Glu Pro Leu Pro Ile His Val
    130                 135                 140

Asp Met Ile Arg Asp Tyr Ile Gly Lys Arg Ile Asn Tyr Phe Glu Arg
145                 150                 155                 160

Glu Leu Ser Gly Gly Val Arg Asp Ala Asn Leu Glu Met Ile Val Glu
                165                 170                 175

Lys Trp Lys Asp Asn Thr Tyr Lys Arg Ile Glu Gly Glu Lys Thr Thr
```

-continued

```
            180                 185                 190

Met Cys Val Arg His Glu Pro Asp Ser Val Leu Gln Met Leu Lys Lys
        195                 200                 205

Met Arg Phe Gly Met Leu Tyr Pro Asn Tyr Tyr Met Leu Asn Thr Asp
    210                 215                 220

Tyr Ile Val Thr Glu Ser Ser Lys Glu Ala Pro Leu Asn Arg Trp Leu
225                 230                 235                 240

Val Lys Glu Lys Thr Val Gly Lys Val Lys Ala Ala Glu Ala Phe Ala
                245                 250                 255

Gly Asn Ser Leu Leu Lys Ser Leu Ala Ser Arg Met Glu Asp Glu Glu
            260                 265                 270

Leu Ser Arg Glu Ile Ile Ile Ala Val Ile Asn Tyr Gly Ser Lys Phe
        275                 280                 285

Gly Thr Arg Ser Gly Lys Lys Lys Asp Leu Met Thr Ile Asp Lys Leu
    290                 295                 300

Glu Lys Tyr Cys Asp Ser Leu Thr Thr Phe Val His Lys Lys Lys Arg
305                 310                 315                 320

Asp Glu Gly Asp Asp Glu Thr Ala Arg Ala Ile Ile Arg Asn Gln Trp
                325                 330                 335

Ile Lys Gly Met Pro Ser Met Asn Leu Lys Lys Glu Met Lys Val Ser
            340                 345                 350

Arg Gly Pro Ile Gln Asn Trp Ser Phe Phe Met Ser Leu Glu Met Phe
        355                 360                 365

Lys Arg Asn Asn Lys Val Asp Ile Asp Pro Asn His Asp Thr Trp Lys
    370                 375                 380

Asn His Val Lys Glu Ile Arg Glu Arg Met Gln Lys Glu Gln Ser Ala
385                 390                 395                 400

Asn Ser Asn Ser Pro Leu Lys Ile Gln Val Asp Gly Val Ser Leu Ser
                405                 410                 415

Thr Gly Glu Phe Tyr Gly Thr Val Glu His Trp Ile Asp Trp Val Val
            420                 425                 430

Asp Leu Ile Met Leu Ala Gln Val Lys Arg Leu Ile Lys Glu Tyr Lys
        435                 440                 445

Phe Val Arg Leu Glu Thr Ser Asn Leu Met Ala Gly Met Asn Lys Leu
    450                 455                 460

Val Gly Ala Leu Arg Cys Tyr Ala Tyr Cys Leu Ile Leu Ala Leu Tyr
465                 470                 475                 480

Asp Phe Tyr Gly Ala Asp Ile Glu Gly Phe Glu Lys Gly Ser Asn Ser
                485                 490                 495

Ser Ala Ile Val Glu Thr Val Val Gln Met Phe Pro Asn Phe Lys Gln
            500                 505                 510

Glu Ile Gln Ala Asn Phe Gly Ile Asn Leu Asn Ile Lys Asp Lys Lys
        515                 520                 525

Gln Ala Leu Phe Val Arg Met Asp Met Asp Ser Glu Phe Ser Glu Asp
    530                 535                 540

Glu Gln Lys Gly Tyr Met Phe Glu Tyr Gly Trp Ala Lys Arg Glu Glu
545                 550                 555                 560

Gln Ile Trp Ser Asn Tyr Gly Asp Ile Leu Thr Asp Leu Val Glu Gln
                565                 570                 575

Leu Tyr Lys Ser Ile Met Asn His Glu Glu Trp Glu Lys Ile Val Asp
            580                 585                 590

Asp Pro Glu Lys Tyr Phe Tyr Asp Asp Leu Phe Asn Ala Ser Pro Glu
        595                 600                 605
```

```
Thr Ala Phe Ile Ser Lys Gly Tyr Asp Pro Asp Asn Asn Ile Val Ile
    610                 615                 620

Glu Gly Lys Val Gly Gln Asp Val Thr Tyr Phe Ser Lys Arg Phe Val
625                 630                 635                 640

Ser Tyr Trp Tyr Arg Val Arg Gln Val Gln Thr Ser Lys Gly Ala Glu
                645                 650                 655

Arg Arg Ser Ile Glu Asp Val Lys Tyr Arg Glu Phe Asp Ile Glu Ser
            660                 665                 670

Phe Lys Pro Tyr Ala Ile Gly Glu Ile Gly Ile His Ala Ser Thr Tyr
        675                 680                 685

Lys Tyr Leu Asp Leu Leu Ala Gly Arg Asn Arg Gly Glu Lys Val Lys
    690                 695                 700

Asp Ser Gln Ala Leu Val Trp Tyr Asp Phe Ala Leu Thr Asn Tyr Thr
705                 710                 715                 720

Leu Val Arg Pro Gln Asp Arg Cys Trp Ile Met Ser Cys Thr Asp Cys
                725                 730                 735

Glu Tyr Thr Leu Arg Phe Ala Thr Ile Thr Met Ile Phe Glu Arg Leu
            740                 745                 750

Ser Glu Glu Ala Asp Leu Ser Tyr His Asp Ile Leu Leu Lys Val Arg
        755                 760                 765

Glu Tyr Pro Ile Gln Ser Phe Ala Ser Tyr Lys His Phe Tyr Val Arg
    770                 775                 780

Val Leu Gln His Val Phe Arg Asp Asn Gln Glu Ile Asp Val Leu Glu
785                 790                 795                 800

Phe Cys Thr Arg Met Leu Asp Pro Arg Thr Arg Glu Ala Gly Leu Asn
                805                 810                 815

Lys Phe Ser Arg Phe Arg Gln Trp Arg Glu Ser Glu Phe Leu Ile Asp
            820                 825                 830

Ala Leu Lys Met Asn Phe Leu Leu Trp Val Val Phe Glu Leu Glu Asn
        835                 840                 845

Ile Asp Val Asp Tyr Ser Lys Lys Arg His Pro Leu Leu Ile Ser Thr
    850                 855                 860

Asp Lys Gly Leu Arg Val Val Ser Val Asp Leu Phe Asn Ser Met Leu
865                 870                 875                 880

Ser Val Ser Leu Ser Gly Trp Ile Pro Tyr Val Glu Arg Val Cys Glu
                885                 890                 895

Arg Ser Glu Ala Lys Arg Arg Leu Asn Ala Asp Glu Leu Lys Leu Lys
            900                 905                 910

Asn Trp Phe Ile Ala Tyr Tyr Val Thr Leu Pro Leu Leu Arg Arg Ala
        915                 920                 925

Glu Pro Arg Met Ser Phe Lys Tyr Glu Gly Ile Thr Thr Trp Ile Gly
    930                 935                 940

Ser Asn Cys Gly Gly Val Arg Asp Tyr Leu Ile Gln Met Leu Pro Ala
945                 950                 955                 960

Arg Lys Pro Lys Pro Gly Val Leu Ile Leu Ala His Gly Ala Glu Ile
                965                 970                 975

Asn Val Ala Trp Leu Asn His Ala Leu Arg Asp Ile Leu Ser Leu Glu
            980                 985                 990

Gly Ser Leu Gly Ile Ile Ile Val  Ser Asp Gly Ser Val  Val Asn Lys
        995                 1000                1005

Ser Lys  Leu Arg Val Arg Asp  Met Lys Ile Tyr Asn  Arg Trp Glu
    1010                 1015                 1020

Val Asp  Arg Leu Ile Leu Ile  Ser Ser Gly Asp Tyr  Thr Phe Gly
    1025                 1030                 1035
```

-continued

```
Asn Lys  Tyr Leu Leu Ser Lys  Leu Met Ala Lys Ile  Glu Gln
    1040                 1045                 1050
```